United States Patent
Gottschling et al.

(10) Patent No.: US 8,952,014 B2
(45) Date of Patent: Feb. 10, 2015

(54) PYRIMIDINE DERIVATIVES WHICH ARE CGRP—ANTAGONISTS

(75) Inventors: Dirk Gottschling, Mittelbiberach (DE); Henri Doods, Warthausen (DE); Annekatrin Heimann, Biberach an der Riss (DE); Stephan Georg Mueller, Warthausen (DE); Klaus Rudolf, Warthausen (DE); Gerhard Schaenzle, Biberach an der Riss (DE); Dirk Stenkamp, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 509 days.

(21) Appl. No.: 13/140,607

(22) PCT Filed: Dec. 17, 2009

(86) PCT No.: PCT/EP2009/067360
§ 371 (c)(1),
(2), (4) Date: Sep. 13, 2011

(87) PCT Pub. No.: WO2010/070022
PCT Pub. Date: Jun. 24, 2010

(65) Prior Publication Data
US 2012/0088755 A1    Apr. 12, 2012

(30) Foreign Application Priority Data
Dec. 19, 2008   (EP) ..................................... 08172320

(51) Int. Cl.
*A01N 43/54*   (2006.01)
*C07D 239/42*   (2006.01)
*C07D 401/04*   (2006.01)

(52) U.S. Cl.
USPC ......................................... 514/256; 544/242

(58) Field of Classification Search
CPC ..... A01N 43/54; C07D 239/42; C07D 401/04
USPC ......................................... 514/256; 544/242
See application file for complete search history.

(56) References Cited

U.S. PATENT DOCUMENTS

| 7,173,028 B2 * | 2/2007 | Dahmann et al. ........... 514/235.8 |
| 7,709,480 B2 | 5/2010 | Dahmann et al. |
| 2008/0113966 A1 | 5/2008 | Burgey et al. |

FOREIGN PATENT DOCUMENTS

| CA | 2463989 A1 | 4/2003 |
| WO | 03032997 A1 | 4/2003 |
| WO | 2006031513 A2 | 3/2006 |
| WO | 2006041830 A2 | 4/2006 |
| WO | 2008060568 A2 | 5/2008 |

OTHER PUBLICATIONS

Paone et al.; Calcitonin gene-related peptide receptor antagonists for the treatment of migraine: a patent review; Expert Opinion on Therapeutic Patents 2009 Informa Healthcare GBR; vol. 19; No. 12; Dec. 2009; pp. 1675-1713.
International Search Report, Form PCT/ISA/210, for corresponding PCT/EP2009/067360; date of mailing: Mar. 24, 2010.

* cited by examiner

*Primary Examiner* — Paul V. Ward
(74) *Attorney, Agent, or Firm* — Michael P. Morris; Alan R. Stempel

(57) ABSTRACT

The present invention relates to the new compounds of general formula I

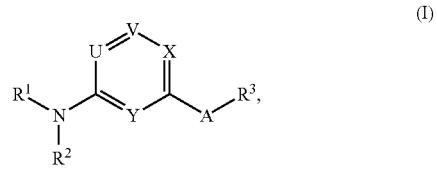

wherein A, U, V, X, Y, $R^1$, $R^2$ and $R^3$ are defined as stated hereinafter, the tautomers, the isomers thereof, the diastereomers, the enantiomers, the hydrates, the mixtures and the salts thereof as well as the hydrates of the salts, particularly the physiologically acceptable salts thereof with inorganic or organic acids or bases, medicaments containing these compounds, their use and processes for preparing them.

8 Claims, No Drawings

PYRIMIDINE DERIVATIVES WHICH ARE CGRP—ANTAGONISTS

The present invention relates to the new compounds of general formula I

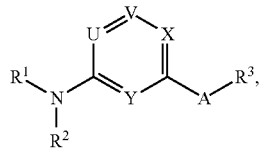

wherein A, U, V, X, Y, $R^1$, $R^2$ and $R^3$ are defined as stated hereinafter, the tautomers, the isomers thereof, the diastereomers, the enantiomers, the hydrates, the mixtures and the salts thereof as well as the hydrates of the salts, particularly the physiologically acceptable salts thereof with inorganic or organic acids or bases, medicaments containing these compounds, their use and processes for preparing them.

The new compounds of general formula I have CGRP-antagonistic properties and are therefore particularly suitable for treating migraine.

DETAILED DESCRIPTION OF THE INVENTION

In the above general formula I in a first embodiment
A denotes —NH, —N($C_{1-3}$-alkyl), —N(C(O)—$C_{1-3}$-alkyl), S, O, SO, $SO_2$,
$R^1$ denotes a group of general formulae IIa or IIb

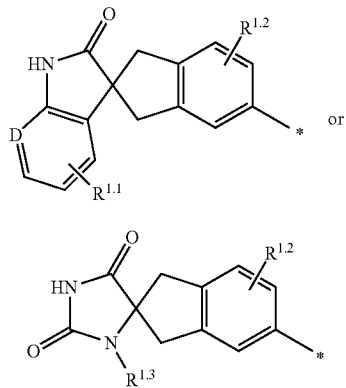

and
$R^2$ denotes H or $C_{1-3}$-alkyl, or
$R^1$ and $R^2$ together with the nitrogen atom to which they are attached denote a group of general formulae IIIa to IIIc

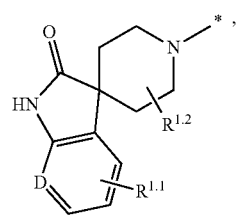

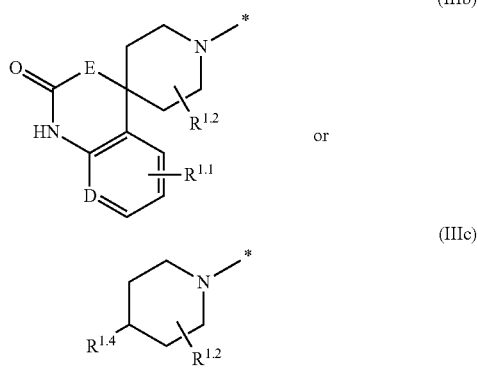

D denotes C—$R^{1.1}$ or N,
E denotes $CH_2$, NH or O,
$R^{1.1}$ independently of one another denote
  (a) H,
  (b) halogen, $C_{1-3}$-alkyl, —OH, —CN, —O—$C_{1-3}$-alkyl, —C(O)—O—$C_{1-3}$-alkyl, $C_{2-4}$-alkenyl, $C_{2-4}$-alkynyl, $C_{1-3}$-alkyl-S, cyclopropyl, —$NH_2$, —COOH, —NH—C(O)—O—$C_{1-3}$-alkyl, —NH—C(O)—$C_{1-3}$-alkyl,
  (c) a $C_{1-3}$-alkyl group or $C_{1-3}$-alkyl-O— group wherein each methylene group is substituted by 1 or 2 fluorine atoms and each methyl group is substituted by 1, 2 or 3 fluorine atoms,
$R^{1.2}$ denotes
  (a) H,
  (b) F, —CN, $C_{1-3}$-alkyl, —$CO_2$—$R^{1.2.1}$ or
  (c) a $C_{1-3}$-alkyl group wherein each methylene group may be substituted by up to two fluorine atoms and each methyl group may be substituted by up to three fluorine atoms,
$R^{1.2.1}$ denotes
  (a) H,
$R^{1.3}$ independently of one another denote
  (a) H or
  (b) $C_{1-3}$-alkyl,
$R^{1.4}$ denotes a group of general formula IV

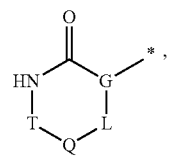

G-L denotes N, N—C($R^{1.4.1}$)$_2$, C═C($R^{1.4.1}$), C═N, C($R^{1.4.1}$), C($R^{1.4.1}$)—C($R^{1.4.1}$)$_2$, C($R^{1.4.1}$)—C($R^{1.4.1}$)$_2$—C($R^{1.4.1}$)$_2$, C═C($R^{1.4.1}$)—C($R^{1.4.1}$)$_2$, C($R^{1.4.1}$)—C($R^{1.4.1}$)═C($R^{1.4.1}$), C($R^{1.4.1}$)—C($R^{1.4.1}$)$_2$—N($R^{1.4.2}$), C═C($R^{1.4.1}$)—N($R^{1.4.2}$), C($R^{1.4.1}$)—C($R^{1.4.1}$)═N, C($R^{1.4.1}$)—N($R^{1.4.2}$)—C($R^{1.4.1}$)$_2$, C═N—C($R^{1.4.1}$)$_2$, C($R^{1.4.1}$)—N═C($R^{1.4.1}$), C($R^{1.4.1}$)—N($R^{1.4.2}$)—N($R^{1.4.2}$), C═N—N($R^{1.4.2}$), N—C($R^{1.4.1}$)$_2$—C($R^{1.4.1}$)$_2$, N—C($R^{1.4.1}$)═C($R^{1.4.1}$), N—C($R^{1.4.1}$)$_2$—N($R^{1.4.2}$), N—C($R^{1.4.1}$)═N, N—N($R^{1.4.2}$)—C($R^{1.4.1}$)$_2$ or N—N═C($R^{1.4.1}$),
Q-T denotes C($R^{1.4.3}$)$_2$—C($R^{1.4.3}$)$_2$, C($R^{1.4.3}$)═C($R^{1.4.3}$), N═C($R^{1.4.3}$), C($R^{1.4.3}$)$_2$—C(═O), C(═O)—C($R^{1.4.3}$)$_2$, C($R^{1.4.3}$)$_2$—S(O)$_m$ or C($R^{1.4.3}$)$_2$—N($R^{1.4.3}$), while a group $C(R^{1.4.3})_2$ contained in Q-T may also denote a cyclic group which is selected from among $C_{3-6}$-cycloalkyl, $C_{5-6}$-cycloalkenyl or heterocyclyl, or while in a group $C(R^{1.4.3})_2$—$C(R^{1.4.3})_2$, $C(R^{1.4.3})$=$C(R^{1.4.3})$ or $C(R^{1.4.3})_2$—$N(R^{1.4.3})$ contained in Q-T in each case a group $R^{1.4.3}$ together with an adjacent group $R^{1.4.3}$ and the atoms to which these groups are linked may also denote a $C_{3-6}$-cycloalkyl, $C_{5-6}$-cycloalkenyl, heterocyclyl, aryl or heteroaryl group which may be substituted independently of one another by 1, 2 or 3 substituents $R^{1.4.4}$, $R^{1.4.1}$ independently of one another denote
  (a) H,
  (b) $C_{1-6}$-alkyl, —CN, —OH, —O—$C_{1-3}$-alkyl,
  (c) a $C_{1-3}$-alkyl or $C_{1-3}$-alkyl-O— group wherein each methylene group is substituted by up to two fluorine atoms and each methyl group is substituted by up to three fluorine atoms, $R^{1.4.2}$ denotes H or $C_{1-6}$-alkyl, $R^{1.4.3}$ independently of one another denote
  (a) H, $C_{1-6}$-alkyl, $C_{2-6}$-alkenyl, $C_{2-6}$-alkynyl, $C_{3-6}$-cycloalkyl,
  (b) an aryl group optionally substituted by 1, 2 or 3 substituents $R^{1.4.3.1}$, wherein the substituents $R^{1.4.3.1}$ may be identical or different,
  (c) a heteroaryl group optionally substituted by 1, 2 or 3 substituents $R^{1.4.3.1}$, wherein the substituents $R^{1.4.3.1}$ may be identical or different,
  (d) a heterocyclic group optionally substituted by 1, 2 or 3 substituents $R^{1.4.3.1}$, wherein the substituents $R^{1.4.3.1}$ may be identical or different, $R^{1.4.3.1}$ independently of one another denote
  (a) halogen, $C_{1-6}$-alkyl, $C_{3-6}$-cycloalkyl,
  (b) —O—$R^{1.4.3.1.1}$, —$(CH_2)_s$—O—$R^{1.4.3.1.1}$, —$CO_2R^{1.4.3.1.1}$, —$C(O)$—$NR^{1.4.3.1.2}R^{1.4.3.1.3}$, —O—$(CO)$—$NR^{1.4.3.1.2}R^{1.4.3.1.3}$, —$N(R^{1.4.3.1.1})$—$C(O)$—$NR^{1.4.3.1.2}R^{1.4.3.1.3}$, —$N(R^{1.4.3.1.2})$—$C(O)$—$O$—$R^{1.4.3.1.3}$, —$N(R^{1.4.3.1.2})$—$C(O)$—$O$—$R^{1.4.3.1.3}$, —$SO_2$—$NR^{1.4.3.1.2}R^{1.4.3.1.3}$, —$N(R^{1.4.3.1.2})$—$SO_2$—$R^{1.4.3.1.3}$, —$S(O)_m$—$R^{1.4.3.1.2}$, —CN, —$NR^{1.4.3.1.2}R^{1.4.3.1.3}$, —O—$C(O)$—$R^{1.4.3.1.1}$ or
  (c) a $C_{1-3}$-alkyl group wherein each methylene group is substituted by up to two fluorine atoms and each methyl group is substituted by up to three fluorine atoms, $R^{1.4.3.1.1}$ denotes
  (a) H,
  (b) $C_{1-6}$-alkyl, $C_{3-6}$-cycloalkyl, aryl, heteroaryl, benzyl, which may be substituted by a group $R^{1.4.3.1.1.1}$, or
  (c) a $C_{1-3}$-alkyl group wherein each methylene group is substituted by up to two fluorine atoms and each methyl group is substituted by up to three fluorine atoms, $R^{1.4.3.1.1.1}$ denotes halogen, HO or $C_{1-6}$-alkyl-O, $R^{1.4.3.1.2}$ denotes
  (a) H,
  (b) $C_{1-6}$-alkyl, $C_{3-6}$-cycloalkyl, aryl, heteroaryl or benzyl, while the groups may be unsubstituted or substituted by halogen, HO or $C_{1-6}$-alkyl-O, or
  (c) a $C_{1-3}$-alkyl group wherein each methylene group is substituted by up to two fluorine atoms and each methyl group is substituted by up to three fluorine atoms, $R^{1.4.3.1.3}$ denotes
  (a) H,
  (b) $C_{1-6}$-alkyl, $C_{3-6}$-cycloalkyl, aryl, heteroaryl or benzyl, while the groups may be unsubstituted or substituted by halogen, HO or $C_{1-6}$-alkyl-O, or
  (c) a $C_{1-3}$-alkyl group wherein each methylene group is substituted by up to two fluorine atoms and each methyl group is substituted by up to three fluorine atoms, or $R^{1.4.3.1.2}$ and $R^{1.4.3.1.3}$ together may also form a ring which is selected from among azetidinyl, pyrrolidinyl, piperidinyl, piperazinyl and morpholinyl, while the ring may be unsubstituted or substituted by 1, 2 or 3 substituents $R^{1.4.3.1.1}$ or fluorine, wherein the substituents $R^{1.4.3.1.1}$ are independent of one another, $R^{1.4.4}$ independently of one another denotes
  (a) H, halogen, $C_{1-6}$-alkyl, $C_{3-6}$-cycloalkyl,
  (b) —O—$C_{1-6}$-alkylene-$NR^{1.4.3.1.2}R^{1.4.3.1.3}$, —O—$R^{1.4.3.1.1}$, —O—$(CH_2)_s$—O—$R^{1.4.3.1.1}$, —$CO_2$—$R^{1.4.3.1.1}$, —$C(O)$—$NR^{1.4.3.1.2}R^{1.4.3.1.3}$, —O—$C(O)$—$NR^{1.4.3.1.2}R^{1.4.3.1.3}$, —$NR^{1.4.3.1.1}$—$C(O)$—$NR^{1.4.3.1.2}R^{1.4.3.1.3}$, —$NR^{1.4.3.1.2}$—$C(O)$—$R^{1.4.3.1.3}$, —$NR^{1.4.3.1.2}$—$C(O)$—$O$—$R^{1.4.3.1.3}$, —$SO_2$—$NR^{1.4.3.1.2}R^{1.4.3.1.3}$, —$NR^{1.4.3.1.2}$—$SO_2$—$R^{1.4.3.1.3}$, —$S(O)_m$—$R^{1.4.3.1.2}$, —CN, —$NR^{1.4.3.1.2}R^{1.4.3.1.3}$, —O—$C(O)$—$R^{1.4.3.1.1}$,
  (c) a $C_{1-3}$-alkyl or $C_{1-3}$-alkyl-O— group wherein each methylene group is substituted by up to two fluorine atoms and each methyl group is substituted by up to three fluorine atoms,
  (d) an aryl group substituted by 1, 2 or 3 substituents $R^{1.4.3.1.1}$, wherein the substituents $R^{1.4.3.1.1}$ may be identical or different,
  (e) a heteroaryl group substituted by with 1, 2 or 3 substituents $R^{1.4.3.1.1}$, wherein the substituents $R^{1.4.3.1.1}$ may be identical or different,
  (f) a heterocyclic group substituted by 1, 2 or 3 substituents $R^{1.4.3.1.1}$, wherein the substituents $R^{1.4.3.1.1}$ may be identical or different, m denotes one of the numbers 0, 1 or 2, s denotes one of the numbers 1, 2 or 3, $R^3$ denotes
  (a) a 6- or 10-membered aryl group substituted by the groups $R^{3.1}$, $R^{3.2}$ and $R^{3.3}$,
  (b) a 5- or 6-membered heteroaryl group substituted by the groups $R^{3.1}$, $R^{3.2}$ and $R^{3.3}$ which is attached via a carbon atom, or
  (c) a 5- or 6-membered heteroaryl group substituted by a group $R^{3.2}$ which is attached via a carbon atom and is additionally fused to a phenyl ring, $R^{3.1}$ denotes
  (a) H,
  (b) halogen, —$NH_2$, $C_{1-4}$-alkyl-NH—, $(C_{1-4}$-alkyl$)_2$N, —CN, —OH
  (c) $C_{1-4}$-alkyl, $R^{3.1.1}$—$C_{1-3}$-alkylene, $C_{2-4}$-alkenyl, $C_{2-4}$-alkynyl, $C_{1-3}$-alkyl-O, cyclopropyl,
  (d) a $C_{1-3}$-alkyl or $C_{1-3}$-alkyl-O— group wherein each methylene group is substituted by up to two fluorine atoms and each methyl group is substituted by up to three fluorine atoms, $R^{3.1.1}$ denotes
  (a) H,
  (b) $C_{3-6}$-cycloalkyl, $C_{5-6}$-cycloalkenyl,
  (c) $(C_{1-4}$-alkyl$)_2$N, $C_{1-4}$-alkyl-NH—, $C_{1-3}$-alkyl-O, $R^{3.2}$ denotes
  (a) H,
  (b) $NH_2$, $C_{1-4}$-alkyl-NH—, $(C_{1-4}$-alkyl$)_2$N, $C_{1-3}$-alkyl-C(O)—NH—, HO, $C_{1-3}$-alkyl-O,
  (c) $C_{1-3}$-alkyl or
  (d) a $C_{1-3}$-alkyl or $C_{1-3}$-alkyl-O— group wherein each methylene group is substituted by up to two fluorine atoms and each methyl group is substituted by up to three fluorine atoms, $R^{3.3}$ denotes
(a) H,
(b) halogen,
(c) $C_{1-3}$-alkyl, $C_{1-3}$-alkyl-O or
(d) a $C_{1-3}$-alkyl or $C_{1-3}$-alkyl-O— group wherein each methylene group is substituted by up to two fluorine atoms and each methyl group is substituted by up to three fluorine atoms, or $R^{3.2}$ and $R^{3.3}$ together with the carbon atoms to which they are bonded form a monounsaturated 5-membered or a mono- or diunsaturated 6-membered heterocyclic group or a 5- to 6-membered heteroaryl group, wherein
the previously mentioned heterocycles may contain a carbonyl, thiocarbonyl or cyanimino group adjacent to a nitrogen atom, and
may optionally additionally be substituted at one or two nitrogen atoms by a group $R^{3.3.1}$ and
may optionally additionally be substituted at one or two carbon atoms by one or two groups $R^{3.3.2}$, $R^{3.3.1}$ independently of one another denote
(a) $C_{1-4}$-alkyl or
(b) $C_{3-6}$-cycloalkyl, $R^{3.3.2}$ independently of one another denote
(a) $R^{3.3.2.1}$—$C_{1-3}$-alkylene,
(b) $C_{3-6}$-cycloalkyl, wherein a $CH_2$ group may be replaced by an oxygen atom,
(c) halogen, CN, —O—$C_{1-3}$-alkyl, —$NH_2$, $C_{1-4}$-alkyl-NH—, ($C_{1-4}$-alkyl)$_2$N—, —NH(CN),
(d) a $C_{1-3}$-alkyl or $C_{1-3}$-alkyl-O— group wherein each methylene group is substituted by up to two and each methyl group is substituted by up to three fluorine atoms, $R^{3.3.2.1}$ denotes
(a) H,
(b) CN, $CF_3$, $NH_2$, $C_{1-4}$-alkyl-NH—, ($C_{1-4}$-alkyl)$_2$N—,
(c) OH, —O—$C_{1-3}$-alkyl,
(d) $C_{3-6}$-cycloalkyl, U denotes N, N-oxide or C—$R^4$,
V denotes N, N-oxide or C—$R^5$,
X denotes N, N-oxide or C—$R^6$,
Y denotes N or CH,
while at most three of the previously mentioned groups U, V, X or Y simultaneously denote a nitrogen atom, $R^4$ denotes
(a) H,
(b) a $C_{1-6}$-alkyl or $C_{1-3}$-alkyl-O— group which is substituted in each case by a group $R^{4.1}$,
(c) $R^{4.2}R^{4.3}N$, $R^{4.2}R^{4.3}N$—$C_{1-3}$-alkylene,
(d) halogen, —CN, —OH, $C_{1-3}$-alkyl-O—$C_{1-3}$-alkylene, $C_{3-6}$-cycloalkyl, $C_{3-6}$-cycloalkyl-$C_{1-4}$-alkylene, $C_{1-3}$-alkyl-C(O)—O—$C_{1-3}$-alkylene,
(e) heterocyclyl,
(f) a $C_{1-3}$-alkyl or $C_{1-3}$-alkyl-O— group wherein each methylene group is substituted by up to two fluorine atoms and each methyl group is substituted by up to three fluorine atoms, $R^{4.1}$ denotes H, —OH or —O—$CH_3$,
$R^{4.2}$ denotes H or $C_{1-3}$-alkyl,
$R^{4.3}$ denotes H or $C_{1-3}$-alkyl, or
$R^{4.2}$ and $R^{4.3}$ together with the nitrogen atom to which they are attached, denote a 3- to 6-membered heterocyclic group, $R^5$ denotes
(a) H,
(b) a $C_{1-6}$-alkyl or $C_{1-3}$-alkyl-O— group which is substituted in each case by a group $R^{5.1}$,
(c) —$NR^{5.2}R^{5.3}$, $NR^{5.2}R^{5.3}$—$C_{1-3}$-alkylene,
(d) halogen, —CN, —OH, $C_{1-3}$-alkyl-O—$C_{1-3}$-alkylene, $C_{3-6}$-cycloalkyl, $C_{3-6}$-cycloalkyl-$C_{1-4}$-alkylene, $C_{1-3}$-alkyl-C(O)—O—$C_{1-3}$-alkylene,
(e) aryl-$C_{0-3}$-alkylene-O,
(f) heterocyclyl,
(g) a $C_{1-3}$-alkyl or $C_{1-3}$-alkyl-O— group wherein each methylene group is substituted by up to two fluorine atoms and each methyl group is substituted by up to three fluorine atoms, $R^{5.1}$ denotes H, OH or —O—$CH_3$,
$R^{5.2}$ denotes H or $C_{1-6}$-alkyl,
$R^{5.3}$ denotes H, $C_{1-6}$-alkyl or —$SO_2$—$C_{1-3}$-alkyl, or
$R^{5.2}$ and $R^{5.3}$ together with the nitrogen atom to which they are attached, denote a 3- to 6-membered heterocyclic group, $R^6$ denotes
(a) H,
(b) a $C_{1-6}$-alkyl or $C_{1-3}$-alkyl-O— group which is substituted in each case by a group $R^{6.1}$,
(c) $R^{6.2}R^{6.3}N$, $R^{6.2}R^{6.3}N$—$C_{1-3}$-alkylene,
(d) halogen, —CN, —OH, $C_{1-3}$-alkyl-O—$C_{1-3}$-alkylene, $C_{3-6}$-cycloalkyl, $C_{3-6}$-cycloalkyl-$C_{1-4}$-alkylene, $C_{1-3}$-alkyl-C(O)—O—$C_{1-3}$-alkylene,
(e) heterocyclyl,
(f) a $C_{1-3}$-alkyl or $C_{1-3}$-alkyl-O— group wherein each methylene group is substituted by up to two fluorine atoms and each methyl group is substituted by up to three fluorine atoms, $R^{6.1}$ denotes H, —OH or —O—$CH_3$,
$R^{6.2}$ denotes H or $C_{1-3}$-alkyl, and
$R^{6.3}$ denotes H or $C_{1-3}$-alkyl, or
$R^{6.2}$ and $R^{6.3}$ together with the nitrogen atom to which they are attached denote a 3- to 6-membered heterocyclic group, the tautomers, the diastereomers, the enantiomers, the hydrates, the mixtures thereof and the salts thereof as well as the hydrates of the salts, particularly the physiologically acceptable salts thereof with inorganic or organic acids or bases.

A second embodiment of the present invention comprises the compounds of the above general formula I, wherein A, U, V, X, Y, $R^2$ and $R^3$ are defined as hereinbefore in the first embodiment and $R^1$ denotes a group selected from

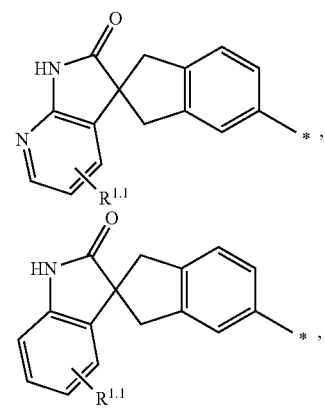

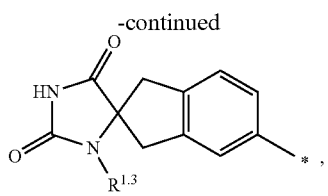

$R^{1.1}$ denotes
(a) H,
(b) halogen, $C_{1-3}$-alkyl, —OH, —CN, —O—$C_{1-3}$-alkyl, —C(O)—O—$C_{1-3}$-alkyl, $C_{2-4}$-alkenyl, $C_{2-4}$-alkynyl, $C_{1-3}$-alkyl-S, —NH$_2$,
(c) a $C_{1-3}$-alkyl group or $C_{1-3}$-alkyl-O— group wherein each methylene group is substituted by up to two fluorine atoms and each methyl group is substituted by up to three fluorine atoms, and $R^{1.3}$ denotes
(a) H or
(b) CH$_3$, the tautomers, the diastereomers, the enantiomers, the hydrates, the mixtures thereof and the salts thereof as well as the hydrates of the salts, particularly the physiologically acceptable salts thereof with inorganic or organic acids or bases.

A third embodiment of the present invention comprises the compounds of the above general formula I, wherein A, U, V, X, Y, $R^2$ and $R^3$ are defined as hereinbefore in the first embodiment and
$R^1$ denotes a group selected from

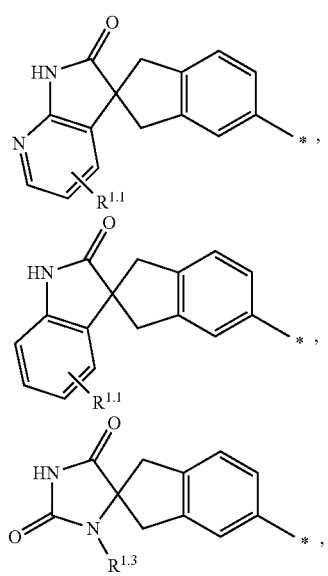

$R^{1.1}$ denotes
(a) H,
(b) F, CH$_3$, —OH, —O—CH$_3$ or
(c) CF$_3$ and
$R^{1.3}$ denotes H or CH$_3$,
the tautomers, the diastereomers, the enantiomers, the hydrates, the mixtures thereof and the salts thereof as well as the hydrates of the salts, particularly the physiologically acceptable salts thereof with inorganic or organic acids or bases.

A fourth embodiment of the present invention comprises the compounds of the above general formula I, wherein A, U, V, X, Y, $R^2$ and $R^3$ are defined as hereinbefore in the first embodiment and
$R^1$ denotes a group selected from

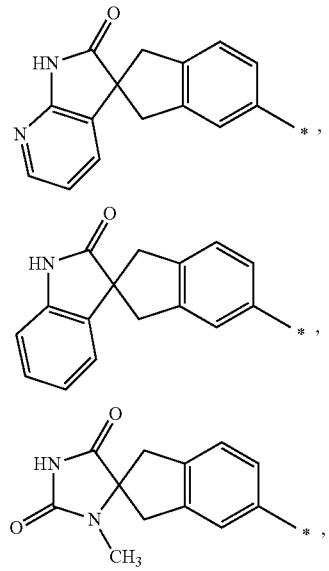

the tautomers, the diastereomers, the enantiomers, the hydrates, the mixtures thereof and the salts thereof as well as the hydrates of the salts, particularly the physiologically acceptable salts thereof with inorganic or organic acids or bases.

A fifth embodiment of the present invention comprises the compounds of the above general formula I, wherein A, U, V, X, Y, $R^2$ and $R^3$ are defined as hereinbefore in the first embodiment and
$R^1$ denotes a group

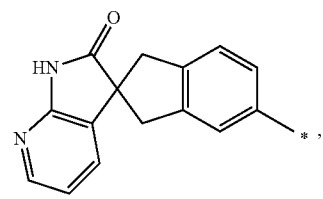 [SMILES: Cc1ccc2c(c1)CC1(C2)C(=O)Nc2ncccc21]

the tautomers, the diastereomers, the enantiomers, the hydrates, the mixtures thereof and the salts thereof as well as the hydrates of the salts, particularly the physiologically acceptable salts thereof with inorganic or organic acids or bases.

A sixth embodiment of the present invention comprises the compounds of the above general formula I, wherein A, U, V, X, Y and $R^3$ are defined as hereinbefore in the first embodiment and
$R^1$ and $R^2$ together with the nitrogen atom to which they are attached denote a group selected from

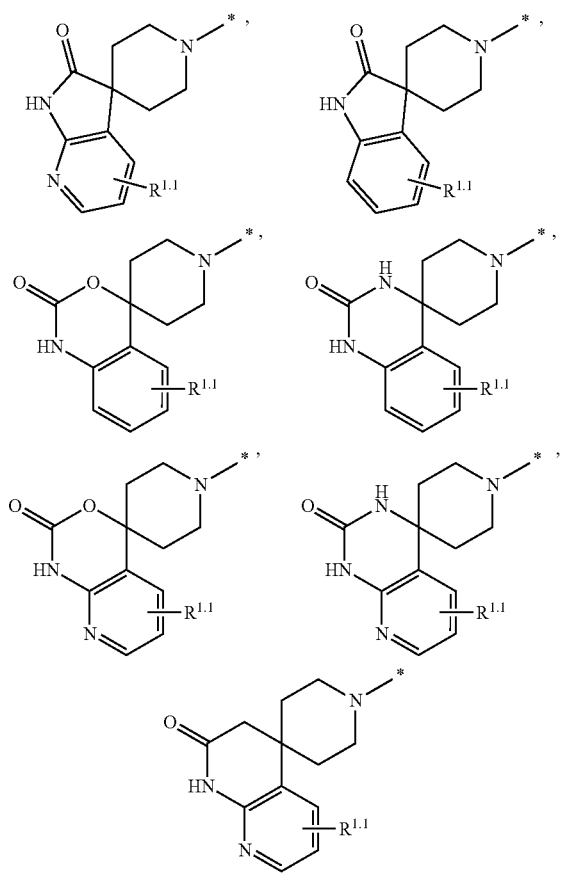

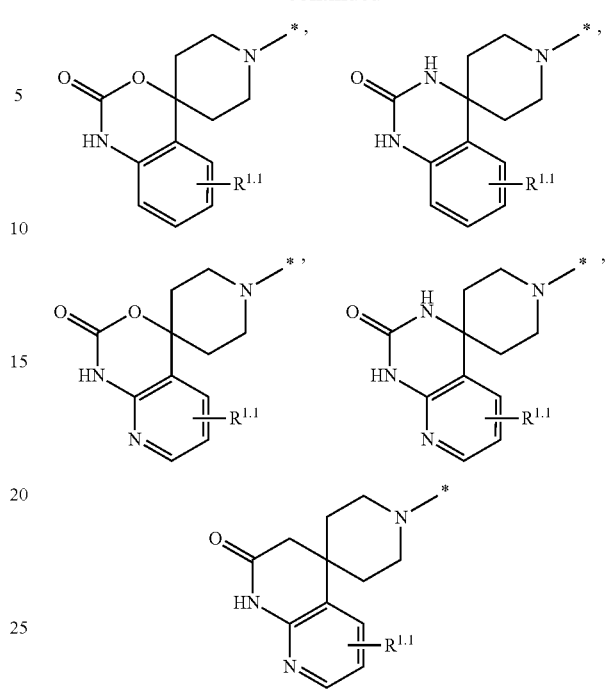

$R^{1.1}$ denotes
(a) H,
(b) halogen, $C_{1-3}$-alkyl, —OH, —CN, —O—$C_{1-3}$-alkyl, —C(O)—O—$C_{1-3}$-alkyl, $C_{2-4}$-alkenyl, $C_{2-4}$-alkynyl, $C_{1-3}$-alkyl-S, —NH$_2$,
(c) a $C_{1-3}$-alkyl group or $C_{1-3}$-alkyl-O— group wherein each methylene group is substituted by up to two fluorine atoms and each methyl group is substituted by up to three fluorine atoms, the tautomers, the diastereomers, the enantiomers, the hydrates, the mixtures thereof and the salts thereof as well as the hydrates of the salts, particularly the physiologically acceptable salts thereof with inorganic or organic acids or bases.

A seventh embodiment of the present invention comprises the compounds of the above general formula I, wherein A, U, V, X, Y and $R^3$ are defined as hereinbefore in the first embodiment and $R^1$ and $R^2$ together with the nitrogen atom to which they are attached denote a group selected from

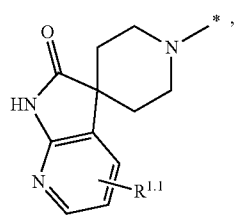

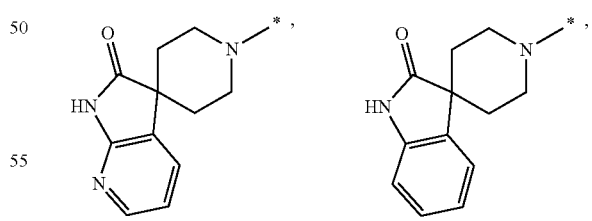

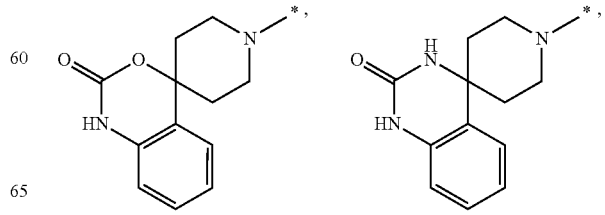

$R^{1.1}$ denotes
(a) H,
(b) F, CH$_3$, —OH, —O—CH$_3$ or
(c) CF$_3$, the tautomers, the diastereomers, the enantiomers, the hydrates, the mixtures thereof and the salts thereof as well as the hydrates of the salts, particularly the physiologically acceptable salts thereof with inorganic or organic acids or bases.

An eighth embodiment of the present invention comprises the compounds of the above general formula I, wherein A, U, V, X, Y and $R^3$ are defined as hereinbefore in the first embodiment and $R^1$ and $R^2$ together with the nitrogen atom to which they are attached denote a group selected from

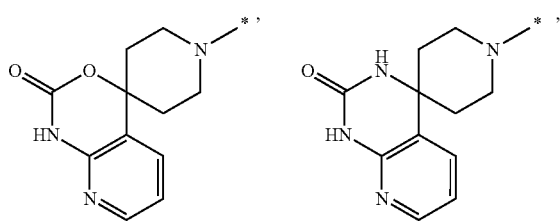

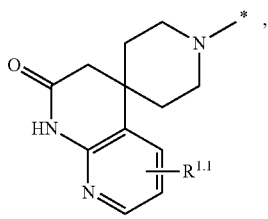

the tautomers, the diastereomers, the enantiomers, the hydrates, the mixtures thereof and the salts thereof as well as the hydrates of the salts, particularly the physiologically acceptable salts thereof with inorganic or organic acids or bases.

A ninth embodiment of the present invention comprises the compounds of the above general formula I, wherein A, U, V, X, Y and $R^3$ are defined as hereinbefore in the first embodiment and $R^1$ and $R^2$ together with the nitrogen atom to which they are attached denote a group

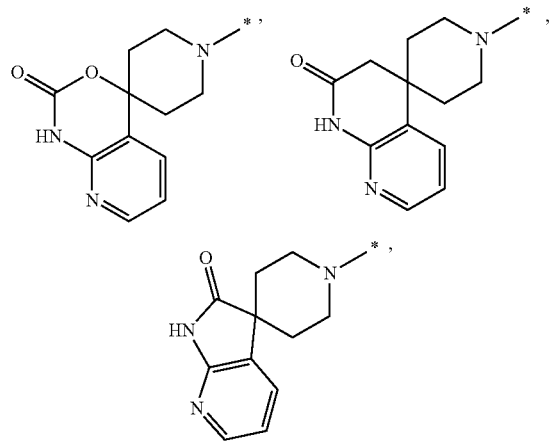

the tautomers, the diastereomers, the enantiomers, the hydrates, the mixtures thereof and the salts thereof as well as the hydrates of the salts, particularly the physiologically acceptable salts thereof with inorganic or organic acids or bases.

A tenth embodiment of the present invention comprises the compounds of the above general formula I, wherein A, U, V, X, Y and $R^3$ are defined as hereinbefore in the first embodiment and $R^1$ and $R^2$ together with the nitrogen atom to which they are attached denote a group of general formula IV

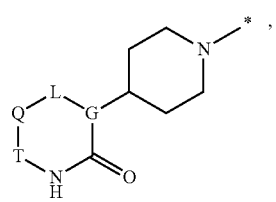

(IV)

wherein

G-L denotes N, N—C($R^{1.4.1}$)$_2$, C=C($R^{1.4.1}$), C=N, C($R^{1.4.1}$), C($R^{1.4.1}$)—C($R^{1.4.1}$)$_2$, C($R^{1.4.1}$)—C($R^{1.4.1}$)$_2$—C($R^{1.4.1}$)$_2$, C=C($R^{1.4.1}$)—C($R^{1.4.1}$)$_2$, C($R^{1.4.1}$)—C($R^{1.4.1}$)=C($R^{1.4.1}$), C($R^{1.4.1}$)—C($R^{1.4.1}$)$_2$—N($R^{1.4.2}$), C=C($R^{1.4.1}$)—N($R^{1.4.2}$), C($R^{1.4.1}$)—C($R^{1.4.1}$)=N, C($R^{1.4.1}$)—N($R^{1.4.2}$)—C($R^{1.4.1}$)$_2$, C=N—C($R^{1.4.1}$)$_2$, C($R^{1.4.1}$)—N=C($R^{1.4.1}$), C($R^{1.4.1}$)—N($R^{1.4.2}$)—N ($R^{1.4.2}$), C=N—N($R^{1.4.2}$), N—C($R^{1.4.1}$)$_2$—C($R^{1.4.1}$)$_2$, N—C($R^{1.4.1}$)=C($R^{1.4.1}$), N—C($R^{1.4.1}$)$_2$—N($R^{1.4.2}$), N—C($R^{1.4.1}$)=N, N—N($R^{1.4.2}$)—C($R^{1.4.1}$)$_2$ or N—N=C ($R^{1.4.1}$), Q-T denotes C($R^{1.4.3}$)$_2$—C($R^{1.4.3}$)$_2$, C($R^{1.4.3}$)=C($R^{1.4.3}$), N=C($R^{1.4.3}$), C($R^{1.4.3}$)$_2$—C(=O), C(=O)—C($R^{1.4.3}$)$_2$, C($R^{1.4.3}$)$_2$—S(O)$_m$ or C($R^{1.4.3}$)$_2$—N($R^{1.4.3}$), while a group C($R^{1.4.3}$)$_2$ contained in Q-T may also denote a cyclic group which is selected from among cyclobutyl, cyclopentyl, cyclohexyl, cyclopentenyl, cyclohexenyl, dioxanyl, morpholinyl, thiomorpholinyl, thiomorpholine-5-oxide, thiomorpholine-S-dioxide, azetidinyl, pyrrolidinyl, piperidinyl, tetrahydrofuranyl, tetrahydropyranyl and piperazinyl, or in a group C($R^{1.4.3}$)$_2$—C($R^{1.4.3}$)$_2$, C($R^{1.4.3}$)=C($R^{1.4.3}$) or C($R^{1.4.3}$)$_2$—N($R^{1.4.3}$) contained in Q-T in each case a group $R^{1.4.3}$ together with an adjacent group $R^{1.4.3}$ and the atoms to which these groups are linked may also denote a group selected from cyclobutyl, cyclopentyl, cyclohexyl, cyclopentenyl, cyclohexenyl, dioxanyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyridazinyl, pyrrolyl, pyrrolinyl, quinolinyl, isoquinolinyl, morpholinyl, thiomorpholinyl, thiomorpholine-S-oxide, thiomorpholine-S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, which may be substituted independently of one another by 1, 2 or 3 substituents $R^{1.4.4}$, $R^{1.4.1}$ denotes
(a) H,
(b) $C_{1-6}$-alkyl, —CN, —OH, —O—$C_{1-3}$-alkyl,
(c) a $C_{1-3}$-alkyl or $C_{1-3}$-alkyl-O— group wherein each methylene group is substituted by up to two fluorine atoms and each methyl group is substituted by up to three fluorine atoms, $R^{1.4.2}$ denotes H or $C_{1-6}$-alkyl, $R^{1.4.3}$ denotes
(a) H, $C_{1-6}$-alkyl, $C_{2-6}$-alkenyl, $C_{2-6}$-alkynyl, $C_{3-6}$-cycloalkyl,
(b) an aryl group optionally substituted by 1, 2 or 3 substituents $R^{1.4.3.1}$, wherein the substituents $R^{1.4.3.1}$ may be identical or different,
(c) a heteroaryl group optionally substituted by 1, 2 or 3 substituents $R^{1.4.3.1}$, wherein the substituents $R^{1.4.3.1}$ may be identical or different, (d) a heterocyclic group optionally substituted by 1, 2 or 3 substituents $R^{1.4.3.1}$, wherein the substituents $R^{1.4.3.1}$ may be identical or different, $R^{1.4.3.1}$ denotes
(a) halogen, $C_{1-6}$-alkyl, $C_{3-6}$-cycloalkyl,
(b) —O—$R^{1.4.3.1.1}$, —O—$(CH_2)_s$—O—$R^{1.4.3.1.1}$, —$CO_2R^{1.4.3.1.1}$, —C(O)—$NR^{1.4.3.1.2}R^{1.4.3.1.3}$, —O—(CO)—$NR^{1.4.3.1.2}R^{1.4.3.1.3}$, —$N(R^{1.4.3.1.1})$—C(O)—$NR^{1.4.3.1.2}R^{1.4.3.1.3}$, —$N(R^{1.4.3.1.2})$—C(O)—$R^{1.4.3.1.3}$, —$N(R^{1.4.3.1.2})$—C(O)—O—$R^{1.4.3.1.3}$, —$SO_2$—$NR^{1.4.3.1.2}R^{1.4.3.1.3}$, —$N(R^{1.4.3.1.2})$—$SO_2$—$R^{1.4.3.1.3}$, —$S(O)_m$—$R^{1.4.3.1.2}$, CN, —$NR^{1.4.3.1.2}R^{1.4.3.1.3}$, —O—C(O)—$R^{1.4.3.1.1}$ or
(c) a $C_{1-3}$-alkyl group wherein each methylene group is substituted by up to two fluorine atoms and each methyl group is substituted by up to three fluorine atoms, $R^{1.4.3.1.1}$ denotes
(a) H,
(b) $C_{1-6}$-alkyl, $C_{3-6}$-cycloalkyl, aryl, heteroaryl, benzyl, which may be substituted by a group $R^{1.4.3.1.1.1}$, or
(c) a $C_{1-3}$-alkyl group wherein each methylene group is substituted by up to two fluorine atoms and each methyl group is substituted by up to three fluorine atoms, $R^{1.4.3.1.1.1}$ denotes halogen, HO— or $C_{1-6}$-alkyl-O, $R^{1.4.3.1.2}$ denotes
(a) H,
(b) $C_{1-6}$-alkyl, $C_{3-6}$-cycloalkyl, aryl, heteroaryl or benzyl, while the groups may be unsubstituted or substituted by halogen, HO— or $C_{1-6}$-alkyl-O, or
(c) a $C_{1-3}$-alkyl group wherein each methylene group is substituted by up to two fluorine atoms and each methyl group is substituted by up to three fluorine atoms, $R^{1.4.3.1.3}$ denotes
(a) H,
(b) $C_{1-6}$-alkyl, $C_{3-6}$-cycloalkyl, aryl, heteroaryl or benzyl, while the groups may be unsubstituted or substituted by halogen, HO— or $C_{1-6}$-alkyl-O, or
(c) a $C_{1-3}$-alkyl group wherein each methylene group is substituted by up to two fluorine atoms and each methyl group is substituted by up to three fluorine atoms, or $R^{1.4.3.1.2}$ and $R^{1.4.3.1.3}$ together may also form a ring which is selected from among azetidinyl, pyrrolidinyl, piperidinyl, piperazinyl and morpholinyl, while the ring may be unsubstituted or substituted by 1, 2 or 3 substituents $R^{1.4.3.1.1}$ or fluorine, wherein the substituents $R^{1.4.3.1.1}$ are independent of one another, $R^{1.4.4}$ denotes
(a) H, halogen, $C_{1-6}$-alkyl, $C_{3-6}$-cycloalkyl,
(b) —O—$C_{1-6}$-alkylene-$NR^{1.4.3.1.2}R^{1.4.3.1.3}$, —O—$R^{1.4.3.1.1}$, —O—$(CH_2)_s$—O—$R^{1.4.3.1.1}$, —$CO_2$—$R^{1.4.3.1.1}$, C(O)—$NR^{1.4.3.1.2}R^{1.4.3.1.3}$, —O—C(O)—$NR^{1.4.3.1.2}R^{1.4.3.1.3}$, —$NR^{1.4.3.1.2}$—C(O)—$NR^{1.4.3.1.2}R^{1.4.3.1.3}$, —$NR^{1.4.3.1.2}$—C(O)—$R^{1.4.3.1.3}$, —$NR^{1.4.3.1.2}$—C(O)—O—$R^{1.4.3.1.3}$, —$SO_2$—$NR^{1.4.3.1.2}R^{1.4.3.1.3}$, —$NR^{1.4.3.1.2}$-$SO_2$—$R^{1.4.3.1.3}$, —$S(O)_m$—$R^{1.4.3.1.2}$, —CN, —$NR^{1.4.3.1.2}R^{1.4.3.1.3}$ —O—C(O)—$R^{1.4.3.1.1}$,
(c) a $C_{1-3}$-alkyl or $C_{1-3}$-alkyl-O— group wherein each methylene group is substituted by up to two fluorine atoms and each methyl group is substituted by up to three fluorine atoms,
(d) an aryl group substituted by 1, 2 or 3 substituents $R^{1.4.3.1.1}$, wherein the substituents $R^{1.4.3.1.1}$ may be identical or different,
(e) a heteroaryl group substituted by 1, 2 or 3 substituents $R^{1.4.3.1.1}$, wherein the substituents $R^{1.4.3.1.1}$ may be identical or different,
(f) a heterocyclic group substituted by 1, 2 or 3 substituents $R^{1.4.3.1.1}$, wherein the substituents $R^{1.4.3.1.1}$ may be identical or different, m denotes one of the numbers 0, 1 or 2 and s denotes one of the numbers 1, 2 or 3, the tautomers, the diastereomers, the enantiomers, the hydrates, the mixtures thereof and the salts thereof as well as the hydrates of the salts, particularly the physiologically acceptable salts thereof with inorganic or organic acids or bases.

An eleventh embodiment of the present invention comprises the compounds of the above general formula I, wherein A, U, V, X, Y and $R^3$ are defined as hereinbefore in the first embodiment and $R^1$ and $R^2$ together with the nitrogen atom to which they are attached denote a group of general formulae

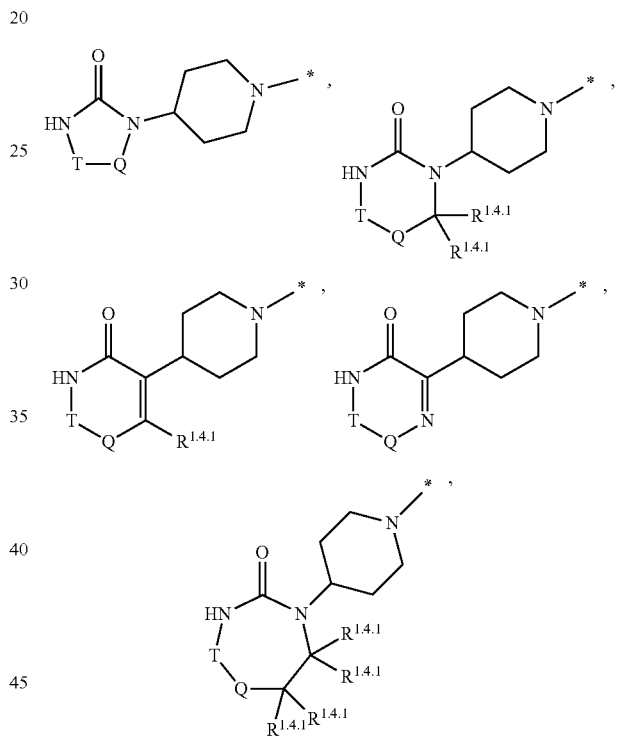

wherein

Q-T denotes $C(R^{1.4.3})_2$—$C(R^{1.4.3})_2$, $C(R^{1.4.3})=C(R^{1.4.3})$, $N=C(R^{1.4.3})$, $C(R^{1.4.3})_2$—$C(=O)$, $C(=O)$—$C(R^{1.4.3})_2$, $C(R^{1.4.3})_2$—$S(O)_m$ or $C(R^{1.4.3})_2$—$N(R^{1.4.3})$, while in a group $C(R^{1.4.3})_2$—$C(R^{1.4.3})_2$, $C(R^{1.4.3})=C(R^{1.4.3})$ or $C(R^{1.4.3})_2$—$N(R^{1.4.3})$ contained in Q-T in each case a group $R^{1.4.3}$ together with an adjacent group $R^{1.4.3}$ and the atoms to which these groups are linked may also denote a group selected from cyclobutyl, cyclopentyl, cyclohexyl, cyclopentenyl, cyclohexenyl, dioxanyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyridazinyl, pyrrolyl, pyrrolinyl, quinolinyl, isoquinolinyl, morpholinyl, thiomorpholinyl, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, which may be substituted independently of one another by 1, 2 or 3 substituents $R^{1.4.4}$, $R^{1.4.1}$ denotes
(a) H,
(b) $C_{1-6}$-alkyl, —CN, —OH, —O—$C_{1-3}$-alkyl,
(c) a $C_{1-3}$-alkyl or $C_{1-3}$-alkyl-O— group wherein each methylene group is substituted by up to two fluorine atoms and each methyl group is substituted by up to three fluorine atoms, $R^{1.4.3}$ independently of one another denote
(a) H, $C_{1-6}$-alkyl, $C_{2-6}$-alkenyl, $C_{2-6}$-alkynyl, $C_{3-6}$-cycloalkyl,
(b) an aryl group optionally substituted by 1, 2 or 3 substituents $R^{1.4.3.1}$, wherein the substituents $R^{1.4.3.1}$ may be identical or different,
(c) a heteroaryl group optionally substituted by 1, 2 or 3 substituents $R^{1.4.3.1}$, wherein the substituents $R^{1.4.3.1}$ may be identical or different,
(d) a heterocyclic group optionally substituted by 1, 2 or 3 substituents $R^{1.4.3.1}$, wherein the substituents $R^{1.4.3.1}$ may be identical or different, $R^{1.4.3.1}$ denotes
(a) halogen, $C_{1-6}$-alkyl, $C_{3-6}$-cycloalkyl,
(b) —O—$R^{1.4.3.1.1}$, —O—$(CH_2)_s$—O—$R^{1.4.3.1.1}$, —$CO_2R^{1.4.3.1.1}$, —$S(O)_m$—$R^{1.4.3.1.2}$, —CN, —O—C(O)—$R^{1.4.3.1.1}$ or
(c) a $C_{1-3}$-alkyl group wherein each methylene group is substituted by up to two fluorine atoms and each methyl group is substituted by up to three fluorine atoms, $R^{1.4.3.1.1}$ denotes
(a) H,
(b) $C_{1-6}$-alkyl, $C_{3-6}$-cycloalkyl, aryl, heteroaryl, benzyl, which may be substituted by a group $R^{1.4.3.1.1.1}$, or
(c) a $C_{1-3}$-alkyl group wherein each methylene group is substituted by up to two fluorine atoms and each methyl group is substituted by up to three fluorine atoms, $R^{1.4.3.1.1.1}$ denotes halogen, HO— or $C_{1-6}$-alkyl-O, $R^{1.4.3.1.2}$ denotes
(a) H,
(b) $C_{1-6}$-alkyl, $C_{3-6}$-cycloalkyl, aryl, heteroaryl, or benzyl, while the groups may be unsubstituted or substituted by halogen, HO— or $C_{1-6}$-alkyl-O, or
(c) a $C_{1-3}$-alkyl group wherein each methylene group is substituted by up to two fluorine atoms and each methyl group is substituted by up to three fluorine atoms, $R^{1.4.3.1.3}$ denotes
(a) H,
(b) $C_{1-6}$-alkyl, $C_{3-6}$-cycloalkyl, aryl, heteroaryl, or benzyl, while the groups may be unsubstituted or substituted by halogen, HO— or $C_{1-6}$-alkyl-O, or
(c) a $C_{1-3}$-alkyl group wherein each methylene group is substituted by up to two fluorine atoms and each methyl group is substituted by up to three fluorine atoms, or $R^{1.4.3.1.2}$ and $R^{1.4.3.1.3}$ together may also form a ring which is selected from among azetidinyl, pyrrolidinyl, piperidinyl, piperazinyl and morpholinyl, while the ring may be unsubstituted or substituted by 1, 2 or 3 substituents $R^{1.4.3.1.1}$, wherein the substituents $R^{1.4.3.1.1}$ are independent of one another, $R^{1.4.4}$ denotes
(a) H, halogen, $C_{1-6}$-alkyl, $C_{3-6}$-cycloalkyl,
(b) —O—$C_{1-6}$-alkylene-$NR^{1.4.3.1.2}R^{1.4.3.1.3}$, —O—$R^{1.4.3.1.1}$, —$CO_2R^{1.4.3.1.1}$, —C(O)$NR^{1.4.3.1.2}R^{1.4.3.1.3}$, —$SO_2$—$NR^{1.4.3.1.2}R^{1.4.3.1.3}$, —$N(R^{1.4.3.1.2})$—$SO_2$—$R^{1.4.3.1.3}$, —$S(O)_m$—$R^{1.4.3.1.2}$, —CN, —$NR^{1.4.3.1.2}R^{1.4.3.1.3}$, —O—C(O)—$R^{1.4.3.1.1}$ or (c) a $C_{1-3}$-alkyl group wherein each methylene group is substituted by up to two fluorine atoms and each methyl group is substituted by up to three fluorine atoms, m denotes one of the numbers 0, 1 or 2 and
s denotes one of the numbers 1, 2 or 3,
the tautomers, the diastereomers, the enantiomers, the hydrates, the mixtures thereof and the salts thereof as well as the hydrates of the salts, particularly the physiologically acceptable salts thereof with inorganic or organic acids or bases.

A twelfth embodiment of the present invention comprises the compounds of the above general formula I, wherein A, U, V, X, Y and $R^3$ are defined as hereinbefore in the first embodiment and $R^1$ and $R^2$ together with the nitrogen atom to which they are attached denote a group of general formulae

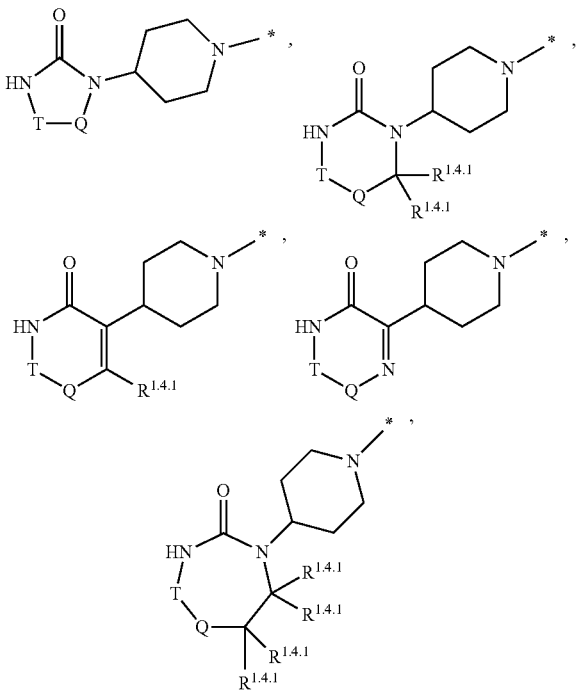

wherein
Q-T denotes $C(R^{1.4.3})_2$—$C(R^{1.4.3})_2$, $C(R^{1.4.3})$=$C(R^{1.4.3})$, N=$C(R^{1.4.3})$, $C(R^{1.4.3})_2$—$C(=O)$, $C(=O)$—$C(R^{1.4.3})_2$, $C(R^{1.4.3})_2$—$S(O)_m$ or $C(R^{1.4.3})_2$—$N(R^{1.4.3})$,
while in a group $C(R^{1.4.3})_2$—$C(R^{1.4.3})_2$, $C(R^{1.4.3})$=$C(R^{1.4.3})$ or $C(R^{1.4.3})_2$—$N(R^{1.4.3})$ contained in Q-T in each case a group $R^{1.4.3}$ together with an adjacent group $R^{1.4.3}$ and the atoms to which these groups are linked may also denote a group selected from cyclopentyl, cyclohexyl, cyclopentenyl, cyclohexenyl, dioxanyl, phenyl, naphthyl, thienyl, pyridyl, pyrazinyl, pyridazinyl, quinolinyl, isoquinolinyl, morpholinyl, pyrrolidinyl, piperidinyl, tetrahydrofuranyl, tetrahydropyranyl and piperazinyl, which may be substituted independently of one another by 1, 2 or 3 substituents $R^{1.4.4}$, $R^{1.4.1}$ denotes
(a) H,
(b) $C_{1-6}$-alkyl, —CN, —OH, —O—$C_{1-3}$-alkyl,
(c) a $C_{1-3}$-alkyl or $C_{1-3}$-alkyl-O— group wherein each methylene group is substituted by up to two fluorine atoms and each methyl group is substituted by up to three fluorine atoms, $R^{1.4.3}$ independently of one another denote
- (a) H, $C_{1-6}$-alkyl, $C_{3-6}$-cycloalkyl,
- (b) an aryl group optionally substituted by 1, 2 or 3 substituents $R^{1.4.3.1}$, wherein the substituents $R^{1.4.3.1}$ may be identical or different,
- (c) a heteroaryl group optionally substituted by 1, 2 or 3 substituents $R^{1.4.3.1}$, wherein the substituents $R^{1.4.3.1}$ may be identical or different,
- (d) a heterocyclic group optionally substituted by 1, 2 or 3 substituents $R^{1.4.3.1}$, wherein the substituents $R^{1.4.3.1}$ may be identical or different, $R^{1.4.3.1}$ denotes
- (a) halogen, $C_{1-6}$-alkyl, $C_{3-6}$-cycloalkyl,
- (b) —O—$R^{1.4.3.1.1}$, —O—$(CH_2)_s$—$OR^{1.4.3.1.1}$, —$CO_2R^{1.4.3.1.1}$, —$S(O)_m$—$R^{1.4.3.1.1}$, —CN, —O—C(O)—$R^{1.4.3.1.1}$ or
- (c) a $C_{1-3}$-alkyl group wherein each methylene group is substituted by up to two fluorine atoms and each methyl group is substituted by up to three fluorine atoms, $R^{1.4.3.1.1}$ denotes
- (a) H,
- (b) $C_{1-6}$-alkyl, $C_{3-6}$-cycloalkyl, aryl, heteroaryl, benzyl, which may be substituted by a group $R^{1.4.3.1.1.1}$, or
- (c) a $C_{1-3}$-alkyl group wherein each methylene group is substituted by up to two fluorine atoms and each methyl group is substituted by up to three fluorine atoms, $R^{1.4.3.1.1.1}$ denotes halogen, HO— or $C_{1-6}$-alkyl-O, $R^{1.4.3.1.2}$ denotes
- (a) H,
- (b) $C_{1-6}$-alkyl, $C_{3-6}$-cycloalkyl, aryl, heteroaryl, or benzyl, while the groups may be unsubstituted or substituted by halogen, HO— or $C_{1-6}$-alkyl-O, or
- (c) a $C_{1-3}$-alkyl group wherein each methylene group is substituted by up to two fluorine atoms and each methyl group is substituted by up to three fluorine atoms, $R^{1.4.3.1.3}$ denotes
- (a) H,
- (b) $C_{1-6}$-alkyl, $C_{3-6}$-cycloalkyl, aryl, heteroaryl, or benzyl, while the groups may be unsubstituted or substituted by halogen, HO— or $C_{1-6}$-alkyl-O, or
- (c) a $C_{1-3}$-alkyl group wherein each methylene group is substituted by up to two fluorine atoms and each methyl group is substituted by up to three fluorine atoms, or $R^{1.4.3.1.2}$ and $R^{1.4.3.1.3}$ together may also form a ring which is selected from among azetidinyl, pyrrolidinyl, piperidinyl, piperazinyl and morpholinyl, while the ring may be unsubstituted or substituted by 1, 2 or 3 substituents $R^{1.4.3.1.1}$ wherein the substituents $R^{1.4.3.1.1}$ are independent of one another, $R^{1.4.4}$ denotes
- (a) H, halogen, $C_{1-6}$-alkyl, $C_{3-6}$-cycloalkyl,
- (b) —O—$C_{1-6}$-alkylene-$NR^{1.4.3.1.2}R^{1.4.3.1.3}$, —O—$R^{1.4.3.1.1}$, —$CO_2R^{1.4.3.1.1}$, —C(O)—$NR^{1.4.3.1.2}R^{1.4.3.1.3}$, —$SO_2$—$NR^{1.4.3.1.2}R^{1.4.3.1.3}$, —$NR^{1.4.3.1.2}$-$SO_2$—$R^{1.4.3.1.3}$, —$S(O)_m$—$R^{1.4.3.1.2}$, —CN, —$NR^{1.4.3.1.2}R^{1.4.3.1.3}$, —O—C(O)—$R^{1.4.3.1.1}$ or
- (c) a $C_{1-3}$-alkyl group wherein each methylene group is substituted by up to two fluorine atoms and each methyl group is substituted by up to three fluorine atoms, m denotes one of the numbers 0, 1 or 2 and
s denotes one of the numbers 1, 2 or 3,
the tautomers, the diastereomers, the enantiomers, the hydrates, the mixtures thereof and the salts thereof as well as the hydrates of the salts, particularly the physiologically acceptable salts thereof with inorganic or organic acids or bases.

A thirteenth embodiment of the present invention comprises the compounds of the above general formula I, wherein A, U, V, X, Y and $R^3$ are defined as hereinbefore in the first embodiment and $R^1$ and $R^2$ together with the nitrogen atom to which they are attached denote a group of general formulae

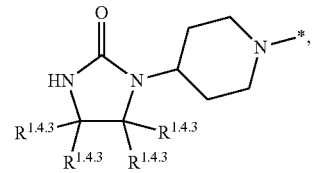

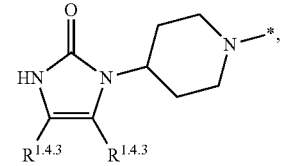

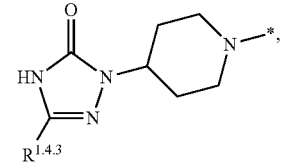

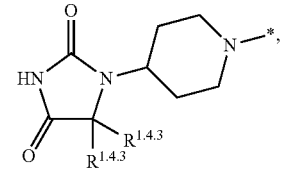

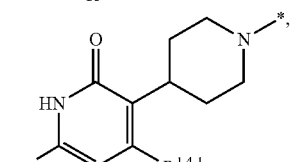

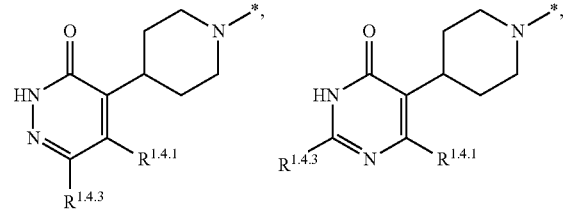

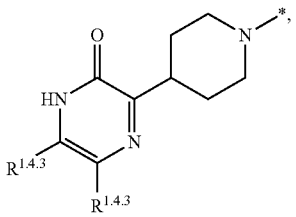

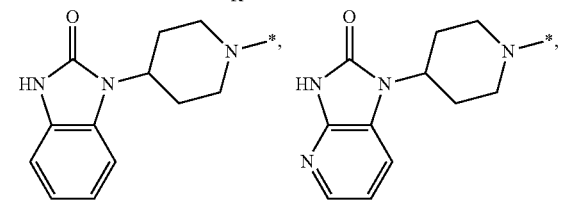

-continued

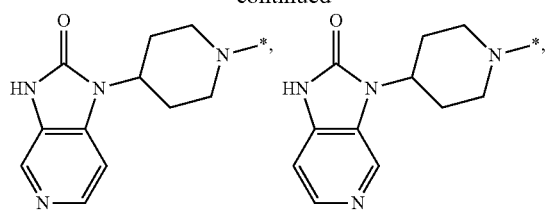

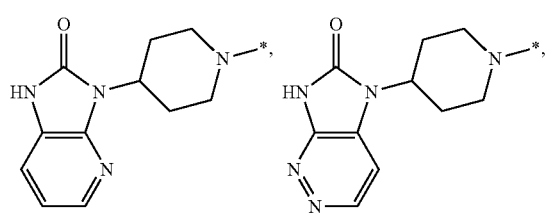

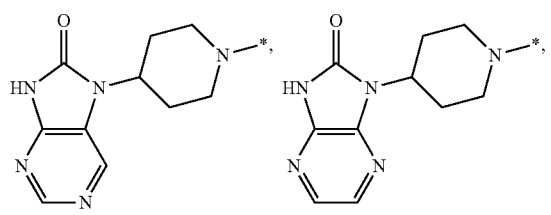

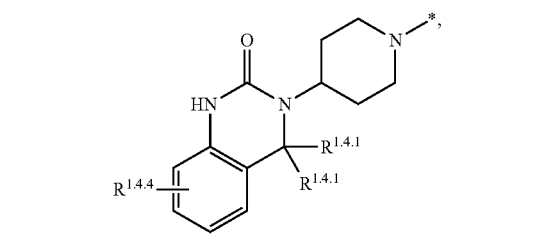

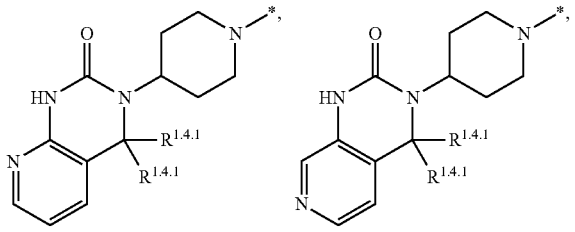

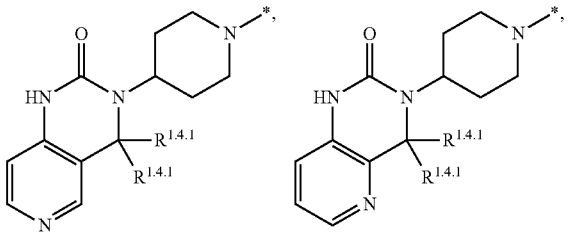

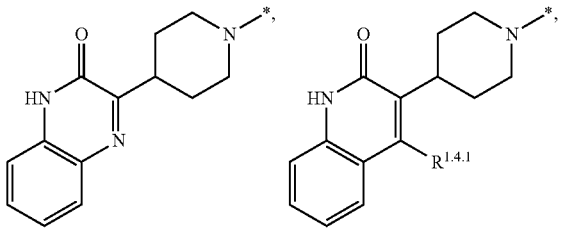

wherein
$R^{1.4.1}$ denotes
- (a) H,
- (b) $C_{1-6}$-alkyl, —OH, —O—$C_{1-3}$-alkyl,
- (c) a $C_{1-3}$-alkyl or $C_{1-3}$-alkyl-O— group wherein each methylene group is substituted by up to two fluorine atoms and each methyl group is substituted by up to three fluorine atoms, $R^{1.4.3}$ denotes
- (a) H, $C_{1-6}$-alkyl, $C_{3-6}$-cycloalkyl,
- (b) a phenyl group optionally substituted by 1, 2, or 3 substituents $R^{1.4.3.1}$, wherein the substituents $R^{1.4.3.1}$ may be identical or different,
- (c) a heteroaryl group optionally substituted by 1, 2 or 3 substituents $R^{1.4.3.1}$ which is selected from among benzimidazole, benzothiophene, furan, imidazole, indole, isoxazole, oxazole, pyrazine, pyrazole, pyridazine, pyridine, pyrimidine, pyrrole, thiazole, thiophene and triazole, wherein the substituents $R^{1.4.3.1}$ may be identical or different,
- (d) a heterocyclic group optionally substituted by 1, 2 or 3 substituents $R^{1.4.3.1}$, wherein the substituents $R^{1.4.3.1}$ may be identical or different, $R^{1.4.3.1}$ denotes
- (a) halogen, $C_{1-6}$-alkyl, $C_{3-6}$-cycloalkyl,
- (b) —O—$R^{1.4.3.1.1}$, —O—$(CH_2)_s$—O—$R^{1.4.3.1.1}$, —$CO_2 R^{1.4.3.1.1}$, —$S(O)_m$—$R^{1.4.3.1.1}$, —CN, —O—C(O)—$R^{1.4.3.1.1}$ or
- (c) a $C_{1-3}$-alkyl group wherein each methylene group is substituted by up to two fluorine atoms and each methyl group is substituted by up to three fluorine atoms, $R^{1.4.3.1.1}$ denotes
- (a) H,
- (b) $C_{1-6}$-alkyl, $C_{3-6}$-cycloalkyl, aryl, heteroaryl, benzyl, which may be substituted by a group $R^{1.4.3.1.1.1}$, or
- (c) a $C_{1-3}$-alkyl group wherein each methylene group is substituted by up to two fluorine atoms and each methyl group is substituted by up to three fluorine atoms, $R^{1.4.3.1.1.1}$ denotes HO— or $C_{1-6}$-alkyl-O, $R^{1.4.3.1.2}$ denotes
- (a) H,
- (b) $C_{1-3}$-alkyl, phenyl or benzyl, while the groups may be unsubstituted or substituted by halogen, HO— or $H_3C$—O, $R^{1.4.3.1.3}$ denotes
(a) H,
(b) $C_{1-3}$-alkyl, phenyl or benzyl, while the groups may be unsubstituted or substituted by halogen, HO— or $H_3C$—O, or $R^{1.4.3.1.2}$ and $R^{1.4.3.1.3}$ together may also form a ring which is selected from among azetidinyl, pyrrolidinyl, piperidinyl, piperazinyl and morpholinyl, while the ring may be unsubstituted or substituted by a substituent $R^{1.4.5}$, $R^{1.4.4}$ denotes
(a) H, halogen, $C_{1-6}$-alkyl, $C_{3-6}$-cycloalkyl,
(b) —O—$C_{1-6}$-alkylene-$NR^{1.4.3.1.2}R^{1.4.3.1.3}$, —O—$R^{1.4.3.1.1}$, —$CO_2R^{1.4.3.1.1}$, —C(O)—$NR^{1.4.3.1.2}R^{1.4.3.1.3}$, —$SO_2$—$NR^{1.4.3.1.2}R^{1.4.3.1.3}$, —$NR^{1.4.3.1.2}$-$SO_2$—$R^{1.4.3.1.3}$, —$S(O)_m$—$R^{1.4.3.1.2}$, —CN, —$NR^{1.4.3.1.2}R^{1.4.3.1.3}$, —O—C(O)—$R^{1.4.3.1.1}$ or
(c) a $C_{1-3}$-alkyl or $C_{1-3}$-alkyl-O— group wherein each methylene group is substituted by up to two fluorine atoms and each methyl group is substituted by up to three fluorine atoms, m denotes one of the numbers 0, 1 or 2, and s denotes one of the numbers 1, 2 or 3, the tautomers, the diastereomers, the enantiomers, the hydrates, the mixtures thereof and the salts thereof as well as the hydrates of the salts, particularly the physiologically acceptable salts thereof with inorganic or organic acids or bases.

A fourteenth embodiment of the present invention comprises the compounds of the above general formula I, wherein A, U, V, X, Y and $R^3$ are defined as hereinbefore in the first embodiment and $R^1$ and $R^2$ together with the nitrogen atom to which they are attached denote a group of general formula

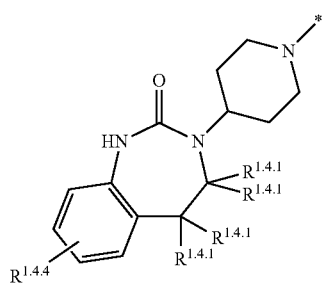

wherein
$R^{1.4.1}$ independently of one another denote H, $C_{1-3}$-alkyl, —OH, $CF_3$ and
$R^{1.4.4}$ denotes H, Cl, F, $CH_3$, $CF_3$ or —O—$CH_3$, the tautomers, the diastereomers, the enantiomers, the hydrates, the mixtures thereof and the salts thereof as well as the hydrates of the salts, particularly the physiologically acceptable salts thereof with inorganic or organic acids or bases.

A fifteenth embodiment of the present invention comprises the compounds of the above general formula I, wherein A, U, V, X, Y and $R^3$ are defined as hereinbefore in the first embodiment and $R^1$ and $R^2$ together with the nitrogen atom to which they are attached denote a group of general formulae

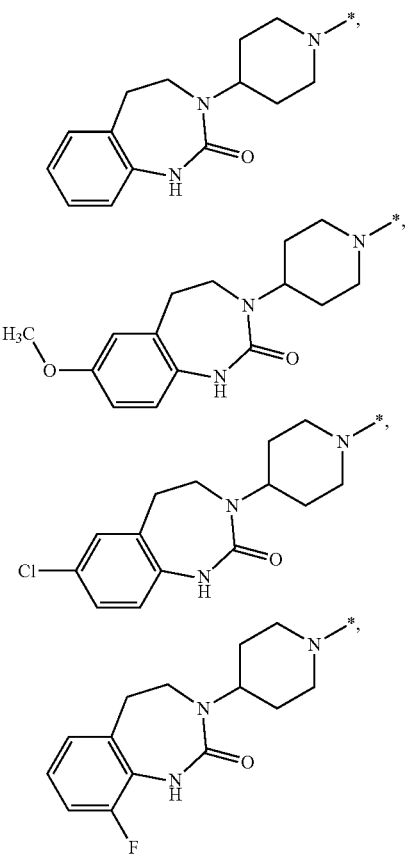

the tautomers, the diastereomers, the enantiomers, the hydrates, the mixtures thereof and the salts thereof as well as the hydrates of the salts, particularly the physiologically acceptable salts thereof with inorganic or organic acids or bases.

A sixteenth embodiment of the present invention comprises the compounds of the above general formula I, wherein A, U, V, X, Y and $R^3$ are defined as hereinbefore in the first embodiment and $R^1$ and $R^2$ together with the nitrogen atom to which they are attached denote a group

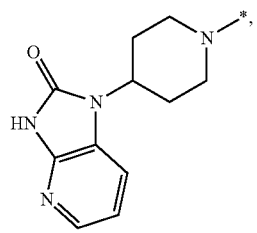

the tautomers, the diastereomers, the enantiomers, the hydrates, the mixtures thereof and the salts thereof as well as the hydrates of the salts, particularly the physiologically acceptable salts thereof with inorganic or organic acids or bases.

A seventeenth embodiment of the present invention comprises the compounds of the above general formula I, wherein A, U, V, X, Y and $R^3$ are defined as hereinbefore in the first embodiment and $R^1$ and $R^2$ together with the nitrogen atom to which they are attached denote a group

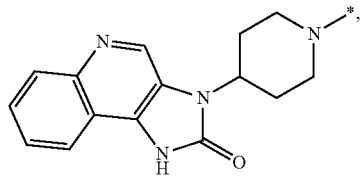

the tautomers, the diastereomers, the enantiomers, the hydrates, the mixtures thereof and the salts thereof as well as the hydrates of the salts, particularly the physiologically acceptable salts thereof with inorganic or organic acids or bases.

An eighteenth embodiment of the present invention comprises the compounds of the above general formula I, wherein A, U, V, X, Y and $R^3$ are defined as hereinbefore in the first embodiment and $R^1$ and $R^2$ together with the nitrogen atom to which they are attached denote a group selected from

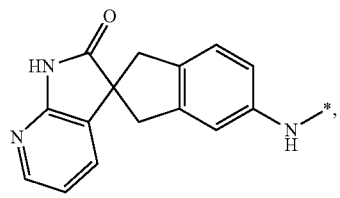

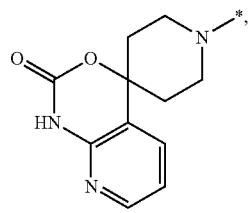

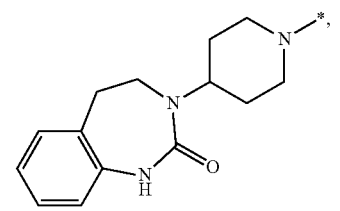

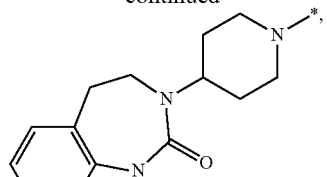

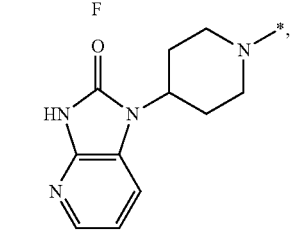

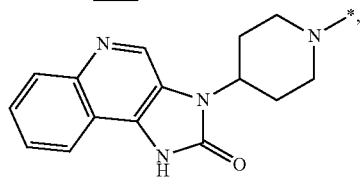

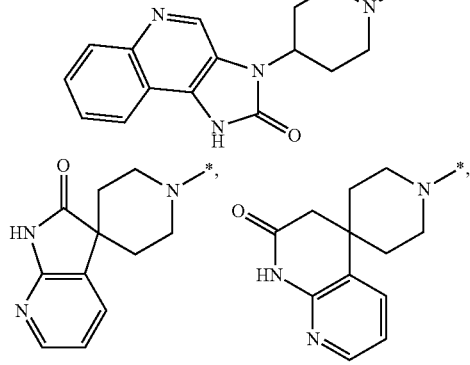

the tautomers, the diastereomers, the enantiomers, the hydrates, the mixtures thereof and the salts thereof as well as the hydrates of the salts, particularly the physiologically acceptable salts thereof with inorganic or organic acids or bases.

A nineteenth embodiment of the present invention comprises the compounds of the above general formula I, wherein A, U, V, X, Y, $R^1$ and $R^2$ are defined as hereinbefore in the first, second, third, fourth, fifth, sixth, seventh, eighth ninth, tenth, eleventh, twelfth, thirteenth, fourteenth, fifteenth, sixteenth, seventeenth or eighteenth embodiment and $R^3$ denotes (a) a 6 or 10-membered aryl group substituted by the groups $R^{3.1}$, $R^{3.2}$ and $R^{3.3}$, (b) a 5- or 6-membered heteroaryl group substituted by the groups $R^{3.1}$, $R^{3.2}$ and $R^{3.3}$ which is attached via a carbon atom, or (c) a 5- or 6-membered heteroaryl group substituted by a group $R^{3.2}$ which is attached via a carbon atom and is additionally fused to a phenyl ring, $R^{3.1}$ denotes (a) H, (b) halogen, —$NH_2$, $C_{1-4}$-alkyl-NH—, ($C_{1-4}$-alkyl)$_2$N—, —CN, —OH (c) $C_{1-4}$-alkyl, $R^{3.1.1}$—$C_{1-3}$-alkylene, $C_{1-3}$-alkyl-O—, cyclopropyl, (d) a $C_{1-3}$-alkyl or $C_{1-3}$-alkyl-O— group wherein each methylene group is substituted by up to two fluorine atoms and each methyl group is substituted by up to three fluorine atoms, $R^{3.1.1}$ denotes
  (a) H,
  (b) $C_{3-6}$-cycloalkyl,
  (c) $(C_{1-4}\text{-alkyl})_2N$, $C_{1-4}\text{-alkyl-NH}—$, $C_{1-3}\text{-alkyl-O}—$,
$R^{3.2}$ denotes
  (a) H,
  (b) $NH_2$, $C_{1-4}\text{-alkyl-NH}—$, $(C_{1-4}\text{-alkyl})_2N—$, $C_{1-3}\text{-alkyl-}$C(O)—NH—, HO, $C_{1-3}\text{-alkyl-O}—$,
  (c) $C_{1-3}$-alkyl or
  (d) a $C_{1-3}$-alkyl- or $C_{1-3}$-alkyl-O— group wherein each methylene group is substituted by up to two fluorine atoms and each methyl group is substituted by up to three fluorine atoms,
$R^{3.3}$ denotes
  (a) H,
  (b) F, Cl, Br,
  (c) $C_{1-3}$-alkyl, $C_{1-3}$-alkyl-O— or
  (d) a $C_{1-3}$-alkyl or $C_{1-3}$-alkyl-O— group wherein each methylene group is substituted by up to two fluorine atoms and each methyl group is substituted by up to three fluorine atoms, or
$R^{3.2}$ and $R^{3.3}$ together with the carbon atoms to which they are bonded form a monounsaturated 5-membered or a mono- or diunsaturated 6-membered heterocyclic group or a 5- to 6-membered heteroaryl group, while
  the previously mentioned heterocycles may contain a carbonyl, thiocarbonyl or cyanimino group adjacent to a nitrogen atom, and
  may optionally additionally be substituted at one or two nitrogen atoms by a group $R^{3.3.1}$ and
  may optionally additionally be substituted at one or two carbon atoms by one or two groups $R^{3.3.2}$,
$R^{3.3.1}$ independently of one another denote
  (a) $C_{1-4}$-alkyl or
  (b) $C_{3-6}$-cycloalkyl,
$R^{3.3.2}$ independently of one another denote
  (a) $R^{3.3.2.1}$—$C_{1-3}$-alkylene,
  (b) $C_{3-6}$-cycloalkyl, wherein a $CH_2$ group may be replaced by an oxygen atom,
  (c) halogen, CN, —O—$C_{1-3}$-alkyl, —$NH_2$, $C_{1-4}$-alkyl-NH—, $(C_{1-4}\text{-alkyl})_2N—$, —NH(CN),
  (d) a $C_{1-3}$-alkyl- or $C_{1-3}$-alkyl-O— group wherein each methylene group is substituted by up to two and each methyl group is substituted by up to three fluorine atoms,
$R^{3.3.2.1}$ denotes
  (a) H,
  (b) CN, $CF_3$, $NH_2$, $C_{1-4}$-alkyl-NH—, $(C_{1-4}\text{-alkyl})_2N—$,
  (c) OH, —O—$C_{1-3}$-alkyl,
  (d) $C_{3-6}$-cycloalkyl,
the tautomers, the diastereomers, the enantiomers, the hydrates, the mixtures thereof and the salts thereof as well as the hydrates of the salts, particularly the physiologically acceptable salts thereof with inorganic or organic acids or bases.

A twentieth embodiment of the present invention comprises the compounds of the above general formula I, wherein A, U, V, X, Y, $R^1$ and $R^2$ are defined as hereinbefore in the first, second, third, fourth, fifth, sixth, seventh, eighth, ninth, tenth, eleventh, twelfth, thirteenth, fourteenth, fifteenth, sixteenth, seventeenth or eighteenth embodiment and $R^3$ denotes a group selected from

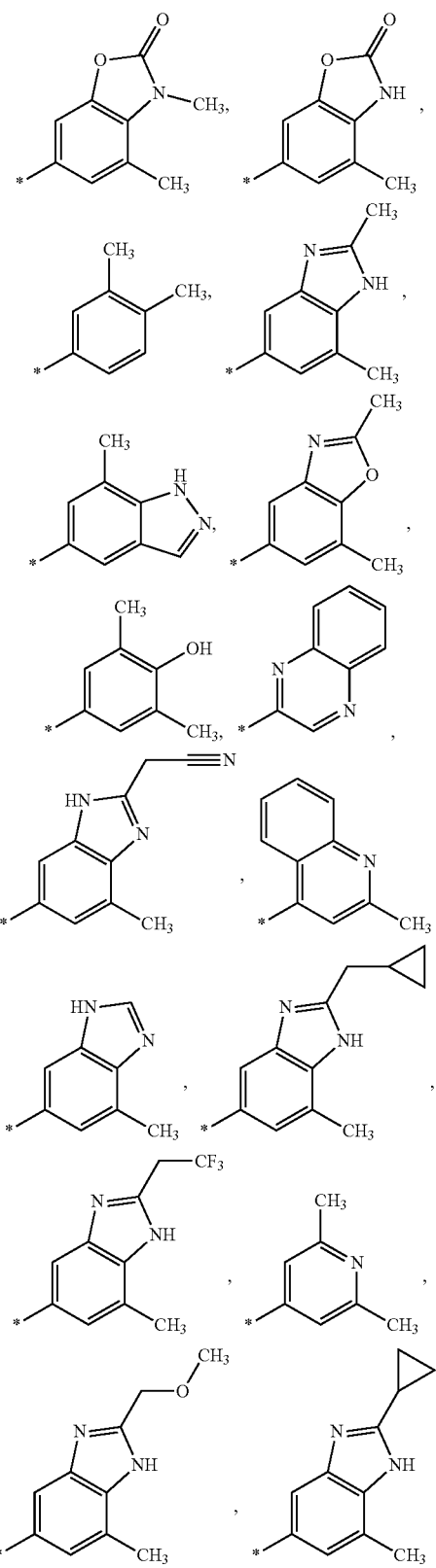

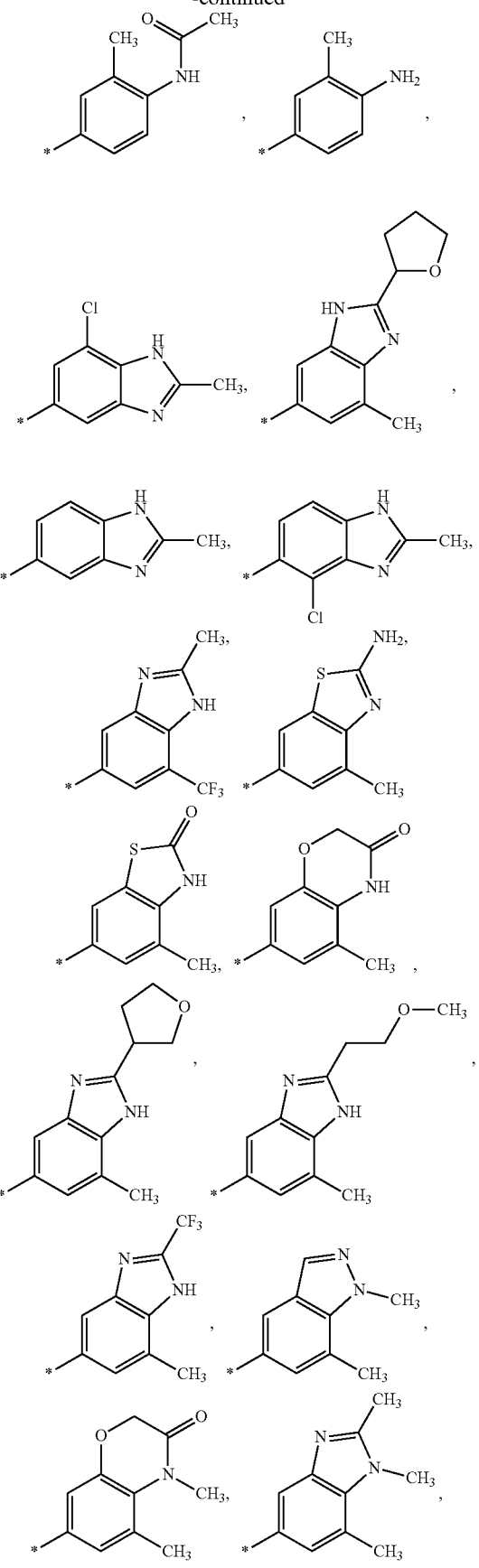

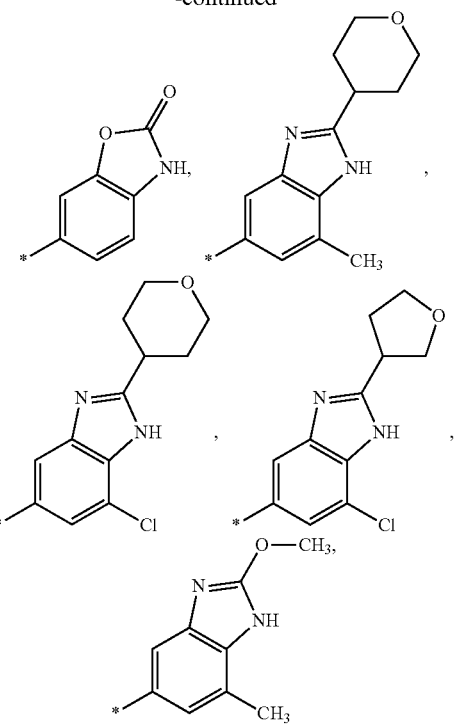

the tautomers, the diastereomers, the enantiomers, the hydrates, the mixtures thereof and the salts thereof as well as the hydrates of the salts, particularly the physiologically acceptable salts thereof with inorganic or organic acids or bases.

A twenty-first embodiment of the present invention comprises the compounds of the above general formula I, wherein A, U, V, X, Y, $R^1$ and $R^2$ are defined as hereinbefore in the first, second, third, fourth, fifth, sixth, seventh, eighth, ninth, tenth, eleventh, twelfth, thirteenth, fourteenth, fifteenth, sixteenth, seventeenth or eighteenth embodiment and $R^3$ denotes a group of general formulae Va, Vb or Vc

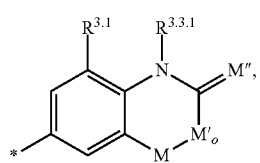

(Va)

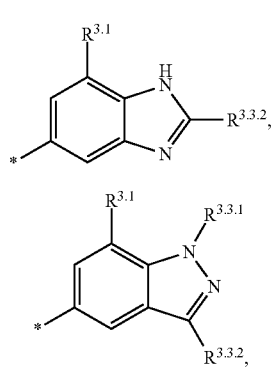

(Vb)

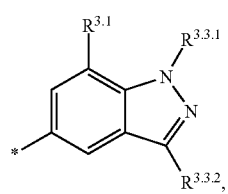

(Vc)

M denotes $CH_2$, NH, O, S,
M' denotes $CH_2$, $C(R^{3.2.2})_2$,
M" denotes O or S,
$R^{3.1}$ denotes
(a) H,
(b) halogen,
(c) $C_{1-3}$-alkyl, $C_{1-3}$-alkyl-O—,
(d) a $C_{1-3}$-alkyl or $C_{1-3}$-alkyl-O— group wherein each methylene group is substituted by up to two fluorine atoms and each methyl group is substituted by up to three fluorine atoms,
$R^{3.2.2}$ denotes
(a) H or
(b) $C_{1-3}$-alkyl- and
$R^{3.3.1}$ independently of one another denote
(a) H,
(b) $C_{3-6}$-cycloalkyl or
(c) $C_{1-3}$-alkyl,
$R^{3.3.2}$ denotes
(a) H,
(b) $R^{3.3.2.1}$—$C_{1-3}$-alkylene,
(c) $C_{3-6}$-cycloalkyl, wherein a $CH_2$ group may be replaced by an oxygen atom,
(d) halogen, CN, —O—$C_{1-3}$-alkyl, $NH_2$, $C_{1-4}$-alkyl-NH—, $(C_{1-4}$-alkyl$)_2$N—, —NH(CN),
(e) a $C_{1-3}$-alkyl or $C_{1-3}$-alkyl-O— group wherein each methylene group is substituted by up to two fluorine atoms and each methyl group is substituted by up to three fluorine atoms,
$R^{3.3.2.1}$ denotes
(a) H,
(b) CN, $CF_3$, $NH_2$, $C_{1-4}$-alkyl-NH—, $(C_{1-4}$-alkyl$)_2$N—,
(c) OH, —O—$C_{1-3}$-alkyl,
(d) $C_{3-6}$-cycloalkyl,
o denotes one of the numbers 0 or 1,
the tautomers, the diastereomers, the enantiomers, the hydrates, the mixtures thereof and the salts thereof as well as the hydrates of the salts, particularly the physiologically acceptable salts thereof with inorganic or organic acids or bases.

A twenty-second embodiment of the present invention comprises the compounds of the above general formula I, wherein A, U, V, X, Y, $R^1$ and $R^2$ are defined as hereinbefore in the first, second, third, fourth, fifth, sixth, seventh, eighth, ninth, tenth, eleventh, twelfth, thirteenth, fourteenth, fifteenth, sixteenth, seventeenth or eighteenth embodiment and $R^3$ denotes a group of general formulae Va

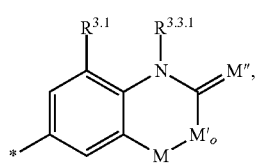

M denotes $CH_2$, NH, O, S,
M' denotes $CH_2$, $C(R^{3.2.2})_2$,
M" denotes O or S,
$R^{3.1}$ denotes
(a) H,
(b) halogen,
(c) $C_{1-3}$-alkyl, $C_{1-3}$-alkyl-O—,
(d) a $C_{1-3}$-alkyl or $C_{1-3}$-alkyl-O— group wherein each methylene group is substituted by up to two fluorine atoms and each methyl group is substituted by up to three fluorine atoms,
$R^{3.2.2}$ denotes
(a) H or
(b) $C_{1-3}$-alkyl- and
$R^{3.3.1}$ denotes H,
o denotes one of the numbers 0 or 1,
the tautomers, the diastereomers, the enantiomers, the hydrates, the mixtures thereof and the salts thereof as well as the hydrates of the salts, particularly the physiologically acceptable salts thereof with inorganic or organic acids or bases.

A twenty-third embodiment of the present invention comprises the compounds of the above general formula I, wherein A, U, V, X, Y, $R^1$ and $R^2$ are defined as hereinbefore in the first, second, third, fourth, fifth, sixth, seventh, eighth, ninth, tenth, eleventh, twelfth, thirteenth, fourteenth, fifteenth, sixteenth, seventeenth or eighteenth embodiment and $R^3$ denotes a group selected from

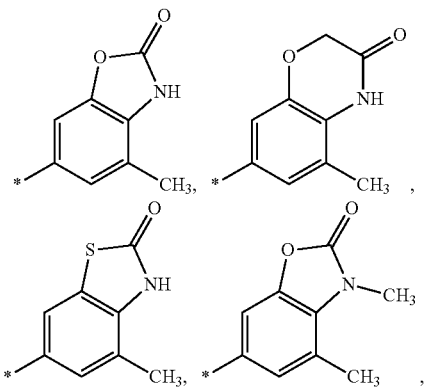

the tautomers, the diastereomers, the enantiomers, the hydrates, the mixtures thereof and the salts thereof as well as the hydrates of the salts, particularly the physiologically acceptable salts thereof with inorganic or organic acids or bases.

A twenty-fourth embodiment of the present invention comprises the compounds of the above general formula I, wherein A, U, V, X, Y, $R^1$ and $R^2$ are defined as hereinbefore in the first, second, third, fourth, fifth, sixth, seventh, eighth, ninth, tenth, eleventh, twelfth, thirteenth, fourteenth, fifteenth, sixteenth, seventeenth or eighteenth embodiment and $R^3$ denotes a group of general formula Vb

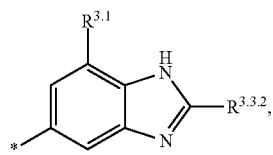

$R^{3.1}$ denotes
(a) H,
(b) halogen,
(c) $C_{1-3}$-alkyl, $C_{1-3}$-alkyl-O—,
(d) a $C_{1-3}$-alkyl or $C_{1-3}$-alkyl-O— group wherein each methylene group is substituted by up to two fluorine atoms and each methyl group is substituted by up to three fluorine atoms, $R^{3.3.2}$ denotes
- (a) H,
- (b) $R^{3.3.2.1}$—$C_{1-3}$-alkylene,
- (c) $C_{3-6}$-cycloalkyl, wherein a $CH_2$ group may be replaced by an oxygen atom,
- (d) halogen, CN, —O—$C_{1-3}$-alkyl, $NH_2$, $C_{1-4}$-alkyl-NH—, $(C_{1-4}$-alkyl$)_2$N—, —NH(CN),
- (e) a $C_{1-3}$-alkyl- or $C_{1-3}$-alkyl-O— group wherein each methylene group is substituted by up to two fluorine atoms and each methyl group is substituted by up to three fluorine atoms, $R^{3.3.2.1}$ denotes
- (a) H,
- (b) CN, $CF_3$, $NH_2$, $C_{1-4}$-alkyl-NH—, $(C_{1-4}$-alkyl$)_2$N—,
- (c) OH, —O—$C_{1-3}$-alkyl,
- (d) $C_{3-6}$-cycloalkyl and o denotes one of the numbers 0 or 1, the tautomers, the diastereomers, the enantiomers, the hydrates, the mixtures thereof and the salts thereof as well as the hydrates of the salts, particularly the physiologically acceptable salts thereof with inorganic or organic acids or bases.

A twenty-fifth embodiment of the present invention comprises the compounds of the above general formula I, wherein A, U, V, X, Y, $R^1$ and $R^2$ are defined as hereinbefore in the first, second, third, fourth, fifth, sixth, seventh, eighth, ninth, tenth, eleventh, twelfth, thirteenth, fourteenth, fifteenth, sixteenth, seventeenth or eighteenth embodiment and $R^3$ denotes a group selected from

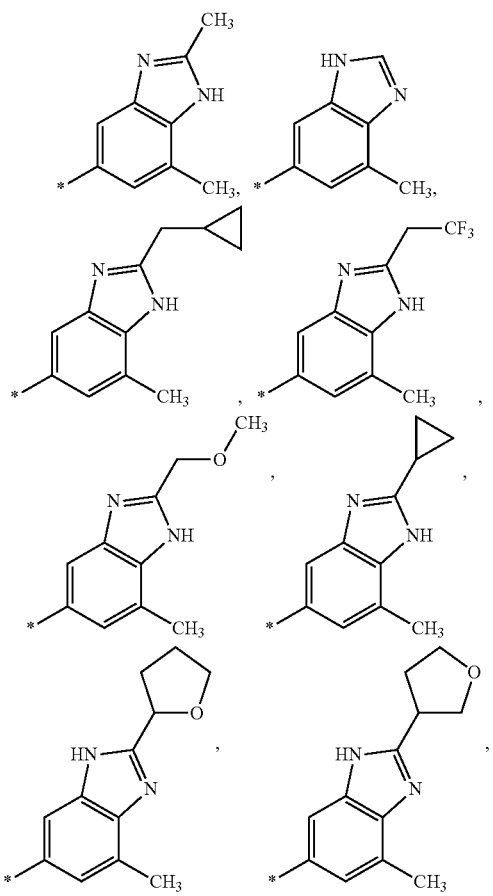

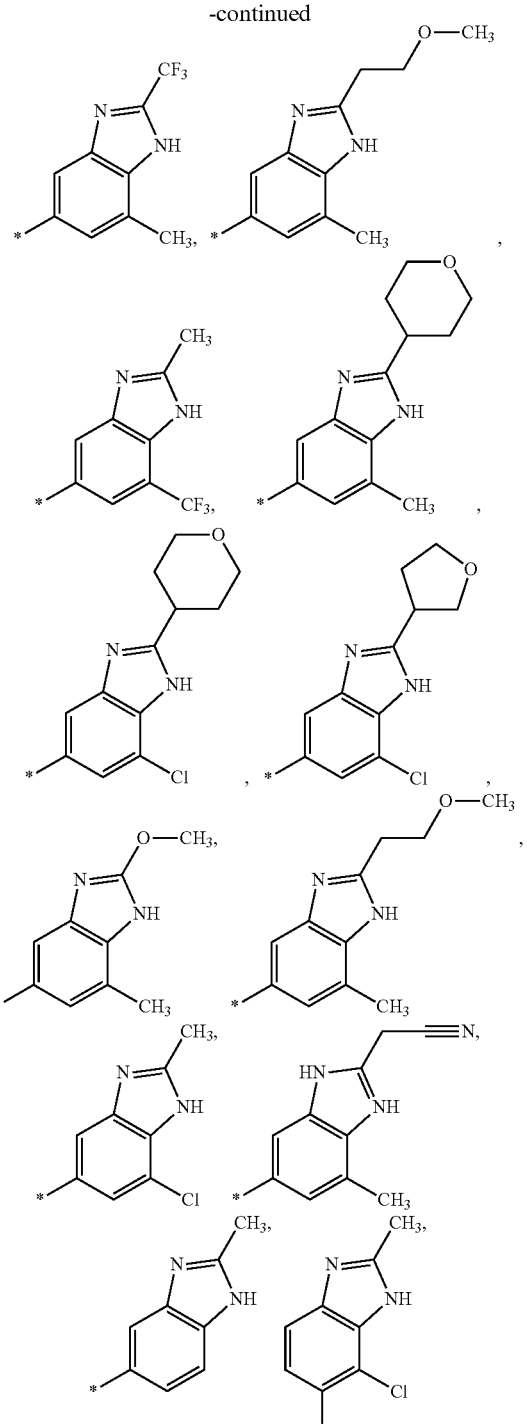

the tautomers, the diastereomers, the enantiomers, the hydrates, the mixtures thereof and the salts thereof as well as the hydrates of the salts, particularly the physiologically acceptable salts thereof with inorganic or organic acids or bases.

A twenty-sixth embodiment of the present invention comprises the compounds of the above general formula I, wherein A, U, V, X, Y, $R^1$ and $R^2$ are defined as hereinbefore in the first, second, third, fourth, fifth, sixth, seventh, eighth, ninth, tenth, eleventh, twelfth, thirteenth, fourteenth, fifteenth, sixteenth, seventeenth or eighteenth embodiment and $R^3$ denotes a group of general formula Vc

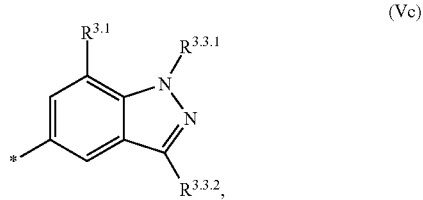

(Vc)

$R^{3.1}$ denotes
(a) H,
(b) halogen,
(c) $C_{1-3}$-alkyl, $C_{1-3}$-alkyl-O—,
(d) a $C_{1-3}$-alkyl- or $C_{1-3}$-alkyl-O— group wherein each methylene group is substituted by up to two fluorine atoms and each methyl group is substituted by up to three fluorine atoms, $R^{3.3.1}$ denotes
(a) H or
(b) —$CH_3$, $R^{3.3.2}$ denotes
(a) H,
(b) $R^{3.3.2.1}$—$C_{1-3}$-alkylene,
(c) $C_{3-6}$-cycloalkyl, wherein a $CH_2$ group may be replaced by an oxygen atom,
(d) halogen, CN, —O—$C_{1-3}$-alkyl, $NH_2$, $C_{1-4}$-alkyl-NH—, $(C_{1-4}$-alkyl$)_2$N—, —NH(CN),
(e) a $C_{1-3}$-alkyl or $C_{1-3}$-alkyl-O— group wherein each methylene group is substituted by up to two fluorine atoms and each methyl group is substituted by up to three fluorine atoms, and $R^{3.3.2.1}$ denotes
(a) H,
(b) CN, $CF_3$, $NH_2$, $C_{1-4}$-alkyl-NH—, $(C_{1-4}$-alkyl$)_2$N—,
(c) OH, —O—$C_{1-3}$-alkyl,
(d) $C_{3-6}$-cycloalkyl, the tautomers, the diastereomers, the enantiomers, the hydrates, the mixtures thereof and the salts thereof as well as the hydrates of the salts, particularly the physiologically acceptable salts thereof with inorganic or organic acids or bases.

A twenty-seventh embodiment of the present invention comprises the compounds of the above general formula I, wherein A, U, V, X, Y, $R^1$ and $R^2$ are defined as hereinbefore in the first, second, third, fourth, fifth, sixth, seventh, eighth, ninth, tenth, eleventh, twelfth, thirteenth, fourteenth, fifteenth, sixteenth, seventeenth or eighteenth embodiment and $R^3$ denotes a group selected from

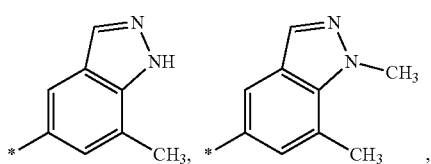

the tautomers, the diastereomers, the enantiomers, the hydrates, the mixtures thereof and the salts thereof as well as the hydrates of the salts, particularly the physiologically acceptable salts thereof with inorganic or organic acids or bases.

A twenty-eighth embodiment of the present invention comprises the compounds of the above general formula I, wherein A, Y, $R^1$, $R^2$ and $R^3$ are defined as hereinbefore in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth or twenty-seventh embodiment and U—V—X denotes a group selected from
N=N—(C—$R^6$)=, —N=(C—$R^5$)—N=, —N=(C—$R^5$)—(C—$R^6$)=, —(N-oxide)=(C—$R^5$)—(C—$R^6$)=, —(C$R^4$)=N—N=, —(C$R^4$)=N—(C—$R^6$)=, —(C—$R^4$)=N(oxide)-(C—$R^6$)=, —(C$R^4$)=(C—$R^5$)—N=, —(C$R^4$)=(C—$R^5$)—(N-oxide)=, —(C$R^4$)=(C—$R^5$)—(C$R^6$)=, and $R^4$ denotes
(a) H,
(b) a $C_{1-6}$-alkyl or $C_{1-3}$-alkyl-O— group which is substituted in each case by a group $R^{4.1}$,
(c) $R^{4.2}R^{4.3}$N—, $R^{4.2}R^{4.3}$N—$C_{1-3}$-alkylene-,
(d) halogen, —CN, —OH, $C_{1-3}$-alkyl-O—$C_{1-3}$-alkylene-, $C_{3-6}$-cycloalkyl-, $C_{3-6}$-cycloalkyl-$C_{1-4}$-alkylene-, $C_{1-3}$-alkyl-C(O)—O—$C_{1-3}$-alkylene,
(e) a $C_{1-3}$-alkyl- or $C_{1-3}$-alkyl-O— group wherein each methylene group is substituted by up to two fluorine atoms and each methyl group is substituted by up to three fluorine atoms, $R^{4.1}$ denotes H, OH or —O—$CH_3$,
$R^{4.2}$ denotes H or $C_{1-3}$-alkyl,
$R^{4.3}$ denotes H or $C_{1-3}$-alkyl, or
$R^{4.2}$ and $R^{4.3}$ together with the nitrogen atom to which they are attached denote a 3- to 6-membered heterocyclic group, $R^5$ denotes
(a) H,
(b) a $C_{1-6}$-alkyl or $C_{1-3}$-alkyl-CO— group which is substituted in each case by a group $R^{5.1}$,
(c) —$NR^{5.1}R^{5.2}$, $NR^{5.1}R^{5.2}$—$C_{1-3}$-alkylene-,
(d) halogen, —CN, —OH, $C_{1-3}$—O—$C_{1-3}$-alkylene, $C_{3-6}$-cycloalkyl, $C_{3-6}$-cycloalkyl-$C_{1-4}$-alkylene, $C_{1-3}$-alkyl-C(O)—O—$C_{1-3}$-alkylene,
(e) aryl-$C_{0-3}$-alkylene-O—,
(f) a $C_{1-3}$-alkyl- or $C_{1-3}$-alkyl-O— group wherein each methylene group is substituted by up to two fluorine atoms and each methyl group is substituted by up to three fluorine atoms, $R^{5.1}$ denotes H, OH or —O—$CH_3$,
$R^{5.2}$ denotes H or $C_{1-6}$-alkyl,
$R^{5.3}$ denotes H, $C_{1-6}$-alkyl or —$SO_2$—$C_{1-3}$-alkyl,
$R^{5.2}$ and $R^{5.3}$ together with the nitrogen atom to which they are attached denote a 3- to 6-membered heterocyclic group, $R^6$ denotes
(a) H,
(b) a $C_{1-6}$-alkyl or $C_{1-3}$-alkyl-O— group which is substituted in each case by a group $R^{6.1}$,
(c) $R^{6.2}R^{6.3}$N, $R^{6.2}R^{6.3}$N—$C_{1-3}$-alkylene-,
(d) halogen, —CN, —OH, $C_{1-3}$-alkyl-O—$C_{1-3}$-alkylene-, $C_{3-6}$-cycloalkyl-, $C_{3-6}$-cycloalkyl-$C_{1-4}$-alkylene-, $C_{1-3}$-alkyl-C(O)—O—$C_{1-3}$-alkylene,
(e) a $C_{1-3}$-alkyl or $C_{1-3}$-alkyl-O— group wherein each methylene group is substituted by up to two fluorine atoms and each methyl group is substituted by up to three fluorine atoms, $R^{6.1}$ denotes H, OH or —O—$CH_3$,
$R^{6.2}$ denotes H or $C_{1-3}$-alkyl,
$R^{6.3}$ denotes H or $C_{1-3}$-alkyl, or $R^{6.2}$ and $R^{6.3}$ together with the nitrogen atom to which they are attached denote a 3- to 6-membered heterocyclic group, the tautomers, the diastereomers, the enantiomers, the hydrates, the mixtures thereof and the salts thereof as well as the hydrates of the salts, particularly the physiologically acceptable salts thereof with inorganic or organic acids or bases.

A twenty-ninth embodiment of the present invention comprises the compounds of the above general formula I, wherein A, $R^1$, $R^2$ and $R^3$ are defined as hereinbefore in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth or twenty-seventh embodiment and the ring

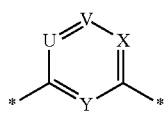

denotes a group selected from

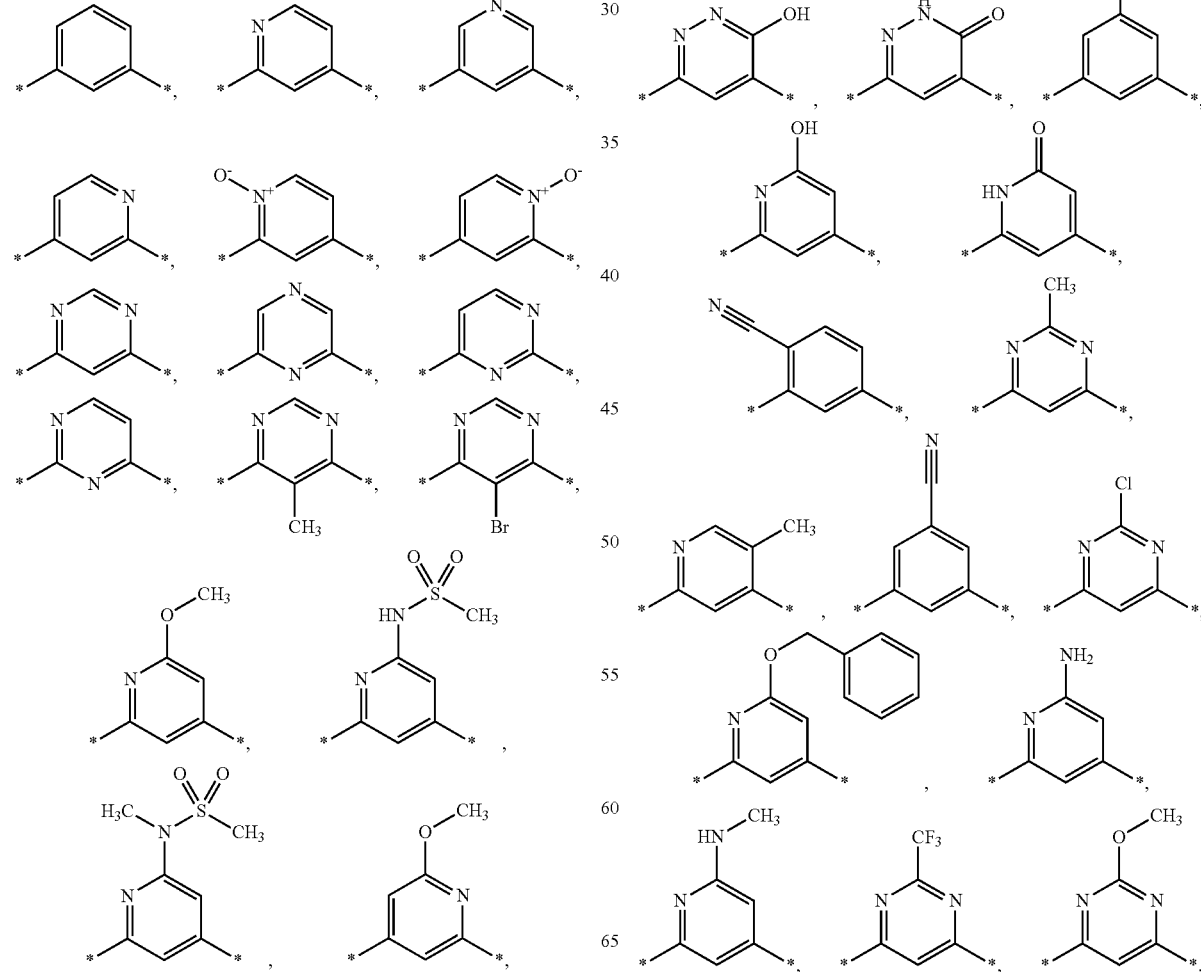

-continued

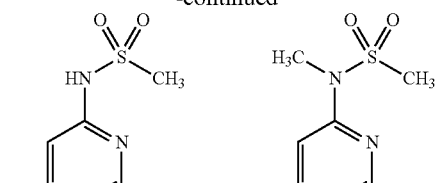

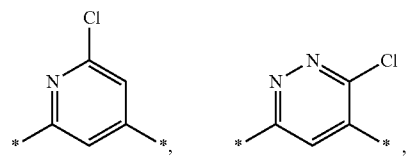

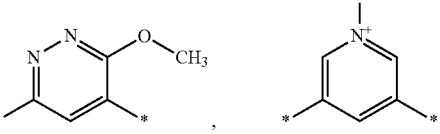

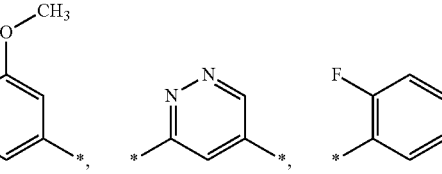

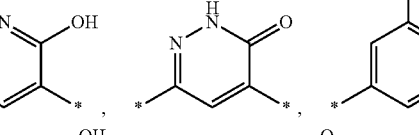

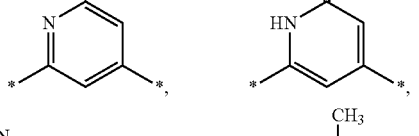

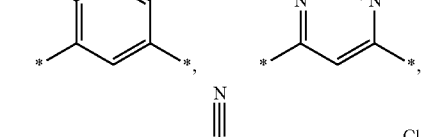

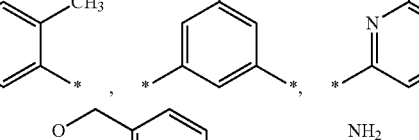

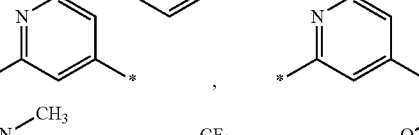

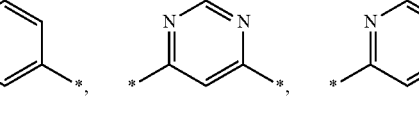

-continued

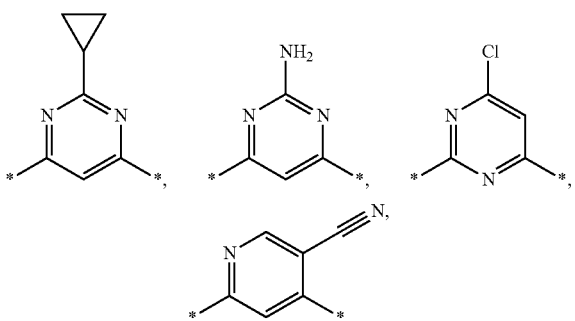

the tautomers, the diastereomers, the enantiomers, the hydrates, the mixtures thereof and the salts thereof as well as the hydrates of the salts, particularly the physiologically acceptable salts thereof with inorganic or organic acids or bases.

A thirtieth embodiment of the present invention comprises the compounds of the above general formula I, wherein A, $R^1$, $R^2$ and $R^3$ are defined as hereinbefore in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth or twenty-seventh embodiment and the ring

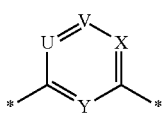

denotes a group selected from

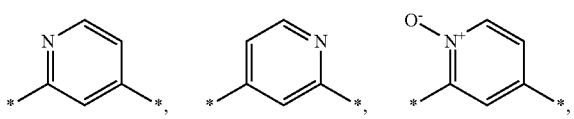

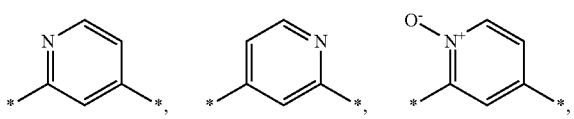

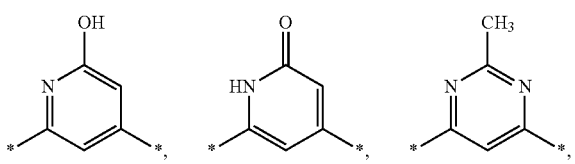

-continued

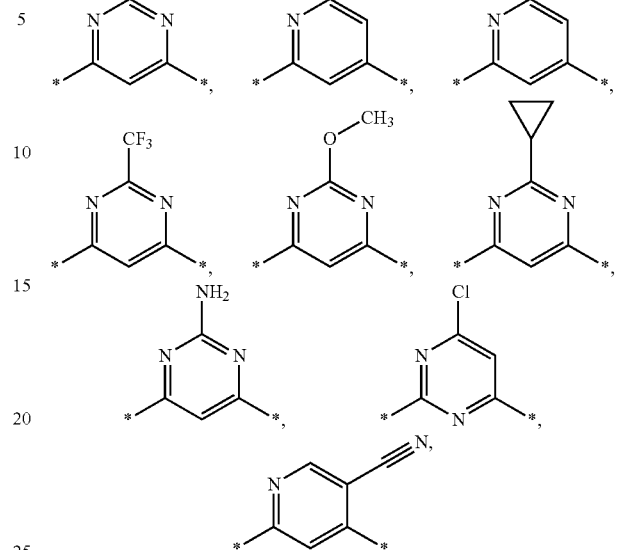

the tautomers, the diastereomers, the enantiomers, the hydrates, the mixtures thereof and the salts thereof as well as the hydrates of the salts, particularly the physiologically acceptable salts thereof with inorganic or organic acids or bases.

A thirty-first embodiment of the present invention comprises the compounds of the above general formula I, wherein A, $R^1$, $R^2$ and $R^3$ are defined as hereinbefore in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth or twenty-seventh embodiment and the ring

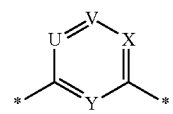

denotes a group

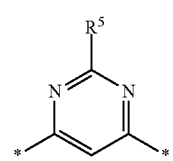

and
$R^5$ denotes H, $CH_3$, —O—$CH_3$, —$CF_3$, —$NH_2$ or cyclopropyl,
the tautomers, the diastereomers, the enantiomers, the hydrates, the mixtures thereof and the salts thereof as well as the hydrates of the salts, particularly the physiologically acceptable salts thereof with inorganic or organic acids or bases.

A thirty-second embodiment of the present invention comprises the compounds of the above general formula I, wherein U, V, X, Y, $R^1$, $R^2$ and $R^3$ are defined as hereinbefore in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth or thirty-first embodiment and A denotes —O— or —NH—, the tautomers, the diastereomers, the enantiomers, the hydrates, the mixtures thereof and the salts thereof as well as the hydrates of the salts, particularly the physiologically acceptable salts thereof with inorganic or organic acids or bases.

A thirty-third embodiment of the present invention comprises the compounds of general formula Ia

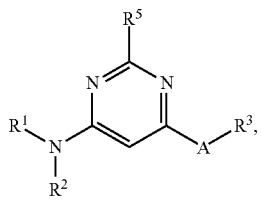

(Ia)

wherein

A denotes —NH— or —O—, $R^1$ and $R^2$ together with the nitrogen atom to which they are attached denote a group selected from

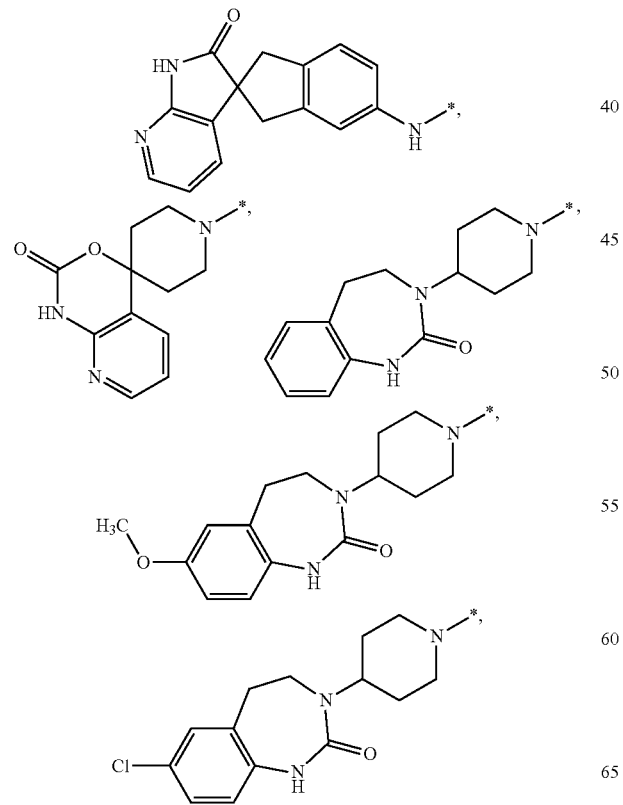

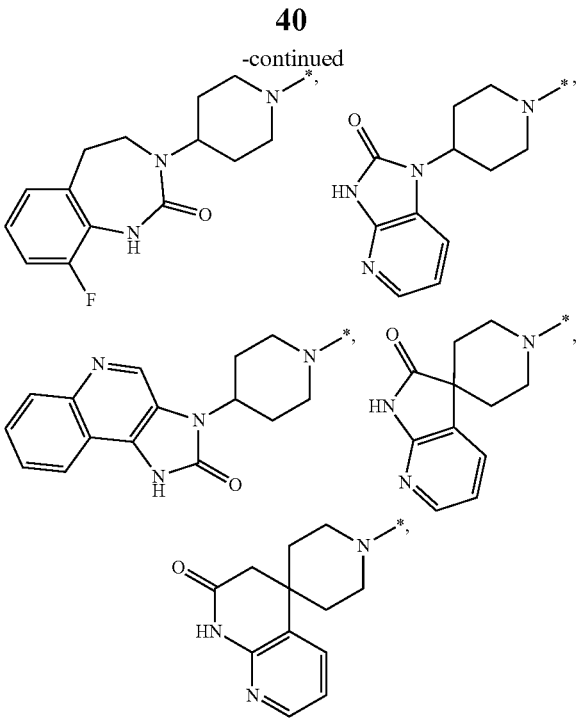

$R^3$ denotes a group of general formulae Va, Vb or Vc

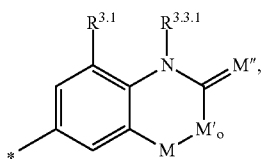
(Va)

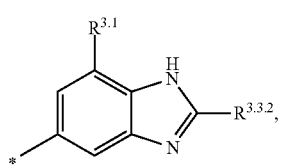
(Vb)

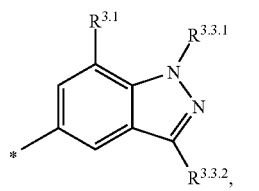
(Vc)

M denotes $CH_2$, NH, O, S,

M' denotes $CH_2$, $C(R^{3.2.2})_2$,

M" denotes O or S, $R^{31}$ denotes (a) H, (b) halogen, (c) $C_{1-3}$-alkyl, $C_{1-3}$-alkyl-O—, (d) a $C_{1-3}$-alkyl- or $C_{1-3}$-alkyl-O— group wherein each methylene group is substituted by up to two fluorine atoms and each methyl group is substituted by up to three fluorine atoms, $R^{3.2.2}$ independently of one another denote
 (a) H or
 (b) $C_{1-3}$-alkyl,
$R^{3.3.1}$ denotes H,
$R^{3.3.2}$ denotes
 (a) H,
 (b) $R^{3.3.2.1}$—$C_{1-3}$-alkylene,
 (c) $C_{3-6}$-cycloalkyl,
 (d) $NH_2$, $C_{1-4}$-alkyl-NH—, $(C_{1-4}$-alkyl$)_2$N—, —NH(CN),
$R^{3.3.2.1}$ denotes
 (a) H,
 (b) $C_{3-6}$-cycloalkyl, wherein a $CH_2$ group may be replaced by an oxygen atom,
 (c) CN, $CF_3$, $NH_2$, $C_{1-4}$-alkyl-NH—, $(C_{1-4}$-alkyl$)_2$N—,
 (d) OH, —O—$C_{1-3}$-alkyl,
$R^5$ denotes H, Cl, $CH_3$, —O—$CH_3$ or cyclopropyl, and
o denotes one of the numbers 0 or 1,
the tautomers, the diastereomers, the enantiomers, the hydrates, the mixtures thereof and the salts thereof as well as the hydrates of the salts, particularly the physiologically acceptable salts thereof with inorganic or organic acids or bases.

A thirty-fourth embodiment of the present invention comprises the compounds of general formula Ia

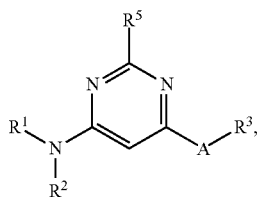

(Ia)

wherein
A denotes —NH— or —O—,
$R^1$ and $R^2$ together with the nitrogen atom to which they are attached denote a group selected from

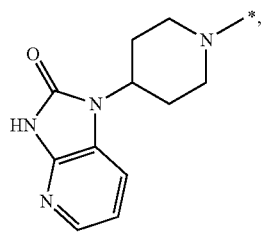

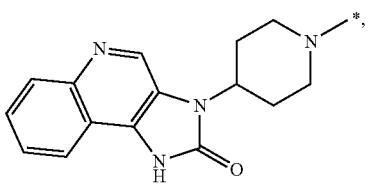

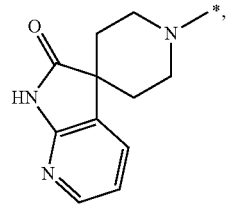

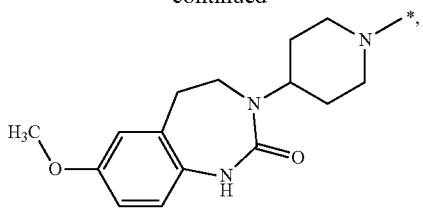

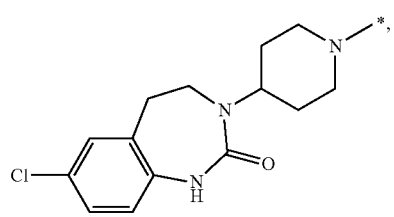

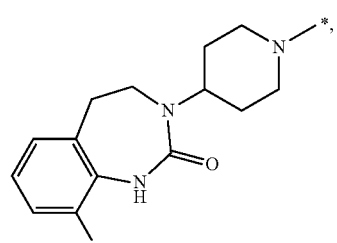

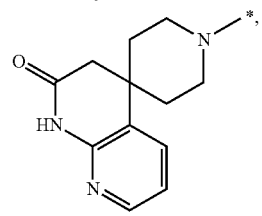

$R^3$ denotes a group selected from

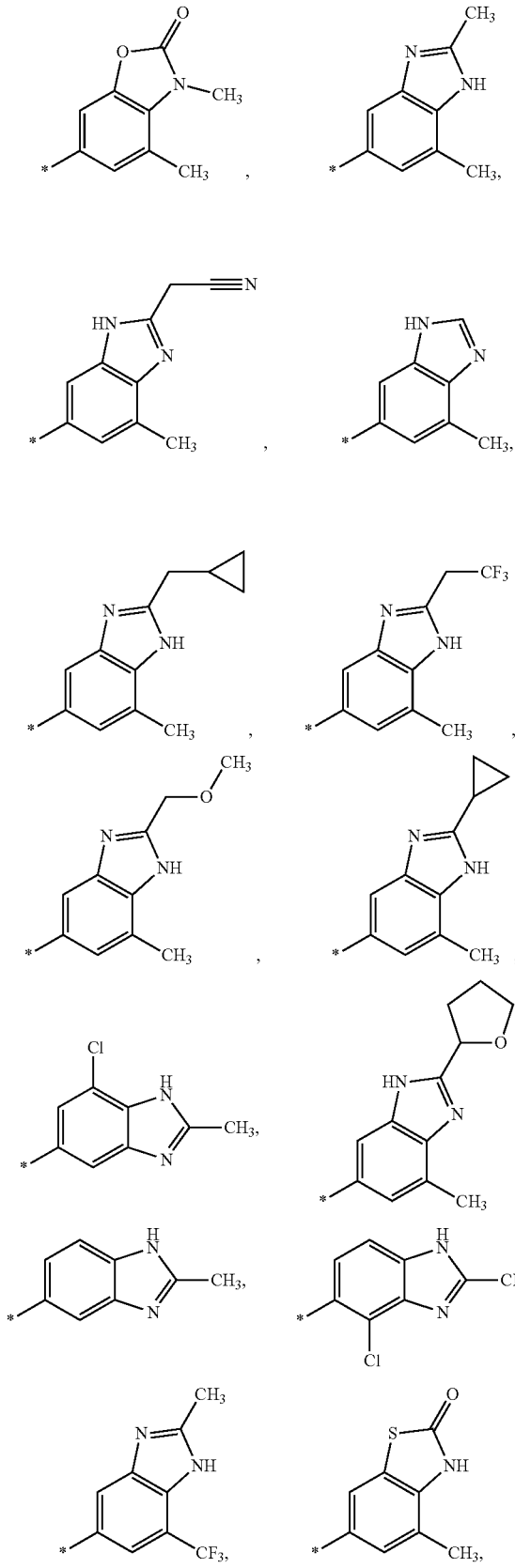

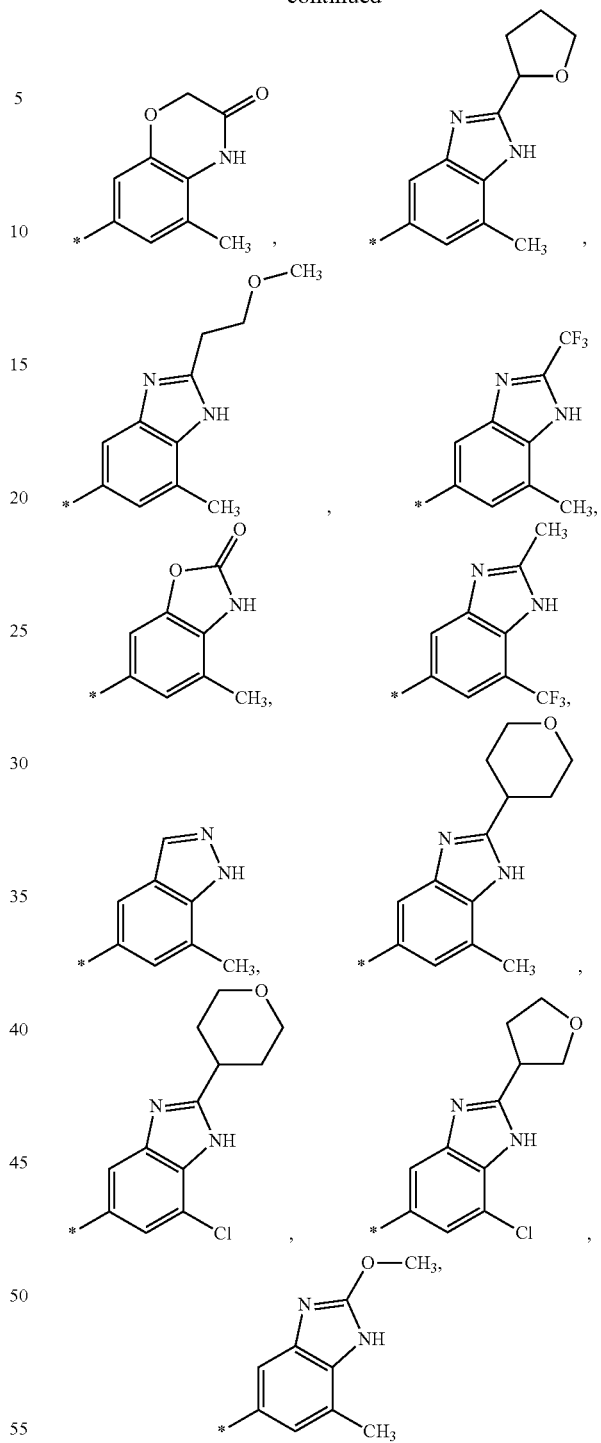

$R^5$ denotes H, Cl, $CH_3$, $CF_3$, —O—$CH_3$ or cyclopropyl, the tautomers, the diastereomers, the enantiomers, the hydrates, the mixtures thereof and the salts thereof as well as the hydrates of the salts, particularly the physiologically acceptable salts thereof with inorganic or organic acids or bases.

The following compounds are mentioned as examples of most particularly preferred compounds of the above general formula I:

| No. | Structure |
|---|---|
| (1) | *chemical structure* |
| (2) | *chemical structure* |
| (3) | *chemical structure* |
| (4) | *chemical structure* |
| (5) | *chemical structure* |
| (6) | *chemical structure* |
| (7) | *chemical structure* |

-continued
| No. | Structure |
|---|---|
| (8) | 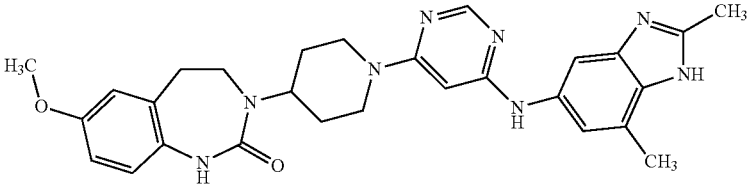 |
| (9) | 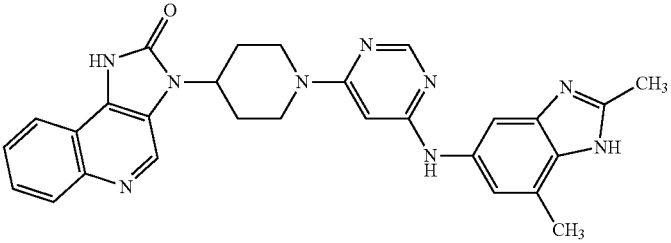 |
| (10) | 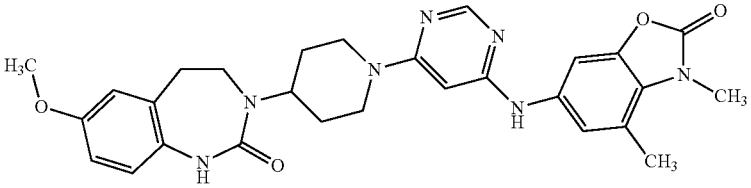 |
| (11) | 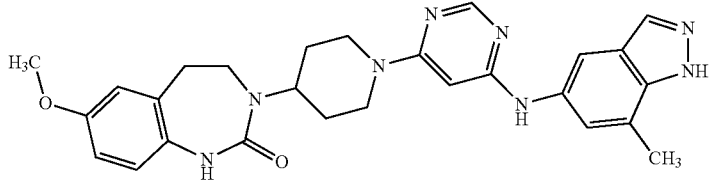 [SMILES: COc1ccc2c(c1)CCN(C1CCN(c3cc(Nc4cc(C)c5[nH]ncc5c4)ncn3)CC1)C(=O)N2] |
| (12) | 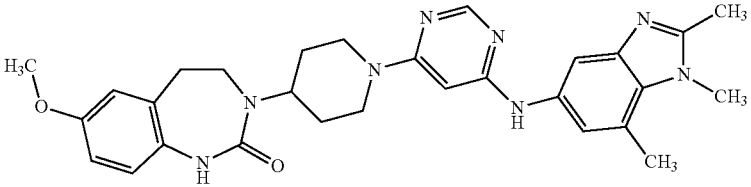 |
| (13) | 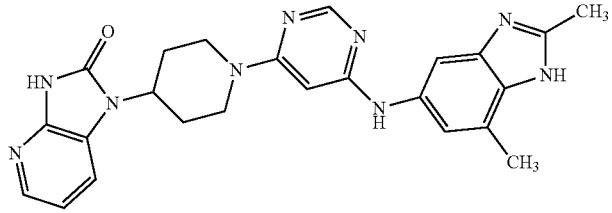 [SMILES: Cc1nc2cc(Nc3cc(N4CCC(n5c(=O)[nH]c6ncccc65)CC4)ncn3)cc(C)c2[nH]1] |
| (14) | 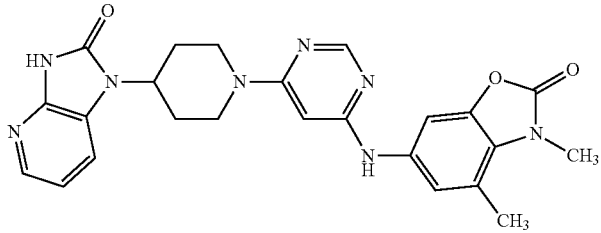 [SMILES: Cc1cc(Nc2cc(N3CCC(n4c(=O)[nH]c5ncccc54)CC3)ncn2)cc2oc(=O)n(C)c12] |

-continued
| No. | Structure |
|---|---|
| (15) | 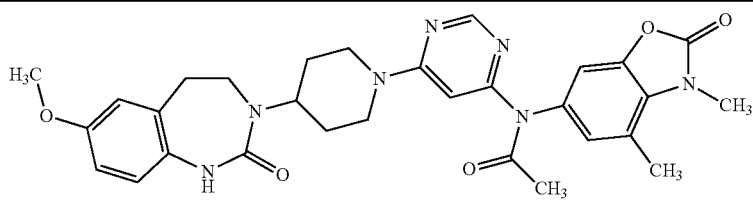 |
| (16) | 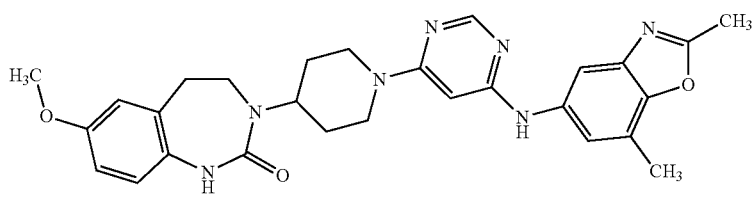 |
| (17) | 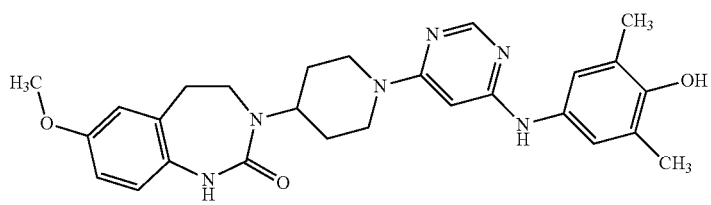 [SMILES: COc1ccc2c(c1)CCN(C1CCN(c3cc(Nc4cc(C)c(O)c(C)c4)ncn3)CC1)C(=O)N2] |
| (18) | 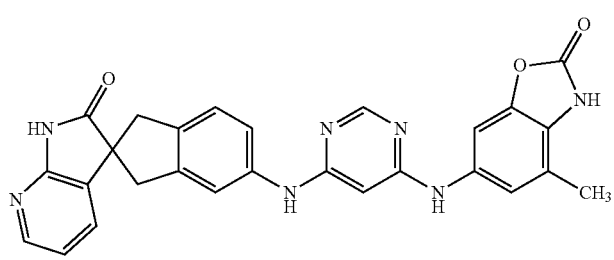 [SMILES: Cc1cc(Nc2cc(Nc3ccc4c(c3)CC3(C4)C(=O)Nc4ncccc43)ncn2)cc2oc(=O)[nH]c12] |
| (19) | 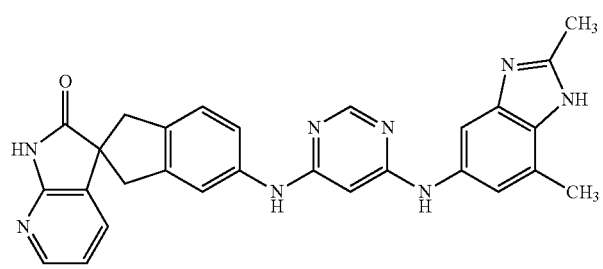 [SMILES: Cc1nc2cc(Nc3cc(Nc4ccc5c(c4)CC4(C5)C(=O)Nc5ncccc54)ncn3)cc(C)c2[nH]1] |
| (20) | 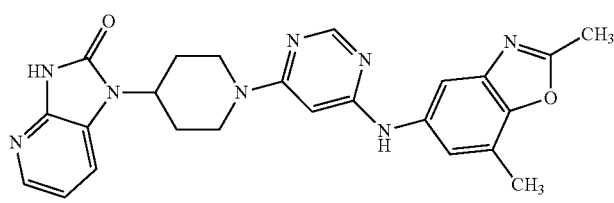 [SMILES: Cc1nc2cc(Nc3cc(N4CCC(n5c(=O)[nH]c6ncccc65)CC4)ncn3)cc(C)c2o1] |
| (21) | 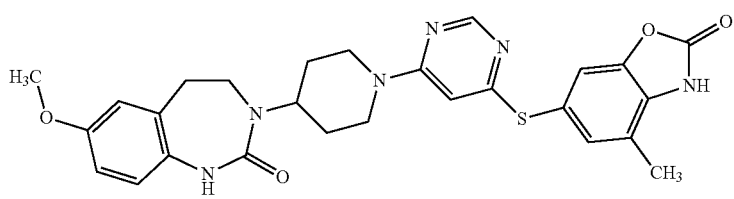 [SMILES: COc1ccc2c(c1)CCN(C1CCN(c3cc(Sc4cc(C)c5[nH]c(=O)oc5c4)ncn3)CC1)C(=O)N2] |

| No. | Structure |
|---|---|
| (22) | 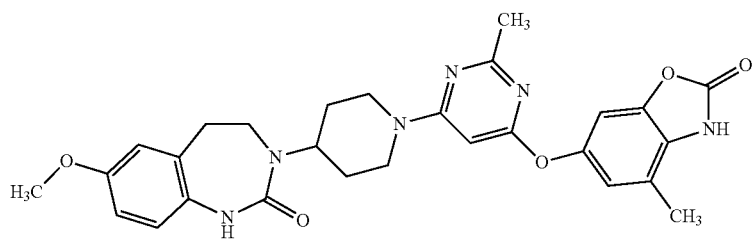 [SMILES: COc1ccc2c(c1)CCN(C1CCN(c3cc(Oc4cc(C)c5[nH]c(=O)oc5c4)nc(C)n3)CC1)C(=O)N2] |
| (23) | 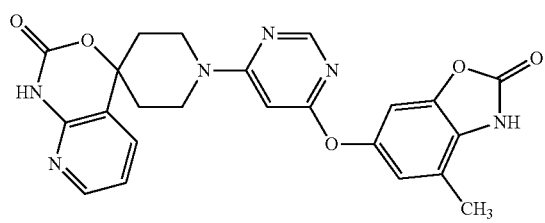 [SMILES: Cc1cc(Oc2cc(N3CCC4(CC3)OC(=O)Nc3ncccc34)ncn2)cc2oc(=O)[nH]c12] |
| (24) | 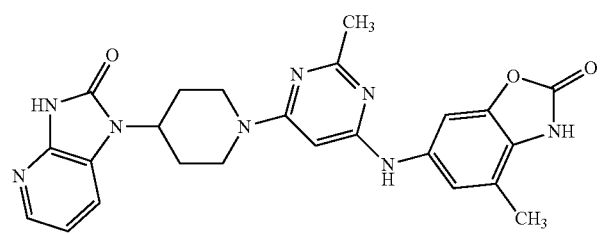 [SMILES: Cc1nc(Nc2cc(C)c3[nH]c(=O)oc3c2)cc(N2CCC(n3c(=O)[nH]c4ncccc43)CC2)n1] |
| (25) | 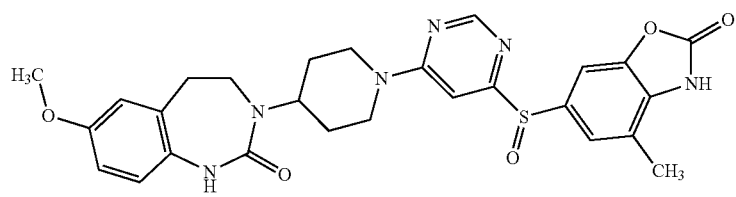 [SMILES: COc1ccc2c(c1)CCN(C1CCN(c3cc(S(=O)c4cc(C)c5[nH]c(=O)oc5c4)ncn3)CC1)C(=O)N2] |
| (26) | 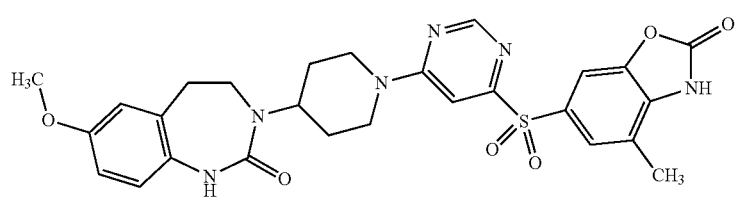 [SMILES: COc1ccc2c(c1)CCN(C1CCN(c3cc(S(=O)(=O)c4cc(C)c5[nH]c(=O)oc5c4)ncn3)CC1)C(=O)N2] |
| (27) | 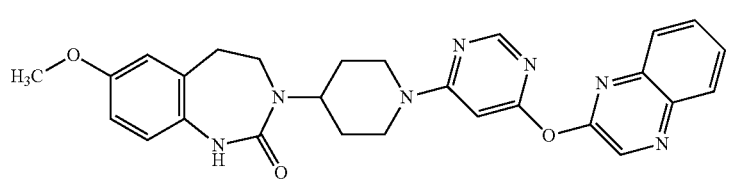 [SMILES: COc1ccc2c(c1)CCN(C1CCN(c3cc(Oc4cnc5ccccc5n4)ncn3)CC1)C(=O)N2] |
| (28) | 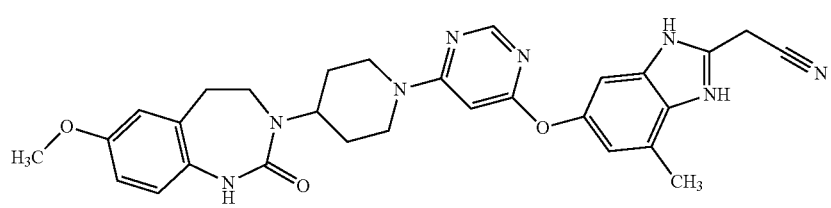 [SMILES: COc1ccc2c(c1)CCN(C1CCN(c3cc(Oc4cc(C)c5nc(CC#N)[nH]c5c4)ncn3)CC1)C(=O)N2] |

| No. | Structure |
|---|---|
| (29) | 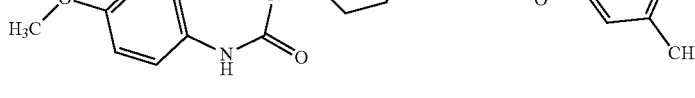 |
| (30) | 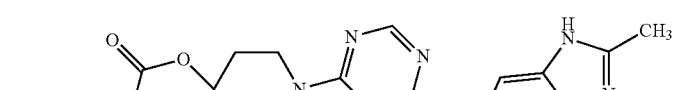 |
| (31) | 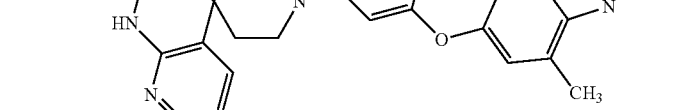 |
| (32) | 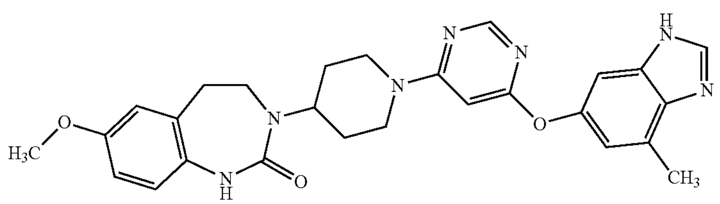 [SMILES: COc1ccc2c(c1)CCN(C1CCN(c3cc(Oc4cc(C)c5nc[nH]c5c4)ncn3)CC1)C(=O)N2] |
| (33) | 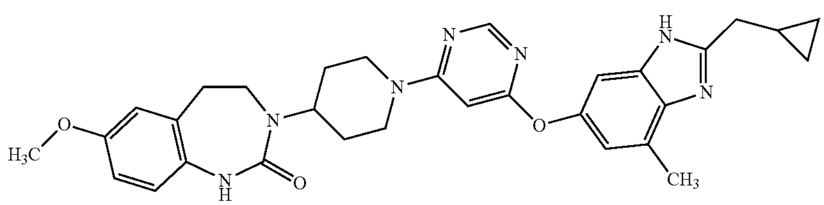 [SMILES: COc1ccc2c(c1)CCN(C1CCN(c3cc(Oc4cc(C)c5nc(CC6CC6)[nH]c5c4)ncn3)CC1)C(=O)N2] |
| (34) | 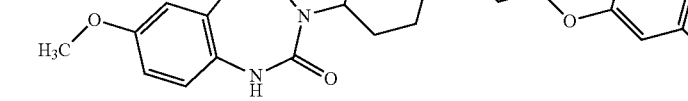 |
| (35) | 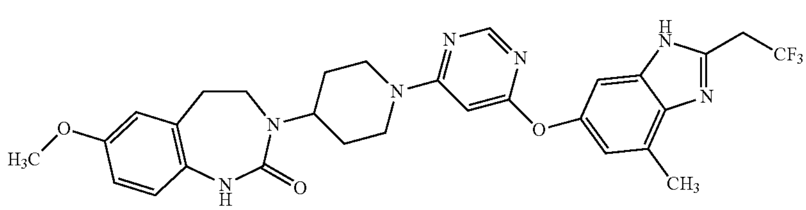 [SMILES: COc1ccc2c(c1)CCN(C1CCN(c3cc(Oc4cc(C)c5nc(CC(F)(F)F)[nH]c5c4)ncn3)CC1)C(=O)N2] |

| No. | Structure |
|---|---|
| (36) | 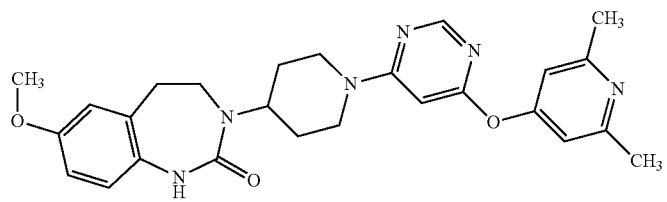 [SMILES: COc1ccc2c(c1)CCN(C1CCN(c3cc(Oc4cc(C)nc(C)c4)ncn3)CC1)C(=O)N2] |
| (37) | 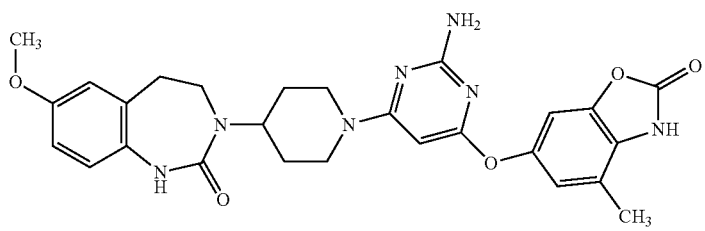 [SMILES: COc1ccc2c(c1)CCN(C1CCN(c3cc(Oc4cc(C)c5[nH]c(=O)oc5c4)nc(N)n3)CC1)C(=O)N2] |
| (38) | 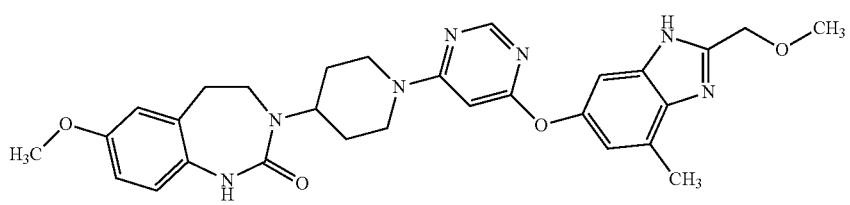 |
| (39) | 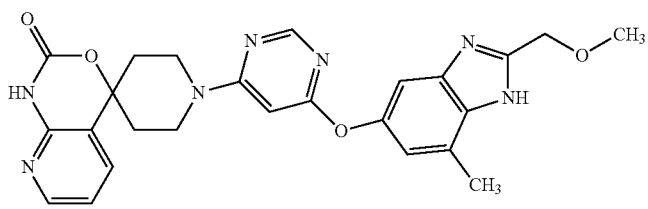 [SMILES: COCc1nc2cc(Oc3cc(N4CCC5(CC4)OC(=O)Nc4ncccc45)ncn3)cc(C)c2[nH]1] |
| (40) | 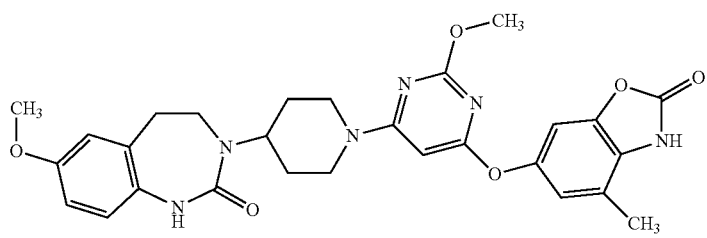 [SMILES: COc1ccc2c(c1)CCN(C1CCN(c3cc(Oc4cc(C)c5[nH]c(=O)oc5c4)nc(OC)n3)CC1)C(=O)N2] |
| (41) | 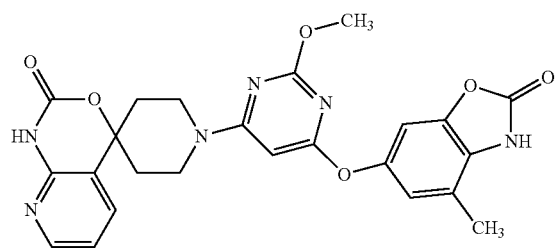 [SMILES: COc1nc(Oc2cc(C)c3[nH]c(=O)oc3c2)cc(N2CCC3(CC2)OC(=O)Nc2ncccc23)n1] |
| (42) | 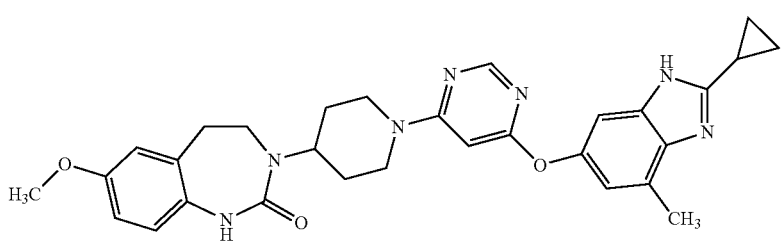 [SMILES: COc1ccc2c(c1)CCN(C1CCN(c3cc(Oc4cc(C)c5nc(C6CC6)[nH]c5c4)ncn3)CC1)C(=O)N2] |

-continued
| No. | Structure |
|---|---|
| (43) | 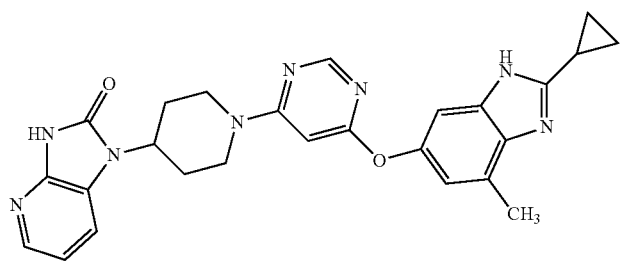 [SMILES: Cc1cc(Oc2cc(N3CCC(n4c(=O)[nH]c5ncccc54)CC3)ncn2)cc2[nH]c(C3CC3)nc12] |
| (44) | 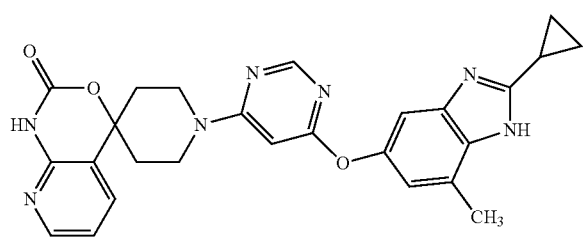 [SMILES: Cc1cc(Oc2cc(N3CCC4(CC3)OC(=O)Nc3ncccc34)ncn2)cc2nc(C3CC3)[nH]c12] |
| (45) | 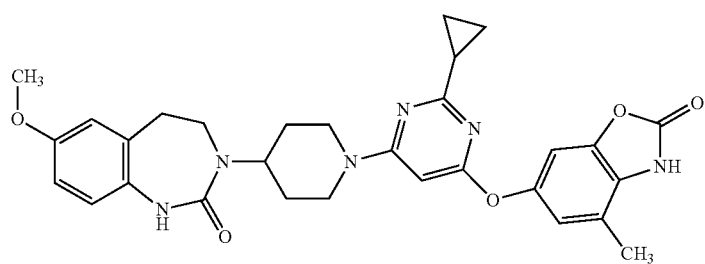 [SMILES: COc1ccc2c(c1)CCN(C1CCN(c3cc(Oc4cc(C)c5[nH]c(=O)oc5c4)nc(C4CC4)n3)CC1)C(=O)N2] |
| (46) | 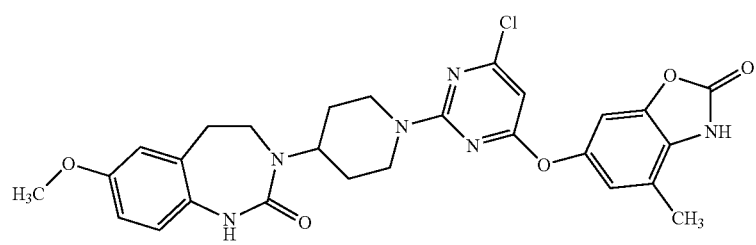 [SMILES: COc1ccc2c(c1)CCN(C1CCN(c3nc(Cl)cc(Oc4cc(C)c5[nH]c(=O)oc5c4)n3)CC1)C(=O)N2] |
| (47) | 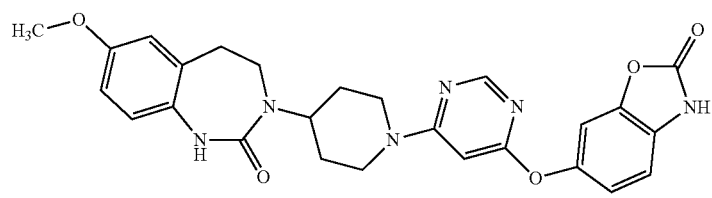 [SMILES: COc1ccc2c(c1)CCN(C1CCN(c3cc(Oc4ccc5[nH]c(=O)oc5c4)ncn3)CC1)C(=O)N2] |
| (48) | 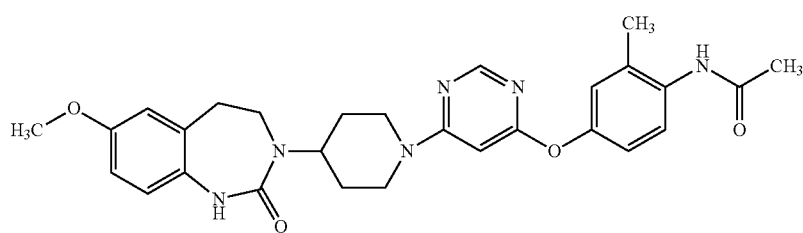 [SMILES: COc1ccc2c(c1)CCN(C1CCN(c3cc(Oc4ccc(NC(C)=O)c(C)c4)ncn3)CC1)C(=O)N2] |

-continued
| No. | Structure |
|---|---|
| (49) | 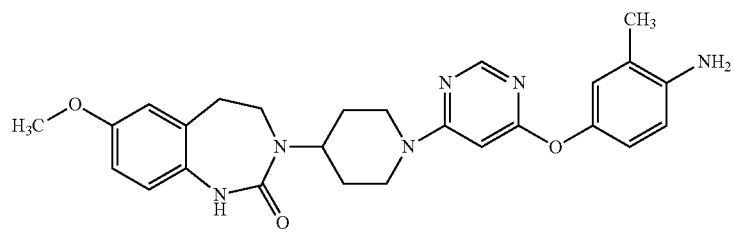 [SMILES: COc1ccc2c(c1)CCN(C1CCN(c3cc(Oc4ccc(N)c(C)c4)ncn3)CC1)C(=O)N2] |
| (50) | 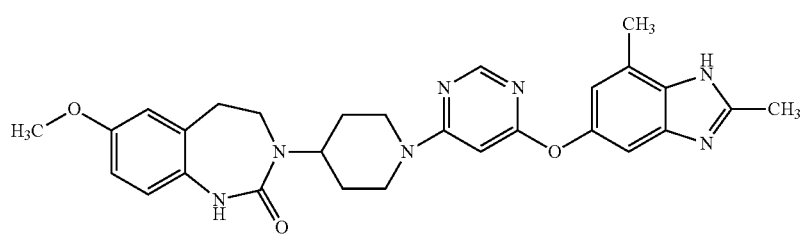 |
| (51) | 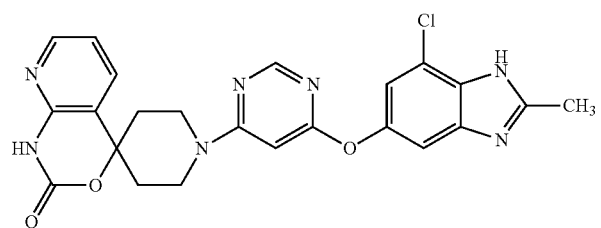 [SMILES: Cc1nc2cc(Oc3cc(N4CCC5(CC4)OC(=O)Nc4ncccc45)ncn3)cc(Cl)c2[nH]1] |
| (52) | 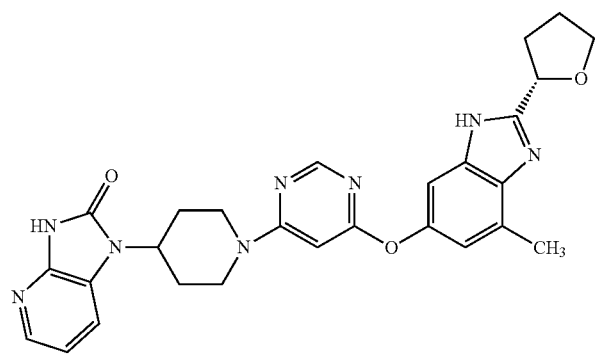 [SMILES: Cc1cc(Oc2cc(N3CCC(n4c(=O)[nH]c5ncccc54)CC3)ncn2)cc2[nH]c([C@@H]3CCCO3)nc12] |
| (53) | 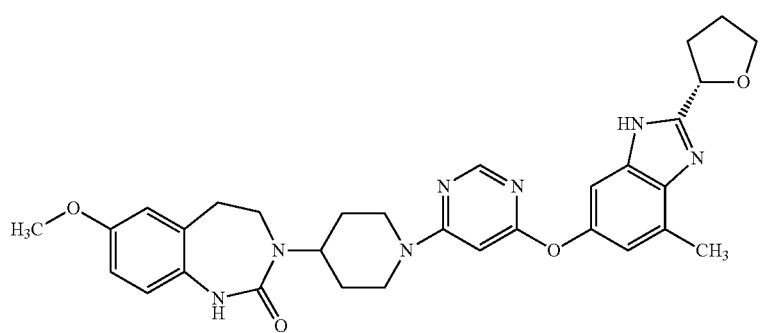 [SMILES: COc1ccc2c(c1)CCN(C1CCN(c3cc(Oc4cc(C)c5nc([C@@H]6CCCO6)[nH]c5c4)ncn3)CC1)C(=O)N2] |

-continued
| No. | Structure |
|---|---|
| (54) | 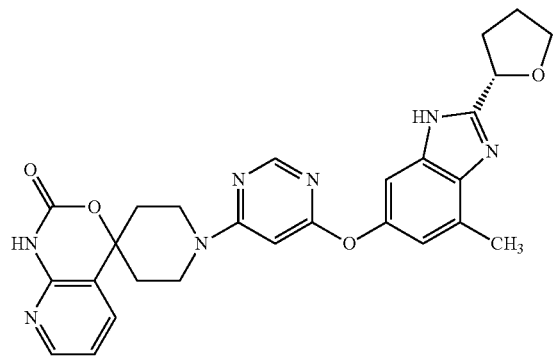 [SMILES: Cc1cc(Oc2cc(N3CCC4(CC3)OC(=O)Nc3ncccc34)ncn2)cc2[nH]c([C@@H]3CCCO3)nc12] |
| (55) | 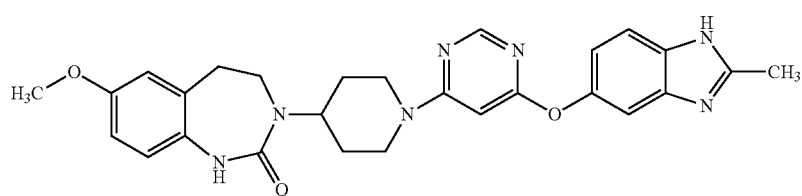 |
| (56) | 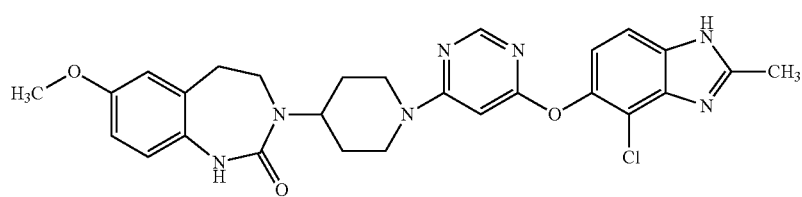 |
| (57) | 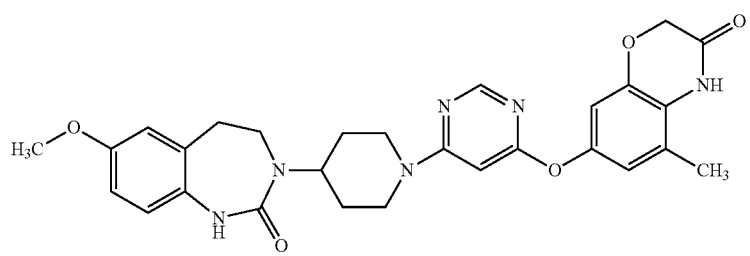 [SMILES: COc1ccc2c(c1)CCN(C1CCN(c3cc(Oc4cc(C)c5c(c4)OCC(=O)N5)ncn3)CC1)C(=O)N2] |
| (58) | 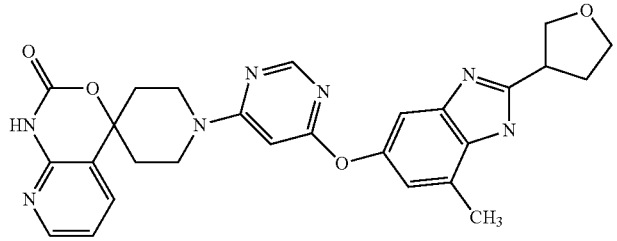 [SMILES: Cc1cc(Oc2cc(N3CCC4(CC3)OC(=O)Nc3ncccc34)ncn2)cc2nc(C3CCOC3)[nH]c12] |
| (59) | 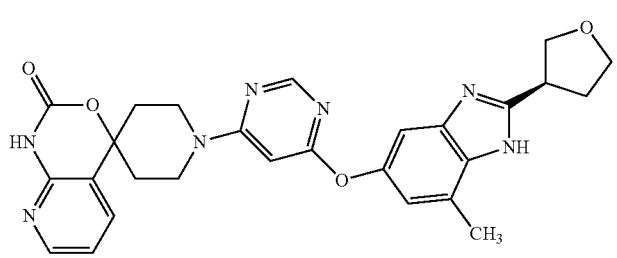 [SMILES: Cc1cc(Oc2cc(N3CCC4(CC3)OC(=O)Nc3ncccc34)ncn2)cc2nc([C@@H]3CCOC3)[nH]c12] |

-continued
| No. | Structure |
|---|---|
| (60) | 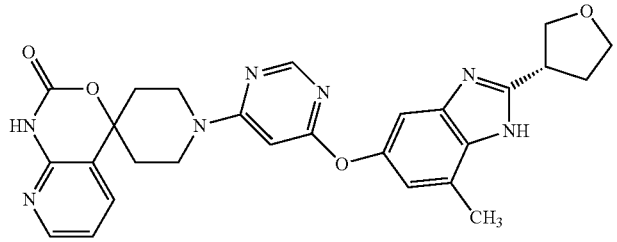 [SMILES: Cc1cc(Oc2cc(N3CCC4(CC3)OC(=O)Nc3ncccc34)ncn2)cc2nc([C@H]3CCOC3)[nH]c12] |
| (61) | 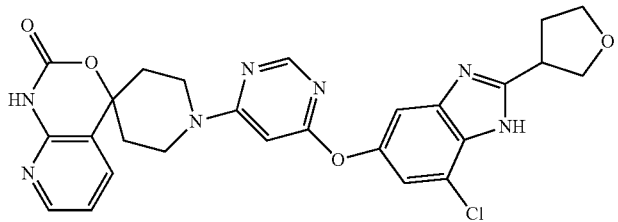 [SMILES: O=C1Nc2ncccc2C2(CCN(c3cc(Oc4cc(Cl)c5[nH]c(C6CCOC6)nc5c4)ncn3)CC2)O1] |
| (62) | 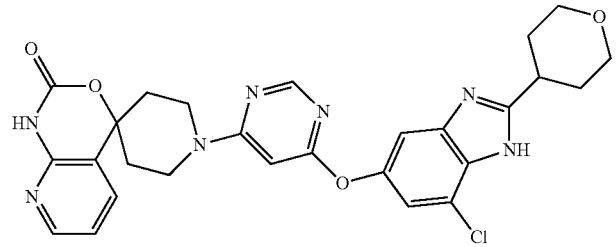 [SMILES: O=C1Nc2ncccc2C2(CCN(c3cc(Oc4cc(Cl)c5[nH]c(C6CCOCC6)nc5c4)ncn3)CC2)O1] |
| (63) | 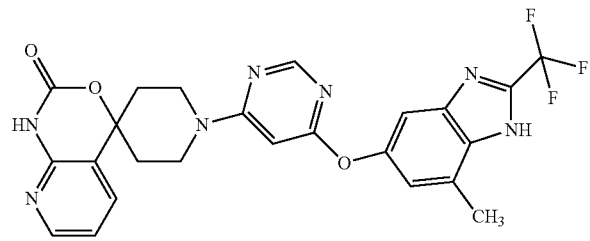 [SMILES: Cc1cc(Oc2cc(N3CCC4(CC3)OC(=O)Nc3ncccc34)ncn2)cc2nc(C(F)(F)F)[nH]c12] |
| (64) | 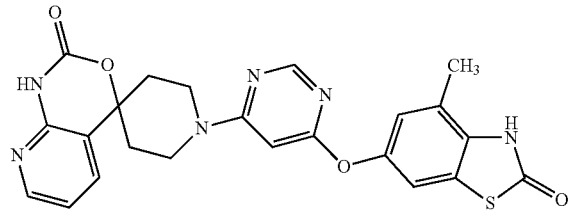 [SMILES: Cc1cc(Oc2cc(N3CCC4(CC3)OC(=O)Nc3ncccc34)ncn2)cc2sc(=O)[nH]c12] |
| (65) | 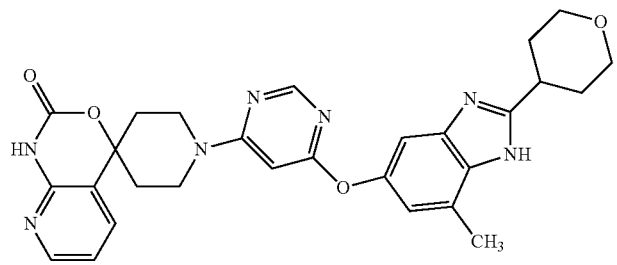 [SMILES: Cc1cc(Oc2cc(N3CCC4(CC3)OC(=O)Nc3ncccc34)ncn2)cc2nc(C3CCOCC3)[nH]c12] |

| No. | Structure |
|---|---|
| (66) | 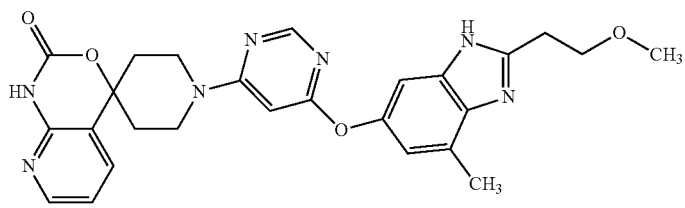 [SMILES: COCCc1nc2c(C)cc(Oc3cc(N4CCC5(CC4)OC(=O)Nc4ncccc45)ncn3)cc2[nH]1] |
| (67) | 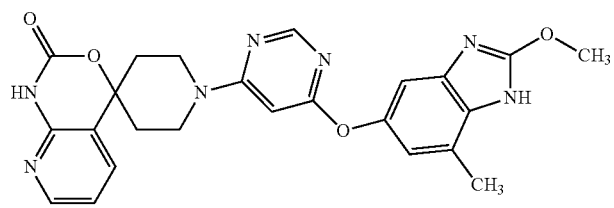 [SMILES: COc1nc2cc(Oc3cc(N4CCC5(CC4)OC(=O)Nc4ncccc45)ncn3)cc(C)c2[nH]1] |
| (68) | 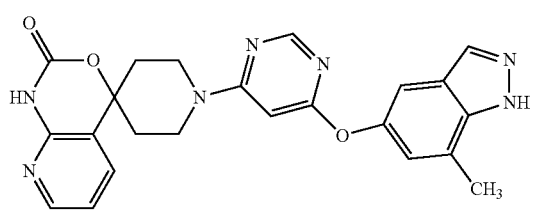 |
| (69) | 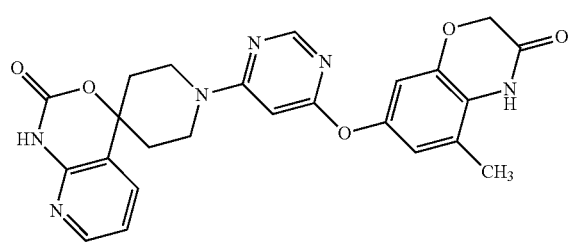 [SMILES: Cc1cc(Oc2cc(N3CCC4(CC3)OC(=O)Nc3ncccc34)ncn2)cc2c1NC(=O)CO2] |
| (70) | 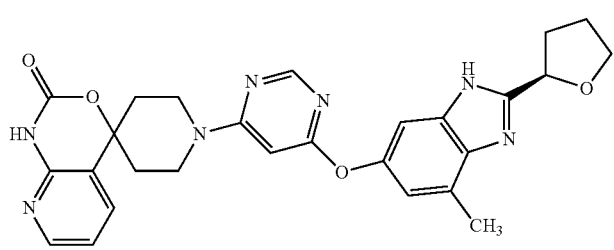 [SMILES: Cc1cc(Oc2cc(N3CCC4(CC3)OC(=O)Nc3ncccc34)ncn2)cc2[nH]c([C@H]3CCCO3)nc12] |
| (71) | 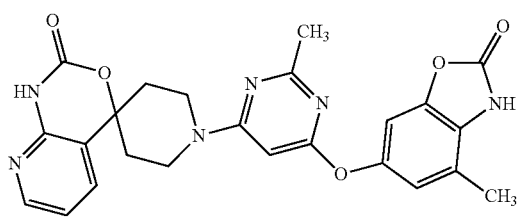 [SMILES: Cc1nc(Oc2cc(C)c3[nH]c(=O)oc3c2)cc(N2CCC3(CC2)OC(=O)Nc2ncccc23)n1] |
| (72) | 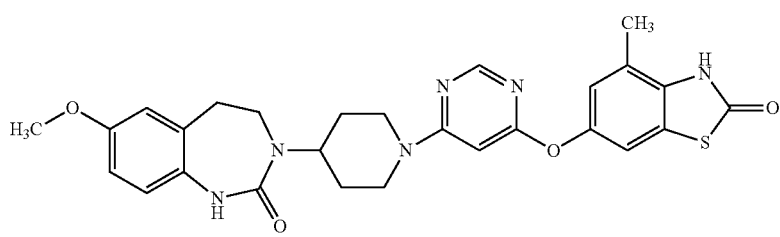 [SMILES: COc1ccc2c(c1)CCN(C1CCN(c3cc(Oc4cc(C)c5[nH]c(=O)sc5c4)ncn3)CC1)C(=O)N2] |

-continued
| No. | Structure |
|---|---|
| (73) | 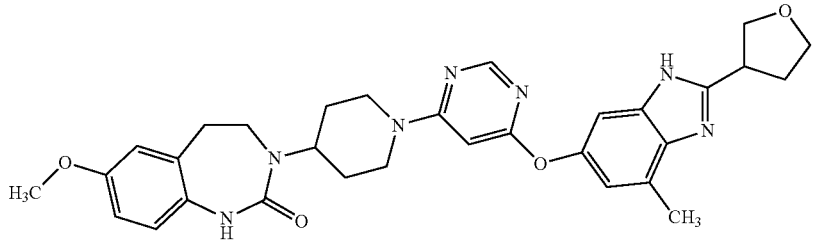 [SMILES: COc1ccc2c(c1)CCN(C1CCN(c3cc(Oc4cc(C)c5nc(C6CCOC6)[nH]c5c4)ncn3)CC1)C(=O)N2] |
| (74) | 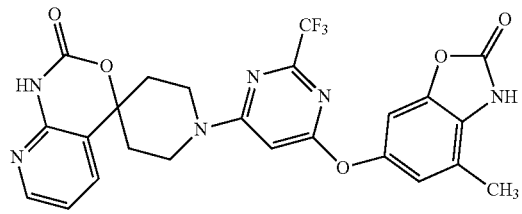 [SMILES: Cc1cc(Oc2cc(N3CCC4(CC3)OC(=O)Nc3ncccc34)nc(C(F)(F)F)n2)cc2oc(=O)[nH]c12] |
| (75) | 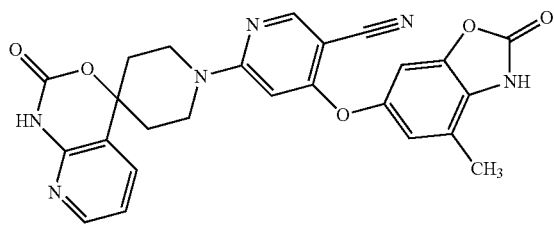 [SMILES: Cc1cc(Oc2cc(N3CCC4(CC3)OC(=O)Nc3ncccc34)ncc2C#N)cc2oc(=O)[nH]c12] |
| (76) | 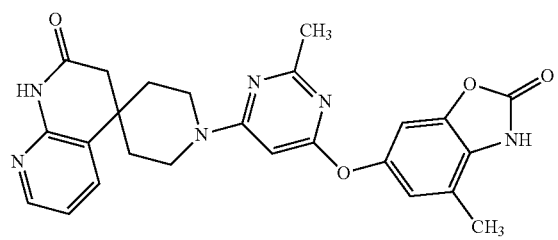 [SMILES: Cc1nc(Oc2cc(C)c3[nH]c(=O)oc3c2)cc(N2CCC3(CC2)CC(=O)Nc2ncccc23)n1] |
| (77) | 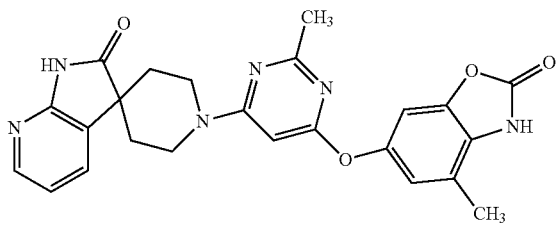 [SMILES: Cc1nc(Oc2cc(C)c3[nH]c(=O)oc3c2)cc(N2CCC3(CC2)C(=O)Nc2ncccc23)n1] |
| (78) | 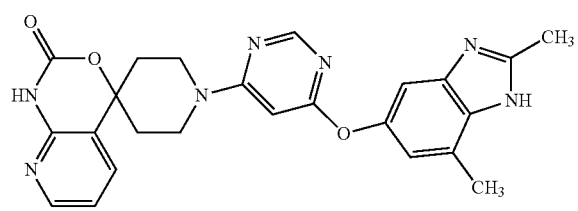 [SMILES: Cc1nc2cc(Oc3cc(N4CCC5(CC4)OC(=O)Nc4ncccc45)ncn3)cc(C)c2[nH]1] |

| No. | Structure |
|---|---|
| (79) | ![structure 79] |
| (80) | ![structure 80] | the tautomers, the diastereomers, the enantiomers, the hydrates, the mixtures thereof and the salts thereof as well as the hydrates of the salts, particularly the physiologically acceptable salts thereof with inorganic or organic acids or bases.

TERMS AND DEFINITIONS USED

The present specification of the invention is to be interpreted in accordance with the conventions and rules of chemical bonds.

The compounds included in this invention are those that are also chemically stable.

Unless otherwise stated, all the substituents are independent of one another. If for example there are a plurality of $C_{1-4}$-alkyl groups as substituents in one group, in the case of three $C_{1-4}$-alkyl substituents, independently of one another, one may represent methyl, one ethyl and one n-propyl.

Within the scope of this application, in the definition of possible substituents, these may also be represented in the form of a structural formula. If present, an asterisk (*) in the structural formula of the substituent is to be understood as being the linking point to the rest of the molecule. For example a phenyl group is shown as follows:

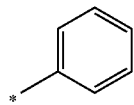

Moreover, the atom of the substituent that follows the linking point is understood as being the atom at position number 1.

The subject-matter of this invention also includes the compounds according to the invention, including the salts thereof, wherein one or more hydrogen atoms, for example one, two, three, four or five hydrogen atoms, are replaced by deuterium.

By the term "$C_{1-3}$-alkyl" (including those which are a part of other groups) are meant branched and unbranched alkyl groups with 1 to 3 carbon atoms, by the term "$C_{1-4}$-alkyl" are meant branched and unbranched alkyl groups with 1 to 4 carbon atoms and by the term "$C_{1-6}$-alkyl" are meant branched and unbranched alkyl groups with 1 to 6 carbon atoms. Examples include: methyl, ethyl, n-propyl, iso-propyl, n-butyl, iso-butyl, sec-butyl, tert-butyl, pentyl, neopentyl or n-hexyl. The abbreviations may optionally also be used for the above-mentioned groups Me, Et, n-Pr, i-Pr, n-Bu, i-Bu, t-Bu, etc. Unless stated otherwise, the definitions propyl and butyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are a part of other groups) are meant branched and unbranched alkylene groups with 1 to 6 carbon atoms, by the term "$C_{1-4}$-alkylene" are meant branched and unbranched alkylene groups with 1 to 4 carbon atoms, by the term "$C_{1-3}$-alkylene" are meant branched and unbranched alkylene groups with 1 to 3 carbon atoms, and by the term "$C_{0-3}$-alkylene" are meant branched and unbranched alkylene groups with 0 to 3 carbon atoms. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definition propylene includes all the possible isomeric forms of the groups in question with the same number of carbons. Thus, for example, propyl also includes 1-methylethylene and butylene includes 1-methylpropylene, 1,1-dimethylethylene, 1,2-dimethylethylene.

The definition for $C_0$-alkylene denotes a bond.

By the term "$C_{2-6}$-alkenyl" (including those which are a part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they comprise at least one double bond. Alkenyl groups with 2 to 4 carbon atoms are preferred. Examples include: ethenyl or vinyl, propenyl, butenyl, pentenyl, or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkynyl" (including those which are a part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they comprise at least one triple bond. Examples include: ethynyl, propynyl, butynyl, pentynyl, or hexynyl. Unless stated otherwise, the definitions propynyl, butynyl, pentynyl and hexynyl include all the possible isomeric forms of the groups in question. Thus, for example propynyl includes 1-propynyl and 2-propynyl, butynyl includes 1-, 2- and 3-butynyl, 1-methyl-1-propynyl, 1-methyl-2-propynyl etc.

By the term "$C_{3-6}$-cycloalkyl" (including those which are a part of other groups) are meant cyclic alkyl groups with 3 to 6 carbon atoms and by the term "$C_{5-6}$-cycloalkyl" are meant cyclic alkyl groups with 5 to 6 carbon atoms. Examples include: cyclopropyl, cyclobutyl, cyclopentyl or cyclohexyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{5-6}$-cycloalkenyl" (including those which are a part of other groups) are meant cyclic alkenyl groups with 5 or 6 carbon atoms, which contain an unsaturated bond. Examples include: cyclopentenyl or cyclohexenyl. Unless otherwise stated, the cyclic alkenyl groups may be substituted by one or more groups selected from among methyl, ethyl, iso-propyl, tert-butyl, hydroxy, fluorine, chlorine, bromine and iodine.

By the term "heterocyclyl" or "heterocyclic group" are meant, unless otherwise described in the definitions, stable 5-, 6- or 7-membered monocyclic or 8-, 9-, 10- or 11-membered bicyclic heterocyclic ring systems, which do not form an aromatic ring system in at least one ring and in addition to carbon atoms may carry one to four heteroatoms selected from among nitrogen, oxygen and sulphur. The two nitrogen atoms and also sulphur atoms may optionally be oxidised and nitrogen atoms may be quaternised. The heterocyclic ring may contain one or two carbonyl, thiocarbonyl or cyanimino groups adjacent to a nitrogen atom. The heterocycles mentioned previously may be linked to the rest of the molecule via a carbon atom or a nitrogen atom.

Unless otherwise stated, the heterocycles may be substituted by one or more groups selected from among:
(a) OH, $NO_2$, CN, $OCF_3$, $OCHF_2$, $OCH_2F$, $NH_2$,
(b) halogen, preferably fluorine or chlorine,
(c) $C_{1-6}$-alkyl, preferably $C_{1-3}$-alkyl, particularly preferably ethyl, methyl, iso-propyl or tert-butyl,
(d) —$SO_2$—O—$C_{1-3}$-alkyl, preferably —O-methyl,
(e) —O—$C_{1-3}$-alkyl, preferably —O-methyl or —O-ethyl,
(f) COOH, COO—$C_{1-3}$-alkyl, preferably CO—O-methyl or CO—O-ethyl, while the groups may be identical or different.

The following compounds are mentioned by way of example, but the invention is not restricted to them: azetidine, oxetane, thietane, thietane dioxide, tetrahydrofuran, dihydrofuran, dioxolane, imidazolidine, imidazoline, imidazolidinone, dihydroimidazolone, oxazoline, oxazolidine, oxazolidinone, pyrrolidinone, dihydropyrazole, pyrrolidine, pyrroline, morpholine, tetrahydropyridine, dihydropyran, tetrahydropyran, dioxane, piperazine, piperidine, piperazinone, piperidinone, pyran, thiomorpholine-S-oxide, thiomorpholine-S-dioxide, thiomorpholine, dihydroxazine, morpholinedione, morpholinethione, perhydrothiazinedioxide, ε-caprolactam, oxazepanone, diazepanone, thiazepanone, perhydroazepine, dihydroquinazolinone, dihydroindole, dihydroisoindole, benzoxazolone, benzimidazolone, chromanone, tetrahydroquinoline, tetrahydrobenzoxazole, tetrahydrobenzisoxazole, tetrahydrobenzothiophene, tetrahydrothieno-pyridine, tetrahydrobenzofuran, tetrahydrooxazolopyridine, tetrahydro-isoxazolopyridine.

The following heterocycles are preferred according to the invention:

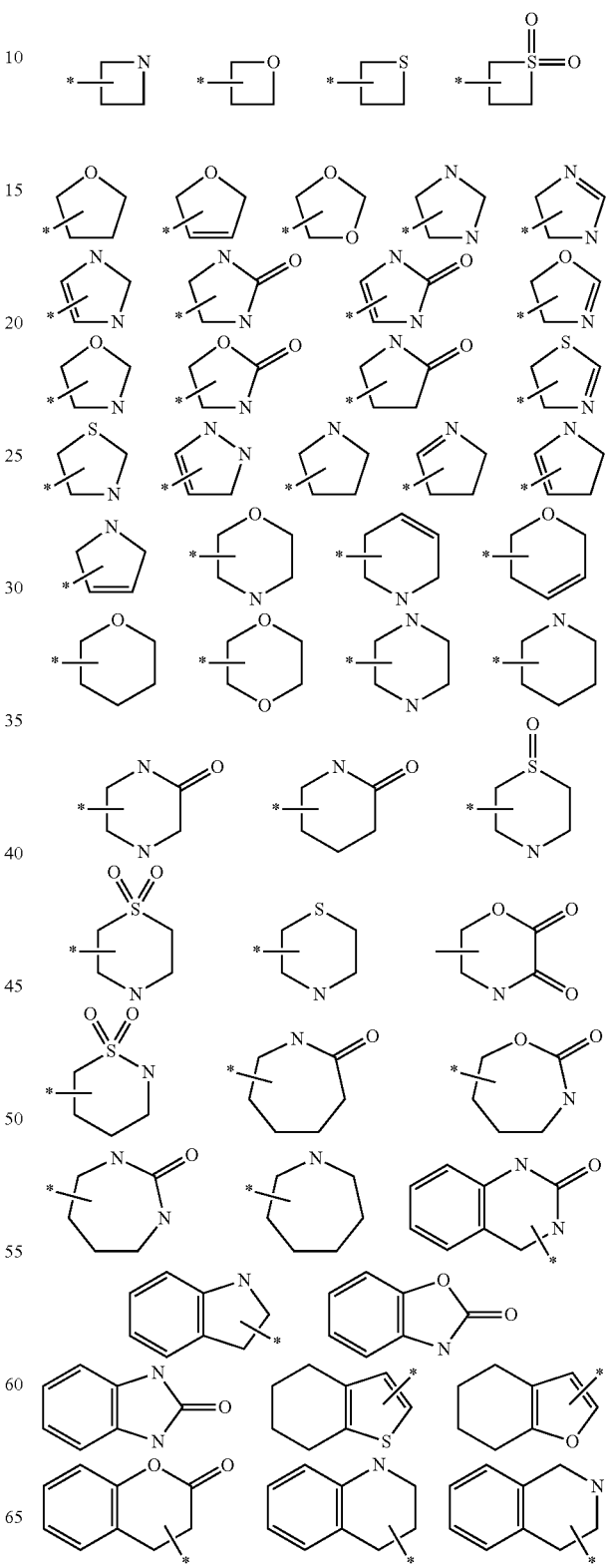

By the term "aryl" (including those which are a part of other groups) are meant monocyclic aromatic ring systems with 6 carbon atoms or bicyclic aromatic ring systems with 10 carbon atoms. Examples include phenyl, 1-naphthyl or 2-naphthyl; the preferred aryl group is phenyl.

Unless otherwise stated, the aromatic groups may be substituted by one or more groups selected from among:

(a) OH, NO$_2$, CN, OCF$_3$, OCHF$_2$, OCH$_2$F, NH$_2$, (b) halogen, preferably fluorine or chlorine, (c) C$_{1-6}$-alkyl, preferably C$_{1-3}$-alkyl, particularly preferably ethyl, methyl, iso-propyl or tert-butyl, (d) —SO$_2$—O—C$_{1-3}$-alkyl, preferably —O-methyl, (e) —O—C$_{1-3}$-alkyl, preferably —O-methyl or —O-ethyl, (f) COOH, CO—O—C$_{1-3}$-alkyl, preferably CO—O-methyl or CO—O-ethyl, while the groups may be identical or different.

By the term "heteroaryl" are meant stable five- or six-membered heterocyclic aromatic groups or 8- to 10-membered bicyclic heteroaryl rings that may contain in each ring one, two or three heteroatoms, selected from among oxygen, sulphur and nitrogen, and additionally sufficient conjugated double bonds to form an aromatic system. Examples of five- or six-membered heterocyclic aromatic groups are as follows, but the invention is not restricted to these:

furan, pyrrole, thiophene, pyrazole, imidazole, oxazole, thiazole, isothiazole, isoxazole, oxadiazole, triazole, tetrazole, furazan, thiadiazole, pyridine, pyrimidine, pyrazine, pyridazine, triazine.

The following five-membered heterocyclic aromatic groups are preferred according to the invention:

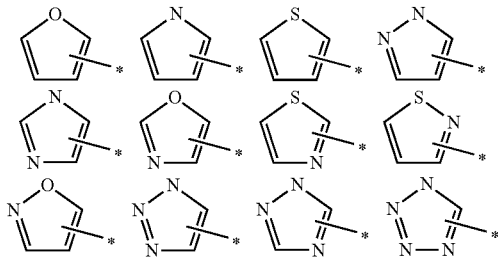

The following six-membered heterocyclic aromatic groups are preferred according to the invention:

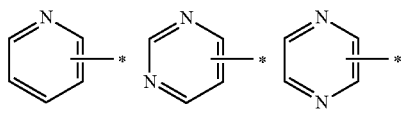

Examples of 9- or 10-membered bicyclic heteroaryl rings are as follows, but the invention is not restricted to these:

indole, isoindole, indazole, indolizine, benzofuran, benzothiophene, benzimidazole, benzoxazole, benzothiazole, benzotriazole, benzisoxazole, benzisothiazole, quinoline, isoquinoline, cinnoline, phthalazine, quinoxaline, quinazoline, pyrimidopyrimidine, pyridopyrazine, pyridopyridazine, pyrimidopyrimidine, pteridine, purine, quinolizine, benzoxazolecarbonitrile, quinoline, isoquinoline, quinolizine, pteridine, purine, quinolizine, benzoxazole-carbonitrile.

The following bicyclic heteroaryl rings are preferred according to this invention:

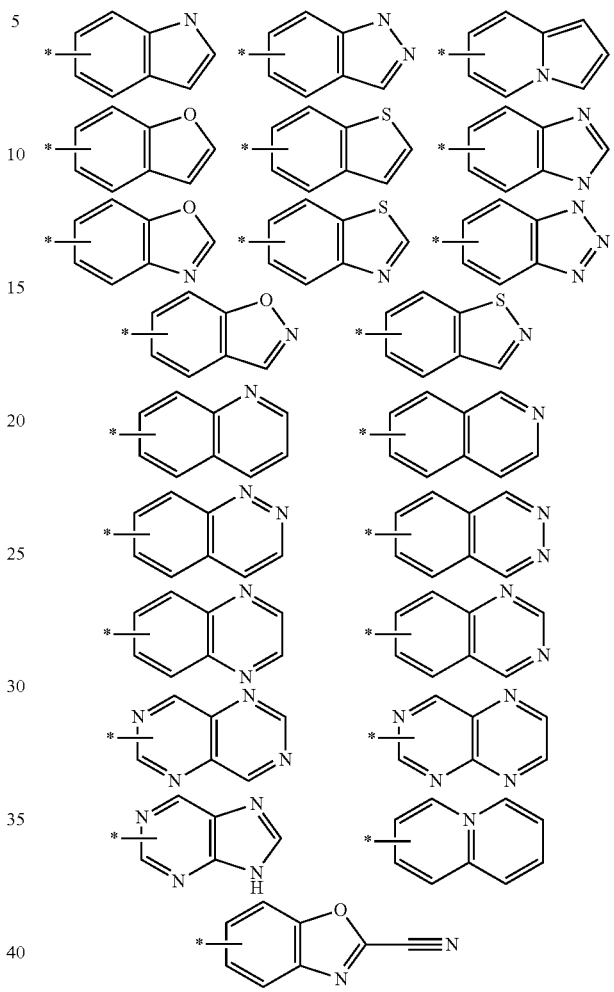

Unless otherwise stated, the heteroaryls previously mentioned may be substituted by one or more groups selected from among:

(a) OH, NO$_2$, CN, OCF$_3$, OCHF$_2$, OCH$_2$F, NH$_2$, (b) halogen, preferably fluorine or chlorine, (c) C$_{1-6}$-alkyl, preferably C$_{1-3}$-alkyl, particularly preferably ethyl, methyl, iso-propyl or tert-butyl, (d) —SO$_2$—O—C$_{1-3}$-alkyl, preferably —O-methyl, (e) —O—C$_{1-3}$-alkyl, preferably —O-methyl or —O-ethyl, (f) COOH, CO—O—C$_{1-3}$-alkyl, preferably CO—O-methyl or CO—O-ethyl, while the groups may be identical or different.

Bicyclic heteroaryl rings may preferably be substituted in the phenyl group.

By the term "halogen" are meant fluorine, chlorine, bromine or iodine atoms.

Compounds of general formula I may have acid groups, mainly carboxyl groups, and/or basic groups such as e.g. amino functions. Compounds of general formula I may therefore be present as internal salts, as salts with pharmaceutically useable inorganic acids such as for example hydrobromic acid, phosphoric acid, nitric acid, hydrochloric acid, sulphuric acid, methanesulphonic acid, ethanesulphonic acid, benzenesulphonic acid, p-toluenesulphonic acid or organic acids such as for example malic acid, succinic acid, acetic acid, fumaric acid, maleic acid, mandelic acid, lactic acid, tartaric acid, citric acid or as salts with pharmaceutically useable bases such as alkali or alkaline earth metal hydroxides, e.g. sodium hydroxide or potassium hydroxide, or carbonates, ammonia, zinc or ammonium hydroxides or organic amines such as e.g. diethylamine, triethylamine, ethanolamine, diethanolamine, triethanolamine, cyclohexylamine, dicyclohexylamine, inter alia.

The compounds according to the invention may be present as racemates, provided that they have only one chiral element, but may also be obtained as pure enantiomers, i.e. in the (R) or (S) form.

Compounds with a substituted carbon double bond may be present in both the E and Z form.

The following nitrogen-containing heteroaryls may be present in different tautomeric forms:

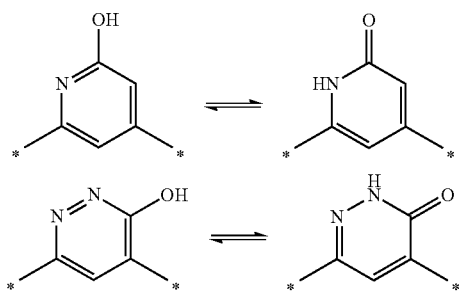

This means that the compound prepared in each case is not limited to one tautomeric form but encompasses all tautomeric forms.

However, the application also includes the individual diastereomeric pairs of antipodes or mixtures thereof, which are obtained if there is more than one chiral element in the compounds of general formula I, as well as the individual optically active enantiomers of which the above-mentioned racemates are made up.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids.

So-called prodrugs of compounds of general formula I are also encompassed by this invention. The term prodrug is used to denote any molecule that releases the active principle of general formula I in-vivo after administration to mammals. The prodrug may have little or no pharmacological activity per se, but releases the active principle of general formula I in-vivo after administration and this has the activity described. Prodrugs for compounds of general formula I may be prepared by modifying suitable functional groups in the compound of general formula I, as known to the skilled man in this field. (H. Bundgaard (Editor), Design of Prodrugs. (1986), Elsevier)

This invention also includes those metabolites that are derived from compounds of general formula I. By metabolites are meant, in this context, compounds that are formed in-vivo from the compound of general formula I after administration. Examples of metabolites include:

methyl groups of the compound of general formula I may be converted into the corresponding hydroxymethyl groups. (—$CH_3$→—$CH_2OH$)

alkoxy groups of the compound of general formula I may be converted into the corresponding hydroxyl groups. (—OR→—OH)

secondary amines of the compound of general formula I may be converted into the corresponding primary amines. (—$NR_1R_2$→—$NHR_1$ or —$NHR_2$)

nitrogen atoms of the compound of general formula I may be converted into the corresponding nitrogen oxides. (=N—→=$N^+$—(O)—)

METHODS OF PREPARATION

The invention further relates to a process for preparing the compounds of general formula I wherein the substituents A, U, V, X, Y, $R^1$, $R^2$ and $R^3$ are defined as mentioned hereinbefore.

Some methods of preparing the novel compounds of general formula I

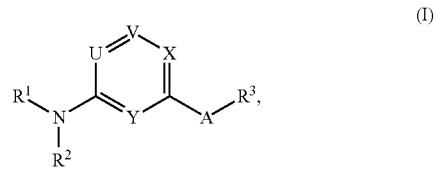

(I)

wherein A, U, V, X, Y, $R^1$, $R^2$ and $R^3$ are defined as mentioned hereinbefore, are shown in the following synthesis schemes and Examples.

In some cases the order of carrying out the reaction schemes may be varied in order to simplify the reactions or prevent unwanted by-products. The Examples that follow are provided to make the invention fully comprehensible. The Examples are intended to illustrate the invention and should in no way restrict it.

The compounds according to the invention may be prepared according to the schemes and specific examples provided or corresponding modifications thereof. Modifications to these reactions which are known to the skilled man but not described in detail here may also be implemented. The general methods of preparing the compounds according to the invention will become apparent to the skilled man from a study of the following schemes.

Starting compounds are commercially available or are prepared by processes which are described in the literature, known in the art or as described herein. Before the reaction is carried out corresponding functional groups in the compounds may be protected by conventional protective groups. These protective groups may be cleaved again at a suitable stage within the reaction sequence using methods familiar to the skilled man.

In the reactions described below, any reactive groups present such as hydroxy, carboxy, amino, alkylamino, amide or imino groups may be protected during the reaction by conventional protective groups that are cleaved again after the reaction.

For example
a suitable protective group for a hydroxy group may be the methoxy-, benzyloxy-, trimethylsilyl-, acetyl-, benzoyl-, tert.-butyl-, trityl, benzyl- or tetrahydropyranyl group, suitable protective groups for a carboxyl group may be the trimethylsilyl-, methyl-, ethyl-, tert.-butyl-, benzyl- or tetrahydropyranyl group, and suitable protective groups for an amide group may be the N-methoxymethyl-(MOM), N-benzyloxymethyl-(BOM), N-(trimethylsilyl)ethoxymethyl (SEM), N-tert-butyldimethylsiloxymethyl-, N-tert-butyldimethylsilyl-(TBDMS), N-triisopropylsilyl-(TIPS), N-benzyl-, N-4-methoxybenzyl-(PMB), N-triphenylmethyl-(Trt), N-tert-butoxycarbonyl-(BOC), N-benzyloxycarbonyl-(Cbz) or N-trimethylsilylethylsulphonyl-(SES)

a suitable protective group for an amino-, alkylamino- or imino group may be the acetyl-, trifluoroacetyl-, benzoyl-, ethoxycarbonyl-, tert.-butoxycarbonyl-, benzyloxycarbonyl-, benzyl-, methoxybenzyl- or 2,4-dimethoxybenzyl group and additionally, for the amino-group, the phthalyl group.

Other protective groups and their cleavage are described in T. W. Greene, P. G. M. Wuts, "Protective Groups in Organic Synthesis", Wiley, 1991 and 1999.

Any protecting group used is optionally subsequently cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide, or by ether splitting, e.g. in the presence of iodotrimethylsilane, at temperatures between 0 and 100° C., preferably at temperatures between 10 and 50° C.

However, a benzyl-, methoxybenzyl- or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 1 to 5 bar.

A methoxybenzyl group may also be cleaved in the presence of an oxidising agent such as cerium(IV) ammonium nitrate in a solvent such as methylene chloride, acetonitrile or acetonitrile/water at temperatures of between 0 and 50° C., but preferably at ambient temperature.

A methoxy group is conveniently cleaved in the presence of boron tribromide in a solvent such as methylene chloride at temperatures between −35 and −25° C.

A 2,4-dimethoxybenzyl group is preferably cleaved in trifluoroacetic acid in the presence of anisole.

A tert.butyl or tert.butyloxycarbonyl group is preferably cleaved by treating with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

A methoxymethyl group may be cleaved in the presence of an acid such as concentrated hydrochloric acid in a solvent such as dimethoxyethane. Alternatively an acid such as trifluoroacetic acid may also be used without a solvent.

An N-(trimethylsilyl)ethoxymethyl group may be cleaved in the presence of tetrabutylammonium fluoride and 1,3-dimethyl-3,4,5,6-tetrahydro-2(1H)-pyrimidone. Alternatively the SEM protective group may also be cleaved with an acid such as hydrogen chloride in an organic solvent such as dioxane or ethanol.

An allyloxycarbonyl group is cleaved by treating with a catalytic amount of tetrakis-(triphenylphosphine)-palladium (0), preferably in a solvent such as tetrahydrofuran and preferably in the presence of an excess of a base such as morpholine at temperatures between 0 and 100° C., preferably at ambient temperature and under an inert gas, or by treating with a catalytic amount of tris-(triphenylphosphine)-rhodium (I) chloride in a solvent such as aqueous ethanol and optionally in the presence of a base such as 1,4-diazabicyclo[2,2,2]octane at temperatures between 20 and 70° C.

The following methods of preparing the compounds of general formula I according to the invention and their precursors have proved particularly suitable:

Scheme 1:

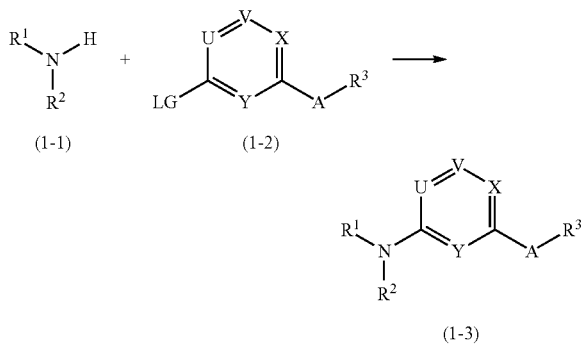

(1-1)     (1-2)

(1-3)

A compound of general formula (1-3), wherein A, U, V, X, Y, $R^1$, $R^2$ and $R^3$ are defined as mentioned hereinbefore, may be prepared by reacting an amino or aniline of general formula (1-1), wherein $R^1$ and $R^2$ are as hereinbefore defined, with an electron-depleted compound of general formula (1-2), wherein U, V, X, Y, A and $R^3$ are as hereinbefore defined and LG denotes a leaving group. The leaving group LG used may be halides, preferably chlorides and bromides, —$SO_2CH_3$, —$OSO_2CH_3$, —$OSO_2C_6H_4$—$CH_3$ or —S—$CH_3$ (—S—$CH_3$ requires further reaction with an organic peroxide in order to be converted into the actual leaving group) etc., but is not restricted to these. It is most particularly preferred to use chlorides.

The reaction may be carried out by nucleophilic aromatic substitution in an inert solvent using an auxiliary base in a temperature range from 0° C. to the reflux temperature of the solvent. Nucleophilic aromatic substitutions are carried out in a suitable inert solvent, such as tetrahydrofuran, toluene, xylene, dialkylformamide (particularly preferably dimethylformamide), cyclic amides (particularly preferably N-methylpyrrolidone), 1,4-dioxane, acetonitrile or in mixtures of solvents. Suitable auxiliary bases that may be used are tertiary amines such as triethylamine or ethyldiisopropylamine, alkali metal carbonates such as potassium carbonate or sodium carbonate, sodium hydride (NaH) or lithium diisopropylamide (LDA). The solvent used must be compatible with the base used. Preferably, the reaction is carried out in dimethylformamide, at temperatures between ambient temperature and the reflux temperature of the solvent, in the presence of a tertiary amine base.

Alternatively structures of general formula (1-3), wherein A, U, V, X, Y, $R^1$, $R^2$ and $R^3$ are defined as mentioned hereinbefore, may be synthesised by transition metal-catalysed reactions. An amine or aniline of general formula (1-1), wherein $R^1$ and $R^2$ are as hereinbefore defined, may react with a compound of general formula (1-2), wherein A, U, V, X, Y, and $R^3$ are as hereinbefore defined and LG denotes a leaving group, in an inert solvent in the presence of a catalyst and an auxiliary base. Additionally a suitable ligand may be used for the catalyst. The leaving group LG used may be chlorides, bromides, iodides, trifluoroacetates, trifluoromethanesulphonates, methanesulphonates and toluenesulphonates, but is not restricted to these. The inert solvents used may be xylene, tetrahydrofuran, dimethylformamide, dimethoxyethane, toluene, benzene, tert-butanol, 1,4-dioxane, acetonitrile or mixtures of solvents. The preferred solvent is xylene. Suitable bases are particularly amine bases such as e.g. triethylamine or diisopropylethylamine or also inorganic bases such as caesium carbonate, caesium acetate, potassium carbonate, potassium-tert-butoxide, sodium carbonate, sodium-tert-butoxide or potassium phosphate. Preferred reaction temperatures are from RT to the reflux temperature of the solvent at normal pressure. Typical catalysts are e.g. transition metal catalysts, such as e.g. palladium catalysts of the tris(dibenzylideneacetone)-dipalladium(0), tetrakis-(triphenylphosphine)-palladium(0), palladium-(II)-acetate, $Pd(PPh_3)_2Cl_2$, $Pd(CH_3CN)_2Cl_2$, $Pd(dppf)Cl_2$ or palladium(II)-chloride type. Typical ligands are e.g. triphenylphosphine, triphenylarsene, 2,2'-bis(diphenylphosphino)-1,1'-binaphthyl (BINAP), 2-di-tert-butylphosphino-2',4',6'-triisopropylbiphenyl (XPhos), 4,5-bis-diphenylphosphanyl-9,9-dimethyl-9H-xanthene (XantPhos), or 2-(di-tert-butylphosphino)biphenyl.

Scheme 2:

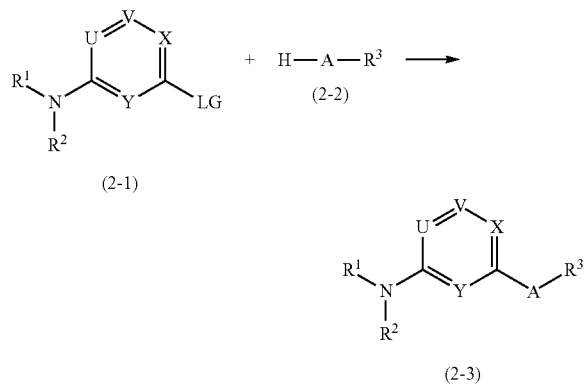

A compound of general formula (2-3), wherein U, V, X, Y, $R^1$, $R^2$ and $R^3$ are defined as mentioned hereinbefore and A denotes a sulphur or oxygen atom or the group —NH—, may—as shown in Scheme 2—be prepared by coupling a nucleophilic compound of general formula (2-2), wherein A denotes a sulphur, nitrogen or oxygen atom and $R^3$ is as hereinbefore defined, with a compound of general formula (2-1), wherein U, V, X, Y, $R^1$ and $R^2$ are defined as mentioned hereinbefore and LG denotes a leaving group. The leaving group LG used may be halides such as e.g. chlorides, bromides and fluorides, $-SO_2CH_3$, $-OSO_2CH_3$, $-NO_2$, $-OSO_2C_6H_4-CH_3$ or $-S-CH_3$ ($-S-CH_3$ requires further reaction with an organic peroxide in order to be converted into the actual leaving group) etc., but is not restricted to these. It is most particularly preferred to use chlorides as the leaving group LG.

The reaction may be carried out by nucleophilic aromatic substitution in an inert solvent using an auxiliary base in a temperature range from 0° C. to the reflux temperature of the solvent. Nucleophilic aromatic substitutions are carried out in a suitable inert solvent, such as tetrahydrofuran, toluene, xylene, dialkylformamide (particularly preferably dimethylformamide), cyclic amides (particularly preferably N-methylpyrrolidone), 1,4-dioxane, acetonitrile or in mixtures of solvents. Suitable auxiliary bases that may be used are for example tertiary amines such as triethylamine or ethyldiisopropylamine, alkoxides of the alkali and alkaline earth metals such as sodium-tert.-butoxide or potassium-tert.-butoxide, alkali metal carbonates such as potassium carbonate or sodium carbonate, sodium hydride (NaH) or lithium diisopropylamide (LDA). The inert solvent used must be compatible with the base used. Preferably, the reaction is carried out in N-methylpyrrolidone at temperatures between ambient temperature and the reflux temperature of the solvent in the presence of potassium-tert-butoxide.

Alternatively structures of general formula (2-3), wherein U, V, X, Y, $R^1$, $R^2$ and $R^3$ are defined as mentioned hereinbefore and A denotes a sulphur or oxygen atom or the group —N—H—, are synthesised by transition metal-catalysed reactions by known methods (cf. for example Alex R. Muci and Stephen L. Buchwald, Topics in Current Chemistry 2002, 219, 133-209.). A nucleophilic compound of general formula (2-2), wherein A denotes a sulphur, nitrogen or oxygen atom and $R^3$ is as hereinbefore defined, may react with a compound of general formula (2-1), wherein U, V, X, Y, $R^1$ and $R^3$ are as hereinbefore defined and LG denotes a leaving group, in an inert solvent in the presence of a catalyst and an auxiliary base. Additionally a suitable ligand may be used for the catalyst. The leaving group LG used may be a chloride, bromide, iodide, trifluoroacetate, trifluoromethanesulphonate, methanesulphonate or toluenesulphonate, but is not restricted to these.

The reaction is carried out in a suitable mixture of solvents that has sufficient dissolving capability for all the reactants involved, while heterogeneous procedures are also possible (e.g. the use of virtually insoluble bases). Preferably the reaction is carried out in polar aprotic or protic solvents. Preferably, a solvent or mixtures of a number of solvents, selected from among tetrahydrofuran, 1,4-dioxane, isopropanol, tert.-butanol, toluene or xylene, is or are used.

Suitable auxiliary bases are for example hydroxides, alkoxides and fluorides of alkali and alkaline earth metals, carbonates, hydrogen carbonates and phosphates of the alkali metals and the mixtures thereof. Particularly suitable are the bases in the group potassium phosphate, sodium phosphate, potassium-tert.-butoxide, sodium-tert.-butoxide, caesium-tert.-butoxide, lithium-tert.-butoxide and the corresponding isopropoxides. The base is normally used in at least equimolar amounts based on the compound (2-2), while preferably 1.2 to 3 equivalents of base are used.

The reaction may be carried out at temperatures between RT and the boiling point of the solvents used at the pressure used. To achieve a faster reaction, it is preferable to carry out the reaction at elevated temperatures in the range from 0° C. to 240° C. Particularly preferred is the temperature range from RT to 200° C., particularly from 50 to 150° C. The concentration of the reactants may be varied within wide limits. The reaction is expediently carried out in the highest possible concentration, while the solubilities of the reaction partners and reagents in the particular reaction medium must be taken into account.

Typical catalysts are e.g. transition metal catalysts, such as e.g. palladium catalysts of the tris(dibenzylideneacetone)-dipalladium(0), tetrakis-(triphenylphosphine)-palladium(0), palladium-(II)-acetate, $Pd(PPh_3)_2Cl_2$, $Pd(CH_3CN)_2Cl_2$, $Pd(dppf)Cl_2$, palladium(II)-chloride or copper(I)-trifluoromethanesulphonate type (cf. J. F. Marcoux, S. Doye, S. L. Buchwald J. Amer. Chem. Soc. 1997, 119, 10539-10540). Typical ligands for palladium-catalysed couplings include e.g. triphenylphosphine, triphenylarsene, BINAP, XPhos, XantPhos, or 2-(di-tert-butylphosphino)biphenyl (cf. e.g. Angew. Chemie. Int. Ed. 2006, 45, 4321-4326). The choice of catalyst and ligand must be matched in each case to the electronic and steric properties of the two reaction partners.

Scheme 3:

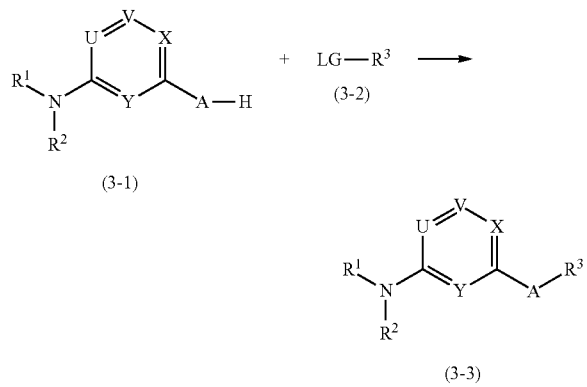

A compound of general formula (3-3), wherein U, V, X, Y, $R^1$, $R^2$ and $R^3$ are defined as mentioned hereinbefore and A denotes a sulphur or oxygen atom or the group —N—H—, may—as shown in Scheme 3—be prepared by coupling a compound of general formula (3-2), wherein $R^3$ is as hereinbefore defined and LG denotes a leaving group, with a compound of general formula (3-1), wherein U, V, X, Y, $R^1$ and $R^2$ are defined as mentioned hereinbefore and A denotes a sulphur or oxygen atom or the group —N—H—. The leaving group LG may be a halide, preferably a bromide or iodide, —$SO_2CF_3$ etc., but is not restricted to these.

The reaction is carried out in an inert solvent using an auxiliary base in a temperature range from 0° C. to the reflux temperature of the solvent. Suitable solvents include e.g. tetrahydrofuran, toluene, xylene, dialkylformamide (particularly preferably dimethylformamide), cyclic amides (particularly preferably N-methylpyrrolidone), 1,4-dioxane, acetonitrile or mixtures of these solvents. Suitable auxiliary bases that may be used are tertiary amines such as triethylamine or ethyldiisopropylamine, alkali metal carbonates such as potassium carbonate or sodium carbonate, sodium hydride (NaH) or lithium diisopropylamide (LDA). The inert solvent used must be compatible with the base used. Preferably, the reaction is carried out in dimethylformamide, at temperatures between ambient temperature and the reflux temperature of the solvent, in the presence of a tertiary amine base.

If A is an oxygen atom, the hydroxy group may be converted into a good leaving group. This may be done by using a phosphine reagent (which may also be bound to solid phases) such as e.g. triphenylphosphine, trimethylphosphine, triisopropylphosphite or tributyl-phosphine combined with an azodicarboxylate such as e.g. diethyl-azodicarboxylate (DEAD), diisopropylazodicarboxylate (DIAD), di-tert-butylazodi-carboxylate (DBAD), N,N,N',N'-tetraisopropylazodicarboxylamide (TIPA), 1,1'-(azodi-carbonyl)-dipiperidine (ADDP) or N,N,N',N'-tetramethylazodicarboxylamide (TMAD). Similarly fluorinated variants of the phosphine reagent and the azo compound may be used (for an Abstract see *Chem. Asian J.* 2007, *Eur. J. Org. Chem.* 2004, 2763-2772.). It is possible to use a phosphine ylide, such as e.g. (cyanomethylene)-trimethylphosphine (CMMP) or (cyanomethylene)-tributylphosphine (CMBP) (*Tetrahedron Lett.* 1996, 37, 2459-2462.). This reaction may particularly conveniently be carried out using polar, aprotic solvents such as e.g. tetrahydrofuran, toluene, xylene, benzene, 1,4-dioxane, dimethoxyethane, acetonitrile, dichloromethane, dichloroethane or mixtures of solvents, but it is also possible to work without solvents. The reaction is usually carried out at a temperature range from 0° C. to the reflux temperature of the solvent, or, if it is carried out without a solvent, in a temperature range from RT to the reflux temperature of the azo compound.

Alternatively structures of general formula (32-3), wherein A, U, V, X, Y, $R^1$, $R^2$ and $R^3$ are defined as mentioned hereinbefore are synthesised by transition metal-catalysed reactions by known methods. A compound of general formula (3-2), wherein $R^3$ is as hereinbefore defined and LG denotes a leaving group, may react with a compound of general formula (3-1), wherein $R^1$ and $R^2$ are as hereinbefore defined, in an inert solvent in the presence of a catalyst and an auxiliary base.

Scheme 4:

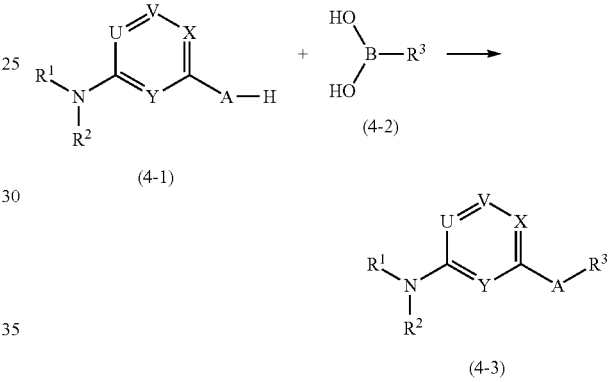

A compound of general formula (4-3), wherein U, V, X, Y, $R^1$, $R^2$ and $R^3$ are defined as mentioned hereinbefore and A denotes an oxygen atom or the group —N—H—, may be prepared—as shown in Scheme 4—by coupling a boric acid (4-2) with a compound of general formula (4-1), wherein U, V, X, Y, $R^1$ and $R^2$ are defined as mentioned hereinbefore and A denotes an oxygen atom or the group —NH—, with the addition of a copper (II) catalyst and an auxiliary base (cf. e.g. D. M. T. Chan, K. L. Monaco, R.-P. Wang, M. P. Winters *Tetrahedron Lett.* 1998, 39, 2933-2936; D. A. Evans, J. L. Katz, T. R. West *Tetrahedron Lett.* 1998, 39, 2937-2940; P. Y. S. Lam, C. G. Clark, S. Saubern, J. Adams, M. P. Winters, D. M. T. Chan, A. Combs *Tetrahedron Lett.* 1998, 39, 2941-2944). The reaction is carried out in an inert solvent in a temperature range from 0° C. to the reflux temperature of the solvent. Suitable solvents include e.g. dichloromethane or dichloroethane. Suitable auxiliary bases are in particular tertiary amines such as triethylamine or ethyldiisopropylamine or pyridine. Preferably the reaction is carried out using copper (II)-acetate as catalyst in dichloromethane, at temperatures between ambient temperature and the reflux temperature of the solvent, in the presence of triethylamine or pyridine.

The compounds of general formula (1-2) shown in Scheme 1 wherein U, V, X, Y, $R^1$, $R^2$ and $R^3$ are defined as mentioned hereinbefore and A denotes a sulphur or oxygen atom or the group —N—H—, may be prepared analogously to the methods described under Schemes 2, 3 and 4.

Compounds of general formula (I) wherein U, V, X, Y, $R^1$, $R^2$ and $R^3$ are defined as mentioned hereinbefore and A denotes a group selected from —S(=O)— (sulphoxide) or —SO$_2$— (sulphone) may conveniently be prepared by oxidation of the respective thioether compounds. Suitable oxidising agents include for example peroxides such as hydrogen peroxide, 4-chloroperbenzoic acid or periodic acid, and optionally Lewis acids may be added to the reaction mixture. The reaction is carried out in a suitable mixture of solvents that has sufficient dissolving capability for all the reactants involved. The preferred solvents are dichloromethane or acetonitrile. The reaction may be carried out at temperatures between the setting point and the boiling point of the solvent used.

Compounds of general formula (I) wherein U, V, X, Y, R$^1$, R$^2$ and R$^3$ are defined as mentioned hereinbefore and A denotes —N(C$_{1-3}$-alkyl), —N(C(O)—C$_{1-3}$-alkyl), may conveniently be prepared by alkylation or acylation of the respective biarylamines (1-3) using methods described in the specialist literature (cf. e.g. J. March, Advanced Organic Reactions, Reactions Mechanism, and Structure, 4th Edition, John Wiley & Sons, Chichester/New York/Brisbane/Toronto/Singapore, 1992 and literature cited therein).

The compounds of general formulae (2-2), (3-2) and (4-2) are either commercially available or may be synthesised by methods that are known in the specialist field of organic chemistry or are described in the specialist literature (cf. e.g. J. March, Advanced Organic Reactions, Reactions Mechanism, and Structure, 4th Edition, John Wiley & Sons, Chichester/New York/Brisbane/Toronto/Singapore, 1992 and literature cited therein). The use of transition metals and organo-metallic compounds for the synthesis is described in detail in monographs (cf. for example L. Brandsma, S. F. Vasilevsky, H. D. Verkruijsse, Application of Transition Metals Catalysts in Organic Synthesis, Springer-Verlag, Berlin/Heidelberg, 1999; M. Schlosser, Organometallics in Synthesis, John Wiley & Sons, Chichester/New York/Brisbane/Toronto/Singapore, 1994, P. J. Stang, F. Diederich, Metal-Catalyzed Cross-Coupling Reactions, Wiley-VCH, Weinheim, 1997 and references contained therein).

In some cases the end product may be further derivatised, e.g. by manipulation of the substituents. These manipulations may be, inter alia, those which are generally known to the skilled man, such as oxidation, reduction, alkylation, acylation and hydrolysis, but need not be restricted to the above.

The new compounds of general formula I according to the invention may contain one or more chiral centres. If for example there are two chiral centres present, the compounds may occur in the form of two diastereomeric pairs of antipodes. The invention includes the individual isomers as well as the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula I may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+) or (−)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula I is reacted with one of the abovementioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. with dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

The new compounds of general formula I and the physiologically acceptable salts thereof have valuable pharmacological properties, based on their selective CGRP-antagonistic properties. The invention further relates to pharmaceutical compositions containing these compounds, their use and the preparation thereof.

The new compounds mentioned above and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC membranes (~20 μg protein) are incubated for 180 minutes at ambient temperature with 50 pM $^{125}$I-iodotyrosyl-Calcitonin-Gene-Related Peptide and increasing concentrations of the test substances in a total volume of 250 μl (assay buffer: 10 mM tris, 50 mM NaCl, 5 mM MgCl$_2$, 1 mM EDTA, pH=7.4). The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity after the presence of 1 μM BIBN4096BS during incubation.

The concentration binding curves are analysed using computer-aided non-linear curve fitting.

The compounds mentioned hereinbefore show K$_i$ values≤50 μm in the test described.

B. CGRP Antagonism in SK-N-MC Cells

SK-N-MC cells (~1000 cells per well) are incubated for 30 minutes in the presence of increasing concentrations of CGRP and different concentrations of the test substance.

The cAMP contents of the samples are determined using an AlphaScreen cAMP assay kit (Perkin Elmer) and the pA$_2$ values of antagonistically acting substances are determined graphically.

The compounds according to the invention exhibit CGRP-antagonistic properties in the in vitro test model described, in a dosage range between 10$^{-12}$ and 10$^{-4}$ M.

To demonstrate that the compounds of general formula I exhibit good to very good CGRP-antagonistic activities with different structural elements, the following Table gives the activity values obtained according to the test procedure described above.

| No. | CGRP binding $K_i$ (nM) |
|---|---|
| (1) | 2 |
| (2) | 20 |
| (3) | 23 |
| (4) | 175 |
| (5) | 3 |
| (6) | 4 |
| (7) | 5 |
| (8) | 12 |
| (9) | 37 |
| (10) | 49 |
| (11) | 54 |
| (12) | 61 |
| (13) | 68 |
| (14) | 81 |
| (15) | 102 |
| (16) | 187 |
| (17) | 198 |
| (18) | 227 |
| (19) | 241 |
| (20) | 481 |
| (21) | 2 |
| (22) | 5 |
| (23) | 1 |
| (24) | 3 |
| (25) | 18 |
| (26) | 45 |
| (27) | 207 |
| (28) | 4 |
| (29) | 3 |
| (30) | 25 |
| (31) | 129 |
| (32) | 15 |
| (33) | 8 |
| (34) | 18 |
| (35) | 16 |
| (36) | 61 |
| (37) | 65 |
| (38) | 10 |
| (39) | 7 |
| (40) | 8 |
| (41) | 3 |
| (42) | 2 |
| (43) | 6 |
| (44) | 1 |
| (45) | 81 |
| (46) | 194 |
| (47) | 47 |
| (48) | 96 |
| (49) | 154 |
| (50) | 11 |
| (51) | 3 |
| (52) | 27 |
| (53) | 5 |
| (54) | 2 |
| (55) | 89 |
| (56) | 29 |
| (57) | 35 |
| (58) | 2 |
| (59) | 2 |
| (60) | 2 |
| (61) | 2 |
| (62) | 2 |
| (63) | 2 |
| (64) | 2 |
| (65) | 3 |
| (66) | 6 |
| (67) | 6 |
| (68) | 4 |
| (69) | 4 |
| (70) | 5 |
| (71) | 8 |
| (72) | 3 |
| (73) | 3 |
| (74) | 29 |
| (75) | 23 |
| (76) | 26 |
| (77) | 21 |
| (78) | 8 |
| (79) | 11 |
| (80) | 11 |

INDICATIONS

In view of their pharmacological properties the compounds according to the invention and the salts thereof with physiologically acceptable acids are thus suitable for the acute and prophylactic treatment of headaches, particularly migraine or cluster headaches and tension headaches. Moreover, the compounds according to the invention also have a positive effect on the following diseases: non-insulin-dependent diabetes mellitus ("NIDDM"), cardiovascular diseases, morphine tolerance, diarrhoea caused by clostridium toxin, skin diseases, particularly thermal and radiation-induced skin damage including sunburn, lichen, pruritis, pruritic toxidermies and severe itching, inflammatory diseases, e.g. inflammatory diseases of the joints (osteoarthritis, rheumatoid arthritis, neurogenic arthritis), generalised soft-tissue rheumatism (fibromyalgia), neurogenic inflammation of the oral mucosa, inflammatory lung diseases, allergic rhinitis, asthma, COPD, diseases accompanied by excessive vasodilatation and resultant reduced blood supply to the tissues, e.g. shock and sepsis, chronic pain, e.g. diabetic neuropathies, neuropathies induced by chemotherapy, HIV-induced neuropathies, postherpetic neuropathies, neuropathies induced by tissue trauma, trigeminal neuralgias, temporomandibular dysfunctions, CRPS (complex regional pain syndrome), back pain, and visceral complaints, such as e.g. irritable bowel syndrome (IBS) and inflammatory bowel syndrome. In addition, the compounds according to the invention have a general pain-relieving effect. The symptoms of menopausal hot flushes caused by vasodilatation and increased blood flow in oestrogen-deficient women and hormone-treated patients with prostate carcinoma and castrated men are favourably affected by the CGRP antagonists of the present application in a preventive and acute-therapeutic capacity, this therapeutic approach being distinguished from hormone replacement by the absence of side effects.

Preferably, the compounds according to the invention are suitable for the acute and prophylactic treatment of migraine and cluster headaches, for treating irritable bowel syndrome (IBS) and for the preventive and acute-therapeutic treatment of hot flushes in oestrogen-deficient women.

The dosage required to achieve a corresponding effect is conveniently 0.0001 to 3 mg/kg of body weight, preferably 0.01 to 1 mg/kg of body weight, when administered intravenously or subcutaneously, and 0.01 to 10 mg/kg of body weight, preferably 0.1 to 10 mg/kg of body weight when administered orally, nasally or by inhalation, 1 to 3× a day in each case.

If the treatment with CGRP antagonists and/or CGRP release inhibitors is given as a supplement to conventional hormone replacement, it is advisable to reduce the doses specified above, in which case the dosage may be from 1/5 of the lower limits mentioned above up to 1/1 of the upper limits specified.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

COMBINATIONS

Categories of active substance which may be used in combination include e.g. antiemetics, prokinetics, neuroleptics, antidepressants, neurokinin antagonists, anticonvulsants, histamine-H1-receptor antagonists, β-blockers, α-agonists and α-antagonists, ergot alkaloids, mild analgesics, non-steroidal anti-inflammatories, corticosteroids, calcium antagonists, 5-HT$_{1B/1D}$-agonists or other anti-migraine agents which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal anti-inflammatories aceclofenac, acemetacin, acetyl-salicylic acid, acetaminophen (paracetamol), azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, zomepirac or the pharmaceutically acceptable salts thereof as well as meloxicam and other selective COX2-inhibitors, such as for example rofecoxib, valdecoxib, parecoxib, etoricoxib and celecoxib, as well as substances that inhibit earlier or later stages of prostaglandin synthesis or prostaglandin receptor antagonists such as e.g. EP2-receptor antagonists and IP-receptor antagonists.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, pregabalin, duloxetine, topiramate, riboflavin, montelukast, lisinopril, micardis, prochloroperazine, dexamethasone, flunarizine, dextropropoxyphene, meperidine, metoprolol, propranolol, nadolol, atenolol, clonidine, indoramin, carbamazepine, phenyloin, valproate, amitryptiline, imipramine, venlafaxine, lidocaine or diltiazem and other 5-HT$_{1B/1D}$-agonists such as, for example, almotriptan, avitriptan, eletriptan, frovatriptan, naratriptan, rizatriptan, sumatriptan and zolmitriptan.

Furthermore, CGRP antagonists with vanilloid receptor antagonists, such as e.g. VR-1 antagonists, glutamate receptor antagonists, such as e.g. MGlu5 receptor antagonists, mGlu1 receptor antagonists, iGlu5 receptor antagonists, AMPA receptor antagonists, purine receptor blockers, such as e.g. P2X3 antagonists, NO-synthase inhibitors, such as e.g. INOS inhibitors, calcium channel blockers, such as e.g. PQ-type blockers, N-type blockers, potassium channel openers, such as e.g. KCNQ channel openers, sodium channel blockers, such as e.g. PN3 channel blockers, NMDA receptor antagonists, acid-sensing ion channel antagonists, such as e.g. ASIC3 antagonists, bradykinin receptor antagonists such as e.g. B1 receptor antagonists, cannabinoid receptor agonists, such as e.g. CB2 agonists, CB1 agonists, somatostatin receptor agonists, such as e.g. Sst2 receptor agonists may be added.

The dosage of these active substances is expediently 1/5 of the lowest usually recommended dose to 1/1 of the normally recommended dose, i.e. for example 20 to 100 mg of sumatriptan.

FORMULATIONS

The compounds prepared according to the invention may be administered either on their own or optionally in combination with other active substances for the treatment of migraine by intravenous, subcutaneous, intramuscular, intraarticular, intrarectal, intranasal route, by inhalation, topically, transdermally or orally, while aerosol formulations are particularly suitable for inhalation. The combinations may be administered either simultaneously or sequentially.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula I according to the preferred embodiments above.

It is particularly preferable if the compounds of formula I are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula I are administered by inhalation, particularly preferably if they are administered once or twice a day. For this purpose, the compounds of formula I have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

EXPERIMENTAL SECTION

As a rule IR, $^1$H-NMR and/or mass spectra have been obtained for the compounds prepared. Unless stated otherwise, $R_f$ values are determined using ready-made TLC silica gel plates 60 F254 (E. Merck, Darmstadt, Item no. 1.05714) without chamber saturation.

The ratios given for the eluants relate to units by volume of the particular solvents. The units by volume given for $NH_3$ relate to a concentrated solution of $NH_3$ in water.

Unless stated otherwise, the acid, base and salt solutions used in working up the reaction solutions are aqueous systems of the specified concentrations. Silica gel made by Millipore (MATREX™, 35-70 μm) is used for chromatographic purifications.

The HPLC data provided are measured under the parameters listed below and using the columns mentioned:
Columns Used:

| | (column temperature: 30° C.; injection volume: 5 μL; detection at 254 nm) |
|---|---|
| S1 | Zorbax column (Agilent Technologies), SB (Stable Bond) C18; 3.5 μm; 4.6 × 75 mm |
| S2 | Zorbax column (Agilent Technologies), SB (Stable Bond) C18; 1.8 μm; 3.0 × 30 mm |
| S3 | Zorbax column (Agilent Technologies), SB (Stable Bond) C18; 5 μm; 4.6 × 75 mm |
| S4 | X-Bridge(Waters) C18; 2.5 μm; 3.0 × 30 mm, |

| | (column temperature: 30° C.; injection volume: 5 μL; detection at 254 nm) |
|---|---|
| S5 | Sunfire C18 (Waters); 3.5 μm; 4.6 × 75 mm |
| S6 | Symmetry C18 (Waters); 3.5 μm; 4.6 × 75 mm |

Solvents Used:
Acidic Conditions:
solvent A: water (with 0.1% formic acid)
solvent B: acetonitrile (with 0.1% formic acid)
(The Percentages Stated Relate to the Total Volume.)
Gradients:

| gradient | time [min] | % A | % B |
|---|---|---|---|
| G1 | 0.00 | 95 | 5 |
| (1.6 mL/min) | 0.10 | 95 | 5 |
| | 1.75 | 5 | 95 |
| | 1.90 | 5 | 95 |
| | 1.95 | 95 | 5 |
| | 2.00 | 95 | 5 |
| G2 | 0.00 | 95 | 5 |
| (1.6 mL/min) | 4.50 | 10 | 90 |
| | 5.00 | 10 | 90 |
| | 5.50 | 95 | 5 |
| G3 | 0.00 | 95 | 5 |
| (1.6 mL/min) | 4.00 | 50 | 50 |
| | 4.50 | 10 | 90 |
| | 5.00 | 10 | 90 |
| | 5.50 | 95 | 5 |
| G4 | 0.00 | 95 | 5 |
| (1.6 mL/min) | 1.00 | 10 | 90 |
| | 2.50 | 50 | 50 |
| | 2.75 | 95 | 5 |
| G5 | 0.00 | 95 | 5 |
| (1.4 mL/min) | 1.80 | 10 | 90 |
| | 2.00 | 10 | 90 |
| | 2.20 | 95 | 5 |
| G6 | 0.00 | 95 | 5 |
| (1.6 mL/min) | 2.00 | 50 | 50 |
| | 2.25 | 10 | 90 |
| | 2.50 | 10 | 90 |
| | 2.75 | 95 | 5 |

Separations with Methanol:
solvent A: water (with 0.2% HCOOH)
solvent B: methanol
(The percentages given are based on the total volume.)

| gradient | time [min] | % A | % B |
|---|---|---|---|
| G7 | 0.00 | 95 | 5 |
| (1.6 mL/min) | 4.50 | 10 | 90 |
| | 6.50 | 10 | 90 |
| | 7.00 | 95 | 5 |

Basic Conditions:
solvent A: water (with 0.1% NH4OH)
solvent B: acetonitrile (with 0.1% NH4OH)
(The percentages stated relate to the total volume.)

| gradient | time [min] | % A | % B |
|---|---|---|---|
| basic_1 | 0.00 | 95 | 5 |
| (0.8 mL/min) | 9.00 | 10 | 90 |

-continued

| gradient | time [min] | % A | % B |
|---|---|---|---|
| | 10.00 | 10 | 90 |
| | 11.00 | 95 | 5 |

| gradient | time [min] | % A | % B |
|---|---|---|---|
| basic_2 | 0.00 | 95 | 5 |
| (1.4 mL/min) | 1.80 | 10 | 90 |
| | 2.00 | 10 | 90 |
| | 2.20 | 95 | 5 |

Methods:

The particular method of HPLC used will be the result of the combination of the columns and gradients described above:

| | column | gradient |
|---|---|---|
| method A | S1 | G1 |
| method B | S2 | G1 |
| method C | S1 | G2 |
| method D | S1 | G3 |
| method E | S2 | G4 |
| method F | S4 | G5 |
| method G | S5 | G2 |
| method H | S4 | basic_1 |
| method I | S2 | G6 |
| method J | S6 | G2 |
| method K | S4 | basic_2 |
| method L | S5 | G3 |
| method M | S1 | G7 |

In preparative HPLC purification, generally the same gradients are used as were used to obtain the analytical HPLC data. The collection of the products is mass-controlled and the fractions containing product are combined and freeze-dried.

In the absence of any more information regarding the configuration, it is unclear whether there are pure enantiomers involved or whether partial or even total racemisation has taken place.

The following abbreviations are used in the test descriptions:
AcOH acetic acid
BINAP 2,2'-bis(diphenylphosphino)-1,1'-binaphthyl
BOC tert.-butyloxycarbonyl
cyc cyclohexane
CDI 1,1'-carbonyldimidazole
DCM dichloromethane
DIPE diisopropylether
DIPEA diisopropylethylamine
DMF N,N-dimethylformamide
DMSO dimethylsulphoxide
dppf 1,1'-bis(diphenyl-phosphino)ferrocene
of th. of theory
EI electron jet ionisation (in MS)
ESI electron spray ionisation (in MS)
EtOAc ethyl acetate
EtOH ethanol
E-water de-ionised water
FM eluant
HCl hydrogen chloride
HCOOH formic acid
HPLC High Performance Liquid Chromatography
HPLC-MS HPLC coupled mass spectrometry
i.vac. in vacuo (under vacuum)
conc. concentrated
MeOH methanol
MS mass spectrometry
MW molecular weight [g/mol]
NaOH sodium hydroxide
NH$_4$OH ammonium hydroxide (aqueous ammonia solution, 30%)
NMP N-methyl-2-pyrrolidine
Pd$_2$dba$_3$ bis(dibenzylideneacetone)-palladium(0)
PE petroleum ether
R$_f$ retention index (in TLC)
RT ambient temperature
R$_t$ retention time (in HPLC)
TEA triethylamine
TFA trifluoroacetic acid
THF tetrahydrofuran
ULTS circulating air dryer Preparation of the Starting Compounds Intermediate 1

7-methoxy-3-piperidin-4-yl-1,3,4,5-tetrahydro-1,3-benzodiazepin-2-one

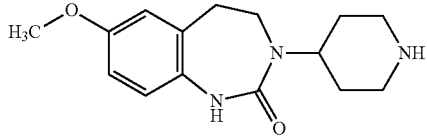 [SMILES: COc1ccc2c(c1)CCN(C1CCNCC1)C(=O)N2]

This compound and its precursors was prepared as described in U.S. Pat. No. 6,313,097.

Intermediate 2

6-(6-chloro-pyrimidin-4-yloxy)-4-methyl-3H-benzoxazol-2-one

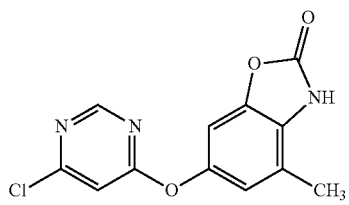

Step 1: 4-methyl-2-oxo-2,3-dihydrobenzo[d]oxazol-6-ylboric acid

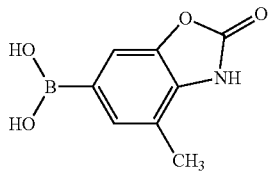

Under an argon atmosphere 1.00 g (4.39 mmol) 6-bromo-4-methyl-3H-benzoxazol-2-one, 1.71 g (6.60 mmol) bis-(pinacolato)-diborane, 0.359 g (0.440 mmol) 1,1'-bis(diphenyl-phosphino)ferrocene-palladium(II) dichloride and 1.30 g (13.2 mmol) potassium acetate were added to 3.0 mL of DMSO and the mixture was stirred for 2 h at 120° C. The mixture was poured onto ice water and extracted several times with DCM. The combined organic phases were washed with water and saturated sodium chloride solution and evaporated down i.vac. The residue was dissolved in DMF and purified by preparative HPLC-MS. The product-containing fractions were combined, made slightly alkaline with 1N aqueous sodium hydroxide solution and evaporated down i.vac. The residue was taken up in water and the precipitate was suction filtered. The filtrate was acidified slightly with 1N aqueous hydrochloric acid solution, the precipitate was suction filtered and dried i. vac.

Yield: 0.3 g (36% of theory)
ESI-MS: m/z=192 (M−H)⁻
R$_f$(HPLC): 0.89 min (method B)

Step 2: 6-hydroxy-4-methyl-3H-benzoxazol-2-one

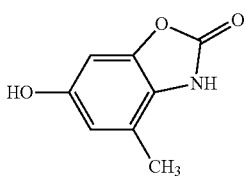

77 mg (0.40 mmol) 4-methyl-2-oxo-2,3-dihydrobenzo[d]oxazol-6-ylboric acid were dissolved in 2.0 mL glacial acetic acid and mixed with 0.20 mL (2.3 mmol) hydrogen peroxide solution (35% in water) and stirred briefly. The reaction mixture was left to stand for 1 h at RT. The precipitate formed was suction filtered, washed with water and dried i. vac.

Yield: 40 mg (61% of theory)
ESI-MS: m/z=164 (M−H)⁻
R$_f$(HPLC): 1.07 min (method B)

Step 3: 6-(6-chloro-pyrimidin-4-yloxy)-4-methyl-3H-benzoxazol-2-one

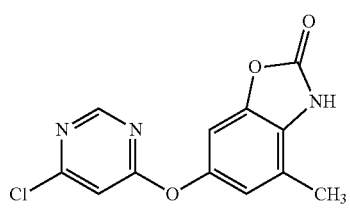 [SMILES: Cc1cc(Oc2cc(Cl)ncn2)cc2oc(=O)[nH]c12]

0.10 g (0.60 mmol) 6-hydroxy-4-methyl-3H-benzoxazol-2-one in 1.5 mL DMF were combined with 0.10 g (0.70 mmol) potassium carbonate and stirred for 15 min at RT. Then 0.10 g (0.60 mmol) 4,6-dichloropyrimidine were added to the reaction mixture and stirred overnight at RT. Then water was added and the precipitate formed was suction filtered, washed and dried i. vac.

Yield: 90 mg (56% of theory)
ESI-MS: m/z=278(M+H)⁺
R$_f$(HPLC): 1.29 min (method B)

Intermediate 3

6-(6-chloro-pyrimidin-4-yloxy)-3,4-dimethyl-3H-benzoxazol-2-one

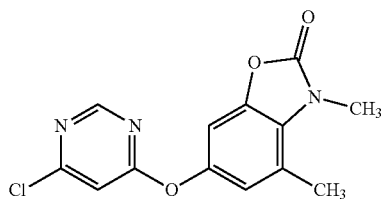

Step 1: 3,4-dimethyl-6-(4,4,5,5-tetramethyl-[1,3,2]dioxaborolan-2-yl)-3H-benzoxazol-2-one

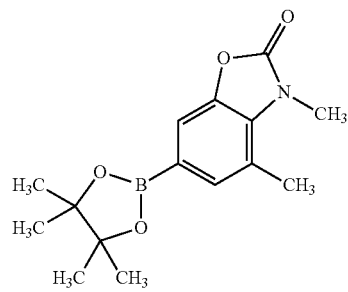

Under an argon atmosphere, 3.20 g (13.4 mmol) 6-bromo-3,4-dimethyl-3H-benzoxazol-2-one, 5.00 g (19.3 mmol) bis-(pinacolato)-diborane, 0.90 g (1.1 mmol) 1,1'-bis(diphenyl-phosphino)ferrocene-palladium(II)dichloride and 3.94 g (40.1 mmol) potassium acetate in 10.0 mL DMSO were combined and stirred for 2 h at 120° C. The mixture was diluted with EtOAc and washed with water and saturated sodium chloride solution. The organic phase was evaporated down and purified by flash chromatography. The product-containing fractions were combined and evaporated down. The residue was triturated with PE and suction filtered. The solid obtained was washed with PE and dried i. vac.

Yield: 2.40 g (62% of theory)
ESI-MS: m/z=290 (M+H)⁺
R$_f$(HPLC): 1.66 min (method B)

Step 2: 6-hydroxy-3,4-dimethyl-3H-benzoxazol-2-one

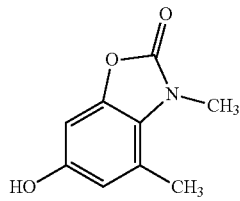

0.20 g (0.70 mmol) 3,4-dimethyl-6-(4,4,5,5-tetramethyl-[1,3,2]dioxaborolan-2-yl)-3H-benzoxazol-2-one were dissolved in 2.0 mL glacial acetic acid and combined with 0.40 mL (4.6 mmol) hydrogen peroxide solution (35% in water) and stirred. The precipitate formed was suction filtered, washed with water and dried i. vac.
Yield: 122 mg (98% of theory)
ESI-MS: m/z=180 (M−H)⁻
$R_t$(HPLC): 1.09 min (method B)

Step 3: 6-(6-chloro-pyrimidin-4-yloxy)-3,4-dimethyl-3H-benzoxazol-2-one

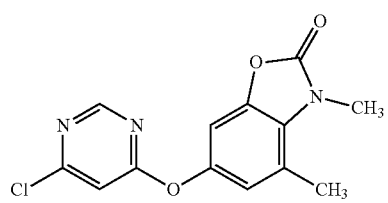 [SMILES: Cc1cc(Oc2cc(Cl)ncn2)cc2oc(=O)n(C)c12]

30 mg (0.70 mmol) sodium hydride (55%, suspension in mineral oil) were added to 0.12 g (0.70 mmol) 6-hydroxy-3,4-dimethyl-3H-benzoxazol-2-one in 5.0 ml DMF and the mixture was stirred for 10 min at RT. Then 0.10 g (0.70 mmol) 4,6-dichloropyrimidine was added and the mixture was stirred for 1 h at RT. Then water and EtOAc were added, the organic phase was separated off, dried on sodium sulphate, filtered and evaporated down.
Yield: 260 mg (quantitative)
ESI-MS: m/z=292 (M+H)⁺
$R_t$(HPLC): 1.50 min (method B)

Intermediate 4a 1-piperidin-4-yl-1,3-dihydroimidazo[4,5-b]pyridin-2-one

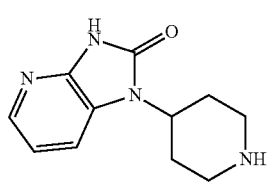 [SMILES: O=c1[nH]c2ncccc2n1C1CCNCC1]

Step 1: benzyl 4-(2-chloro-pyridin-3-yl-amino)-piperidine-1-carboxylate

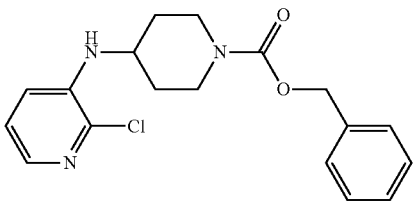 [SMILES: O=C(OCc1ccccc1)N1CCC(Nc2cccnc2Cl)CC1]

560 mL (7.25 mol) TFA were added dropwise at approx. 15° C. to 930 g (3.99 mol) N-benzyloxy carbonyl-4-piperidone and 466 g (3.63 mol) 2-chloro-3-aminopydridine in 9.5 L isopropyl acetate. 922 g (4.35 mol) sodium triacetoxyborohydride were added batchwise. The mixture was stirred until the reaction was complete. At RT the reaction mixture was combined with 860 mL sodium hydroxide solution (2 mol/L). The organic phase was separated off, washed with 5 L water and evaporated down.
Yield: 1250 g (crude 100% of theory)
ESI-MS: m/z=346 (M+H)⁺

Step 2: benzyl 4-[1-(2-chloro-pyridin-3-yl)-ureido]-piperidine-1-carboxylate

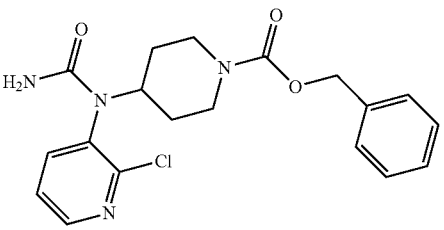 [SMILES: NC(=O)N(c1cccnc1Cl)C1CCN(C(=O)OCc2ccccc2)CC1]

530 mL (6.1 mol) chlorosulphonyl isocyanate were placed in 6 L of THF and cooled to −15° C. A solution of 1.25 kg (3.63 mol) benzyl 4-(2-chloro-pyridin-3-yl-amino)-piperidine-1-carboxylate in 7 L THF was then added dropwise to this mixture within one hour in such a way that the temperature of the reaction mixture did not exceed −7° C. The mixture was stirred for 90 minutes at approx. −8° C. and then 700 mL water was added dropwise within 30 minutes. The mixture was stirred for 30 minutes at approx. 10° C. and then slowly combined with 8.1 L sodium hydroxide solution (2 mol/L). The reaction mixture was then heated to 50° C. and the phases were separated. The organic phase was washed with 2 L water. Then 10 L solvent were distilled off from the organic phase, 15 L butyl acetate were added to the residue and another 8 L were distilled off again. The product was crystallised by slowly cooling to 0° C. The precipitate was suction filtered, washed with 2 L butyl acetate and dried at 40° C.
Yield: 1108 g (78.8% of theory)
ESI-MS: m/z=389/391(M+H)⁺

Step 3: benzyl 4-(2-oxo-2,3-dihydro-imidazo[4,5-b]pyridin-1-yl)-piperidine-1-carboxylate

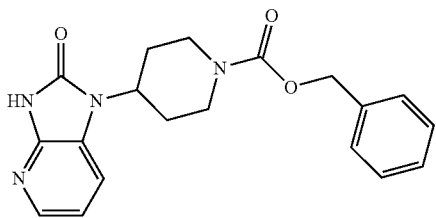 [SMILES: O=C(OCc1ccccc1)N1CCC(n2c(=O)[nH]c3ncccc32)CC1]

1108 g (2.85 mol) benzyl 4-[1-(2-chloro-pyridin-3-yl)ureido]-piperidine-1-carboxylate were refluxed with 720 g (8.57 mol) sodium hydrogen carbonate in 14.5 L tert-amylalcohol. During this time 3 L solvent were distilled off. The reaction mixture was cooled to 35° C. and mixed with 11 mL water. Then 13 g (0.058 mol) palladium acetate and 49 g (0.115 mol) 1,4-bis-(diphenylphosphino)-butane (DPPB) were added and the mixture was heated to reflux temperature. It was stirred at 100° C. until the reaction was complete, then cooled to RT and 7.5 L of water were added. The organic phase was separated off, washed with 5 L water and then evaporated down. The oily residue was combined twice with 3 L isopropyl acetate and distilled off. Then the residue was dissolved hot in 7 L isopropyl acetate and slowly cooled to RT. The precipitated solid was suction filtered, washed with 2 L isopropyl acetate and tert.-butyl-methylether and dried at 50° C.

Yield: 690 g (69% of theory)
ESI-MS: m/z=353 (M+H)$^+$

Step 4: 1-piperidin-4-yl-1,3-dihydro-imidazo[4,5-b]pyridin-2-one

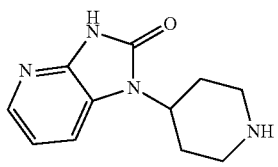 [SMILES: O=c1[nH]c2ncccc2n1C1CCNCC1]

690 g (1.96 mol) benzyl 4-(2-oxo-2,3-dihydro-imidazo[4,5-b]pyridin-1-yl)-piperidine-1-carboxylate were dissolved in 5.4 L methanol and hydrogenated with the addition of 46 g Pd/C (10%; 6.6 wt. %) at 60° C. under a hydrogen pressure of 60 psi until all the hydrogen had been taken up. The catalyst was filtered off. 4 L methanol were distilled off from the filtrate. 2 L of methylcyclohexane were added and a further 1.5 L solvent were distilled off. The suspension thus obtained was suction filtered, the residue was washed with methylcyclohexane and dried at 40° C.

Yield: 446 g (100% of theory)
ESI-MS: m/z=219 (M+H)$^+$

Intermediate 4b 1-piperidin-4-yl-1,3-dihydroimidazo[4,5-b]pyridin-2-one-dihydrochloride

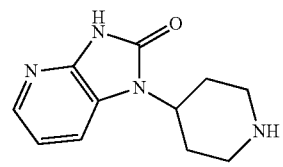

This compound and its precursors were synthesised as described in WO 2005/013894.

Intermediate 5

4-chloro-6-(3,4-dimethyl-phenoxy)-pyrimidine

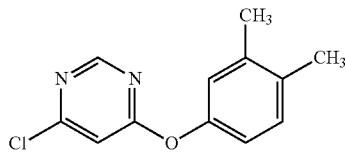 [SMILES: Cc1ccc(Oc2cc(Cl)ncn2)cc1C]

218 mg (5.00 mmol) sodium hydride (55%, suspension in mineral oil) were added to 617 mg (5.00 mmol) 3,4-dimethylphenol in 10 ml DMF and the mixture was stirred for 10 min at RT. Then 768 mg (5.00 mmol) 4,6-dichloropyrimidine were added and the mixture was stirred for 48 h at RT. Water and EtOAc were added to the reaction mixture, the organic phase was separated off, dried on sodium sulphate, filtered and evaporated down. The residue was dried i. vac.

Yield: 1.3 g (94% of theory)
purity: 85%
ESI-MS: m/z=235/37 (Cl) (M+H)$^+$
R$_t$(HPLC): 1.64 min (method B)

Intermediate 6

6-(6-chloro-pyrimidin-4-ylamino)-4-methyl-3H-benzoxazol-2-one

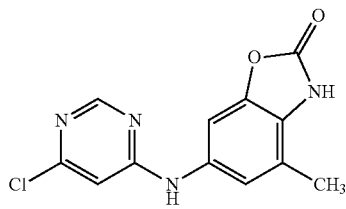 [SMILES: Cc1cc(Nc2cc(Cl)ncn2)cc2oc(=O)[nH]c12]

Step 1: methyl 4-methyl-2-oxo-2,3-dihydro-benzoxazole-6-carboxylate

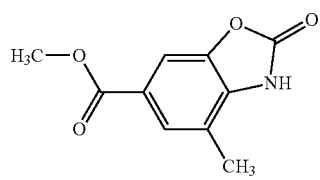

12 g (53 mmol) 6-bromo-4-methyl-3H-benzoxazol-2-one, 30 mg (0.13 mmol) palladium(II)-acetate, 1.0 g (1.8 mmol) dppf and 12 g (0.14 mol) sodium acetate were placed in 600 mL MeOH and left to react under a pressure of 5 bar in a carbon monoxide atmosphere for 8 h at 100° C. and then cooled to RT. The precipitate formed was suction filtered and the mother liquor was evaporated almost to dryness by rotary evaporation, combined with ice water and the precipitate formed was suction filtered, washed with water and dried.

Yield: 11 g (82% of theory)
ESI-MS: m/z=206 (M–H)⁻
R$_f$: 0.30 (silica gel: PE/EtOAc=2/1)

Step 2: 4-methyl-2-oxo-2,3-dihydro-benzoxazole-6-carboxylic acid

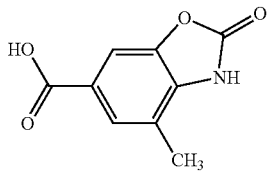

20 mL 4N aqueous sodium hydroxide solution were added to 5.00 g (24.1 mmol) methyl 4-methyl-2-oxo-2,3-dihydro-benzoxazole-6-carboxylate in 50 mL MeOH and the mixture was stirred for 24 h at RT. Then 10 mL of 4N aqueous sodium hydroxide solution were added and the mixture was stirred for a further 8 h at RT. Then the MeOH was eliminated i.vac., water was added and while cooling with ice the mixture was acidified with conc. hydrochloric acid solution until a precipitate formed. This was suction filtered, washed with water and dried i. vac.

Yield: 4.6 g (99% of theory)
R$_t$(HPLC): 1.96 min (method C)

Step 3: 4-methyl-2-oxo-2,3-dihydro-benzoxazole-6-carboxylic acid azide

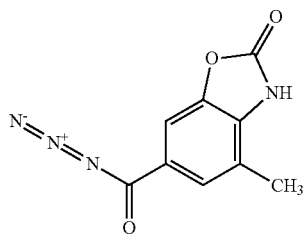 [SMILES: Cc1cc(C(=O)N=[N+]=[N-])cc2oc(=O)[nH]c12]

1.00 g (5.20 mmol) 4-methyl-2-oxo-2,3-dihydro-benzoxazole-6-carboxylic acid, 3.00 ml (41.1 mmol) thionyl chloride, 20 mL DCM and 1.0 mL DMF were combined and stirred for 4 h at 40° C. The reaction mixture was evaporated to dryness and co-evaporated with toluene. The residue was dissolved in acetone, combined with 340 mg (5.20 mmol) sodium azide and stirred for 1 h at RT. Then water was added, the precipitate formed was suction filtered and dried.

Yield: 1.40 g (81% of theory)
purity: 65%
ESI-MS: m/z=217 (M–H)⁻

Step 4: tert-butyl (4-methyl-2-oxo-2,3-dihydro-benzoxazol-6-yl)-carbamate

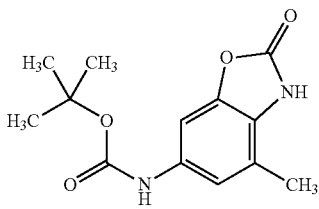 [SMILES: Cc1cc(NC(=O)OC(C)(C)C)cc2oc(=O)[nH]c12]

1.00 g (2.98 mmol) 4-methyl-2-oxo-2,3-dihydro-benzoxazole-6-carboxylic acid azide were refluxed in 15 mL tert-butanol 2.5 with stirring. After cooling to RT the solvent was eliminated i.vac., the residue was taken up in methanol and filtered through Alox. The filtrate was evaporated down and the residue was dried.

Yield: 500 mg (64% of theory)
ESI-MS: m/z=263 (M–H)⁻
R$_t$(HPLC): 1.30 min (method B)

Step 5: 6-amino-4-methyl-3H-benzoxazol-2-one

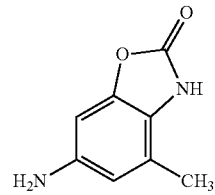

400 μL (5.30 mmol) TFA were added to 230 mg (0.900 mmol) tert-butyl (4-methyl-2-oxo-2,3-dihydro-benzoxazol-6-yl)-carbamate in 5.0 ml DCM and the mixture was stirred for 1.5 h at RT. The reaction mixture was evaporated down and the residue was divided between semisaturated sodium hydrogen carbonate solution and EtOAc. The organic phase was dried on sodium sulphate, filtered and evaporated down.

Yield: 120 mg (84% of theoretical)
ESI-MS: m/z=165 (M+H)⁺
R$_t$(HPLC): 0.23 min (method B)

Step 6: 6-(6-chloro-pyrimidin-4-ylamino)-4-methyl-3H-benzoxazol-2-one

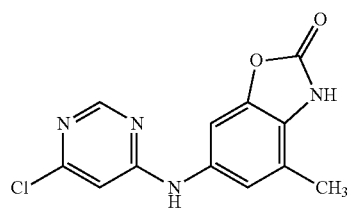 [SMILES: Cc1cc(Nc2cc(Cl)ncn2)cc2oc(=O)[nH]c12]

400 mg (2.40 mmol) 6-amino-4-methyl-3H-benzoxazol-2-one, 400 mg (2.70 mmol) 4,6-dichloropyrimidine and 1.10 mL (8.00 mmol) TEA in 5 mL 1-butanol were stirred for 1 h at 100° C. After cooling to RT the reaction mixture was evaporated down and the residue was washed with water and saturated sodium hydrogen carbonate solution. The organic phase was dried on sodium sulphate, filtered and evaporated down.

Yield: 500 mg (58% of theory)
purity: 78%
ESI-MS: m/z=277 (M+H)+
R$_t$(HPLC): 1.35 min (method B)

Intermediate 7

(6-chloro-pyrimidin-4-yl)-(2,7-dimethyl-1H-benz-imidazol-5-yl)-amine

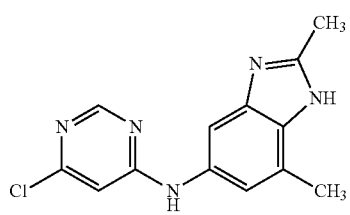 [SMILES: Cc1nc2cc(Nc3cc(Cl)ncn3)cc(C)c2[nH]1]

Step 1: N-(2-methyl-4,6-dinitro-phenyl)-acetamide

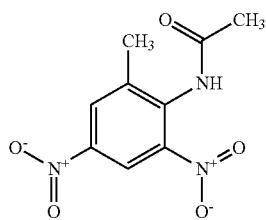 [SMILES: CC(=O)Nc1c(C)cc([N+](=O)[O-])cc1[N+](=O)[O-]]

50.0 g (0.257 mol) N-(2-methyl-4-nitro-phenyl)-acetamide were added in small batches to 400 mL fuming nitric acid, which was being stirred at −5° C., such that the temperature in the reaction vessel did not rise above 0° C. After the addition had ended the reaction mixture was stirred for 15 min at 0° C. and then added to 2 kg of a mixture of ice and water. The product precipitated as a solid was suction filtered, washed with water and dried. It was used directly for the next step.

Yield: 55.3 (90% of theory)
R$_f$: 0.77 (silica gel: DCM)

Step 2: N-(2,4-diamino-6-methyl-phenyl)-acetamide

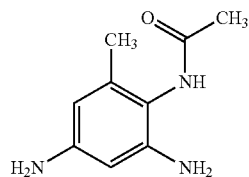

A mixture of 45.0 g (0.188 mol) N-(2-methyl-4,6-dinitro-phenyl)-acetamide and 4.50 g palladium on charcoal (Pd/C 10%) in 1.400 L methanol was hydrogenated for 2 h at RT under a hydrogen atmosphere. The catalyst was removed by suction filtering and the filtrate was evaporated to dryness i.vac. The residue was triturated in diethyl ether, suction filtered and dried. The crude product obtained was used directly for the next step.

Step 3: 2,7-dimethyl-benzimidazol-5-ylamine

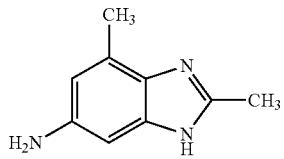

33.0 g (0.184 mol) N-(2,4-diamino-6-methyl-phenyl)-acetamide were stirred in 400 mL glacial acetic acid for 1.5 h at 100° C. The glacial acetic acid was eliminated i.vac. and the residue remaining was triturated with ether, suction filtered and dried. The free base thus obtained was taken up in methanolic hydrochloric acid and left to stand. The hydrochloride slowly settling out as a precipitate was suction filtered, washed with acetone and dried.

Yield: 22.6 g (76% of theory) as free base
ESI-MS: m/z=161 (M)+

Step 4: (6-chloro-pyrimidin-4-yl)-(2,7-dimethyl-1H-benzimidazol-5-yl)-amine

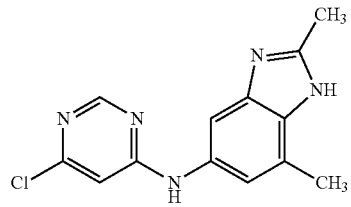 [SMILES: Cc1nc2cc(Nc3cc(Cl)ncn3)cc(C)c2[nH]1]

Under a nitrogen atmosphere 3.00 g (15.2 mmol) 2,7-dimethyl-benzimidazol-5-ylamine-hydrochloride, 2.30 g (15.4 mmol) 4,6-dichloropyrimidine and 6.50 mL (47.0 mmol) TEA in 15 mL 1-butanol were stirred for 3 h at 100° C. After cooling to RT the reaction mixture was evaporated down, the residue was stirred in DCM and the precipitate formed was suction filtered and dried.

Yield: 3.10 g (75% of theory)
ESI-MS: m/z=274/6 (Cl) (M+H)+
R$_t$(HPLC): 0.84 min (method B)

Intermediate 8

3-piperidin-4-yl-1,3-dihydro-imidazo[4,5-c]quinolin-2-one

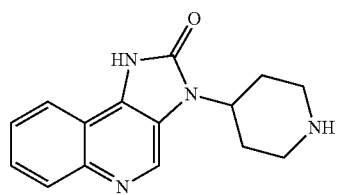 [SMILES: O=c1[nH]c2c3ccccc3ncc2n1C1CCNCC1]

Step 1: 3-bromoquinoline-1-oxide

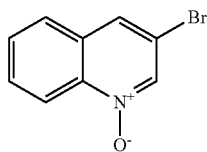 [SMILES: [O-][n+]1cc(Br)cc2ccccc21]

A solution of 72% 3-chloroperbenzoic acid (98 g, 0.41 mol) dissolved in 1 L dichloromethane was added dropwise to a solution of 85 g (0.41 mol) 3-bromoquinoline in 100 mL DCM cooled to 5° C. Care was taken to ensure that the temperature of the reaction mixture did not rise above 10° C. After the addition had ended the mixture was stirred for 5 h, then a solution of 72% 3-chloroperbenzoic acid (25 g, 0.10 mol) dissolved in 200 mL DCM, dried on sodium sulphate and filtered off) was again added dropwise and stirred overnight at RT. Saturated aqueous sodium carbonate solution was added, the phases were separated and the organic phase was dried on sodium sulphate. The solution was filtered through activated charcoal and then evaporated down i.vac.

Yield: 224 g (99% of theory)
ESI-MS: m/z=223/225 (Br)
$R_f$=0.15 (silica gel, PE/EtOAc=2:1)

Step 2: 3-bromo-4-nitroquinoline-1-oxide

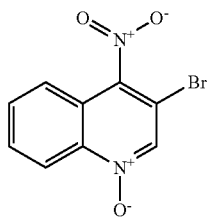 [SMILES: O=[N+]([O-])c1c(Br)c[n+]([O-])c2ccccc12]

A solution of 190 g (0.85 mol) 3-bromoquinoline-1-oxide in 500 mL concentrated sulphuric acid was heated to 90° C. Then 120 g (1.2 mol) potassium nitrate were added in small batches over a period of 100 min such that the temperature of the reaction did not rise above 95° C. The mixture was stirred for 3 h at 90° C.; it was left to cool to RT and the mixture was poured onto ice. The precipitated product was filtered off and the filter cake was washed with water. The residue was dissolved in dichloromethane and washed with saturated aqueous sodium hydrogen carbonate solution until the solution reacted in alkaline manner. The phases were separated and the aqueous phase was again extracted with dichloromethane. The combined organic phases were dried on sodium sulphate and evaporated down i.vac. After comminution of the residue and exhaustive drying i.vac. the product was obtained as a yellow solid.

Yield: 269 g (46% of theory)
ESI-MS: m/z=268/270 (M+H)⁺ (Br)
$R_f$=0.77 (silica gel, EtOAc)

Step 3 (1-benzylpiperidin-4-yl)-(4-nitro-1-oxyquinolin-3-yl)-amine

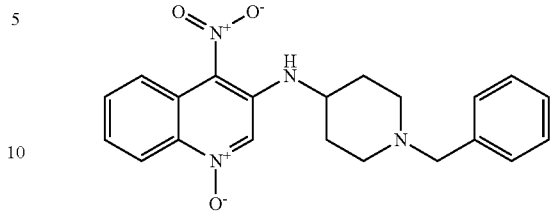

104 g (0.387 mol) 3-bromo-4-nitroquinoline-1-oxide were added to 320 mL (1.54 mol) of 4-amino-1-benzylpiperidine. Then 500 mL THF were added and the mixture was heated somewhat until the substances were fully dissolved. Then it was stirred for 3 h at 70° C. and the reaction mixture was then evaporated down i.vac. The residue obtained was dissolved in 2.5 L dichloromethane and washed with saturated aqueous sodium hydrogen carbonate solution. The aqueous phase was again extracted with 300 mL dichloromethane. Then the organic phases were combined, dried on sodium sulphate and evaporated down i.vac. The residue was dissolved in 250 mL methanol. The product precipitated as a solid was suction filtered and dried i. vac.

Yield: 104 g (71% of theory)
ESI-MS: m/z=379 (M+H)⁺
$R_f$ 0.75 (silica gel, EtOAc)

Step 4 N³-(1-benzylpiperidin-4-yl)quinoline-3,4-diamine

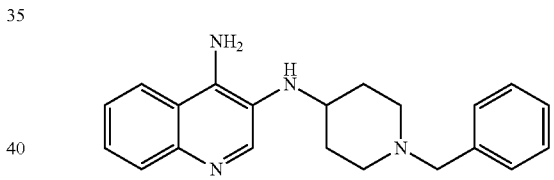

12 g rhodium charcoal (5%, moistened with water) were added to a solution of 76 g (0.20 mol) (1-benzylpiperidin-4-yl)-(4-nitro-1-oxyquinolin-3-yl)-amine in 1.0 L THF. The reaction was shaken for 4.5 h under hydrogen atmosphere (50 psi) at RT. The catalyst was filtered off and the solvent was eliminated i.vac. On account of its susceptibility to oxidation the crude product was used immediately for the next step.

Yield: 66.0 g (99% of theory)
$R_f$: 0.30 (silica gel, DCM/MeOH/cyc/NH₄OH=70:15:15:2)

Step 5 3-(1-benzylpiperidin-4-yl)-1,3-dihydroimidazo[4,5-c]quinolin-2-one

23 g (0.14 mol) 1,1'-carbonyldiimidazole were added to a solution of 9.0 g (27 mmol) N³-(1-benzylpiperidin-4-yl)-quinoline-3,4-diamine in 100 mL DMF. The mixture was heated to 100° C. and stirred for 1.5 h at this temperature. After the reaction mixture had cooled it was poured onto 300 mL water. The precipitated solid was filtered off, washed with water and dried at 30° C. i. vac. The residue was triturated with diethyl ether, suction filtered and the solid product was dried i. vac.

Yield: 7.42 g (77% of theory)
ESI-MS: m/z=359 (M+H)⁺

Step 6 3-piperidin-4-yl-1,3-dihydroimidazo[4,5-c]quinolin-2-one

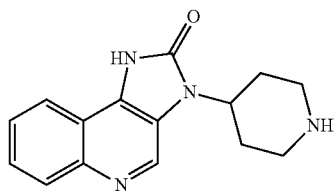 [SMILES: O=c1[nH]c2c3ccccc3ncc2n1C1CCNCC1]

A mixture of 44 g (0.12 mol) 3-(1-benzylpiperidin-4-yl)-1,3-dihydroimidazo[4,5-c]quinolin-2-one and 10 g palladium on charcoal (Pd/C 10%) in 500 mL methanol was hydrogenated for 16 h at 50° C. in a hydrogen atmosphere of 50 psi. After filtration of the reaction mixture the solvent was eliminated in vacuo. By the addition of isopropanol the product was precipitated out. The precipitate was filtered off and then dried in vacuo.

Yield: 31.2 g (95% of theory)
ESI-MS: m/z=269 (M+H)⁺
R_f: 0.20 (silica gel, DCM/MeOH/cyc/NH₄OH=70:15:15:2)

Intermediate 9

6-(6-chloro-pyrimidin-4-ylamino)-3,4-dimethyl-3H-benzoxazol-2-one

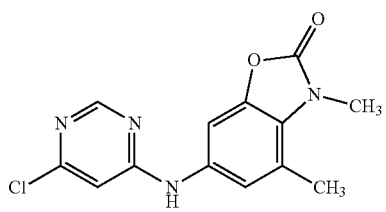 [SMILES: Cc1cc(Nc2cc(Cl)ncn2)cc2oc(=O)n(C)c12]

Step 1: 3,4-dimethyl-2-oxo-2,3-dihydro-benzoxazole-6-carboxylic acid azide

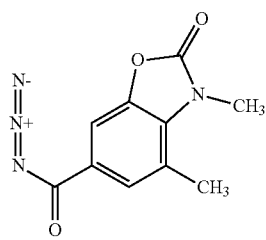 [SMILES: Cc1cc(C(=O)N=[N+]=[N-])cc2oc(=O)n(C)c12]

550 mg (2.50 mmol) 4-methyl-2-oxo-2,3-dihydro-benzoxazole-6-carboxylic acid azide and 400 mg (2.90 mmol) potassium carbonate were stirred in DMF for 20 min at RT. Then 0.200 mL (3.21 mmol) of methyl iodide were added and the mixture was stirred for 1.5 h at RT. Water was added to the reaction mixture, the precipitate formed was suction filtered and dried.

Yield: 530 mg (91% of theory)
ESI-MS: m/z=233 (M+H)⁺
R_t(HPLC): 1.39 min (method B)

Step 2: tert-butyl (3,4-dimethyl-2-oxo-2,3-dihydro-benzoxazol-6-yl)-carbamate

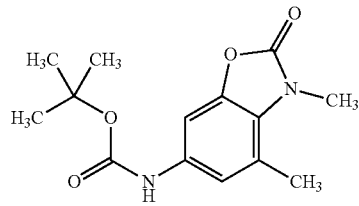 [SMILES: Cc1cc(NC(=O)OC(C)(C)C)cc2oc(=O)n(C)c12]

520 mg (2.20 mmol) 3,4-dimethyl-2-oxo-2,3-dihydro-benzoxazole-6-carboxylic acid azide were refluxed in 10 mL tert-butanol for 3.5 h. After cooling to RT the reaction mixture was evaporated down i.vac. and the residue was stirred in diethyl ether. The precipitate formed was suction filtered and dried.

Yield: 550 mg (79% of theory)
purity: 90%
ESI-MS: m/z=296 (M+NH₄)⁺
R_t(HPLC): 1.44 min (method B)

Step 3: 6-amino-3,4-dimethyl-3H-benzoxazol-2-one

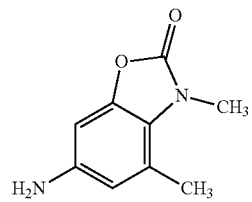

500 µL (6.58 mmol) TFA were added to 500 mg (1.80 mmol) tert-butyl (3,4-dimethyl-2-oxo-2,3-dihydro-benzoxazol-6-yl)-carbamate in 10 mL DCM and the mixture was stirred for 1.5 h at RT. Then the reaction mixture was evaporated down, the residue was made alkaline and extracted with DCM. The organic phase was dried on sodium sulphate, filtered and evaporated down.

Yield: 305 mg (95% of theory)
ESI-MS: m/z=179 (M+H)⁺
R_t(HPLC): 0.39 min (method B)

Step 4: 6-(6-chloro-pyrimidin-4-ylamino)-3,4-dimethyl-3H-benzoxazol-2-one

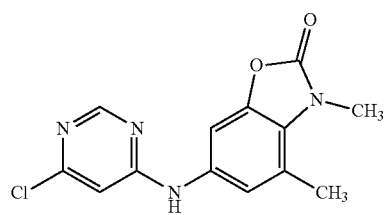 [SMILES: Cc1cc(Nc2cc(Cl)ncn2)cc2oc(=O)n(C)c12]

300 mg (1.70 mmol) 6-amino-3,4-dimethyl-3H-benzoxazol-2-one, 276 mg (1.90 mmol) 4,6-dichloropyrimidine and 0.77 mL (60 μmol) TEA were combined in 5.0 mL 1-butanol and the mixture was stirred for 1 h at 100° C. The reaction mixture was cooled to RT, evaporated down and the residue was triturated in diethyl ether. The precipitate was washed with water and dried i. vac.
Yield: 325 mg (66% of theory)
ESI-MS: m/z=291/3 (Cl) (M+H)+
$R_f$(HPLC): 1.28 min (method B)

Intermediate 10

(6-chloro-pyrimidin-4-yl)-(7-methyl-1H-indazol-5-yl)-amine

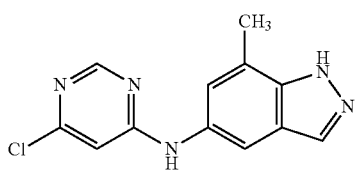 [SMILES: Cc1cc(Nc2cc(Cl)ncn2)cc2cn[nH]c12]

500 mg (3.40 mmol) 4,6-dichloropyrimidine, 500 mg (3.40 mmol) 7-methyl-1H-indazol-5-ylamine and 1.30 mL (7.60 mmol) DIPEA were combined in 5.0 mL DMF and refluxed for 5 h. The reaction mixture was cooled to RT and evaporated down i.vac. The residue was taken up in EtOAc and extracted several times with saturated sodium chloride solution. The organic phases were combined, dried on magnesium sulphate, filtered and evaporated down. The residue was stirred with DIPE, suction filtered and dried i. vac.
Yield: 800 mg (92% of theory)
ESI-MS: m/z=258/260 (Cl) (M−H)−

Intermediate 11

(6-iodo-pyrimidin-4-yl)-(1,2,7-trimethyl-1H-benzimidazol-5-yl)-amine

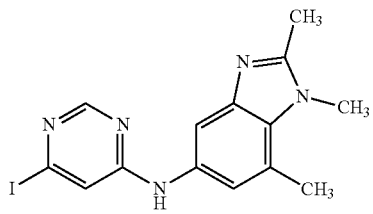 [SMILES: Cc1cc(Nc2cc(I)ncn2)cc2nc(C)n(C)c12]

Step 1:
(4-bromo-2-methyl-6-nitro-phenyl)-methyl-amine

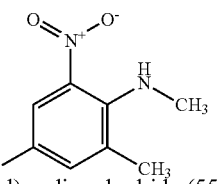

3.80 g (86.6 mmol) sodium hydride (55%, suspension in mineral oil) were added batchwise to 20.0 g (86.6 mmol) 4-bromo-2-methyl-6-nitroaniline in 250 mL DMF with slight cooling and the mixture was stirred for 30 min. Then 5.40 mL (86.6 mmol) methyl iodide were slowly added dropwise, the cooling was stopped and the mixture was stirred overnight at RT. Then water was slowly added while the mixture was cooled and it was extracted several times with EtOAc. The organic phases were combined, dried on sodium sulphate, filtered and evaporated down i.vac. The residue was recrystallised from DIPE, cooled and the precipitate was suction filtered and dried.
Yield: 17.0 g (80% of theory)
ESI-MS: m/z=244/46 (Br) (M+)
$R_f$(HPLC): 1.63 min (method B)

Step 2: 5-bromo-3,$N^2$-dimethyl-benzol-1,2-diamine

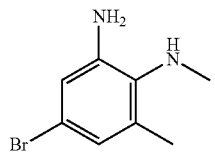

1.50 g (5.50 mmol) (4-bromo-2-methyl-6-nitro-phenyl)-methylamine were hydrogenated with 150 mg platinum charcoal in 20 mL EtOAc in a 50 psi hydrogen atmosphere for 2.5 h at RT. The catalyst was removed by suction filtering and the solution was concentrated by rotary evaporation.
Yield: 1.30 g (93% of theory)
purity: 85%
ESI-MS: m/z=215/17 (Br) (M+H)+
$R_f$(HPLC): 0.89 min (method B)

Step 3: 5-bromo-1,2,7-trimethyl-1H-benzimidazole

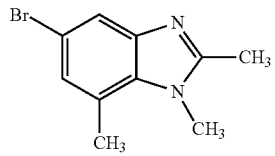

0.60 mL (6.5 mmol) acetic anhydride were added to 1.3 g (5.4 mmol) 5-bromo-3,$N^2$-dimethyl-benzol-1,2-diamine in 5.0 mL glacial acetic acid and the mixture was heated for 30 min to 130° C. Then conc. ammonia was slowly added dropwise and the mixture was stirred for 10 min. The precipitate was suction filtered and dried.
Yield: 1.40 g (93% of theory)
purity: 85%
ESI-MS: m/z=239/41 (Br) (M+H)+
$R_f$(HPLC): 0.94 min (method B)

Step 4: 5-azido-1,2,7-trimethyl-1H-benzimidazole

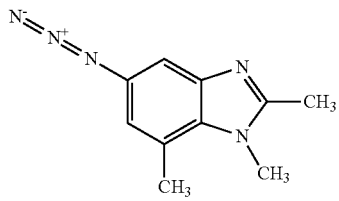

0.59 g (2.50 mmol) 5-bromo-1,2,7-trimethyl-1H-benzimidazole, 0.32 g (4.9 mmol) sodium azide, 75 mg (0.50 mmol) trans-(1R,2R)—N,N'-bismethyl-1,2-cyclohexane-diamine, 50 mg (0.30 mmol) copper(I) iodide and 50 mg (0.30 mmol) L-ascorbic acid sodium salt were added to 2.0 ml of a mixture of ethanol and water (EtOH/water=7/3) and the mixture was stirred for 1 h at 100° C. Then the EtOH was distilled off and the residue was mixed with water. The precipitate formed was suction filtered, washed with water and diethyl ether and dried.
Yield: 0.30 g (60% of theory)
ESI-MS: m/z=202 (M+H)+
$R_f$(HPLC): 0.85 min (method B)

Step 5: 1,2,7-trimethyl-1H-benzimidazol-5-ylamine hydrochloride

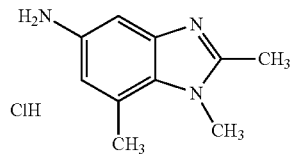

Under a nitrogen atmosphere, 200 mg (1.00 mmol) 5-azido-1,2,7-trimethyl-1H-benzimidazole, 420 mg (1.50 mmol) tris(2-carboxyethyl)phosphine-hydrochloride, 1.5 mL dioxane and 0.5 mL E-water were combined and the mixture was stirred at RT overnight. Then the reaction mixture was acidified and extracted with EtOAc. The aqueous phase was made alkaline with aqueous sodium hydroxide solution and extracted with DCM. The organic phase was dried on sodium sulphate, filtered and evaporated down. The residue was combined with ethereal hydrochloric acid and the hydrochloride that settled out as precipitate was suction filtered and dried.
Yield: 155 mg (74% of theory)
ESI-MS: m/z=176 (M+H)$^+$
R$_f$(HPLC): 0.27 min (method B)

Step 6: (6-iodo-pyrimidin-4-yl)-(1,2,7-trimethyl-1H-benzimidazol-5-yl)-amine

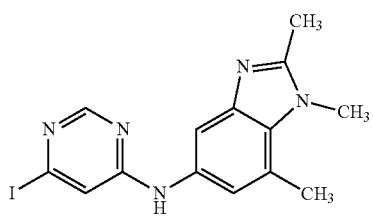 [SMILES: Cc1cc(Nc2cc(I)ncn2)cc2nc(C)n(C)c12]

150 mg (0.700 mmol) 1,2,7-trimethyl-1H-benzimidazol-5-ylamine hydrochloride, 260 mg (0.800 mmol) 4,6-diiodopyrimidine, 0.300 mL (2.00 mmol) TEA and 5.0 mL 1-butanol were combined and stirred for 1 h at RT. The reaction mixture was evaporated down and the residue was extracted with DCM and 1N aqueous sodium hydroxide solution. The organic phase was dried on sodium sulphate, filtered and evaporated down.
Yield: 286 mg (85% of theory)
purity: 80%
ESI-MS: m/z=380 (M+H)$^+$
R$_f$(HPLC): 0.97 min (method B)

Intermediate 12

N-(6-chloro-pyrimidin-4-yl)-N-(3,4-dimethyl-2-oxo-2,3-dihydro-benzoxazol-6-yl)-acetamide

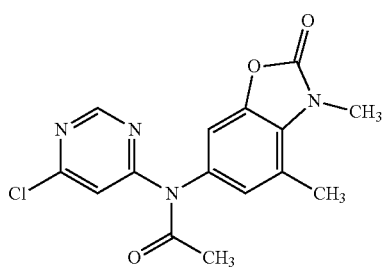 [SMILES: CC(=O)N(c1cc(C)c2c(c1)oc(=O)n2C)c1cc(Cl)ncn1]

100 mg (0.300 mmol) 6-(6-chloro-pyrimidin-4-ylamino)-3,4-dimethyl-3H-benzoxazol-2-one were placed together with 1.00 ml (10.6 mmol) acetic anhydride in a microwave container and stirred for 20 min at 150° C. The reaction mixture was diluted with water and extracted with DCM. The organic phase was separated off, dried and evaporated down. The residue was purified by preparative HPLC. The product-containing fractions were combined and evaporated down.
Yield: 70 mg (61% of theory)
ESI-MS: m/z=333/5 (Cl) (M+H)$^+$
R$_f$(HPLC): 1.31 min (method B)

Intermediate 13

(6-chloro-pyrimidin-4-yl)-(2,7-dimethyl-benzoxazol-5-yl)-amine

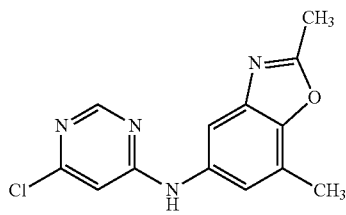 [SMILES: Cc1nc2cc(Nc3cc(Cl)ncn3)cc(C)c2o1]

Step 1: 2,4-diamino-6-methyl-phenol

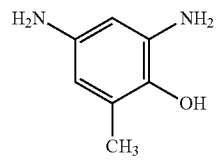

11.0 g (50.0 mmol) 4,6-dinitro-o-cresol were hydrogenated with 2.0 g Raney nickel in 100 mL MeOH under a 5 bar hydrogen atmosphere for 4 h at RT. Then the catalyst was suction filtered and the filtrate was concentrated by rotary evaporation.
Yield: 7.5 g (98% of theory)

Step 2: 2,7-dimethyl-benzoxazol-5-ylamine

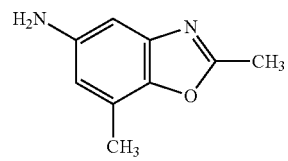

1.00 g (7.20 mmol) 2,4-diamino-6-methyl-phenol, 5.00 mL acetic acid and 15.0 mL (81.8 mmol) triethylorthoacetate were combined and refluxed. The reaction mixture was cooled to RT overnight and evaporated down. The residue was extracted with 0.5 N sodium hydroxide solution and EtOAc and the organic phase was evaporated down. The flask residue was triturated with diethyl ether and the precipitate formed was suction filtered. The mother liquor was evaporated down and the residue was purified by flash chromatography. The product-containing fractions were combined and evaporated down.
Yield: 600 mg (26% of theory)
purity: 50%
ESI-MS: m/z=162 (M+H)$^+$
R$_f$(HPLC): 0.70 min (method B)

Step 3: (6-chloro-pyrimidin-4-yl)-(2,7-dimethyl-benzoxazol-5-yl)-amine

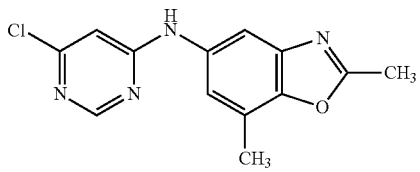 [SMILES: Cc1nc2cc(Nc3cc(Cl)ncn3)cc(C)c2o1]

600 mg (1.90 mmol) 2,7-dimethyl-benzoxazol-5-ylamine, 400 mg (2.70 mmol) 4,6-dichloropyrimidine and 1.50 mL (11.0 mmol) TEA were combined in 8.0 mL 1-butanol and stirred for 2 h at 90° C. The reaction mixture was cooled to RT and purified by preparative HPLC. The product-containing fractions were combined, evaporated down and the residue was triturated with diethyl ether, suction filtered and dried.

Yield: 120 mg (24% of theory)
ESI-MS: m/z=275/7 (Cl) (M+H)$^+$
R$_t$(HPLC): 1.33 min (method B)

Intermediate 14

4-(6-chloro-pyrimidin-4-ylamino)-2,6-dimethyl-phenol

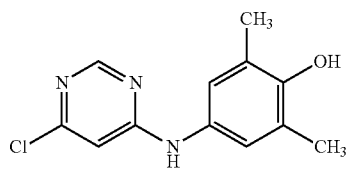 [SMILES: Cc1cc(Nc2cc(Cl)ncn2)cc(C)c1O]

Step 1: 4-amino-2,6-dimethyl-phenol

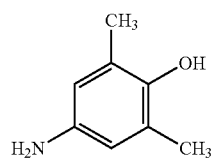

3.00 g (18.0 mmol) 2,6-dimethyl-4-nitrophenol were hydrogenated with 0.50 g palladium on charcoal (Pd/C, 10%) in 50 mL MeOH in a 3 bar hydrogen atmosphere at RT. After the end of the reaction the catalyst was suction filtered and the filtrate was concentrated by rotary evaporation. The residue was triturated with DIPE and the precipitate was suction filtered and dried i. vac.

Yield: 2.10 g (85% of theory)
ESI-MS: m/z=138 (M+H)$^+$
R$_f$: 0.5 (silica gel: DCM/MeOH/cyc/NH$_4$OH=70:15:15:2)

Step 2: 4-(6-chloro-pyrimidin-4-ylamino)-2,6-dimethyl-phenol

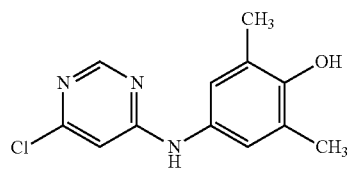 [SMILES: Cc1cc(Nc2cc(Cl)ncn2)cc(C)c1O]

250 mg (1.68 mmol) 4,6-dichloropyrimidine, 240 mg (1.75 mmol) 4-amino-2,6-dimethyl-phenol and 0.650 mL (3.78 mmol) DIPEA in 5 mL DMF were combined and refluxed for 5 h. The reaction mixture was evaporated down, the residue was taken up in EtOAC and extracted with saturated sodium chloride solution. The organic phase was dried on magnesium sulphate, filtered and evaporated down. The residue was stirred with DIPE, the precipitate formed was suction filtered and dried i. vac.

Yield: 260 mg (62% of theory)
ESI-MS: m/z=250/252 (Cl) (M+H)$^+$
R$_f$: 0.3 (silica gel: PE/EtOAc=2:1)

Intermediate 15

5-amino-1,3-dihydrospiro[indene-2,3'-pyrrolo[2,3-b]pyridin]-2'(1'H)-one

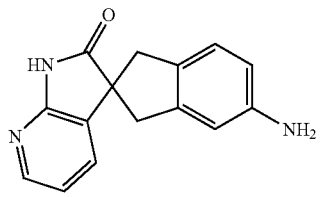 [SMILES: Nc1ccc2c(c1)CC1(C2)C(=O)Nc2ncccc21]

This compound and its precursors were synthesised analogously to WO 2006/31513.

Intermediate 16

6-(6-chloro-pyrimidin-4-ylsulphanyl)-4-methyl-3H-benzoxazol-2-one

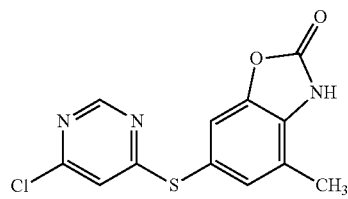 [SMILES: Cc1cc(Sc2cc(Cl)ncn2)cc2oc(=O)[nH]c12]

Step 1:
4-methyl-2-oxo-2,3-dihydro-benzoxazol-6-sulphonic acid chloride

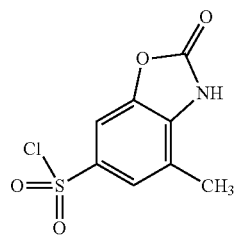

1.10 g (6.60 mmol) 4-methyl-3H-benzoxazol-2-one in 5.0 mL (75 mmol) chlorosulphonic acid were stirred for 2 h at RT. Then the reaction mixture was very slowly added dropwise to a large amount of ice and stirred at RT. The precipitate formed was suction filtered and dried.
Yield: 1.4 g (85% of theory)
ESI-MS: m/z=247 (M)$^+$
$R_t$: 1.25 min (method B)

Step 2: 6-mercapto-4-methyl-3H-benzoxazol-2-one

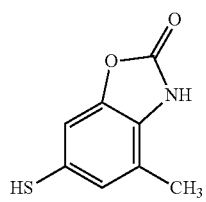

Under a nitrogen atmosphere a solution of 1.40 g (5.60 mmol) 4-methyl-2-oxo-2,3-dihydro-benzoxazol-6-sulphonic acid chloride and 1.60 g (16.8 mmol) N,N-dimethylacetamide in 1,2-dichloroethane was slowly added dropwise to 1.30 g (19.9 mmol) zinc and 2.40 mL (19.5 mmol) dichlorodimethylsilane in 20 mL of 1,2-dichloroethane. The reaction mixture was stirred for 2 h at 75° C. After cooling the mixture was filtered and the filtrate was evaporated down. The residue remaining was combined with MeOH, the precipitate formed was filtered and the filtrate was evaporated down. The residue was further reacted as the crude product.
Yield: 1.0 g (quantitative)
ESI-MS: m/z=180 (M−H)$^−$
$R_t$: 1.23 (method B)

Step 3: 6-(6-chloro-pyrimidin-4-ylsulphanyl)-4-methyl-3H-benzoxazol-2-one

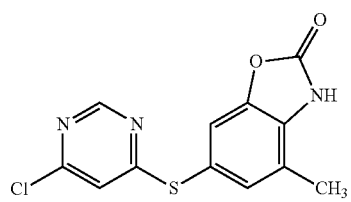 [SMILES: Cc1cc(Sc2cc(Cl)ncn2)cc2oc(=O)[nH]c12]

820 mg (5.50 mmol) 4,6-dichloropyrimidine, 1.00 g (5.50 mmol) 6-mercapto-4-methyl-3H-benzoxazol-2-one and 5.00 mL (29.1 mmol) DIPEA were combined in 20 mL DCM and stirred overnight at 40° C. The reaction mixture was evaporated down, the residue was taken up in EtOAc and combined with sodium hydrogen carbonate solution. The precipitate formed was suction filtered, washed with copious amounts of water and dried.
Yield: 185 mg (9% of theory)
purity: 80%
ESI-MS: m/z=294 (M+H)$^+$ Intermediate 17

6-(6-chloro-2-methyl-pyrimidin-4-yloxy)-4-methyl-3H-benzoxazol-2-one

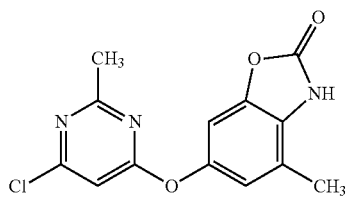 [SMILES: Cc1nc(Cl)cc(Oc2cc(C)c3[nH]c(=O)oc3c2)n1]

Step 4: 6-(6-chloro-2-methyl-pyrimidin-4-yloxy)-4-methyl-3H-benzoxazol-2-one

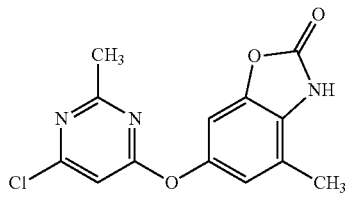 [SMILES: Cc1nc(Cl)cc(Oc2cc(C)c3[nH]c(=O)oc3c2)n1]

100 mg (0.724 mmol) potassium carbonate and 110 mg (0.655 mmol) 4,6-dichloro-2-methyl-pyrimidine were added to 100 mg (0.575 mmol) 6-hydroxy-4-methyl-3H-benzoxazol-2-one in 1.5 mL DMF and the mixture was stirred for 2 h at RT. Then 15 mL water were added and the mixture was stirred overnight at RT. The precipitate formed was suction filtered, washed with water and dried i. vac.
Yield: 145 mg (86% of theory)
ESI-MS: m/z=292(M+H)$^+$
$R_t$(HPLC): 1.26 min (method B)

Intermediate 18

Spiro[benzo[d][1,3]oxazin-4,4'-piperidin]-2(1H)-one hydrochloride

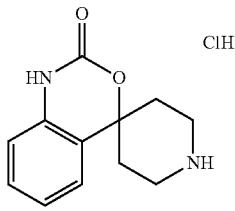 [SMILES: O=C1Nc2ccccc2C2(CCNCC2)O1 ; Cl]

This compound and its precursors were synthesised as described in U.S. Pat. No. 6,436,962.

ESI-MS: m/z=219 (M+H)+

R$_f$: 0.14 (silica gel, DCM/cyc/MeOH/NH$_4$OH=70/15/15/2)

Intermediate 19

2-(6-chloro-pyrimidin-4-yloxy)-quinoxaline

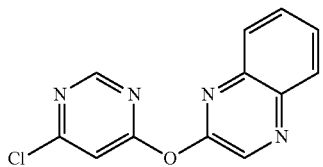 [SMILES: Clc1cc(Oc2cnc3ccccc3n2)ncn1]

40 mg (0.92 mmol) sodium hydride (55%, suspension in mineral oil) were added to 0.10 g (0.68 mmol) 2-hydroxyquinoxaline in 1.5 mL DMF and the mixture was stirred for 15 min. Then 0.11 g (0.69 mmol) 4,6-dichloropyrimidine were added and the mixture was stirred overnight at RT. The reaction mixture was purified by preparative HPLC-MS. The product-containing fractions were combined, the acetonitrile was eliminated i.vac., and the precipitated product was suction filtered and dried.

Yield: 24 mg (13% of theory)

ESI-MS: m/z=259 (M+H)+

Intermediate 20

4-amino-3-methyl-5-nitro-phenol

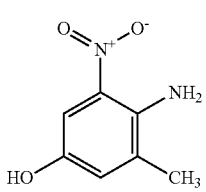

Step 1: 4-acetylamino-3-methyl-phenyl acetate

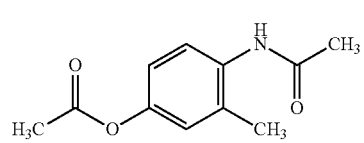

4.66 g (37.5 mmol) 4-amino-3-methylphenol, 5.00 mL glacial acetic acid, 0.500 g (6.09 mmol) sodium acetate and 7.87 mL (83.3 mmol) acetic anhydride were combined and stirred for 1 h at 125° C. After cooling to RT, ice water was added to the reaction mixture. The precipitate formed was suction filtered, washed with water and dried under HV.

Yield: 5.20 g (67% of theory)

ESI-MS: m/z=208 (M+H)+

R$_t$(HPLC): 0.92 min (method B)

Step 2: 4-acetylamino-3-methyl-5-nitro-phenyl acetate

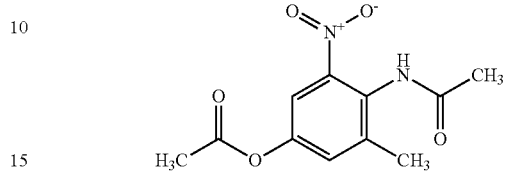

While cooling with ice 748 mg (3.61 mmol) 4-acetylamino-3-methyl-phenyl acetate were added batchwise to 0.60 mL (14.4 mmol) nitric acid (90%). After the addition had ended the cooling was stopped and the mixture was stirred for 2 h at RT. Then the reaction mixture was poured onto ice water, the precipitate formed was suction filtered, washed with water and dried under HV.

Yield: 550 mg (60% of theory)

ESI-MS: m/z=253 (M+H)+

R$_t$(HPLC): 0.98 min (method B)

Step 3: 4-amino-3-methyl-5-nitro-phenol

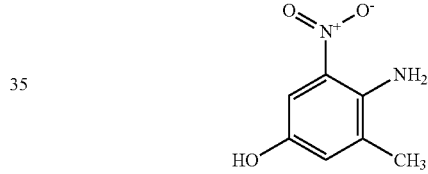

20.4 g (80.7 mmol) 4-acetylamino-3-methyl-5-nitro-phenyl acetate in 100 mL semi-concentrated aqueous hydrochloric acid were refluxed for 2 h. Then the reaction mixture was evaporated down, the residue was triturated with acetone and suction filtered. After washing with acetone and diethyl ether the precipitate was dried under HV. The mother liquor was evaporated down, the residue was taken up in water and freeze-dried.

Yield: 6.00 g (44% of theory)

ESI-MS: m/z=169 (M+H)+

R$_t$(HPLC): 0.96 min (method B)

Intermediate 21

3-{1-[6-(3,4-diamino-5-methyl-phenoxy)-pyrimidin-4-yl]-piperidin-4-yl}-7-methoxy-1,3,4,5-tetrahydro-benzo[d][1,3]diazepin-2-one

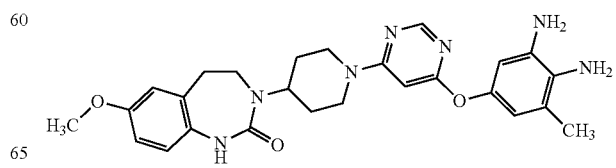

Step 1: 4-(6-chloro-pyrimidin-4-yloxy)-2-methyl-6-nitro-phenylamine

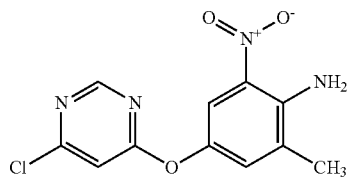 [SMILES: Cc1cc(Oc2cc(Cl)ncn2)cc([N+](=O)[O-])c1N]

1.66 g (12.0 mmol) potassium carbonate were added to 0.922 g (6.00 mmol) 4,6-dichloropyrimidine and 1.11 g (6.60 mmol) 4-amino-3-methyl-5-nitro-phenol in 1.5 mL DMF and the mixture was stirred for 6 h at 50° C. Then the mixture was added to ice water and extracted several times with EtOAc. The combined organic phases were dried on sodium sulphate, evaporated down and purified by flash chromatography. The product-containing fractions were combined and evaporated down. The residue was triturated with EtOAc, suction filtered and dried under HV.

Yield: 0.50 g (30% of theory)
ESI-MS: m/z=281 (M+H)$^+$
R$_t$(HPLC): 1.43 min (method B)

Step 2: 3-{1-[6-(4-amino-3-methyl-5-nitro-phenoxy)-pyrimidin-4-yl]-piperidin-4-yl}-7-methoxy-1,3,4,5-tetrahydro-benzo[d][1,3]diazepin-2-one

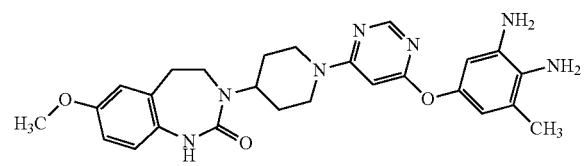 [SMILES: COc1ccc2c(c1)CCN(C1CCN(c3cc(Oc4cc(C)c(N)c(N)c4)ncn3)CC1)C(=O)N2]

496 mg (1.80 mmol) 7-methoxy-3-piperidin-4-yl-1,3,4,5-tetrahydro-1,3-benzodiazepin-2-one, 480 mg (1.71 mmol) 4-(6-chloro-pyrimidin-4-yloxy)-2-methyl-6-nitro-phenylamine and 0.697 mL (4.00 mmol) DIPEA were combined in 10.0 mL DMF and stirred overnight at RT. The reaction mixture was added to ice water, the precipitate formed was suction filtered, washed with water and dried under HV.

Yield: 840 mg (90% of theory)
ESI-MS: m/z=520 (M+H)$^+$
R$_t$(HPLC): 1.45 min (method B)

Step 3: 3-{1-[6-(3,4-diamino-5-methyl-phenoxy)-pyrimidin-4-yl]-piperidin-4-yl}-7-methoxy-1,3,4,5-tetrahydro-benzo[d][1,3]diazepin-2-one 830 mg (1.60 mmol) 3-{1-[6-(4-amino-3-methyl-5-nitro-phenoxy)-pyrimidin-4-yl]-piperidin-4-yl}-7-methoxy-1,3,4,5-tetrahydro-benzo[d][1,3]diazepin-2-one in 20 mL MeOH were combined with 100 mg palladium on charcoal (Pd/C 10%) and hydrogenated for 8 h under a hydrogen atmosphere of 50 psi. After the catalyst had been removed by suction filtering, the filtrate was evaporated down and the residue was reacted further as the crude product.

Yield: 800 mg (quantitative)

Intermediate 22

3,4-diamino-5-methyl-phenol

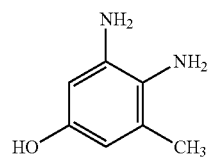

6.00 g (35.7 mmol) 4-amino-3-methyl-5-nitro-phenol in 200 mL MeOH was combined with 0.600 g palladium on charcoal (Pd/C 10%) and hydrogenated for 4 h under a hydrogen atmosphere of 60 psi at 50° C. The catalyst was removed by suction filtering, the filtrate was evaporated down and the residue was dried under HV.

Yield: 4.90 g (99% of theory)
ESI-MS: m/z=139 (M+H)$^+$
R$_t$(HPLC): 0.26 min and 0.69 min (method H) (salt effects)

Intermediate 23

6-(6-chloro-pyrimidin-4-yloxy)-2,4-dimethyl-1H-benzimidazole

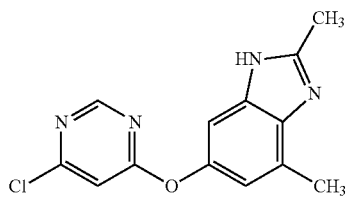 [SMILES: Cc1nc2c(C)cc(Oc3cc(Cl)ncn3)cc2[nH]1]

Step 1: 2,7-dimethyl-3H-benzimidazol-5-ol

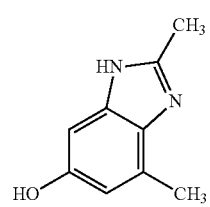

0.553 g (4.00 mml) 3,4-diamino-5-methyl-phenol in 5.00 mL glacial acetic acid were boiled for 3 h. Then the reaction mixture was evaporated down and dried under HV.

Yield: 0.65 g (quantitative)
ESI-MS: m/z=163 (M+H)+
$R_f$(HPLC): 0.50 min (method I)

Step 2: 6-(6-chloro-pyrimidin-4-yloxy)-2,4-dimethyl-1H-benzimidazole

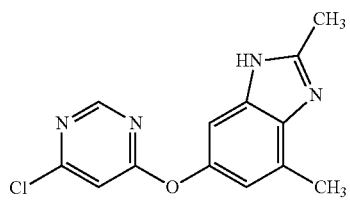

1.66 g (12.0 mmol) potassium carbonate were added to 0.676 g (4.40 mmol) 4,6-dichloropyrimidine and 0.649 g (4.00 mmol) 2,7-dimethyl-3H-benzimidazol-5-ol in 5.00 mL DMF and stirred for 8 h at 50° C. Then the mixture was added to ice water and extracted several times with EtOAc. The combined organic phases were dried on sodium sulphate, evaporated down and purified by preparative HPLC-MS. The product-containing fractions were combined and the acetonitrile was evaporated down. The residue was made alkaline with 1N aqueous sodium hydroxide solution and extracted with EtOAc. The organic phase was dried on sodium sulphate, filtered, evaporated down and dried under HV.
Yield: 0.50 g (41% of theoretical)
ESI-MS: m/z=275 (M+H)+
$R_f$(HPLC): 0.90 min (method B)

Intermediate 24

Spiro[piperidin-4,4'-pyrido[2,3-d][1,3]oxazin]-2'(1'H)-one hydrochloride

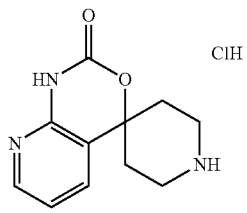 [SMILES: O=C1Nc2ncccc2C2(CCNCC2)O1 ; Cl]

This compound and its precursors were synthesised as described in WO 2006/99268.
ESI-MS: m/z=220 (M+H)+
$R_f$(HPLC): 0.90 min (method C)

Intermediate 25

4-(6-chloro-pyrimidin-4-yloxy)-2-methyl-quinoline

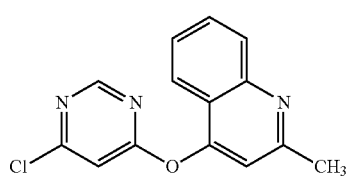

36 mg (0.83 mmol) sodium hydride (55%, suspension in mineral oil) were added to 0 10 g (0.68 mmol) 2-hydroxy-2-methylquinoline in 1.5 mL DMF and the mixture was stirred for 15 min. Then 97 mg (0.63 mmol) 4,6-dichloropyrimidine were added and the mixture was stirred overnight at RT. The reaction mixture was mixed with water and left to stand overnight. The precipitate formed was suction filtered, washed with water and dried i. vac.
Yield: 140 mg (65% of theory)
purity: 80%
ESI-MS: m/z=272 (M+H)+
$R_f$(HPLC): 1.03 min (method B)

Intermediate 26

6-(6-chloro-pyrimidin-4-yloxy)-4-methyl-1H-benzimidazole

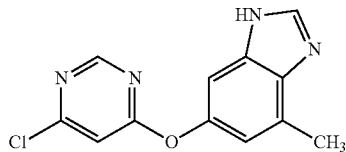 [SMILES: Cc1cc(Oc2cc(Cl)ncn2)cc2[nH]cnc12]

Step 1: 7-methyl-3H-benzimidazol-5-ol

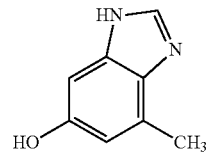

276 mg (2.00 mmol) 3,4-diamino-5-methyl-phenol in 3.00 mL formic acid (98%) were refluxed for 1 h. The reaction mixture was then evaporated down and the residue was dried under HV.
Yield: 295 mg (quantitative)
ESI-MS: m/z=149 (M+H)+
$R_f$(HPLC): 0.36 min (method B)

Step 2: 6-(6-chloro-pyrimidin-4-yloxy)-4-methyl-1H-benzimidazole

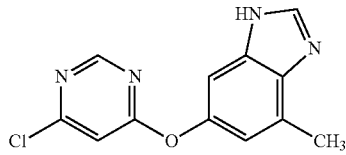

0.830 g (6.00 mmol) potassium carbonate were added to 307 mg (2.00 mmol) 4,6-dichloropyrimidine and 295 mg (2.00 mmol) 7-methyl-3H-benzimidazol-5-ol in 1.50 mL DMF and the mixture was stirred for 8 h at 50° C. Then the mixture was added to ice water added and extracted several times with EtOAc. The combined organic phases were dried on sodium sulphate, evaporated down and purified by preparative HPLC-MS. The product-containing fractions were combined and the acetonitrile was evaporated down. The residue was made alkaline with 1N aqueous sodium hydroxide solution and extracted with EtOAc. The organic phase was dried on sodium sulphate, filtered, evaporated down and dried under HV.
Yield: 120 mg (23% of theory)
ESI-MS: m/z=261 (M+H)+
$R_f$(HPLC): 0.90 min (method B)

Intermediate 27

6-chloro-N-(2,6-dimethylpyridin-4-yl)pyrimidin-4-amine

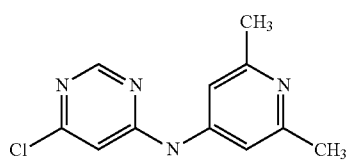 [SMILES: Cc1cc(Nc2cc(Cl)ncn2)cc(C)n1]

0.12 g (0.97 mmol) 2,6-dimethyl-4-hydroxypyridine and 55 mg (1.26 mmol) sodium hydride (60% dispersion in mineral oil) were dissolved in 1.5 mL DMF and stirred for 15 min. 0.15 g (0.98 mmol) 4,6-dichloropyrimidine were added and the mixture was stirred overnight at RT. The reaction mixture was acidified with a 4M hydrochloric acid, filtered and purified by preparative HPLC-MS. The fractions containing product were combined and freeze-dried.
Yield: 105 mg (46% of theory)
ESI-MS: m/z=236/238 (Cl) (M+H)$^+$
$R_t$ (HPLC): 0.78 (method B)

Intermediate 28

6-(2-amino-6-chloropyrimidin-4-yloxy)-4-methyl-benzo[d]oxazol-2(3H)-one

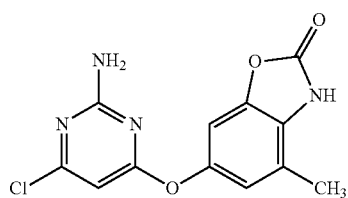

Step 1: 4-methylbenzo[d]oxazol-2(3H)-one

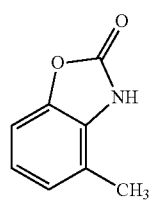

50.0 g (0.39 mol) 2-amino-m-cresol and 0.21 L (1.23 mol) DIPEA in 400 mL dichloromethane were cooled to 0° C. A mixture of 76.0 g (0.45 mol) CDI in 1.2 L dichloromethane was added dropwise and stirred overnight at RT. The reaction mixture was washed with a 1M KHSO$_4$ solution and water. The organic phase was separated off and evaporated down i.vac. The residue was combined with boiling ethyl acetate and while the mixture cooled PE was added dropwise. The precipitate formed was suction filtered, washed with PE and dried.

Yield: 42.62 g (73% of theory)
ESI-MS: m/z=150 (M+H)$^+$

Step 2: 6-acetyl-4-methylbenzo[d]oxazol-2(3H)-one

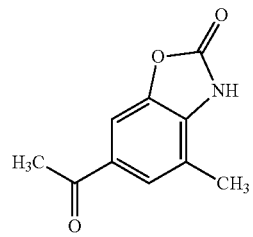

20.0 g (149.99 mmol) aluminium(III) chloride were combined with 5.0 mL DMF, with cooling. After 15 min stirring, first of all 5.0 g (33.52 mmol) 4-methylbenzo[d]oxazol-2(3H)-one and then 5.0 mL (52.90 mmol) acetanhydride were added and the mixture was stirred for 1 h at 80° C. The cooled reaction mixture was mixed with water. The precipitate formed was suction filtered, washed and dried.
Yield: 4.40 g (58% of theory)
ESI-MS: m/z=192 (M+H)$^+$
$R_t$(HPLC): 1.02 min (method B)

Step 3: 4-methyl-2-oxo-2,3-dihydrobenzo[d]oxazol-6-yl-acetate

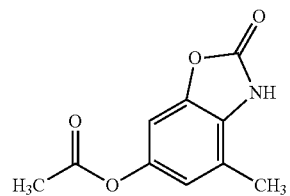

Under a nitrogen atmosphere 4.40 g (19.56 mmol) 6-acetyl-4-methylbenzo[d]oxazol-2(3H)-on were added to 50.0 mL AcOH and combined with 4.65 g (26.93 mmol) metachloroperbenzoic acid. After the mixture had been stirred overnight at 50° C., another 1.0 g (5.79 mmol) metachloroperbenzoic acid were added and the mixture was stirred for a further 3 h at 60° C. The reaction mixture was evaporated down i.vac. and the residue was taken up in ethyl acetate. The organic phase was washed with saturated Na$_2$SO$_3$ solution and saturated NaHCO$_3$ solution and then evaporated down.
Yield: 4.20 g (93% of theory)
ESI-MS: m/z=208 (M+H)$^+$
$R_t$(HPLC): 1.07 min (method B)

Step 4: 6-hydroxy-4-methylbenzo[d]oxazol-2(3H)-one

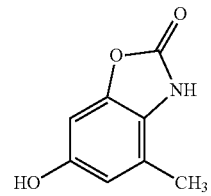

4.20 g (18.24 mmol) 4-methyl-2-oxo-2,3-dihydrobenzo[d]oxazol-6-yl-acetate in 50.0 mL of a 4M hydrochloric acid were stirred for 3 h at 80° C. The reaction mixture was cooled to RT and the precipitate formed was suction filtered. The substance obtained was purified by chromatography. The fractions containing product were combined and evaporated down i.vac.

Yield: 2.10 g (70% of theory)
ESI-MS: m/z=166 (M+H)$^+$
$R_t$(HPLC): 0.75 min (method B)

Step 5: 6-(2-amino-6-chloropyrimidin-4-yloxy)-4-methylbenzo[d]oxazol-2(3H)-one

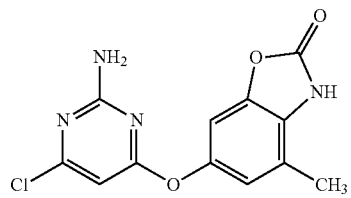

0.20 g (1.15 mmol) 6-hydroxy-4-methylbenzo[d]oxazol-2(3H)-one and 0.19 g (1.16 mmol) 2-amino-4,6-dichloropyrimidine in 3.0 mL DMF were combined with 0.22 g (1.59 mmol) potassium carbonate and stirred overnight at 60° C. Then water was added and the precipitate formed was suction filtered, washed and dried. The substance was purified by preparative HPLC-MS. The fractions containing product were combined and evaporated down i.vac.

Yield: 70 mg (20% of theory)
ESI-MS: m/z=293 (M+H)$^+$
$R_t$(HPLC): 1.22 min (method B)

Intermediate 29

6-(6-chloropyrimidin-4-yloxy)-2-(methoxymethyl)-4-methyl-1H-benzo[d]imidazole

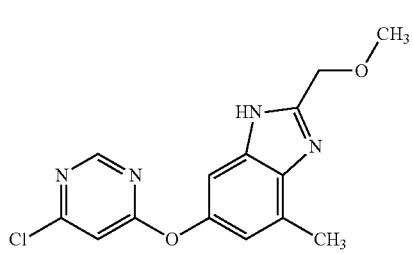 [SMILES: COCc1nc2c(C)cc(Oc3cc(Cl)ncn3)cc2[nH]1]

Step 1: 2-(methoxymethyl)-4-methyl-1H-benzo[d]imidazol-6-ol

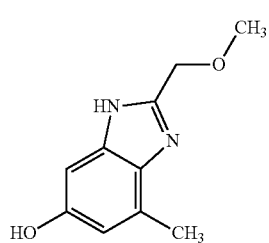

0.55 g (4.00 mmol) 3,4-diamino-5-methyl-phenol and 1.57 mL (20.00 mmol) methoxy-acetic acid were stirred for 1 h at 120° C. Then the reaction mixture was evaporated down and further reacted as crude product.

Yield: 0.77 g (quantitative)
ESI-MS: m/z=193 (M+H)$^+$
$R_t$(HPLC): 0.65 min (method B)

Step 2: 6-(6-chloropyrimidin-4-yloxy)-2-(methoxymethyl)-4-methyl-1H-benzo[d]-imidazole

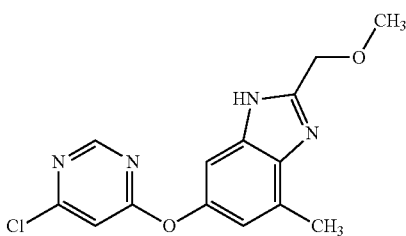 [SMILES: COCc1nc2c(C)cc(Oc3cc(Cl)ncn3)cc2[nH]1]

0.77 g (4.00 mmol) 2-(methoxymethyl)-4-methyl-1H-benzo[d]imidazol-6-ol and 0.68 g (4.40 mmol) 4,6-dichloropyrimidine in 5.0 mL DMF were combined with 1.66 g (12.0 mmol) potassium carbonate and stirred for 8 h at 70° C. Then ice water was added and the substance was extracted with ethyl acetate and concentrated by rotary evaporation i.vac. The residue was purified by preparative HPLC-MS. The fractions containing product were combined and evaporated down i.vac.

Yield: 0.10 g (7.5% of theory)
ESI-MS: m/z=305 (M+H)$^+$
$R_t$(HPLC): 0.99 min (method B)

Intermediate 30

6-(6-chloro-2-methoxypyrimidin-4-yloxy)-4-methyl-benzo[d]oxazol-2(3H)-one

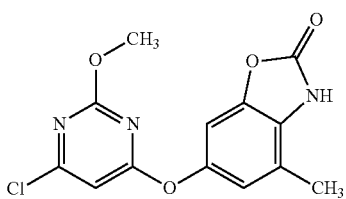

Step 1: 2-methoxypyrimidine-4,6-diol

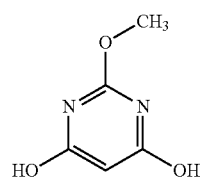

Under a nitrogen atmosphere 3.10 mL (27.0 mmol) dimethylmalonate, 3.00 g (27.1 mmol) o-methylisourea hydrochloride and 15.0 mL (80.8 mmol) sodium methoxide solution (30%) were refluxed for 1.25 h with stirring. The reaction mixture was cooled. The precipitate formed was suction filtered, washed and dried.

Yield: 2.27 g (30% of theory)
ESI-MS: m/z=143 (M+H)$^+$

Step 2: 4,6-dichloro-2-methoxypyrimidine

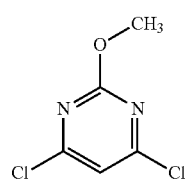

2.25 g (7.92 mmol) 2-methoxypyrimidine-4,6-diol and 10.0 mL (108.92 mmol) phosphorus oxychloride were boiled for 2 h. The reaction mixture was poured onto alkaline ice water and made alkaline with NaOH. The aqueous phase was extracted with DCM. The organic phase was separated off, dried and evaporated down i.vac.

Yield: 0.20 g (14% of theory)
ESI-MS: m/z=179 (M+H)$^+$
$R_t$(HPLC): 1.38 min (method B)

Step 3: 6-(6-chloro-2-methoxypyrimidin-4-yloxy)-4-methylbenzo[d]oxazol-2(3H)-one

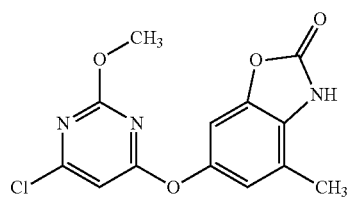 [SMILES: COc1nc(Cl)cc(Oc2cc(C)c3[nH]c(=O)oc3c2)n1]

0.19 g (1.01 mmol) 4,6-dichloro-2-methoxypyrimidine, 0.18 g (1.04 mmol) 6-hydroxy-4-methyl-3H-benzoxazol-2-one and 0.15 g (1.09 mmol) potassium carbonate in 1.5 mL DMF were stirred for 2 h at RT. Then water was added and the precipitate formed was suction filtered, washed and dried.

Yield: 145 mg (42% of theory)
ESI-MS: m/z=308/310 (Cl) (M+H)$^+$
$R_t$(HPLC): 1.41 min (method B)

Intermediate 31

6-(6-chloropyrimidin-4-yloxy)-2-cyclopropyl-4-methyl-1H-benzo[d]imidazole

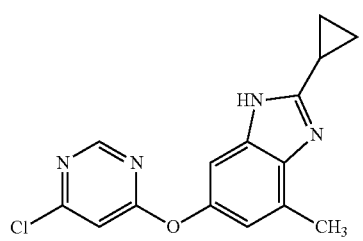 [SMILES: Cc1cc(Oc2cc(Cl)ncn2)cc2[nH]c(C3CC3)nc12]

Step 1: 2-cyclopropyl-4-methyl-1H-benzo[d]imidazol-6-ol

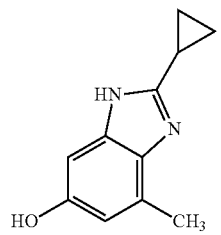

0.55 g (4.00 mmol) 3,4-diamino-5-methyl-phenol and 1.67 mL (20.00 mmol) cyclopropanecarboxylic acid were stirred for 1 h at 120° C. Then the reaction mixture w evaporated down i.vac. and further reacted as crude product.

Yield: 90 mg (12% of theory)
ESI-MS: m/z=189 (M+H)$^+$

Step 2: 6-(6-chloropyrimidin-4-yloxy)-2-cyclopropyl-4-methyl-1H-benzo[d]imidazole

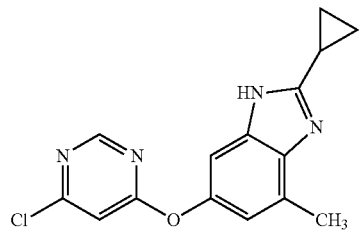

90 mg (0.48 mmol) 2-cyclopropyl-4-methyl-1H-benzo[d]imidazol-6-ol and 77 mg (0.50 mmol) 4,6-dichloropyrimidine in 2.0 mL DMF were combined with 70 mg (0.50 mmol) potassium carbonate and stirred for 8 h at 50° C. Then ice water was added and the substance was extracted with ethyl acetate and concentrated by rotary evaporation i.vac.

Yield: 120 mg (80% of theory)
ESI-MS: m/z=301 (M+H)$^+$
$R_t$(HPLC): 1.02 min (method B)

Intermediate 32

6-(6-chloro-2-cyclopropylpyrimidin-4-yloxy)-4-methylbenzo[d]oxazol-2(3H)-one

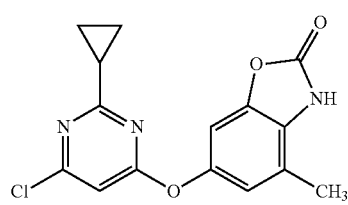 [SMILES: Cc1cc(Oc2cc(Cl)nc(C3CC3)n2)cc2oc(=O)[nH]c12]

Step 1: 2-cyclopropylpyrimidine-4,6-diol

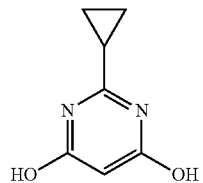

Under a nitrogen atmosphere 1.50 mL (13.06 mmol) dimethylmalonat, 1.60 g (13.27 mmol) cyclopropanecarboxamidine hydrochloride and 15.0 mL (80.80 mmol) sodium methoxide solution (30%) were refluxed for 1.25 h with stirring. The reaction mixture was slightly acidified and the precipitate formed was suction filtered, washed and dried.
Yield: 1.35 g (64% of theory)
ESI-MS: m/z=153 (M+H)$^+$
R$_t$(HPLC): 0.75 min (method K)

Step 2: 4,6-dichloro-2-cyclopropylpyrimidine

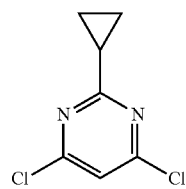 [SMILES: Clc1cc(Cl)nc(C2CC2)n1]

1.34 g (8.40 mmol) 2-cyclopropylpyrimidine-4,6-diol and 15.0 mL (163.37 mmol) phosphorus oxychloride were boiled for 2 h. The reaction mixture was poured onto ice water and made alkaline with NaOH. The precipitate formed was suction filtered, washed and dried.
Yield: 1.02 g (61% of theory)
R$_t$(HPLC): 1.57 min (method B)

Step 3: 6-(6-chloro-2-cyclopropylpyrimidin-4-yloxy)-4-methylbenzo[d]oxazol-2(3H)-one

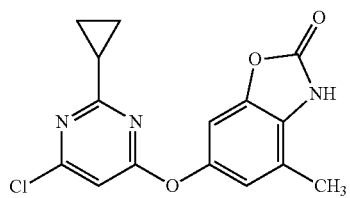 [SMILES: Cc1cc(Oc2cc(Cl)nc(C3CC3)n2)cc2oc(=O)[nH]c12]

0.10 g (0.53 mmol) 4,6-dichloro-2-cyclopropylpyrimidine were added to 95 mg (0.55 mmol) 6-hydroxy-4-methylbenzo[d]oxazol-2(3H)-one and 0.21 g (0.63 mmol) caesium carbonate in 1.5 mL DMF after 15 min and the mixture was stirred overnight at RT. The reaction mixture was purified by preparative HPLC-MS. The fractions containing product were combined and freeze-dried.
Yield: 43 mg (24% of theory)
ESI-MS: m/z=318/320 (Cl) (M+H)$^+$
R$_t$(HPLC): 1.47 min (method B)

Intermediate 33

6-(2,6-dichloropyrimidin-4-yloxy)-4-methylbenzo[d]oxazol-2(3H)-one

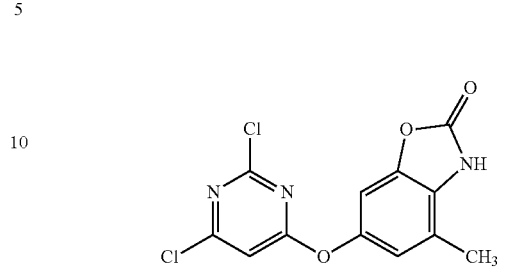

0.15 g (0.82 mmol) 2,4,6-trichloropyrimidine were added to 0.15 g (0.83 mmol) 6-hydroxy-4-methylbenzo[d]oxazol-2(3H)-one and 0.32 g (0.98 mmol) caesium carbonate in 1.5 mL DMF after 15 min and stirred for 1.5 h at RT. The reaction mixture was mixed with water. The precipitate formed was suction filtered, washed and dried.
Yield: 210 mg (78% of theory)
ESI-MS: m/z=312/314/316 (Cl2) (M+H)$^+$
R$_t$(HPLC): 1.41 min (method B)

Intermediate 34

6-(6-chloropyrimidin-4-yloxy)benzo[d]oxazol-2(3H)-one

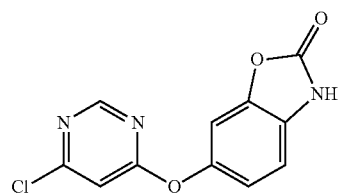 [SMILES: O=c1[nH]c2ccc(Oc3cc(Cl)ncn3)cc2o1]

0.20 g (1.34 mmol) 4,6-dichloropyrimidine, 0.21 g (1.39 mmol) 6-hydroxy-2-benzoxazolinone and 0.20. g (1.45 mmol) potassium carbonate in 2.0 mL DMF were stirred for 2 h at RT. The reaction mixture was mixed with water. The precipitate formed was suction filtered, washed and dried.
Yield: 0.23 g (65% of theory)
ESI-MS: m/z=264/266 (Cl) (M+H)$^+$
R$_t$(HPLC): 3.21 min (method C)

Intermediate 35

7-methoxy-3-(1-(6-(3-methyl-4-nitrophenoxy)pyrimidin-4-yl)piperidin-4-yl)-4,5-dihydro-1H-benzo[d][1,3]diazepin-2(3H)-one

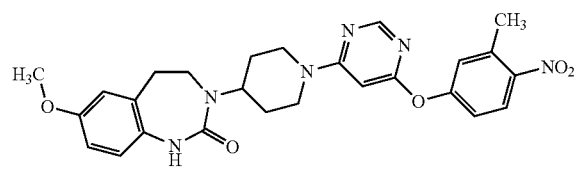 [SMILES: COc1ccc2c(c1)CCN(C1CCN(c3cc(Oc4ccc([N+](=O)[O-])c(C)c4)ncn3)CC1)C(=O)N2]

Step 1:
4-chloro-6-(3-methyl-4-nitrophenoxy)pyrimidine

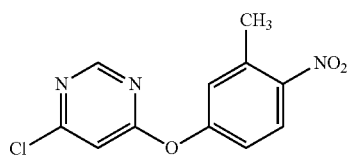 [SMILES: Cc1cc(Oc2cc(Cl)ncn2)ccc1[N+](=O)[O-]]

0.40 g (2.68 mmol) 4,6-dichloropyrimidine, 0.42 g (2.74 mmol) 3-methyl-4-nitrophenol and 0.40 g (2.89 mmol) potassium carbonate in 2.0 mL DMF were stirred for 2 h at RT. The reaction mixture was mixed with water and the precipitate formed was suction filtered, washed and dried.

Yield: 660 mg (93% of theory)
ESI-MS: m/z=266/268 (Cl) (M+H)$^+$
$R_t$(HPLC): 1.51 min (method B)

Step 2: 7-methoxy-3-(1-(6-(3-methyl-4-nitrophenoxy)pyrimidin-4-yl)piperidin-4-yl)-4,5-dihydro-1H-benzo[d][1,3]diazepines-2(3H)-one

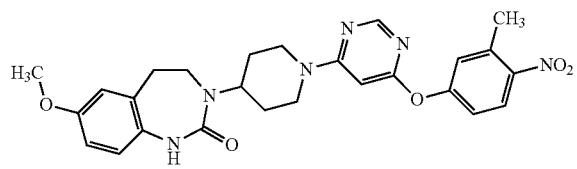 [SMILES: COc1ccc2c(c1)CCN(C1CCN(c3cc(Oc4ccc([N+](=O)[O-])c(C)c4)ncn3)CC1)C(=O)N2]

0.69 g (2.51 mmol) 7-methoxy-3-piperidin-4-yl-1,3,4,5-tetrahydro-1,3-benzodiazepin-2-one, 0.66 g (2.48 mmol) 4-chloro-6-(3-methyl-4-nitrophenoxy)pyrimidine and 1.0 mL (5.81 mmol) DIPEA in 1.0 mL DMF were stirred overnight at 40° C. The reaction mixture was mixed with water. The precipitate formed was suction filtered, washed and dried.

Yield: 0.93 g (74% of theory)
ESI-MS: m/z=505 (M+H)$^+$
$R_t$(HPLC): 1.59 min (method B)

Intermediate 36

7-chloro-5-(6-chloropyrimidin-4-yloxy)-2-methyl-1H-benzo[d]imidazole

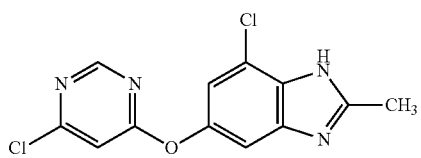 [SMILES: Cc1nc2cc(Oc3cc(Cl)ncn3)cc(Cl)c2[nH]1]

Step 1: 2-chloro-4-methoxy-6-nitroaniline

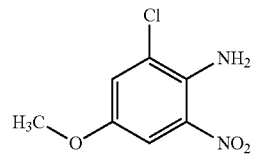

20.0 g (118.94 mmol) 4-methoxy-2-nitroaniline and 10.0 mL sulphuryl chloride were placed in 300.0 mL acetic acid and stirred for 3 h at RT. The reaction mixture was poured onto water and the precipitate formed was suction filtered, washed and dried. The substance obtained was purified by chromatography. The fractions containing product were combined and evaporated down i.vac.

Yield: 2.40 g (10% of theory)
ESI-MS: m/z=203/205 (Cl) (M+H)$^+$
$R_t$(HPLC): 1.41 min (method B)

Step 2: 3-chloro-5-methoxybenzol-1,2-diamine

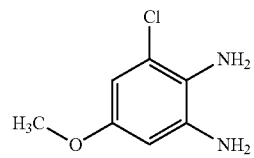

2.40 g (11.85 mmol) 2-chloro-4-methoxy-6-nitroaniline were placed in 50.0 mL ethyl acetate and hydrogenated under a hydrogen atmosphere with the addition of 0.22 g Raney nickel at RT and a hydrogen pressure of 3 bar until all the hydrogen had been taken up. The catalyst was filtered off. The filtrate was evaporated down i.vac.

Yield: 2.00 g (98% of theory)
ESI-MS: m/z=173/175 (Cl) (M+H)$^+$
$R_t$(HPLC): 0.89 min (method B)

Step 3:
7-chloro-5-methoxy-2-methyl-1H-benzo[d]imidazole

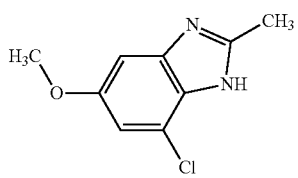

1.00 g (5.79 mmol) 3-chloro-5-methoxybenzol-1,2-diamine and 20.0 mL acetic acid were refluxed for 60 h with stirring. The reaction mixture was evaporated down i.vac. The residue was mixed with an aqueous, saturated NaHCO$_3$ solution. The precipitate was suction filtered, washed and dried.

Yield: 0.98 g (86% of theory)
ESI-MS: m/z=197/199
$R_t$(HPLC): 0.88 min (method B) (Cl) (M+H)$^+$ Step 4:
7-chloro-5-hydroxy-2-methyl-1H-benzo[d]imidazole

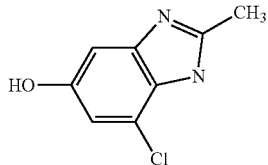

Under a nitrogen atmosphere 0.95 g (4.83 mmol) 7-chloro-5-methoxy-2-methyl-1H-benzo[d]imidazole and 7.0 g (0.06 mol) pyridine hydrochloride were stirred for 15 h at a bath temperature of 180° C. The reaction mixture was poured onto water while still hot and made alkaline with an aqueous $K_2CO_3$ solution. The substance was extracted with ethyl acetate and washed with water. The organic phase was separated off, dried and evaporated down i.vac.

Yield: 600 mg (68% of theory)
ESI-MS: m/z=183/185 (Cl) (M+H)$^+$
$R_f$(HPLC): 0.69 min (method B)

Step 5: 7-chloro-5-(6-chloropyrimidin-4-yloxy)-2-methyl-1H-benzo[d]imidazole

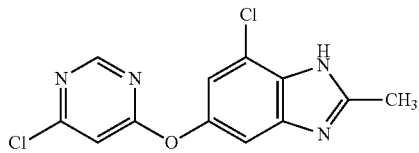 [SMILES: Cc1nc2cc(Oc3cc(Cl)ncn3)cc(Cl)c2[nH]1]

0.49 g (3.29 mmol) 4,6-dichloropyrimidine, 0.60 g (3.29 mmol) 7-chloro-5-hydroxy-2-methyl-1H-benzo[d]imidazole and 0.50 mg (3.62 mmol) potassium carbonate in 2.0 mL DMF were stirred for 2 h at RT. The reaction mixture was mixed with water and the precipitate formed was suction filtered, washed and dried.

Yield: 0.78 g (80% of theory)
ESI-MS: m/z=295/297 (Cl) (M+H)$^+$
$R_f$(HPLC): 1.02 min (method B)

Intermediate 37

(S)-6-(6-chloropyrimidin-4-yloxy)-4-methyl-2-(tetrahydrofuran-2-yl)-1H-benzo[d]imidazole

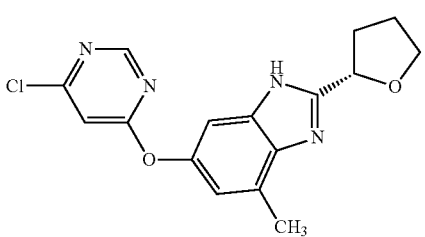 [SMILES: Cc1cc(Oc2cc(Cl)ncn2)cc2[nH]c([C@@H]3CCCO3)nc12]

Step 1: 4-amino-3-methyl-5-nitro-phenyl tetrahydro-furan-2-carboxylate

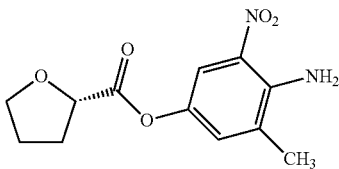 [SMILES: Cc1cc(OC(=O)[C@@H]2CCCO2)cc([N+](=O)[O-])c1N]

0.84 g (5.00 mmol) 4-amino-3-methyl-5-nitro-phenol, 0.58 g (5.00 mmol) (R)-tetrahydro-furan-2-carboxylic acid, 1.77 g (5.50 mmol) TBTU and 1.92 mL (11.00 mmol) DIPEA in 10.0 mL DMF were stirred overnight at RT. The reaction mixture was poured onto ice water and extracted with ethyl acetate. The organic phase was separated off, dried and evaporated down i.vac. The residue was purified by preparative HPLC-MS. The fractions containing product were partially evaporated down i.vac. and neutralised with an aqueous 1M sodium hydroxide solution. The precipitate formed was suction filtered, washed and dried.

Yield: 0.62 g (47% of theory)
ESI-MS: m/z=267 (M+H)$^+$
$R_f$(HPLC): 1.33 min (method B)

Step 2: (S)-4-methyl-2-(tetrahydrofuran-2-yl)-1H-benzo[d]imidazol-6-ol

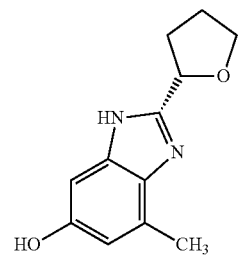

0.62 g (2.33 mmol) 4-amino-3-methyl-5-nitro-phenyl tetrahydrofuran-2-carboxylate were placed in 20.0 mL acetic acid and hydrogenated under a hydrogen atmosphere with the addition of 0.50 g Raney nickel at 50° C. and a hydrogen pressure of 60 psi until all the hydrogen had been taken up. The catalyst was filtered off. The filtrate was purified by chromatography. The fractions containing product were combined and evaporated down i.vac.

Yield: 140 mg (28% of theory)
ESI-MS: m/z=219 (M+H)$^+$
$R_f$(HPLC): 0.75 min (method B)

Step 3: (S)-6-(6-chloropyrimidin-4-yloxy)-4-methyl-2-(tetrahydrofuran-2-yl)-1H-benzo[d]imidazole

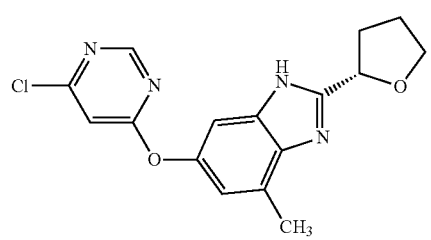 [SMILES: Cc1cc(Oc2cc(Cl)ncn2)cc2[nH]c([C@@H]3CCCO3)nc12]

135 mg (0.62 mmol) (S)-4-methyl-2-(tetrahydrofuran-2-yl)-1H-benzo[d]imidazol-6-ol and 97 mg (0.63 mmol) 4,6-dichloropyrimidine in 2.0 mL DMF were combined with 97 mg (0.70 mmol) potassium carbonate and stirred overnight at 50° C. Then ice water was added and the mixture was extracted with ethyl acetate. The organic phase was concentrated by rotary evaporation i.vac.

Yield: 210 mg (quantitative)
ESI-MS: m/z=331 (M+H)+
$R_f$(HPLC): 1.08 min (method B)

Intermediate 38

4-chloro-5-(6-chloropyrimidin-4-yloxy)-2-methyl-1H-benzo[d]imidazole

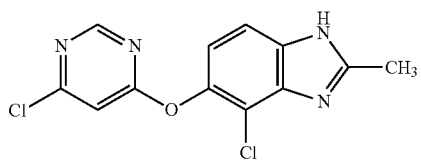 [SMILES: Cc1nc2c(Cl)c(Oc3cc(Cl)ncn3)ccc2[nH]1]

Step 1: 5-methoxy-2-methyl-1H-benzo[d]imidazole

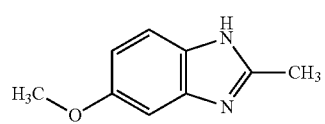

1.95 g (14.11 mmol) 4-methoxy-o-phenylenediamine were refluxed in 30.0 mL acetic acid for 2 h with stirring. The reaction mixture was evaporated down i.vac. The residue was taken up in an aqueous NaHCO$_3$ solution and filtered. The filtrate was extracted with dichloromethane. The organic phase was separated off, dried and evaporated down i.vac.

Yield: 1.30 g (57% of theory)
ESI-MS: m/z=163 (M+H)+
$R_f$(HPLC): 0.69 min (method B)

Step 2:
4-chloro-5-methoxy-2-methyl-1H-benzo[d]imidazole

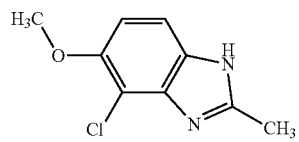

1.30 g (8.02 mmol) 5-methoxy-2-methyl-1H-benzo[d]imidazole and 0.70 mL (8.56 mmol) sulphuryl chloride in 30.0 mL acetic acid were stirred for 2 h. Another 0.3 mL sulphuryl chloride were added and the mixture was stirred for a further 2 h. The reaction mixture was mixed with water and evaporated down i.vac. The residue was stirred with DIPE and isopropanol, suction filtered and dried.

Yield: 1.50 g (95% of theory)
ESI-MS: m/z=197/199 (Cl) (M+H)+
$R_f$(HPLC): 0.82 min (method B)

Step 3:
4-chloro-5-hydroxy-2-methyl-1H-benzo[d]imidazole

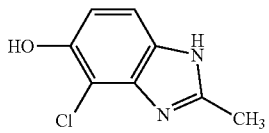

Under a nitrogen atmosphere 1.50 g (7.63 mmol) 4-chloro-5-methoxy-2-methyl-1H-benzo[d]imidazole and 11.20 g (0.10 mol) pyridine hydrochloride were stirred for 15 min at a bath temperature of 180° C. The reaction mixture was poured onto water while hot. The substance was extracted with ethyl acetate and washed with water. The organic phase was separated off, dried and evaporated down i.vac. The residue was stirred with DIPE and ethyl acetate, suction filtered and dried.

Yield: 0.66 g (47% of theory)
ESI-MS: m/z=183/185 (Cl) (M+H)+
$R_f$(HPLC): 0.43 min (method B)

Step 4: 4-chloro-5-(6-chloropyrimidin-4-yloxy)-2-methyl-1H-benzo[d]imidazole

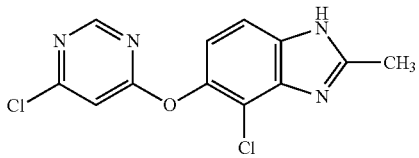 [SMILES: Cc1nc2c(Cl)c(Oc3cc(Cl)ncn3)ccc2[nH]1]

270 mg (1.81 mmol) 4,6-dichloropyrimidine, 330 mg (1.81 mmol) 4-chloro-5-hydroxy-2-methyl-1H-benzo[d]imidazole and 270 mg (1.95 mmol) potassium carbonate in 1.5 mL DMF were stirred for 2 h at RT. The reaction mixture was mixed with water and the precipitate formed was suction filtered, washed and dried.

Yield: 400 mg (75% of theory)
ESI-MS: m/z=295/297 (Cl) (M+H)+
$R_f$(HPLC): 0.98 min (method B)

Intermediate 39

5-chloro-7-(6-chloropyrimidin-4-yloxy)-2H-benzo[b][1.4]oxazin-3(4H)-one

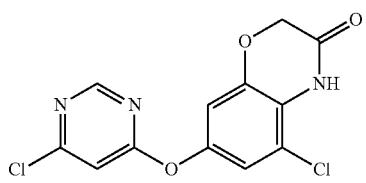 [SMILES: O=C1COc2cc(Oc3cc(Cl)ncn3)cc(Cl)c2N1]

Step 1: 5-methyl-1,3-phenylene diacetate

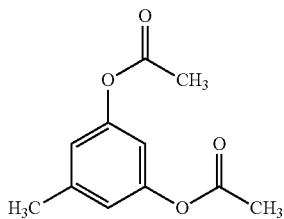

5.80 g (0.04 mol) 5-methylresorcin monohydrate, 20.0 mL (0.21 mol) acetic anhydride and 0.05 g 4-dimethylaminopyridine were stirred in 40.0 mL acetic acid for 2.5 h at 100° C. The reaction mixture was evaporated down i.vac. The residue was taken up in dichloromethane and washed with water. The organic phase was separated off, dried and evaporated down i.vac.

Yield: 8.20 g (quantitative)
ESI-MS: m/z=209 (M+H)$^+$
R$_t$(HPLC): 3.79 min (method C)
R$_f$: 0.6 (silica gel: PE/ethyl acetate=2:1)

Step 2: 5-methyl-4-nitro-1,3-phenylenediacetate

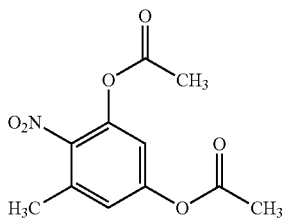 [SMILES: CC(=O)Oc1cc(C)c([N+](=O)[O-])c(OC(C)=O)c1]

Under an argon atmosphere 1.00 g (4.80 mmol) 5-methyl-1,3-phenylenediacetate in 20.0 mL acetonitrile was cooled to −30° C. 700 mg (5.27 mmol) nitronium tetrafluoroborate were added and the mixture was stirred for 1.5 h. The reaction mixture was poured onto ice water and extracted with diethyl ether. The organic phase was separated off, dried and evaporated down i.vac.

Yield: 1.30 g (86 of theory)
ESI-MS: m/z=271 (M+H)$^+$
R$_t$(HPLC): 1.50 min (method B)

Step 3: 5-methyl-4-nitrobenzene-1,3-diol

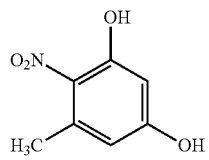

A mixture of 1.15 g (3.63 mmol) 5-methyl-4-nitro-1,3-phenylenediacetate and 10.0 mL (10.0 mmol) 1M aqueous lithium hydroxide solution in 10.0 mL methanol was stirred overnight at RT. The reaction mixture was acidified with 4M hydrochloric acid and extracted with dichloromethane. The organic phase was separated off, dried and evaporated down i.vac. The residue was purified by chromatography. The fractions containing product were combined and evaporated down i.vac.

Yield: 530 mg (86% of theory)
ESI-MS: m/z=168 (M+H)$^+$
R$_t$(HPLC): 3.22 min (method C)

Step 4: 4-amino-5-methylbenzene-1,3-diol

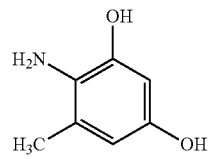

2.43 g (14.4 mmol) 5-methyl-4-nitrobenzene-1,3-diol were placed in 200 mL methanol and hydrogenated under a hydrogen atmosphere and with the addition of 0.20 g Pd/C (10%) at 50° C. and a hydrogen pressure of 5 bar until all the hydrogen had been taken up. The catalyst was filtered off and the filtrate was evaporated down i.vac.

Yield: 2.00 g (quantitative)
ESI-MS: m/z=140 (M+H)$^+$
R$_t$(HPLC): 0.20 min (method B)

Step 5: 7-hydroxy-5-methyl-2H-benzo[b][1.4]oxazin-3(4H)-one

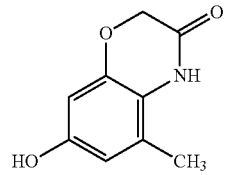

1.0 g (7.2 mmol) 4-amino-5-methylbenzene-1,3-diol and 2.2 g (15.8 mmol) potassium carbonate in 20.0 mL acetonitrile were cooled in the ice bath. 0.65 mL (7.9 mmol) bromoacetyl chloride were added dropwise and the reaction mixture was stirred for 30 min at RT and for 1 h at 70° C. The mixture was combined with water, acidified with aqueous hydrochloric acid and extracted with dichloromethane. The organic phase was separated off, dried and evaporated down i.vac.

Yield: 620 mg (48% of theory)
ESI-MS: m/z=180 (M+H)$^+$
R$_t$(HPLC): 0.83 min (method B)

Step 6: 7-(6-chloropyrimidin-4-yloxy)-5-methyl-2H-benzo[b][1.4]oxazin-3(4H)-one

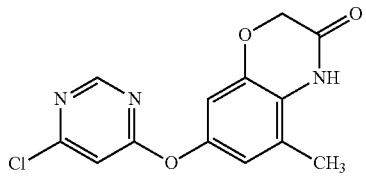 [SMILES: Cc1cc(Oc2cc(Cl)ncn2)cc2c1NC(=O)CO2]

0.10 g (0.56 mmol) 7-hydroxy-5-methyl-2H-benzo[b][1.4]oxazin-3(4H)-one and 0.10 g (0.73 mmol) potassium carbonate were placed in 2.0 mL DMF. After 15 min 86 mg (0.56 mmol) 4,6-dichloropyrimidine were added andtmw stirred at RT over the weekend. The reaction mixture was mixed with water, the substance was extracted with ethyl acetate and evaporated down i.vac.

Yield: 135 mg (79% of theory)
ESI-MS: m/z=292 (M+H)$^+$
R$_t$(HPLC): 1.29 min (method B)

Intermediate 40

6-(6-chloropyrimidin-4-yloxy)-4-methyl-2-(tetrahydrofuran-3-yl)-1H-benzo[d]-imidazole

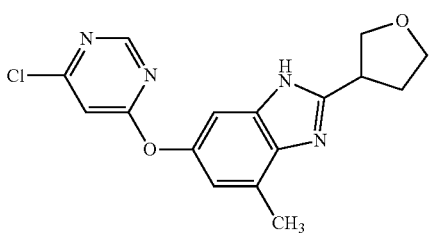 [SMILES: Cc1cc(Oc2cc(Cl)ncn2)cc2[nH]c(C3CCOC3)nc12]

Step 1: 4-acetamido-3-methylphenylacetate

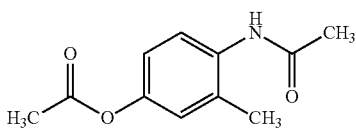

25.0 g (0.20 mol) 4-amino-3-methylphenol, 42.5 mL (0.45 mol) acetic anhydride and 2.50 g sodium acetate were stirred in 25.0 mL acetic acid for 1 h at 125° C. The reaction mixture was combined with ice water and the precipitate formed was suction filtered, washed and dried.

Yield: 27.0 g (65% of theory)
ESI-MS: m/z=208 (M+H)$^+$
R$_t$(HPLC): 0.95 min (method B)

Step 2: 4-acetamido-3-methyl-5-nitrophenylacetate

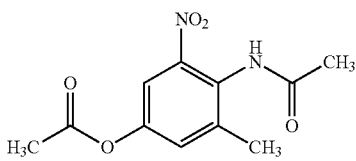

25.0 mL 90% nitric acid were taken and at 10-15° C. 26.9 g (0.13 mol) 4-acetamido-3-methylphenylacetate was added batchwise. The reaction mixture was stirred for 1 h at 18° C. and then combined with ice water and the precipitate formed was suction filtered, washed and dried.

Yield: 22.0 g (67% of theory)
ESI-MS: m/z=253 (M+H)$^+$
R$_t$(HPLC): 1.05 min (method B)

Step 3: 4-amino-3-methyl-5-nitrophenol

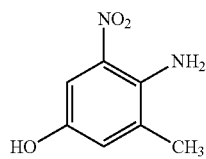

22.0 g (87.2 mmol) 4-acetamido-3-methyl-5-nitrophenylacetate were boiled in 100 mL semiconcentrated hydrochloric acid for 2 h. The reaction mixture was evaporated down i.vac. and dried.

Yield: 15.7 g (quantitative)
ESI-MS: m/z=169 (M+H)$^+$
R$_t$(HPLC): 0.96 min (method B)

Step 4: 3,4-diamino-5-methylphenol

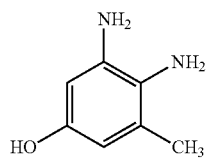

2.00 g (11.06 mmol) 4-amino-3-methyl-5-nitrophenol were placed in 50 mL methanol and hydrogenated under a hydrogen atmosphere and with the addition of 1.00 g Pd/C (10%) at 50° C. and a hydrogen pressure of 5 bar until all the hydrogen had been taken up. The catalyst was filtered off and the filtrate was evaporated down i.vac.

Yield: 1.80 g (quantitative)
ESI-MS: m/z=139 (M+H)$^+$

Step 5: 4-methyl-2-(tetrahydro-3-yl)-1H-benzo[d]imidazol-6-ol

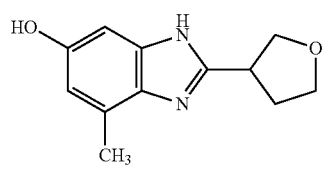

0.66 g (4.78 mmol) 3,4-diamino-5-methylphenol were placed in a little methanol and 1.17 g (10.00 mmol) tetrahydrofuran-3-carboxylic acid was added. First methanol was distilled off and then the mixture was stirred for 2 h at 140° C. The reaction mixture was taken up in DMF/MeOH and purified by chromatography. The fractions containing product were combined and evaporated down i.vac. to leave the aqueous residue. This was neutralised with an aqueous 4M NaOH solution and extracted with ethyl acetate. The organic phase was dried and evaporated down i.vac. and dried.

Yield: 0.21 g (20% of theory)
ESI-MS: m/z=219 (M+H)$^+$
R$_t$(HPLC): 0.73 min (method B)

Step 6: 6-(6-chloropyrimidin-4-yloxy)-4-methyl-2-(tetrahydrofuran-3-yl)-1H-benzo[d]-imidazole

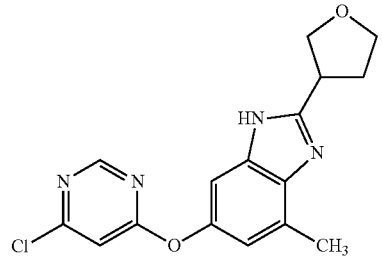 [SMILES: Cc1cc(Oc2cc(Cl)ncn2)cc2[nH]c(C3CCOC3)nc12]

0.20 g (0.92 mmol) 4-methyl-2-(tetrahydro-3-yl)-1H-benzo[d]imidazol-6-ol and 0.15 g (1.00 mmol) 4,6-dichloropyrimidine were placed in 5.0 mL DMF. 0.42 mg (3.00 mmol) potassium carbonate were added and the mixture was stirred overnight at 50° C. The reaction mixture was combined with ice water. The substance was extracted with ethyl acetate and evaporated down i.vac.

Yield: 262 mg (20% of theory)
ESI-MS: m/z=331 (M+H)$^+$
R$_t$(HPLC): 1.06 min (method B)

Intermediate 41

7-chloro-5-(6-chloropyrimidin-4-yloxy)-2-(tetrahydrofuran-3-yl)-1H-benzo[d]imidazole

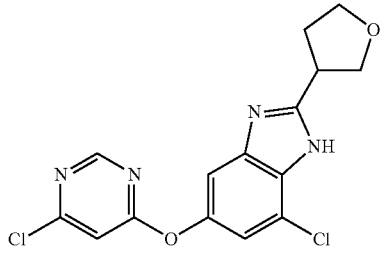 [SMILES: Clc1cc(Oc2cc(Cl)c3[nH]c(C4CCOC4)nc3c2)ncn1]

Step 1: 4-acetamido-3-chlorophenylacetate

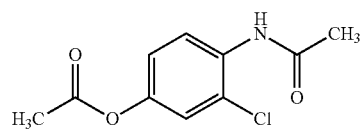

5.0 g (27.8 mmol) 4-amino-3-chlorophenol hydrochloride and 2.6 g sodium acetate were placed in 10.0 mL acetic acid. Then 5.9 mL (62.09 mmol) acetic anhydride were added and the mixture was stirred for 2 h at 125° C. The reaction mixture was combined with ice water, stirred for 1 h and the precipitate formed was suction filtered, washed and dried.

Yield: 5.20 g (82% of theory)
ESI-MS: m/z=228 (M+H)$^+$
R$_t$(HPLC): 1.01 min (method B)

Step 2: N-(2-chloro-4-hydroxy-6-nitrophenyl)acetamide

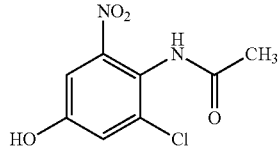

4.85 mL 90% nitric acid were taken and at 10-15° C., 5.20 g (22.84 mmol) 4-acetamido-3-chlorophenylacetate were added batchwise. The reaction mixture was stirred for 2 h at RT, then combined with ice water and the precipitate formed was suction filtered, washed and dried. The crude product was purified by chromatography. The fractions containing product were combined and evaporated down i.vac.

Yield: 1.00 g (19% of theory)
ESI-MS: m/z=231 (M+H)$^+$
R$_t$(HPLC): 1.03 min (method B)

Step 3: 4-amino-3-chloro-5-nitrophenol

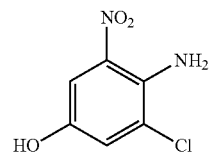 [SMILES: Nc1c(Cl)cc(O)cc1[N+](=O)[O-]]

1.00 g (4.24 mmol) N-(2-chloro-4-hydroxy-6-nitrophenyl)acetamid were refluxed in 10 mL semiconcentrated hydrochloric acid for 2 h. The reaction mixture was evaporated down i.vac. and dried.

Yield: 0.80 g (98% of theory)
ESI-MS: m/z=189 (M+H)$^+$
R$_t$(HPLC): 1.07 min (method B)

Step 4: N-(2-chloro-4-hydroxy-6-nitrophenyl)tetrahydrofuran-3-carboxamide

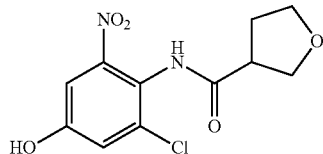 [SMILES: O=C(Nc1c(Cl)cc(O)cc1[N+](=O)[O-])C1CCOC1]

0.40 g (2.12 mmol) 4-amino-3-chloro-5-nitrophenol were placed in 5 mL DCM. 0.44 mL DIPEA and 0.34 g tetrahydrofuran-3-carbonyl chloride were added and the mixture was stirred for 2 h at RT. A further 0.34 g tetrahydrofuran-3-carbonyl chloride was added and the mixture was stirred overnight at RT. The reaction mixture was diluted with DCM and washed with water. The organic phase was evaporated down i.vac.

Yield: 0.60 g (99% of theory)

Step 5: N-(2-amino-6-chloro-4-hydroxyphenyl)tetrahydrofuran-3-carboxamide

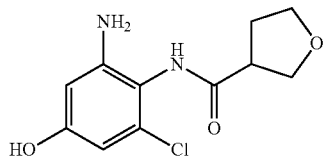

0.60 g (2.09 mmol) N-(2-chloro-4-hydroxy-6-nitrophenyl)tetrahydrofuran-3-carboxamide were placed in 10 mL ethyl acetate and hydrogenated under a hydrogen atmosphere and with the addition of 0.20 g Raney nickel at RT and a hydrogen pressure of 3 bar until all the hydrogen had been taken up. The catalyst was filtered off and the filtrate was evaporated down i.vac.
Yield: 120 mg (22% of theory)
ESI-MS: m/z=257 (M+H)$^+$
R$_t$(HPLC): 0.71 min (method B)

Step 6: 7-chloro-2-(tetrahydrofuran-3-yl)-1H-benzo[d]imidazol-5-ol

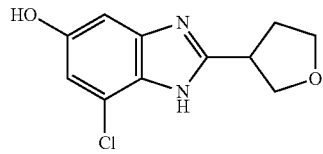 [SMILES: Oc1cc(Cl)c2[nH]c(C3CCOC3)nc2c1]

0.10 g (0.39 mmol) N-(2-amino-6-chloro-4-hydroxyphenyl)tetrahydrofuran-3-carboxamide were placed in 20 mL methanol, a spatula tip of p-toluenesulphonic acid monohydrate was added and the mixture was boiled for 2 h. The reaction mixture was evaporated down i.vac. and purified by chromatography. The fractions containing product were combined and evaporated down i.vac.
Yield: 80 mg (86% of theory)
ESI-MS: m/z=239 (M+H)$^+$
R$_t$(HPLC): 3.10 min (method M)

Step 7: 7-chloro-5-(6-chloropyrimidin-4-yloxy)-2-(tetrahydrofuran-3-yl)-1H-benzo[d]-imidazole

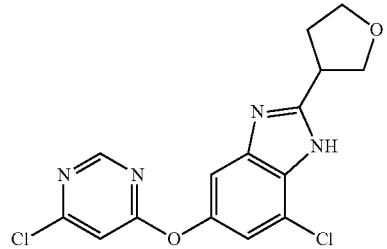 [SMILES: Clc1cc(Oc2cc(Cl)c3[nH]c(C4CCOC4)nc3c2)ncn1]

80 mg (0.34 mmol) 7-chloro-2-(tetrahydrofuran-3-yl)-1H-benzo[d]imidazol-5-ol and 51 mg (0.34 mmol) 4,6-dichloropyrimidine were placed in 2.0 mL DMF. 55 mg (0.40 mmol) potassium carbonate were added and the mixture was stirred overnight at RT. The reaction mixture was filtered and purified by chromatography. The fractions containing product were combined and evaporated down i.vac.
Yield: 60 mg (51% of theory)
ESI-MS: m/z=351 (M+H)$^+$
R$_t$(HPLC): 1.13 min (method B)

Intermediate 42

7-chloro-5-(6-chloropyrimidin-4-yloxy)-2-(tetrahydro-2H-pyran-4-yl)-1H-benzo[d]imidazole

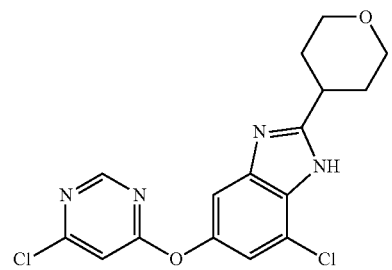 [SMILES: Clc1cc(Oc2cc(Cl)c3[nH]c(C4CCOCC4)nc3c2)ncn1]

Step 1: N-(2-chloro-4-hydroxy-6-nitrophenyl)tetrahydro-2H-pyran-4-carboxamide

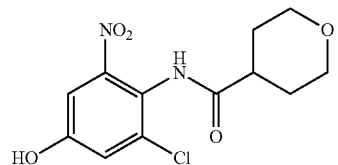

0.40 g (2.12 mmol) 4-amino-3-chloro-5-nitrophenol were placed in 5 mL DCM. 0.44 mL (2.54 mmol) DIPEA and 0.26 mL (2.54 mmol) tetrahydro-2H-pyran-4-carbonyl chloride were added and at RT the mixture was stirred for 2 h. A further 0.26 mL (2.54 mmol) tetrahydro-2H-pyran-4-carbonyl chloride were added and the mixture was stirred overnight at RT. The reaction mixture was diluted with DCM and washed with water. The organic phase was evaporated down i.vac.
Yield: 0.60 g (94% of theory)
ESI-MS: m/z=299 (M−H)$^−$
R$_t$(HPLC): 0.87 min (method B)

Step 2: N-(2-amino-6-chloro-4-hydroxyphenyl)tetrahydro-2H-pyran-4-carboxamide

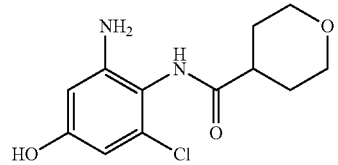

0.60 g (2.00 mmol) N-(2-chloro-4-hydroxy-6-nitrophenyl)tetrahydro-2H-pyran-4-carboxamide were placed in 10 mL ethyl acetate and hydrogenated under a hydrogen atmosphere and with the addition of 0.20 g Raney nickel at RT and a Step 3: 7-chloro-2-(tetrahydro-2H-pyran-4-yl)-1H-benzo[d]imidazol-5-ol

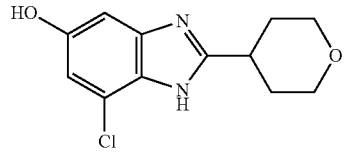 [SMILES: Oc1cc(Cl)c2[nH]c(C3CCOCC3)nc2c1]

0.50 g (1.85 mmol) N-(2-amino-6-chloro-4-hydroxyphenyl)tetrahydro-2H-pyran-4-carboxamide were placed in 20 mL methanol, a spatula tip of p-toluenesulphonic acid monohydrate was added and the mixture was boiled overnight. The reaction mixture was evaporated down i.vac. and purified by chromatography. The fractions containing product were combined and evaporated down i.vac.
Yield: 0.10 g (21% of theory)
ESI-MS: m/z=253 (M+H)⁺
$R_t$(HPLC): 0.75 min (method B)

Step 4: 7-chloro-5-(6-chloropyrimidin-4-yloxy)-2-(tetrahydro-2H-pyran-4-yl)-1H-benzo[d]imidazole

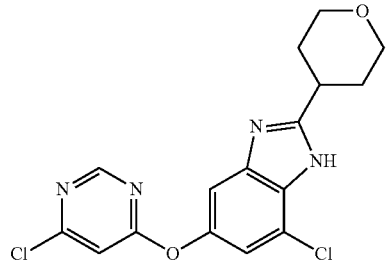 [SMILES: Clc1cc(Oc2cc(Cl)c3[nH]c(C4CCOCC4)nc3c2)ncn1]

0.10 g (0.40 mmol) 7-chloro-2-(tetrahydro-2H-pyran-4-yl)-1H-benzo[d]imidazol-5-ol and 60 mg (0.40 mmol) 4,6-dichloropyrimidine were placed in 2.0 mL DMF. 61 mg (0.40 mmol) potassium carbonate were added and the mixture was stirred overnight at RT. The reaction mixture was filtered and purified by chromatography. The fractions containing product were combined and evaporated down i.vac.
Yield: 80 mg (51% of theory)
ESI-MS: m/z=365 (M+H)⁺
$R_t$(HPLC): 1.12 min (method B)

Intermediate 43

6-(6-chloropyrimidin-4-yloxy)-4-methyl-2-(trifluoromethyl)-1H-benzo[d]imidazole

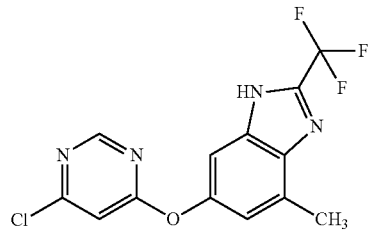 [SMILES: Cc1cc(Oc2cc(Cl)ncn2)cc2[nH]c(C(F)(F)F)nc12]

Step 1: 7-methyl-2-(trifluoromethyl)-1H-benzo[d]imidazol-5-ol

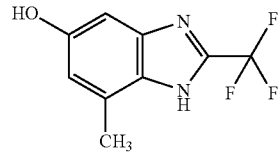

0.20 g (1.45 mmol) 3,4-diamino-5-methylphenol were stirred together with 1 mL (13.07 mmol) trifluoroacetic acid for 1 h at 100° C. The reaction mixture was cooled and purified by chromatography. The fractions containing product were combined and evaporated down i.vac. to leave the aqueous residue. This was neutralised with an aqueous 1M NaOH solution and extracted with ethyl acetate. The organic phase was evaporated down i.vac.
Yield: 60 mg (19% of theory)
ESI-MS: m/z=217 (M+H)⁺
$R_t$(HPLC): 1.07 min (method B)

Step 2: 6-(6-chloropyrimidin-4-yloxy)-4-methyl-2-(trifluoromethyl)-1H-benzo-[d]imidazole

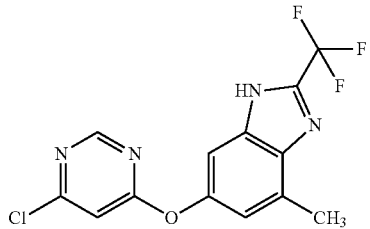 [SMILES: Cc1cc(Oc2cc(Cl)ncn2)cc2[nH]c(C(F)(F)F)nc12]

57 mg (0.26 mmol) 7-methyl-2-(trifluoromethyl)-1H-benzo[d]imidazol-5-ol and 46 mg (0.30 mmol) 4,6-dichloropyrimidine were placed in 2.0 mL DMF. 0.11 g (0.78 mmol) potassium carbonate were added and the mixture was stirred overnight at 70° C. The reaction mixture was combined with ice water. The substance was extracted with ethyl acetate and evaporated down i.vac. The crude product was purified by chromatography. The fractions containing product were combined and i evaporated down.vac. to leave the aqueous residue. This was neutralised with an aqueous 4M NaOH solution and extracted with ethyl acetate. The organic phase was evaporated down i.vac.
Yield: 24 mg (24% of theory)
ESI-MS: m/z=329 (M+H)⁺
$R_t$(HPLC): 1.41 min (method B)

Intermediate 44

6-(6-chloropyrimidin-4-yloxy)-4-methylbenzo[d]thiazol-2(3H)-one

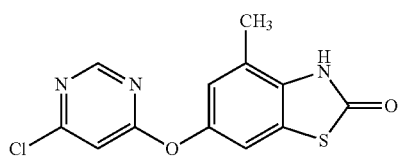 [SMILES: Cc1cc(Oc2cc(Cl)ncn2)cc2sc(=O)[nH]c12]

Step 1:
6-hydroxy-4-methylbenzo[d]thiazol-2(3H)-one

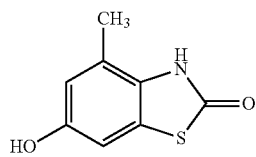

1.00 g (4.78 mmol) 6-ethoxy-4-methylbenzo[d]thiazol-2 (3H)-one and 7.00 g (60.57 mmol) pyridine hydrochloride were thoroughly mixed and stirred for 15 h under a nitrogen atmosphere at 180° C. The reaction mixture was poured onto water and extracted with ethyl acetate. The organic phase was washed with water and evaporated down i.vac. The residue was stirred with diisopropylether and suction filtered.
Yield: 0.65 g (75% of theory)
ESI-MS: m/z=182 (M+H)+
$R_t$(HPLC): 0.89 min (method B)

Step 2: 6-(6-chloropyrimidin-4-yloxy)-4-methyl-benzo[d]thiazol-2(3H)-one

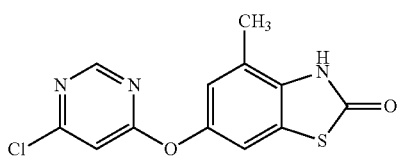 [SMILES: Cc1cc(Oc2cc(Cl)ncn2)cc2sc(=O)[nH]c12]

0.30 g (1.66 mmol) 6-hydroxy-4-methylbenzo[d]thiazol-2 (3H)-one and 0.25 g (1.68 mmol) 4,6-dichloropyrimidine were placed in 2.0 mL DMF. 0.25 g (1.81 mmol) potassium carbonate were added and the mixture was stirred for 2 h at RT. The reaction mixture was mixed with water and stirred overnight. The precipitate formed was suction filtered, washed and dried.
Yield: 0.37 g (75% of theory)
ESI-MS: m/z=294 (M+H)+
$R_t$(HPLC): 1.32 min (method B)

Intermediate 45

5-(6-chloropyrimidin-4-yloxy)-7-methyl-2-(tetrahydro-2H-pyran-4-yl)-1H-benzo[d]imidazole

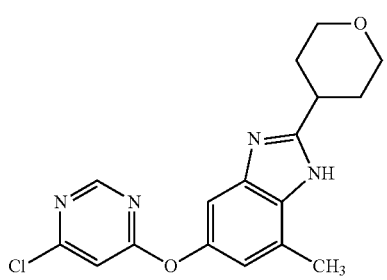 [SMILES: Cc1cc(Oc2cc(Cl)ncn2)cc2nc(C3CCOCC3)[nH]c12]

Step 1: 4-(benzyloxy)-2-methyl-6-nitroaniline

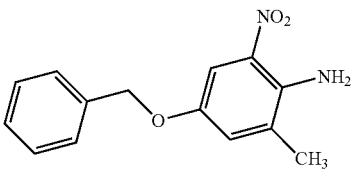 [SMILES: Cc1cc(OCc2ccccc2)cc([N+](=O)[O-])c1N]

0.84 g (5.00 mmol) 4-amino-3-methyl-5-nitrophenol was placed in 10 mL DMF, combined with 0.78 g (5.50 mmol) potassium carbonate and stirred for 10 min at RT. Then 0.65 mL (5.50 mmol) benzylbromide were added and the mixture was stirred for a further 30 min at RT and for 1 h at 60° C. Another 0.33 mL benzylbromide were added and the mixture was stirred for 1 h at 60° C. The reaction mixture was poured onto ice water, extracted with ethyl acetate and evaporated down i.vac. The residue was purified by chromatography. The fractions containing product were combined and evaporated down i.vac. to leave the aqueous residue. This was neutralised with a 1M aqueous NaOH solution and extracted with ethyl acetate. The organic phase was evaporated down i.vac.
Yield: 0.23 g (18% of theory)
ESI-MS: m/z=259 (M+H)+
$R_t$(HPLC): 1.60 min (method B)

Step 2: N-(4-(benzyloxy)-2-methyl-6-nitrophenyl) tetrahydro-2H-pyran-4-carboxamide

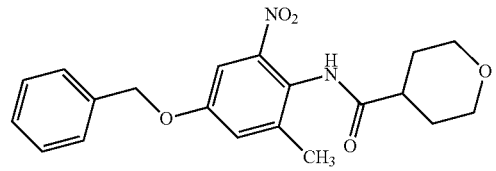 [SMILES: Cc1cc(OCc2ccccc2)cc([N+](=O)[O-])c1NC(=O)C1CCOCC1]

0.22 g (0.85 mmol) 4-(benzyloxy)-2-methyl-6-nitroaniline were placed in 5 mL DCM. 0.17 mL (1.00 mmol) DIPEA and 0.10 mL (1.00 mmol) tetrahydro-2H-pyran-4-carbonyl chloride were added and the mixture was stirred for 2 h at RT. A further 0.10 mL (1.00 mmol) tetrahydro-2H-pyran-4-carbonyl chloride were added and the mixture was stirred overnight at RT. The reaction mixture was diluted with DCM and washed with water. The organic phase was evaporated down i.vac.
Yield: 0.34 g (quantitative)
ESI-MS: m/z=371 (M+H)+
$R_t$(HPLC): 1.40 min (method B)

Step 3: 7-methyl-2-(tetrahydro-2H-pyran-4-yl)-1H-benzo[d]imidazol-5-ol

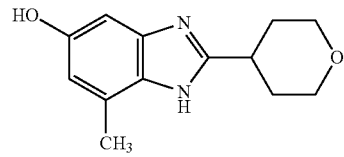 [SMILES: Cc1cc(O)cc2nc(C3CCOCC3)[nH]c12]

0.33 g (0.84 mmol) N-(4-(benzyloxy)-2-methyl-6-nitrophenyl)tetrahydro-2H-pyran-4-carboxamide were placed in 10 mL acetic acid and hydrogenated under a hydrogen atmosphere and with the addition of 0.10 g palladium/charcoal (10%) at 50° C. and a hydrogen pressure of 5 bar until all the hydrogen had been taken up. The catalyst was filtered off and the filtrate was evaporated down i.vac.

Yield: 0.35 g (quantitative)
ESI-MS: m/z=233 (M+H)$^+$
$R_t$(HPLC): 0.64 min (method B)

Step 4: 5-(6-chloropyrimidin-4-yloxy)-7-methyl-2-(tetrahydro-2H-pyran-4-yl)-1H-benzo[d]imidazole

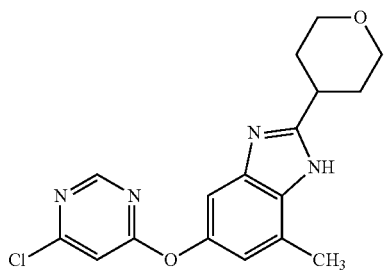 [SMILES: Cc1cc(Oc2cc(Cl)ncn2)cc2nc(C3CCOCC3)[nH]c12]

0.35 g (0.84 mmol) 7-methyl-2-(tetrahydro-2H-pyran-4-yl)-1H-benzo[d]imidazol-5-ol and 0.14 mg (0.90 mmol) 4,6-dichloropyrimidine were placed in 5.0 mL DMF. 0.35 g (2.52 mmol) potassium carbonate were added and the mixture was stirred overnight at 60° C. The reaction mixture was poured onto ice water, extracted with ethyl acetate and evaporated down i.vac. The residue was purified by chromatography. The fractions containing product were combined and evaporated down i.vac. to leave the aqueous residue. This was neutralised with an aqueous NaHCO$_3$ solution and extracted with ethyl acetate. The organic phase was dried and evaporated down i.vac.

Yield: 42 mg (14% of theory)
ESI-MS: m/z=345 (M+H)$^+$
$R_t$(HPLC): 0.96 min (method B)

Intermediate 46

6-(6-chloropyrimidin-4-yloxy)-2-(2-methoxymethyl)-4-methyl-1H-benzo[d]imidazol

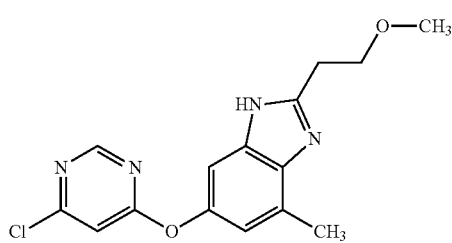 [SMILES: COCCc1nc2c(C)cc(Oc3cc(Cl)ncn3)cc2[nH]1]

Stufe 1: 2-(2-methoxyethyl)-4-methyl-1H-benzo[d]imidazol-6-ol

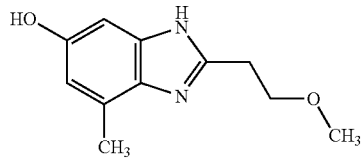

0.65 g (4.70 mmol) 3,4-diamino-5-methylphenol were placed in a little methanol and 0.94 mL (10.00 mmol) 3-methoxypropionic acid was added. First the methanol was distilled off and then the mixture was stirred for 2 h at 140° C. The reaction mixture was taken up in DMF/MeOH and purified by chromatography. The fractions containing product were combined and evaporated down i.vac. to leave the aqueous residue. This was neutralised with an aqueous 4M NaOH solution and extracted with ethyl acetate. The organic phase was dried and evaporated down i.vac. and dried.

Yield: 0.16 g (17% of theory)
ESI-MS: m/z=207 (M+H)$^+$
$R_t$(HPLC): 0.78 min (method B)

Step 2: 6-(6-chloropyrimidin-4-yloxy)-2-(2-methoxymethyl)-4-methyl-1H-benzo-[d]imidazole

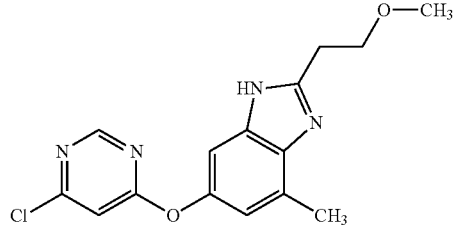 [SMILES: COCCc1nc2c(C)cc(Oc3cc(Cl)ncn3)cc2[nH]1]

0.15 g (0.74 mmol) 2-(2-methoxyethyl)-4-methyl-1H-benzo[d]imidazol-6-ol and 0.12 g (0.80 mmol) 4,6-dichloropyrimidine were placed in 5.0 mL DMF. 0.33 g (2.40 mmol) potassium carbonate were added and the mixture was stirred overnight at 50° C. The reaction mixture was combined with ice water, the substance was extracted with ethyl acetate and evaporated down i.vac. The residue was purified by chromatography. The fractions containing product were combined and evaporated down i.vac. to leave the aqueous residue. This was neutralised with a 1 M aqueous NaOH solution and extracted with ethyl acetate. The organic phase was dried and evaporated down i.vac.

Yield: 33 mg (13% of theory)
ESI-MS: m/z=319 (M+H)$^+$
$R_t$(HPLC): 2.71 min (method B)

Intermediate 47

6-(6-chloropyrimidin-4-yloxy)-2-methoxy-4-methyl-1H-benzo[d]imidazole

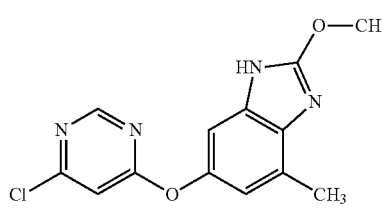

Step 1:
2-methoxy-4-methyl-1H-benzo[d]imidazol-6-ol

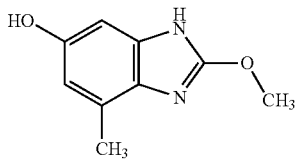

0.60 g (4.34 mmol) 3,4-diamino-5-methylphenol were placed in 2 mL acetic acid. 4.0 mL (0.03 mol) tetramethyl orthocarbonate were added and the mixture was stirred for 4 h at RT. The reaction mixture was purified by chromatography. The fractions containing product were combined and evaporated down i.vac. to leave the aqueous residue. This was neutralised with a 1M aqueous NaOH solution and extracted with ethyl acetate. The organic phase was dried and evaporated down i.vac.
Yield: 80 mg (10% of theory)
ESI-MS: m/z=179 (M+H)$^+$
R$_f$(HPLC): 0.61 min (method B)

Step 2: 6-(6-chloropyrimidin-4-yloxy)-2-methoxy-4-methyl-1H-benzo[d]imidazole

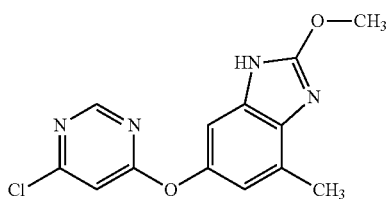 [SMILES: COc1nc2c(C)cc(Oc3cc(Cl)ncn3)cc2[nH]1]

74 mg (0.42 mmol) 2-methoxy-4-methyl-1H-benzo[d]imidazol-6-ol and 68 mg (0.44 mmol) 4,6-dichloropyrimidine were placed in 2.0 mL DMF. 0.12 g (0.88 mmol) potassium carbonate were added and the mixture was stirred for 4 h at 50° C. The reaction mixture was combined with ice water, the substance was extracted with ethyl acetate and evaporated down i.vac.
Yield: 120 mg (94% of theory)
ESI-MS: m/z=291 (M+H)$^+$
R$_f$(HPLC): 1.16 min (method B)

Intermediate 48

6-(6-chloro-2-trifluoromethyl-pyrimidin-4-yloxy)-4-methyl-3H-benzoxazol-2-one

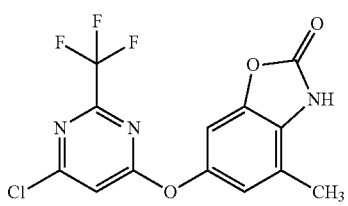 [SMILES: Cc1cc(Oc2cc(Cl)nc(C(F)(F)F)n2)cc2oc(=O)[nH]c12]

0.40 g (1.86 mmol) 4,6-dichloro-2-trifluoromethylpyrimidine, 0.31 g (1.88 mmol) 6-hydroxy-2-benzoxazolinone and 0.28 g (2.03 mmol) potassium carbonate in 2.0 mL DMF were stirred for 2 h at RT. The reaction mixture was mixed with water and stirred for 1 h at RT. The precipitate formed was suction filtered, washed and dried.
Yield: 0.42 g (65% of theory)
ESI-MS: m/z=346 (M+H)$^+$
R$_f$(HPLC): 1.53 min (method B)

Intermediate 49

6-chloro-4-(4-methyl-2-oxo-2,3-dihydro-benzoxazol-6-yloxy)-nicotinonitrile

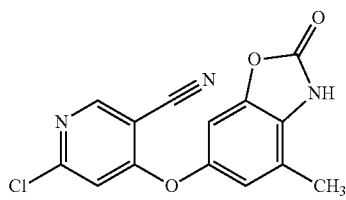 [SMILES: Cc1cc(Oc2cc(Cl)ncc2C#N)cc2oc(=O)[nH]c12]

0.12 g (0.69 mmol) 4,6-dichloro-nicotinonitrile, 0.15 g (0.91 mmol) 6-hydroxy-2-benzoxazolinone and 90 mg (0.80 mmol) potassium-tert.-butoxide in 0.8 mL NMP were stirred for 2 h at 70° C. The reaction mixture was combined with ice water. The precipitate formed was suction filtered and dried.
Yield: 0.12 g (52% of theory)
ESI-MS: m/z=302 (M+H)$^+$
R$_f$(HPLC): 1.31 min (method B)

Intermediate 50

6-(6-chloro-pyrimidin-4-yloxy)-2-methyl-4-trifluoromethyl-1H-benzimidazole

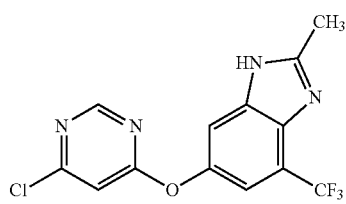

Step 1:
N-(4-fluoro-2-trifluoromethyl-phenyl)-acetamide

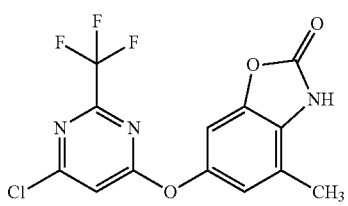 [SMILES: Cc1cc(Oc2cc(Cl)nc(C(F)(F)F)n2)cc2oc(=O)[nH]c12]

10.0 g (0.56 mol) 4-fluoro-2-trifluoromethyl-phenylamine were stirred overnight at RT in 40 mL acetic anhydride. The reaction mixture was poured onto 300 g ice water. The precipitate formed was suction filtered, washed with 100 mL water and dried i. vac.

Yield: 8.80 g (71% of theory)
ESI-MS: m/z=222 (M+H)⁺
R$_t$(HPLC): 3.0 min (method C)

Step 2: N-(4-fluoro-2-nitro-6-trifluoromethyl-phenyl)-acetamide

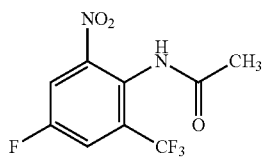 [SMILES: CC(=O)Nc1c([N+](=O)[O-])cc(F)cc1C(F)(F)F]

8.80 g (39.7 mmol) N-(4-fluoro-2-trifluoromethyl-phenyl)-acetamide were added to 60 mL 97% sulphuric acid while cooling with ice. 6.60 mL (95.3 mmol) nitric acid were slowly added dropwise to this mixture at 0° C. and with constant stirring. After the addition had ended the mixture was stirred for 30 min at 0° C. Then the cooling was removed and the reaction mixture was stirred for a further 1.5 h to complete the reaction. The reaction mixture was carefully poured onto 500 g ice and stirred for 30 min. The precipitate formed was filtered off, washed with 150 mL water and dried i. vac.

Yield: 8.60 g (81% of theory)
ESI-MS: m/z=267 (M+H)⁺
R$_t$(HPLC): 3.16 min (method C)

Step 3: N-(4-methoxy-2-nitro-6-trifluoromethyl-phenyl)-acetamide

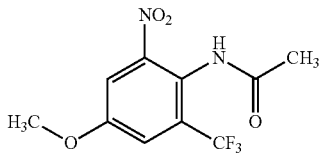

A well stirred mixture of 3.00 g (11.2 mmol) N-(4-fluoro-2-nitro-6-trifluoromethyl-phenyl)-acetamide and 6.00 g (18.4 mmol) caesium carbonate in 90 mL methanol was heated for 10 min at 100° C. in the microwave. After cooling the solvent was eliminated i.vac. and the residue remaining was combined with 100 mL water. The aqueous phase was acidified with 10% citric acid and the product was extracted with 100 mL ethyl acetate. The organic phase was dried and evaporated down i.vac. The residue obtained was purified by flash chromatography. The fractions containing product were combined and evaporated down i.vac.

Yield: 550 mg (17% of theory)
ESI-MS: m/z=279 (M+H)⁺
R$_t$(HPLC): 1.18 min (method B)

Step 4: 6-methoxy-2-methyl-4-trifluoromethyl-1H-benzimidazole

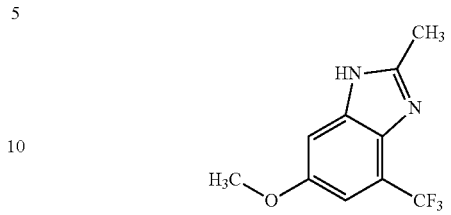

A mixture of 0.55 g (1.98 mmol) N-(4-methoxy-2-nitro-6-trifluoromethyl-phenyl)-acetamide and 100 mg Pd/C in 30 mL acetic acid was hydrogenated for 5 h under a hydrogen atmosphere at 80° C. until all the hydrogen had been taken up. The catalyst was filtered off and the filtrate was evaporated down i.vac.

Yield: 450 mg (99% of theory)
ESI-MS: m/z=231 (M+H)⁺
R$_t$(HPLC): 2.6 min (method C)

Step 5: 2-methyl-7-trifluoromethyl-3H-benzimidazol-5-ol

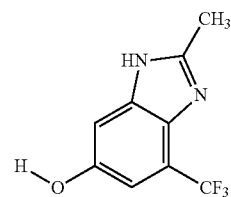

A well stirred mixture of 450 mg (1.95 mmol) 6-methoxy-2-methyl-4-trifluoromethyl-1H-benzimidazole and 2.50 g (21.6 mmol) pyridine hydrochloride was heated for 15 min to 200° C. After cooling to RT the reaction mixture was combined with 3.0 mL DMF and purified by preparative HPLC. The fractions containing product were combined and evaporated down i.vac.

Yield: 330 mg (78% of theory)
ESI-MS: m/z=217 (M+H)⁺
R$_t$(HPLC): 2.0 min (method C)

Step 6: 6-(6-chloro-pyrimidin-4-yloxy)-2-methyl-4-trifluoromethyl-1H-benzimidazole

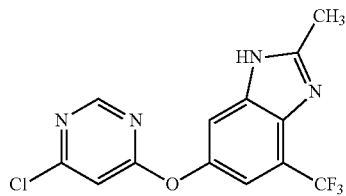 [SMILES: Cc1nc2c(C(F)(F)F)cc(Oc3cc(Cl)ncn3)cc2[nH]1]

221 mg (1.60 mmol) potassium carbonate were added at RT to 245 mg (1.60 mmol) 4,6-dichloropyrimidine and 330 mg (1.52 mmol) 2-methyl-7-trifluoromethyl-3H-benzimidazole-5-ol in 5.0 mL DMF and the mixture was stirred overnight at RT. The reaction mixture was poured onto water. The precipitate formed was filtered off, washed with water and dried.
Yield: 500 mg (95% of theory)
ESI-MS: m/z=329/331 (Cl) (M+H)$^+$
R$_f$(HPLC): 3.18 min (method C)

Intermediate 51

7-methoxy-3-(4'-nitro-1'-oxy-3,4,5,6-tetrahydro-2H-[1,2']bipyridinyl-4-yl)-1,3,4,5-tetrahydro-benzo[d][1,3]diazepin-2-one

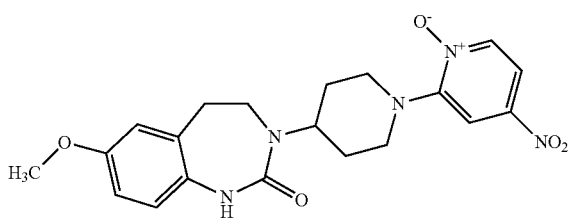 [SMILES: COc1ccc2c(c1)CCN(C1CCN(c3cc([N+](=O)[O-])cc[n+]3[O-])CC1)C(=O)N2]

A mixture of 160 mg (0.581 mmol) 7-methoxy-3-piperidin-4-yl-1,3,4,5-tetrahydro-1,3-benzodiazepin-2-one, 100 mg (0.573 mmol) 2-chloro-4-nitro-pyridin-N-oxide and 100 mg (0.724 mmol) potassium carbonate in 2.0 mL DMF was stirred for 2 h at 60° C. until the reaction was complete. After cooling to RT the reaction mixture was poured onto water. The precipitate formed was filtered off, washed with water and dried i. vac.
Yield: 180 mg (75% of theory)
ESI-MS: m/z=414 (M+H)$^+$ Preparation of the End Compounds Example 1

7-methoxy-3-{1-[6-(4-methyl-2-oxo-2,3-dihydro-benzoxazol-6-yloxy)-pyrimidin-4-yl]-piperidin-4-yl}-1,3,4,5-tetrahydro-benzo[d][1,3]diazepin-2-one

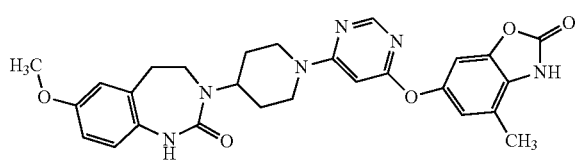 [SMILES: COc1ccc2c(c1)CCN(C1CCN(c3cc(Oc4cc(C)c5[nH]c(=O)oc5c4)ncn3)CC1)C(=O)N2]

64 mg (0.23 mmol) 7-methoxy-3-piperidin-4-yl-1,3,4,5-tetrahydro-1,3-benzodiazepin-2-one, 64 mg (0.23 mmol) 6-(6-chloro-pyrimidin-4-yloxy)-4-methyl-3H-benzoxazol-2-one and 0.10 mL (0.58 mmol) DIPEA were combined in 1.8 mL DMF and stirred for 1 h at RT. Then 40 mg (0.15 mmol) 7-methoxy-3-piperidin-4-yl-1,3,4,5-tetrahydro-1,3-benzodiazepin-2-one were added and the mixture was stirred overnight. The reaction mixture was purified by preparative HPLC-MS. The product-containing fractions were combined, the acetonitrile was evaporated down, the precipitate was suction filtered and dried i. vac.
Yield: 30 mg (25% of theory)
ESI-MS: m/z=517 (M+H)$^+$
R$_f$(HPLC): 1.62 min (method B)

Example 2

1-{-1-[6-(3,4-dimethyl-2-oxo-2,3-dihydro-benzoxazol-6-yloxy)-pyrimidin-4-yl]-piperidin-4-yl}-1,3-dihydro-imidazo[4,5-b]pyridin-2-one

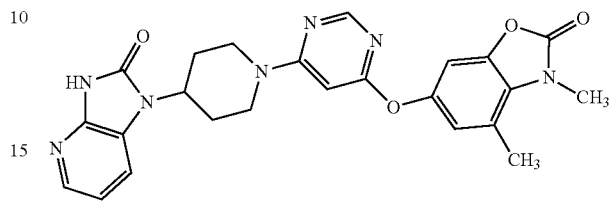

75 mg (0.34 mmol) 1-piperidin-4-yl-1,3-dihydroimidazo[4,5-b]pyridin-2-one-dihydrochloride, 100 mg (0.34 mmol) 6-(6-chloro-pyrimidin-4-yloxy)-3,4-dimethyl-3H-benzoxazol-2-one and 0.15 mL (0.86 mmol) DIPEA were combined in 1.8 mL DMF and stirred overnight at RT. The reaction mixture was purified by preparative HPLC-MS. The product-containing fractions were combined, the acetonitrile was evaporated down and the precipitate was suction filtered and dried i. vac.
Yield: 82 mg (51% of theory)
ESI-MS: m/z=474(M+H)$^+$
R$_f$(HPLC): 1.36 min (method B)

Example 3

3-{-1-[6-(3,4-dimethyl-2-oxo-2,3-dihydro-benzoxazol-6-yloxy)-pyrimidin-4-yl]-piperidin-4-yl}-7-methoxy-1,3,4,5-tetrahydro-benzo[d][1,3]diazepin-2-one

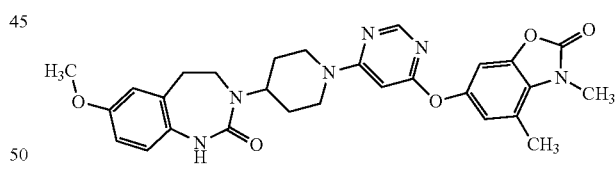

95 mg (0.35 mmol) 7-methoxy-3-piperidin-4-yl-1,3,4,5-tetrahydro-1,3-benzodiazepin-2-one, 0.10 g (0.34 mmol) 6-(6-chloro-pyrimidin-4-yloxy)-3,4-dimethyl-3H-benzoxazol-2-one and 0.15 mL (0.86 mmol) DIPEA were combined in 1.8 mL DMF and stirred overnight at RT. The reaction mixture was purified by preparative HPLC-MS. The product-containing fractions were combined, the acetonitrile was evaporated down, the precipitate was suction filtered and dried i. vac.
Yield: 81 mg (45% of theory)
ESI-MS: m/z=531(M+H)$^+$
R$_f$(HPLC): 1.52 min (method B)

Example 4

1-{-1-[6-(3,4-dimethyl-phenoxy)-pyrimidin-4-yl]-piperidin-4-yl}-1,3-dihydro-imidazo[4,5-b]-pyridin-2-one

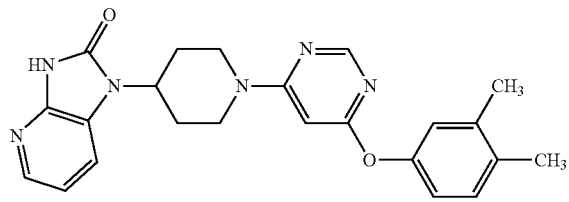 [SMILES: Cc1ccc(Oc2cc(N3CCC(n4c(=O)[nH]c5ncccc54)CC3)ncn2)cc1C]

291 mg (1.00 mmol) 1-piperidin-4-yl-1,3-dihydroimidazo[4,5-b]pyridin-2-one-dihydrochloride, 276 mg (1.00 mmol) 4-chloro-6-(3,4-dimethyl-phenoxy)-pyrimidine and 0.697 mL (4.00 mmol) DIPEA were combined in 3.0 mL DMF and stirred for 4 h at 150° C. The reaction mixture was purified by preparative HPLC-MS. The product-containing fractions were combined, the acetonitrile was evaporated down and the residue was neutralised with 1N aqueous sodium hydroxide solution. The precipitate formed was suction filtered, washed with water and dried i. vac.

Yield: 285 mg (68% of theory)
ESI-MS: m/z=417 (M+H)$^+$
R$_t$(HPLC): 1.47 min (method B)

Example 5

1-{1-[6-(4-methyl-2-oxo-2,3-dihydro-benzoxazol-6-yloxy)-pyrimidin-4-yl]-piperidin-4-yl}-1,3-dihydro-imidazo[4,5-b]pyridin-2-one

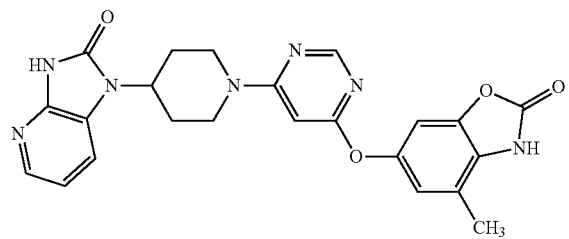 [SMILES: Cc1cc(Oc2cc(N3CCC(n4c(=O)[nH]c5ncccc54)CC3)ncn2)cc2oc(=O)[nH]c12]

40 mg (0.18 mmol) 1-piperidin-4-yl-1,3-dihydroimidazo[4,5-b]pyridin-2-one, 50 mg (0.18 mmol) 6-(6-chloro-pyrimidin-4-yloxy)-4-methyl-3H-benzoxazol-2-one and 0.10 mL (0.58 mmol) DIPEA were combined in 1.8 mL DMF and stirred for 1 h at RT. Then another 40 mg (0.18 mmol) 1-piperidin-4-yl-1,3-dihydroimidazo-[4,5-b]pyridin-2-one were added and the mixture was stirred overnight. The reaction mixture was purified by preparative HPLC-MS. The product-containing fractions were combined, the acetonitrile was evaporated down, the precipitate was suction filtered and dried i. vac.

Yield: 45 mg (25% of theory)
ESI-MS: m/z=460 (M+H)$^+$
R$_t$(HPLC): 1.22 min (method B)

Example 6

1-{1-[6-(4-methyl-2-oxo-2,3-dihydro-benzoxazol-6-ylamino)-pyrimidin-4-yl]-piperidin-4-yl}-1,3-dihydro-imidazo[4,5-b]pyridin-2-one

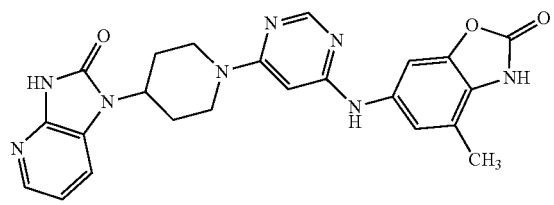

276 mg (1.26 mmol) 1-piperidin-4-yl-1,3-dihydroimidazo[4,5-b]pyridin-2-one, 350 mg (0.987 mmol) 6-(6-chloro-pyrimidin-4-ylamino)-4-methyl-3H-benzoxazol-2-one and 350 mg (2.53 mmol) potassium carbonate in 2 mL NMP were stirred for 2 h at 130° C. After cooling to RT the reaction mixture was diluted with DMF and purified by preparative HPLC. The product-containing fractions were combined and freeze-dried.

Yield: 50 mg (11% of theory)
ESI-MS: m/z=459 (M+H)$^+$
R$_t$(HPLC): 0.96 min (method B)

Example 7

7-methoxy-3-{-1-[6-(4-methyl-2-oxo-2,3-dihydro-benzoxazol-6-ylamino)-pyrimidin-4-yl]-piperidin-4-yl}-1,3,4,5-tetrahydro-benzo[d][1,3]diazepin-2-one

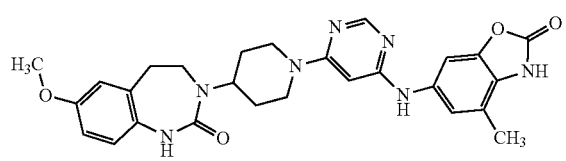

80 mg (0.29 mmol) 7-methoxy-3-piperidin-4-yl-1,3,4,5-tetrahydro-1,3-benzodiazepin-2-one, 90 mg (0.26 mmol) 6-(6-chloro-pyrimidin-4-ylamino)-4-methyl-3H-benzoxazol-2-one and 0.15 mL (0.87 mmol) DIPEA in 1.5 mL DMF were stirred at 150° C. After the reaction of the reactants the reaction mixture was purified by preparative HPLC. The product-containing fractions were combined and evaporated down. The residue was dried.

Yield: 13 mg (25% of theory)
ESI-MS: m/z=514 (M−H)$^-$
R$_t$(HPLC): 1.15 min (method B)

Example 8

3-{1-[6-(2,7-dimethyl-1H-benzimidazol-5-ylamino)-pyrimidin-4-yl]-piperidin-4-yl}-7-methoxy-1,3,4,5-tetrahydro-benzo[d][1,3]diazepin-2-one

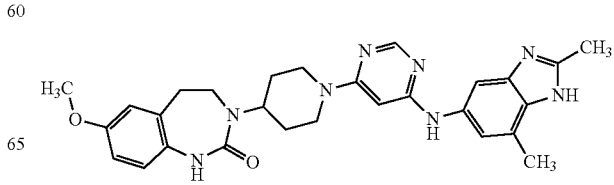

265 mg (0.962 mmol) 7-methoxy-3-piperidin-4-yl-1,3,4,5-tetrahydro-1,3-benzodiazepin-2-one, 250 mg (0.913 mmol) (6-chloro-pyrimidin-4-yl)-(2,7-dimethyl-1H-benzimidazol-5-yl)-amine and 1.00 mL (5.81 mmol) DIPEA were refluxed in 1.5 mL DMF. After the reaction had ended the reaction mixture was diluted with some DMF and microfiltered. The filtrate was purified by preparative HPLC. The product-containing fractions were combined and freeze-dried.
Yield: 170 mg (36% of theoretical)
ESI-MS: m/z=513 (M+H)$^+$
$R_t$(HPLC): 0.97 min (method B)

Example 9

3-{1-[6-(2,7-dimethyl-1H-benzimidazol-5-ylamino)-pyrimidin-4-yl]-piperidin-4-yl}-1,3-di-hydro-imidazo[4,5-c]quinolin-2-one

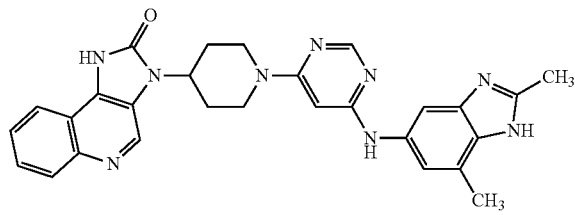 [SMILES: Cc1nc2cc(Nc3cc(N4CCC(n5c(=O)[nH]c6c7ccccc7ncc65)CC4)ncn3)cc(C)c2[nH]1]

150 mg (0.548 mmol) (6-chloro-pyrimidin-4-yl)-(2,7-dimethyl-1H-benzimidazol-5-yl)-amine, 150 mg (0.559 mmol) 3-piperidin-4-yl-1,3-dihydro-imidazo[4,5-c]quinolin-2-one and 1.00 mL (5.81 mmol) DIPEA were refluxed in 1.0 mL DMF. After the reaction had ended the reaction mixture was diluted with MeOH and purified by preparative HPLC. The product-containing fractions were combined and freeze-dried.
Yield: 20 mg (7% of theory)
ESI-MS: m/z=506 (M+H)$^+$
$R_t$(HPLC): 0.74 min (method B)

Example 10

3-{1-[6-(3,4-dimethyl-2-oxo-2,3-dihydro-benzoxazol-6-ylamino)-pyrimidin-4-yl]-piperidin-4-yl}-7-methoxy-1,3,4,5-tetrahydro-benzo[d][1,3]diazepin-2-one

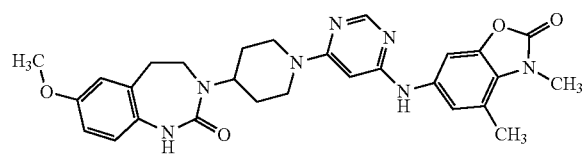 [SMILES: COc1ccc2c(c1)CCN(C1CCN(c3cc(Nc4cc(C)c5c(c4)oc(=O)n5C)ncn3)CC1)C(=O)N2]

90 mg (0.33 mmol) 7-methoxy-3-piperidin-4-yl-1,3,4,5-tetrahydro-1,3-benzodiazepin-2-one, 90 mg (0.31 mmol) 6-(6-chloro-pyrimidin-4-ylamino)-3,4-dimethyl-3H-benzoxazol-2-one and 0.15 mL (0.87 mmol) DIPEA were combined in 1.5 mL DMF and stirred at 150° C. After the reaction had ended the reaction mixture was purified by preparative HPLC. The product-containing fractions were combined and dried.
Yield: 60 mg (37% of theory)
ESI-MS: m/z=530 (M+H)$^+$
$R_t$(HPLC): 3.30 min (method C)

Example 11

7-methoxy-3-{1-[6-(7-methyl-1H-indazol-5-ylamino)-pyrimidin-4-yl]-piperidin-4-yl}-1,3,4,5-tetrahydro-benzo[d][1,3]diazepin-2-one

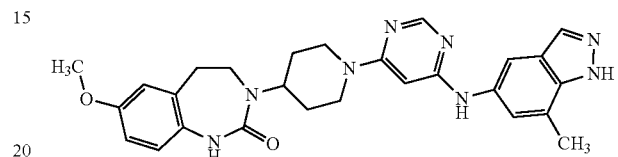

210 mg (0.763 mmol) 7-methoxy-3-piperidin-4-yl-1,3,4,5-tetrahydro-1,3-benzodiazepin-2-one, 200 mg (0.770 mmol) (6-chloro-pyrimidin-4-yl)-(7-methyl-1H-indazol-5-yl)-amine and 3.50 mL (20.3 mmol) DIPEA were combined in 1.5 mL DMF and stirred at 150° C. After the reaction had ended the reaction mixture was purified by preparative HPLC. The product-containing fractions were combined and freeze-dried.
Yield: 40 mg (11% of theory)
ESI-MS: m/z=497 (M−H)$^−$
$R_f$: 0.5 (silica gel: DCM/MeOH/cyc/NH$_4$OH=70:15:15:2)

Example 12

7-methoxy-3-{1-[6-(1,2,7-trimethyl-1H-benzimidazol-5-ylamino)-pyrimidin-4-yl]-piperidin-4-yl}-1,3,4,5-tetrahydro-benzo[d][1,3]diazepin-2-one

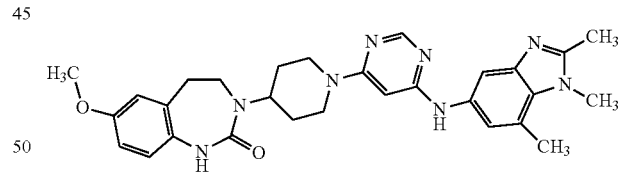

80 mg (0.29 mmol) 7-methoxy-3-piperidin-4-yl-1,3,4,5-tetrahydro-1,3-benzodiazepin-2-one, 0.10 g (0.26 mmol) (6-iodo-pyrimidin-4-yl)-(1,2,7-trimethyl-1H-benzimidazol-5-yl)-amine and 0.15 mL (0.87 mmol) DIPEA were combined in 1.5 mL DMF and stirred at 150° C. The reaction mixture was then purified by preparative HPLC. The product-containing fractions were combined, evaporated down and the residue was dried. This was taken up in DMF and purified again by preparative HPLC. The product-containing fractions were combined and freeze-dried.
Yield: 10 mg (7% of theory)
ESI-MS: m/z=527 (M+H)$^+$
$R_t$(HPLC): 0.97 min (method B)

Example 13

1-{1-[6-(2,7-dimethyl-1H-benzimidazol-5-ylamino)-pyrimidin-4-yl]-piperidin-4-yl}-1,3-dihydro-imidazol-[4,5-b]pyridin-2-one

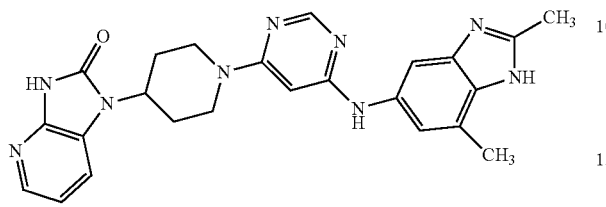

85 mg (0.3 mmol) 1-piperidin-4-yl-1,3-dihydroimidazo[4,5-b]pyridin-2-one-dihydrochloride were added to 80 mg (0.3 mmol) (6-chloro-pyrimidin-4-yl)-(2,7-dimethyl-1H-benzimidazol-5-yl)-amine, 0.2 mL (1.1 mmol) DIPEA in 2 mL DMF and stirred overnight at 60° C., then heated for 3 h at 120° C. in the microwave and then again for 1 h 15 min at 150° C. in the microwave. Then another 30 mg 1-piperidin-4-yl-1,3-dihydroimidazo[4,5-b]pyridin-2-one-dihydrochloride and DIPEA were added and the mixture was stirred for a further 30 min at 150° C. in the microwave. The reaction mixture was then purified by preparative HPLC. The product-containing fractions were combined and freeze-dried.

Yield: 46 mg (31% of theoretical)

ESI-MS: m/z=456 (M+H)$^+$ $R_t$(HPLC): 0.79 min (method B)

Example 14

1-{1-[6-(3,4-dimethyl-2-oxo-2,3-dihydro-benzoxazol-6-ylamino)-pyrimidin-4-yl]-piperidin-4-yl}-1,3-dihydro-imidazo[4,5-b]pyridin-2-one

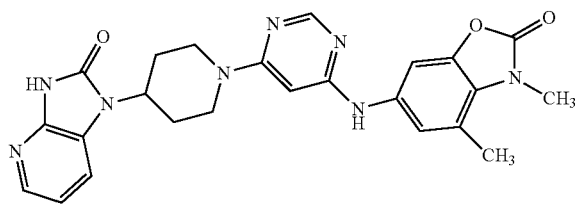 [SMILES: Cc1cc(Nc2cc(N3CCC(n4c(=O)[nH]c5ncccc54)CC3)ncn2)cc2oc(=O)n(C)c12]

0.10 g (0.34 mmol) 1-piperidin-4-yl-1,3-dihydroimidazo[4,5-b]pyridin-2-one-dihydrochloride, 90 mg (0.31 mmol) 6-(6-chloro-pyrimidin-4-ylamino)-3,4-dimethyl-3H-benzoxazol-2-one and 0.15 mL (0.87 mmol) DIPEA in 1.5 mL DMF were combined and stirred at 150° C. After the reaction had ended the reaction mixture was diluted with water. The precipitate formed was suction filtered, taken up in DMF and purified by preparative HPLC. The product-containing fractions were combined, evaporated down and the residue dried.

Yield: 25 mg (17% of theory)

ESI-MS: m/z=473 (M+H)$^+$ $R_t$(HPLC): 1.04 min (method B)

Example 15

N-(3,4-dimethyl-2-oxo-2,3-dihydro-benzoxazol-6-yl)-N-{6-[4-(7-methoxy-2-oxo-1,2,4,5-tetrahydro-benzo[d][1,3]diazepin-3-yl)-piperidin-1-yl]-pyrimidin-4-yl}-acetamide

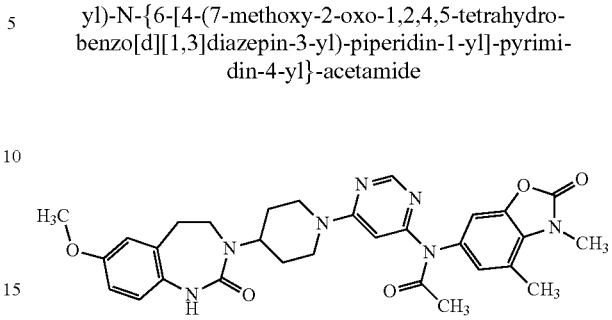

59 mg (0.21 mmol) 7-methoxy-3-piperidin-4-yl-1,3,4,5-tetrahydro-1,3-benzodiazepin-2-one, 65 mg (0.19 mmol) N-(6-chloro-pyrimidin-4-yl)-N-(3,4-dimethyl-2-oxo-2,3-dihydro-benzoxazol-6-yl)-acetamide and 81 mg (0.59 mmol) potassium carbonate in 1.5 mL NMP were combined and stirred at 80° C. The reaction mixture was purified by preparative HPLC. The product-containing fractions were combined and evaporated down. The solid obtained was washed with diethyl ether and dried.

Yield: 6 mg (5% of theory)

ESI-MS: m/z=572 (M+H)$^+$ $R_t$(HPLC): 1.53 min (method F)

Example 16

3-{1-[6-(2,7-dimethyl-benzoxazol-5-ylamino)-pyrimidin-4-yl]-piperidin-4-yl}-7-methoxy-1,3,4,5-tetrahydro-benzo[d][1,3]diazepin-2-one

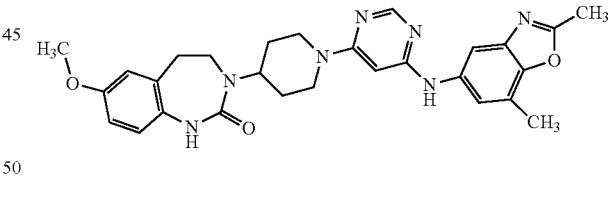

70 mg (0.25 mmol) 7-methoxy-3-piperidin-4-yl-1,3,4,5-tetrahydro-1,3-benzodiazepin-2-one, 55 mg (0.20 mmol) (6-chloro-pyrimidin-4-yl)-(2,7-dimethyl-benzoxazol-5-yl)-amine and 0.15 mL (0.87 mmol) DIPEA were combined in 1.5 mL DMF and stirred for 2.5 h at 150° C. The reaction mixture was purified by preparative HPLC. The product-containing fractions were combined and freeze-dried. The residue was stirred with MeOH and DMF, left to stand for 1 h and filtered. The precipitate was washed with MeOH and dried.

Yield: 25 mg (24% of theory)

ESI-MS: m/z=514 (M+H)$^+$ $R_t$(HPLC): 1.25 min (method B)

Example 17

3-{1-[6-(4-hydroxy-3,5-dimethyl-phenylamino)-pyrimidin-4-yl]-piperidin-4-yl}-7-methoxy-1,3,4,5-tetrahydro-benzo[d][1,3]diazepin-2-one

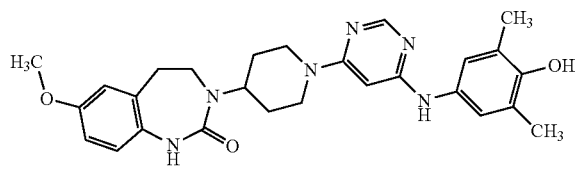 [SMILES: COc1ccc2c(c1)CCN(C1CCN(c3cc(Nc4cc(C)c(O)c(C)c4)ncn3)CC1)C(=O)N2]

140 mg (0.508 mmol) 7-methoxy-3-piperidin-4-yl-1,3,4,5-tetrahydro-1,3-benzodiazepin-2-one, 130 mg (0.521 mmol) 4-(6-chloro-pyrimidin-4-ylamino)-2,6-dimethyl-phenol and 2.50 mL (14.5 mmol) DIPEA were combined and heated to 150° C. overnight. The reaction mixture was evaporated down, the residue was dissolved in DMF and purified by preparative HPLC. The product-containing fractions were combined and freeze-dried. The freeze-dried product was stirred with MeOH, the precipitate was suction filtered and dried.

Yield: 35 mg (14% of theory)

ESI-MS: m/z=489 (M+H)$^+$ $R_f$: 0.62 (silica gel: DCM/MeOH/cyc/NH$_4$OH=70:15:15:2)

Example 18

4-methyl-6-(6-(2'-oxo-1.1'.2'.3-tetrahydrospiro[indene-2,3'-pyrrolo[2,3-b]pyridin]-5-ylamino)pyrimidin-4-ylamino)benzo[d]oxazol-2(3H)-one

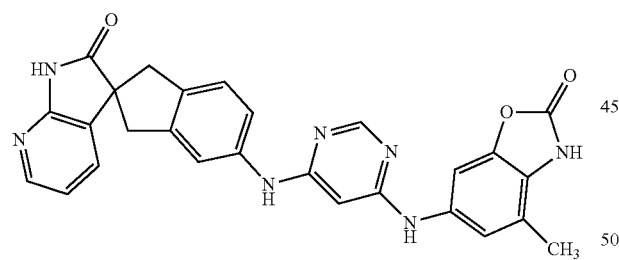

57 mg (0.23 mmol) 5-amino-1,3-dihydrospiro[indene-2,3'-pyrrolo[2,3-b]pyridin]-2'(1'H)-one, 80 mg (0.23 mmol) 6-(6-chloro-pyrimidin-4-ylamino)-4-methyl-3H-benzoxazol-2-one and 69 mg (0.50 mmol) potassium carbonate were combined in 1.5 mL NMP and stirred for 2 h at 130° C. Then the reaction mixture was cooled, acidified with 1M aqueous hydrochloric acid solution and stirred for 1 h at 50° C. The reaction mixture was diluted with water, the precipitate was taken up in DMF and purified by preparative HPLC. The product-containing fractions were combined and freeze-dried.

Yield: 30 mg (27% of theory)

ESI-MS: m/z=492 (M+H)$^+$ $R_t$(HPLC): 1.27 min (method B)

Example 19

5-(6-(2,7-dimethyl-1H-benzo[d]imidazol-5-ylamino)pyrimidin-4-ylamino)-1,3-dihydrospiro-[indene-2,3'-pyrrolo[2,3-b]pyridin]-2'(1'H)-one

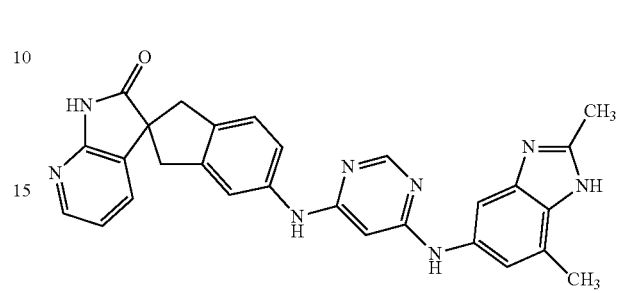

140 mg (0.557 mmol), 150 mg (0.548 mmol) (6-chloro-pyrimidin-4-yl)-(2,7-dimethyl-1H-benzimidazol-5-yl)-amine and 1.00 mL (5.81 mmol) DIPEA were combined with 1.5 mL DMF and refluxed. 20.0 mg (0.126 mmol) benzenesulphonic acid were added and the mixture was stirred for a further 3 h. The reaction mixture was diluted with DMF and purified by preparative HPLC. The product-containing fractions were combined and freeze-dried.

Yield: 15 mg (5% of theory)

ESI-MS: m/z=489 (M+H)$^+$ $R_t$(HPLC): 0.90 min (method B)

Example 20

1-{1-[6-(2,7-dimethyl-benzoxazol-5-ylamino)-pyrimidin-4-yl]-piperidin-4-yl}-1,3-dihydro-imidazol-[4,5-b]pyridin-2-one

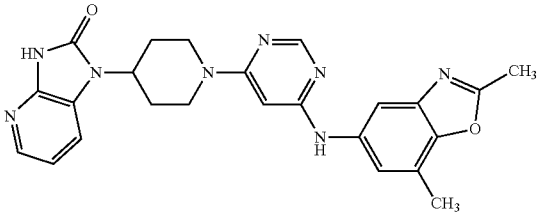 [SMILES: Cc1nc2cc(Nc3cc(N4CCC(n5c(=O)[nH]c6ncccc65)CC4)ncn3)cc(C)c2o1]

75 mg (0.26 mmol) of 1-piperidin-4-yl-1,3-dihydroimidazo[4,5-b]pyridin-2-one-dihydrochloride, 55 mg (0.20 mmol) (6-chloro-pyrimidin-4-yl)-(2,7-dimethyl-benzoxazol-5-yl)-amine and 0.15 mL (0.87 mmol) DIPEA were combined in 1.5 mL DMF and stirred at 150° C. for 2.5 h. The reaction mixture was purified by preparative HPLC. The product-containing fractions were combined and freeze-dried.

Yield: 25 mg (27% of theory)

ESI-MS: m/z=457 (M+H)$^+$ $R_t$(HPLC): 1.11 min (method B)

Example 21

7-methoxy-3-{-1-[6-(4-methyl-2-oxo-2,3-dihydro-benzoxazol-6-ylsulphanyl)-pyrimidin-4-yl]-piperidin-4-yl}-1,3,4,5-tetrahydro-benzo[d][1,3]diazepin-2-one

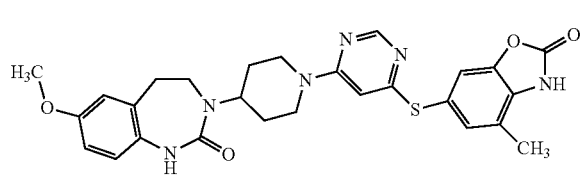 [SMILES: COc1ccc2c(c1)CCN(C1CCN(c3cc(Sc4cc(C)c5[nH]c(=O)oc5c4)ncn3)CC1)C(=O)N2]

187 mg (0.681 mmol) 7-methoxy-3-piperidin-4-yl-1,3,4,5-tetrahydro-1,3-benzodiazepin-2-one, 180 mg (0.490 mmol) 6-(6-chloro-pyrimidin-4-ylsulphanyl)-4-methyl-3H-benzoxazol-2-one and 200 mg (1.45 mmol) potassium carbonate were combined in 5.0 mL NMP and stirred for 2 h at 130° C. The reaction mixture was cooled overnight, filtered and the filtrate was purified by preparative HPLC. The product-containing fractions were combined, evaporated down and dried i. vac.

Yield: 130 mg (50% of theory)

ESI-MS: m/z=533 (M+H)$^+$ $R_t$(HPLC): 1.00 min (method B)

Example 22

7-methoxy-3-{1-[2-methyl-6-(4-methyl-2-oxo-2,3-dihydro-benzoxazol-6-yloxy)-pyrimidin-4-yl]-piperidin-4-yl}-1,3,4,5-tetrahydro-benzo[d][1,3]diazepin-2-one

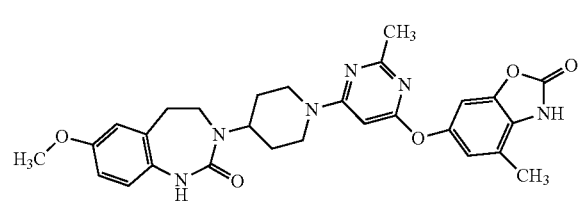 [SMILES: COc1ccc2c(c1)CCN(C1CCN(c3cc(Oc4cc(C)c5[nH]c(=O)oc5c4)nc(C)n3)CC1)C(=O)N2]

48 mg (0.17 mol) 7-methoxy-3-piperidin-4-yl-1,3,4,5-tetrahydro-1,3-benzodiazepin-2-one, 50 mg (0.17 mmol) 6-(6-chloro-2-methyl-pyrimidin-4-yloxy)-4-methyl-3H-benzoxazol-2-one and 0.10 mL (0.58 mmol) DIPEA were combined in 1.8 mL DMF and stirred overnight at 80° C. The reaction mixture was diluted with water and the precipitate formed was suction filtered and dried.

Yield: 62 mg (68% of theory)

ESI-MS: m/z=531 (M+H)$^+$ $R_t$ (HPLC): 1.24 min (method B)

Example 23

1-(6-(4-methyl-2-oxo-2,3-dihydrobenz-[d]oxazol-6-yloxy)pyrimidin-4-yl)spiro[piperidin-4,4'-pyrido[2,3-d][1.3]oxazin]-2'(1'H)-one

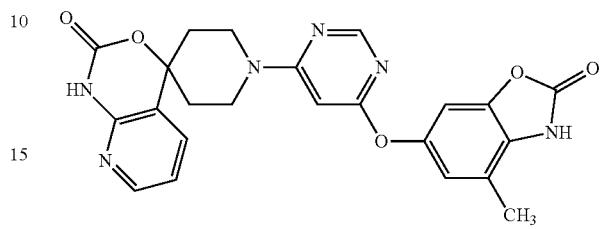

20 mg (0.078 mol) spiro[piperidin-4,4'-pyrido[2,3-d][1,3]oxazin]-2'(1'H)-one hydrochloride, 20 mg (0.072 mmol) 6-(6-chloro-pyrimidin-4-ylamino)-4-methyl-3H-benzoxazol-2-one and 0.10 mL (0.57 mmol) DIPEA were combined in 1.0 mL DMF and stirred overnight at RT. The reaction mixture was purified by preparative HPLC. The product-containing fractions were combined and freeze-dried.

Yield: 3 mg (9% of theory)

ESI-MS: m/z=461 (M+H)$^+$ $R_t$ (HPLC): 1.24 min (method B)

Example 24

1-{1-[2-methyl-6-(4-methyl-2-oxo-2,3-dihydro-benzoxazol-6-yloxy)-pyrimidin-4-yl]-piperidin-4-yl}-1,3-dihydro-imidazo[4,5-b]pyridin-2-one

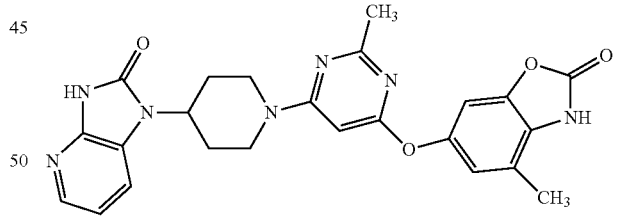

38 mg (0.17 mmol) 1-piperidin-4-yl-1,3-dihydroimidazo[4,5-b]pyridin-2-one, 50 mg (0.17 mmol) 6-(6-chloro-2-methyl-pyrimidin-4-yloxy)-4-methyl-3H-benzoxazol-2-one and 0.10 mL (0.57 mmol) DIPEA were combined in 1.8 mL DMF and stirred overnight at 80° C. Then another 15 mg (0.069 mmol) 1-piperidin-4-yl-1,3-dihydroimidazo[4,5-b]pyridin-2-one were added and the mixture was further stirred overnight at RT. The reaction mixture was diluted with water, the precipitate formed was suction filtered and dried i. vac.

Yield: 49 mg (60% of theory)

ESI-MS: m/z=474 (M+H)$^+$ $R_t$ (HPLC): 1.09 min (method B)

Example 25

7-methoxy-3-{1-[6-(4-methyl-2-oxo-2,3-dihydro-benzoxazol-6-sulphinyl)-pyrimidin-4-yl]-piperidin-4-yl}-1,3,4,5-tetrahydro-benzo[d][1,3]diazepin-2-one

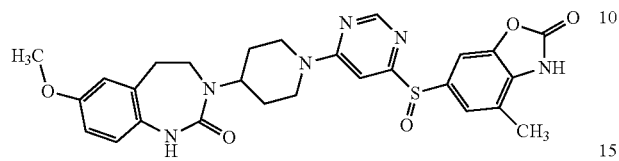

Under a nitrogen atmosphere 28 mg (0.11 mmol) 3-chloroperoxybenzoic acid (70%) in 5 mL dichloromethane was added dropwise to 60 mg (0.11 mmol) 7-methoxy-3-{1-[6-(4-methyl-2-oxo-2,3-dihydro-benzoxazol-6-ylsulphanyl)-pyrimidin-4-yl]-piperidin-4-yl}-1,3,4,5-tetrahydro-benzo[d][1,3]diazepin-2-one in 5 mL dichloromethane and 1 mL methanol. After the reaction had ended the reaction mixture was evaporated down, dissolved in MeOH/DMF and purified by preparative HPLC-MS. The product-containing fractions were combined and freeze-dried.

Yield: 50 mg (73% of theory)
ESI-MS: m/z=549 (M+H)$^+$
$R_t$(HPLC): 1.26 min (method B)

Example 26

7-methoxy-3-{1-[6-(4-methyl-2-oxo-2,3-dihydro-benzoxazol-6-sulphonyl)-pyrimidin-4-yl]-piperidin-4-yl}-1,3,4,5-tetrahydro-benzo[d][1,3]diazepin-2-one

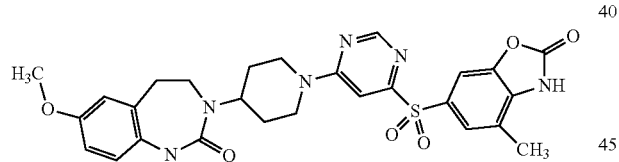

Under a nitrogen atmosphere 56 mg (0.23 mmol) 3-chloroperoxybenzoic acid (70%) in 5 mL dichloromethane was added dropwise to 60 mg (0.11 mmol) 7-methoxy-3-{1-[6-(4-methyl-2-oxo-2,3-dihydro-benzoxazol-6-ylsulphanyl)-pyrimidin-4-yl]-piperidin-4-yl}-1,3,4,5-tetrahydro-benzo[d][1,3]diazepin-2-one in 5 mL dichloromethane while cooling with ice. After the reaction had ended the reaction mixture was purified by preparative HPLC-MS. The product-containing fractions were combined and freeze-dried.

Yield: 19 mg (28% of theory)
ESI-MS: m/z=565 (M+H)$^+$
$R_t$(HPLC): 1.42 min (method B)

Example 27

7-methoxy-3-{1-[6-(quinoxaline-2-yloxy)-pyrimidin-4-yl]-piperidin-4-yl}-1,3,4,5-tetrahydro-benzo[d][1,3]diazepin-2-one

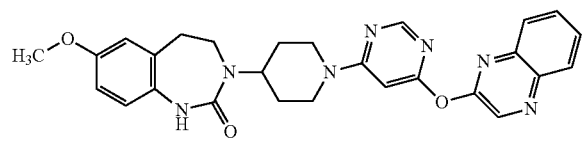 [SMILES: COc1ccc2c(c1)CCN(C1CCN(c3cc(Oc4cnc5ccccc5n4)ncn3)CC1)C(=O)N2]

24 mg (0.087 mmol) 7-methoxy-3-piperidin-4-yl-1,3,4,5-tetrahydro-1,3-benzodiazepin-2-one, 20 mg (0.077 mmol) 2-(6-chloro-pyrimidin-4-yloxy)-quinoxaline and 0.050 mL (0.29 mmol) DIPEA were combined in 1.0 mL DMF and stirred overnight at 90° C. The reaction mixture was purified by preparative HPLC-MS. The product-containing fractions were combined and freeze-dried.

Yield: 10 mg (26% of theory)
ESI-MS: m/z=498 (M+H)$^+$
$R_t$(HPLC): 1.48 min (method B)

Example 28

(6-{6-[4-(7-methoxy-2-oxo-1,2,4,5-tetrahydro-benzo[d][1,3]diazepin-3-yl)-piperidin-1-yl]-pyrimidin-4-yloxy}-4-methyl-1H-benzimidazole-2-yl)-acetonitrile

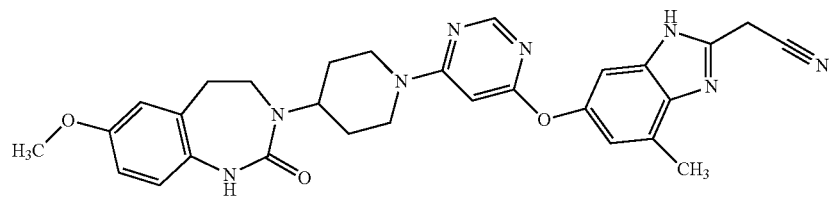 [SMILES: COc1ccc2c(c1)CCN(C1CCN(c3cc(Oc4cc(C)c5nc(CC#N)[nH]c5c4)ncn3)CC1)C(=O)N2]

0.20 g (0.42 mmol) 3-{1-[6-(3,4-diamino-5-methyl-phenoxy)-pyrimidin-4-yl]-piperidin-4-yl}-7-methoxy-1,3,4,5-tetrahydro-benzo[d][1,3]diazepin-2-one, 40 mg (0.46 mmol) cyanoacetic acid, 0.15 g (0.47 mmol) TBTU and 0.14 mL (1.00 mmol) TEA in 2.00 mL DMF were stirred for 4 h at RT. Then 2.00 mL glacial acetic acid was added and the mixture was stirred overnight at RT. The reaction mixture was also stirred for 1 h at 100° C., then cooled and purified by preparative HPLC-MS. The product-containing fractions were combined and the acetonitrile was evaporated down. The residue was made alkaline with 4N aqueous sodium hydroxide solution, the precipitate formed was suction filtered, washed with water and dried under HV.

Yield: 17 mg (8% of theory)
ESI-MS: m/z=539 (M+H)$^+$
$R_t$ (HPLC): 1.23 min (method B)

Example 29

3-{1-[6-(2,7-dimethyl-3H-benzimidazol-5-yloxy)-pyrimidin-4-yl]-piperidin-4-yl}-7-methoxy-1,3,4,5-tetrahydro-benzo[d][1,3]diazepin-2-one

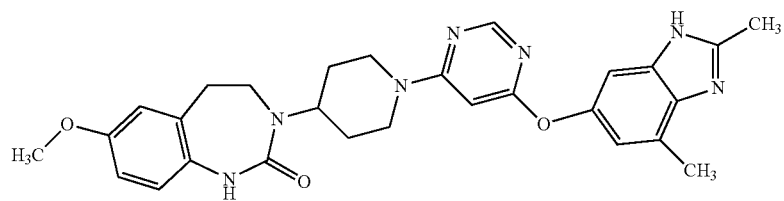

0.16 g (0.59 mmol) 7-methoxy-3-piperidin-4-yl-1,3,4,5-tetrahydro-1,3-benzodiazepin-2-one, 0.15 g (0.55 mmol) 6-(6-chloro-pyrimidin-4-yloxy)-2,4-dimethyl-1H-benzimidazole and 0.21 mL (1.2 mmol) DIPEA were combined in 2.0 mL DMF and stirred overnight at RT. The reaction mixture was purified by preparative HPLC-MS. The product-containing fractions were combined and the acetonitrile was evaporated down. The residue was made alkaline with 4N aqueous sodium hydroxide solution, the precipitate formed was suction filtered, washed with water and dried under HV.

Yield: 70 mg (26% of theory)
ESI-MS: m/z=514 (M+H)$^+$
$R_t$(HPLC): 1.15 min (method B)

Example 30

1-(6-(2,4-dimethyl-1H-benzo[d]imidazol-6-yloxy)pyrimidin-4-yl)spiro[piperidine-4,4'-pyrido-[2,3-d][1,3]oxazin]-2'(1'H)-one

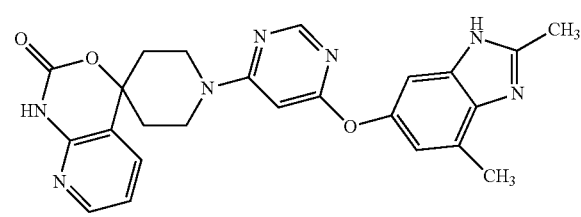 [SMILES: Cc1nc2c(C)cc(Oc3cc(N4CCC5(CC4)OC(=O)Nc4ncccc45)ncn3)cc2[nH]1]

0.15 g (0.59 mmol) spiro[piperidine-4,4'-pyrido[2,3-d][1,3]oxazin]-2'(1'H)-one hydrochloride, 0.15 g (0.55 mmol) 6-(6-chloro-pyrimidin-4-yloxy)-2,4-dimethyl-1H-benzimidazole and 0.31 mL (1.8 mmol) DIPEA were combined in 1.5 mL DMF and stirred first of all overnight at RT then for 2 h at 50° C. The reaction mixture was purified by preparative HPLC-MS. The product-containing fractions were combined and the acetonitrile was evaporated down. The residue was made alkaline with 4N aqueous sodium hydroxide solution, the precipitate formed was suction filtered, washed with water and dried under HV.

Yield: 130 mg (48% of theory)
ESI-MS: m/z=458 (M+H)$^+$
$R_t$(HPLC): 0.96 min (method B)

Example 31

7-methoxy-3-{1-[6-(2-methyl-quinoline-4-yloxy)-pyrimidin-4-yl]-piperidin-4-yl}-1,3,4,5-tetrahydro-benzo[d][1,3]diazepin-2-one

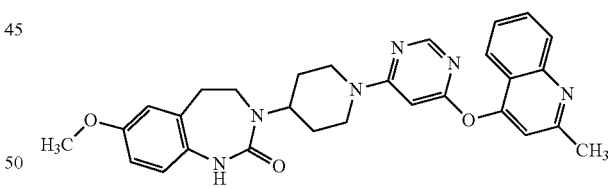

75 mg (0.27 mmol) 7-methoxy-3-piperidin-4-yl-1,3,4,5-tetrahydro-1,3-benzodiazepin-2-one, 70 mg (0.26 mmol) 4-(6-chloro-pyrimidin-4-yloxy)-2-methyl-quinoline and 0.10 mL (0.58 mmol) DIPEA were combined in 1.8 mL DMF and stirred overnight at 90° C. The reaction mixture was purified by preparative HPLC-MS. The product-containing fractions were combined and freeze-dried.

Yield: 35 mg (25% of theory)
ESI-MS: m/z=511 (M+H)$^+$
$R_t$(HPLC): 1.22 min (method B)

Example 32

7-methoxy-3-{-1-[6-(7-methyl-3H-benzimidazol-5-yloxy)-pyrimidin-4-yl]-piperidin-4-yl}-1,3,4,5-tetrahydro-benzo[d][1,3]diazepin-2-one

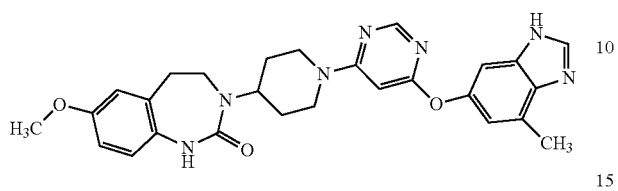

47 mg (0.17 mmol) 7-methoxy-3-piperidin-4-yl-1,3,4,5-tetrahydro-1,3-benzodiazepin-2-one, 45 mg (0.17 mmol) 6-(6-chloro-pyrimidin-4-yloxy)-4-methyl-1H-benzimidazole and 0.06 mL (0.34 mmol) DIPEA were combined in 2.0 mL DMF and stirred for 48 h at RT. The reaction mixture was purified by preparative HPLC-MS. The product-containing fractions were combined and the acetonitrile was evaporated down. The residue was made alkaline with 4N aqueous sodium hydroxide solution, the precipitate formed was suction filtered, washed with water and dried under HV.

Yield: 55 mg (65% of theory)
ESI-MS: m/z=500 (M+H)+
$R_t$(HPLC): 1.14 min (method B)

Example 33

3-{1-[6-(2-cyclopropylmethyl-7-methyl-3H-benzimidazol-5-yloxy)-pyrimidin-4-yl]-piperidin-4-yl}-7-methoxy-1,3,4,5-tetrahydro-benzo[d][1,3]diazepin-2-one

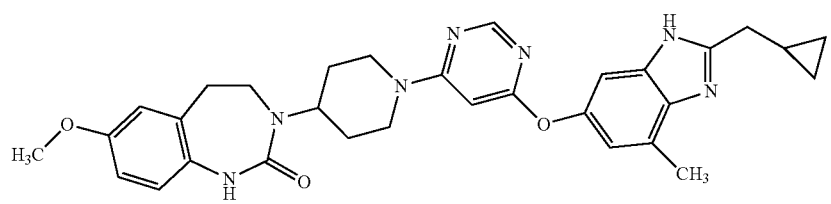 [SMILES: COc1ccc2c(c1)CCN(C1CCN(c3cc(Oc4cc(C)c5nc(CC6CC6)[nH]c5c4)ncn3)CC1)C(=O)N2]

0.20 g (0.42 mmol) 3-{1-[6-(3,4-diamino-5-methyl-phenoxy)-pyrimidin-4-yl]-piperidin-4-yl}-7-methoxy-1,3,4,5-tetrahydro-benzo[d][1,3]diazepin-2-one, 46 mg (0.46 mmol) cyclopropyl-acetic acid, 151 mg (0.47 mmol) TBTU and 0.14 mL (1.00 mmol) TEA in 2.00 mL DMF were stirred for 4 h at RT. Then 2.00 mL glacial acetic acid was added and the mixture was stirred overnight at RT. In addition the reaction mixture was stirred for 1 h at 100° C., then cooled and purified by preparative HPLC-MS. The product-containing fractions were combined and the acetonitrile was evaporated down. The residue was made alkaline with 4N aqueous sodium hydroxide solution, the precipitate formed was suction filtered, washed with water and dried under HV.

Yield: 45 mg (20% of theory)

ESI-MS: m/z=554 (M+H)+

$R_t$ (HPLC): 1.24 min (method B)

Example 34

1-{1-[6-(2,7-dimethyl-3H-benzimidazol-5-yloxy)-pyrimidin-4-yl]-piperidin-4-yl}-1,3-dihydro-imidazol-[4,5-b]pyridin-2-one

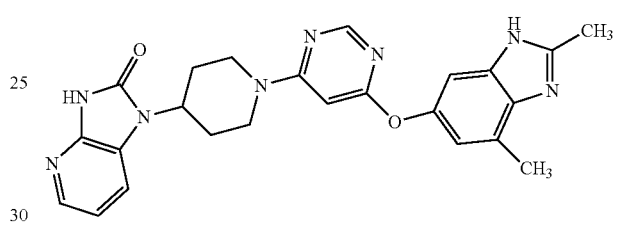

0.13 g (0.59 mmol) 1-piperidin-4-yl-1,3-dihydroimidazo[4,5-b]pyridin-2-one, 150 mg (0.55 mmol) 6-(6-chloro-pyrimidin-4-yloxy)-2,4-dimethyl-1H-benzimidazole and 0.21 mL (1.20 mmol) DIPEA were combined in 2.00 mL DMF and stirred overnight at RT. The reaction mixture was purified by preparative HPLC-MS. The product-containing fractions were combined and the acetonitrile was evaporated down. The residue was made alkaline with 1N aqueous sodium hydroxide solution, the precipitate formed was suction filtered, washed with water and dried under HV.

Yield: 72 mg (27% of theory)
ESI-MS: m/z=457 (M+H)+

Example 35

7-methoxy-3-(1-{6-[7-methyl-2-(2,2,2-trifluoroethyl)-3H-benzimidazol-5-yloxy]-pyrimidin-4-yl}-piperidin-4-yl)-1,3,4,5-tetrahydro-benzo[d][1,3]diazepin-2-one

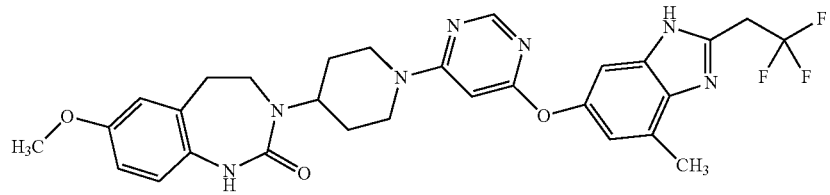 [SMILES: COc1ccc2c(c1)CCN(C1CCN(c3cc(Oc4cc(C)c5nc(CC(F)(F)F)[nH]c5c4)ncn3)CC1)C(=O)N2]

0.20 g (0.42 mmol) 3-{1-[6-(3,4-diamino-5-methyl-phenoxy)-pyrimidin-4-yl]-piperidin-4-yl}-7-methoxy-1,3,4,5-tetrahydro-benzo[d][1,3]diazepin-2-one, 60 mg (0.46 mmol) 3,3,3-tri-fluoropropionic acid, 0.15 g (0.47 mmol) TBTU and 0.14 mL (1.0 mmol) TEA in 2.0 mL DMF were stirred for 4 h at RT. Then 2.0 mL glacial acetic acid was added and the mixture was stirred overnight at RT. In addition the reaction mixture was stirred for 1 h at 100° C., then cooled and purified by preparative HPLC-MS. The product-containing fractions were combined and the acetonitrile was evaporated down. The residue was made alkaline with 4N aqueous sodium hydroxide solution, the precipitate formed was suction filtered, washed with water and dried under HV.

Yield: 13 mg (5% of theory)

ESI-MS: m/z=582 (M+H)$^+$

R$_t$ (HPLC): 1.31 min (method B)

Example 36

3-{1-[6-(2,6-dimethylpyridin-4-yloxy)pyrimidin-4-yl]piperidin-4-yl}-7-methoxy-4,5-dihydro-1H-benzo[d][1,3]diazepin-2(3H)-one

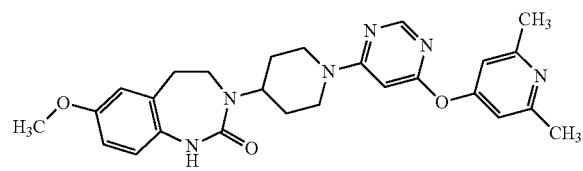

62 mg (0.23 mmol) 7-methoxy-3-piperidin-4-yl-1,3,4,5-tetrahydro-1,3-benzodiazepin-2-one, 50 mg (0.21 mmol)6-chloro-N-(2,6-dimethylpyridin-4-yl)pyrimidin-4-amine and 0.10 mL (0.57 mmol) DIPEA in 1.0 mL DMF were stirred for 1 h at 90° C. The reaction mixture was mixed with water and the precipitate formed was suction filtered and dried.

Yield: 72 mg (68% of theory)

ESI-MS: m/z=475 (M+H)$^+$

R$_t$ (HPLC): 1.11 min (method B)

Example 37

3-{1-[2-amino-6-(4-methyl-2-oxo-2,3-dihydrobenzofuran-6-yloxy)piperidin-4-yl)7-methoxy-4,5-dihydro-1H-benzo[d][1,3]diazepin-2(3H)-one

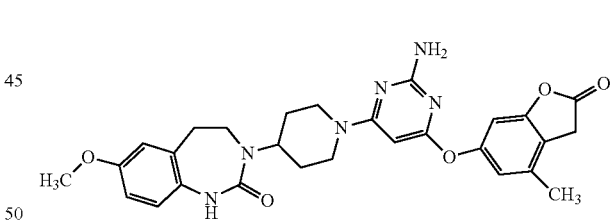

78 mg (0.28 mmol) 7-methoxy-3-piperidin-4-yl-1,3,4,5-tetrahydro-1,3-benzodiazepin-2-one, 80 mg (0.23 mmol) 6-(2-amino-6-chloropyrimidin-4-yloxy)-4-methylbenzo[d]oxazol-2(3H)-one and 0.10 mL (0.57 mmol) DIPEA in 1.0 mL DMF were stirred for 1 h at 90° C. The reaction mixture was purified by preparative HPLC-MS. The fractions containing product were combined and freeze-dried.

Yield: 43 mg (34% of theory)

ESI-MS: m/z=532 (M+H)$^+$

R$_t$ (HPLC): 1.19 min (method B)

Example 38

7-methoxy-3-{1-[6-(2-(methoxymethyl)-4-methyl-1H-benzo[d]imidazol-6-yloxy)pyrimidin-4-yl]piperidin-4-yl}-4,5-dihydro-1H-benzo[d][1,3]diazepin-2(3H)-one

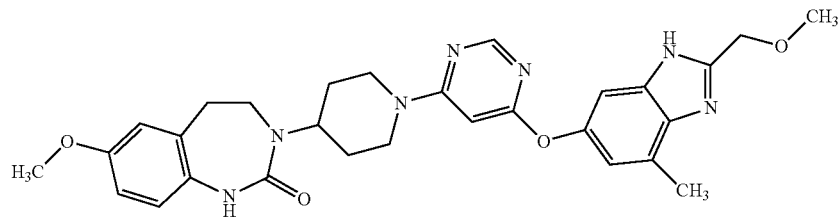

52 mg (0.19 mmol) 7-methoxy-3-piperidin-4-yl-1,3,4,5-tetrahydro-1,3-benzodiazepin-2-one, 50 mg (0.16 mmol) 6-(6-chloropyrimidin-4-yloxy)-2-(methoxymethyl)-4-methyl-1H-benzo[d]imidazole and 0.07 mL (0.40 mmol) DIPEA in 2.0 mL DMF were stirred at RT over the weekend. The reaction mixture was purified by preparative HPLC-MS. The fractions containing product were partially evaporated down i.vac. and neutralised with 4M sodium hydroxide solution. The precipitate formed was suction filtered, washed and dried.

Yield: 30 mg (29% of theory)
ESI-MS: m/z=544 (M+H)+
$R_t$ (HPLC): 1.16 min (method B)

Example 39

1-{6-[2-(methoxymethyl)-4-methyl-1H-benzo[d]imidazol-6-yloxy]pyrimidin-4-yl}spiro-(piperidin-4,4'-pyrido[2,3-d][1,3]oxazin)-2'(1'H)-one

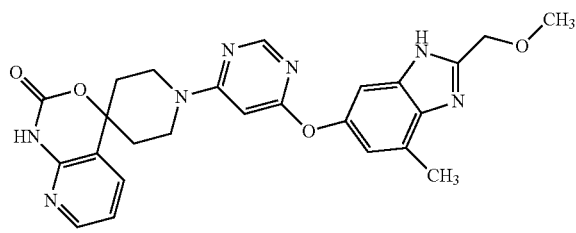 [SMILES: COCc1nc2c(C)cc(Oc3cc(N4CCC5(CC4)OC(=O)Nc4ncccc45)ncn3)cc2[nH]1]

49 mg (0.19 mmol) spiro[piperidin-4,4'-pyrido[2,3-d][1,3]oxazin]-2'(1'H)-one hydrochloride, 50 mg (0.16 mmol) 6-(6-chloropyrimidin-4-yloxy)-2-(methoxymethyl)-4-methyl-1H-benzo-[d]imidazole and 0.10 mL (0.57 mmol) DIPEA in 2.0 mL DMF were stirred at 40° C. over the weekend. The reaction mixture was purified by preparative HPLC-MS. The fractions containing product were partially evaporated down i.vac. and neutralised with 4M sodium hydroxide solution. The precipitate formed was suction filtered, washed and dried.

Yield: 37 mg (40% of theory)
ESI-MS: m/z=488 (M+H)+
$R_t$ (HPLC): 0.99 min (method B)

Example 40

6-{2-methoxy-6-[4-(7-methoxy-2-oxo-4,5-dihydro-1H-benzo[d][1,3]diazepin-3(2H)-yl)-piperidin-1-yl]pyrimidin-4-yloxy}-4-methylbenzo[d]oxazol-2(3H)-one

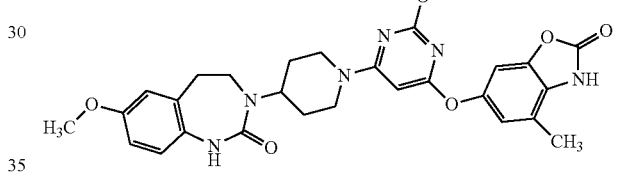

45 mg (0.16 mmol) 7-methoxy-3-piperidin-4-yl-1,3,4,5-tetrahydro-1,3-benzodiazepin-2-one, 50 mg (0.15 mmol) 6-(6-chloro-2-methoxypyrimidin-4-yloxy)-4-methylbenzo[d]oxazol-2(3H)-one and 0.10 mL (0.57 mmol) DIPEA in 1.0 mL DMF were stirred for 3 h at 90° C. The reaction mixture was purified by preparative HPLC-MS. The fractions containing product were combined and freeze-dried.

Yield: 20 mg (21% of theory)
ESI-MS: m/z=547 (M+H)+
$R_t$ (HPLC): 1.42 min (method B)

Example 41

1-[2-methoxy-6-(4-methyl-2-oxo-2,3-dihydrobenzo[d]oxazol-6-yloxy)pyrimidin-4-yl]spiro-[piperidin-4,4'-pyrido[2,3-d][1,3]oxazin]-2'(1'H)-one

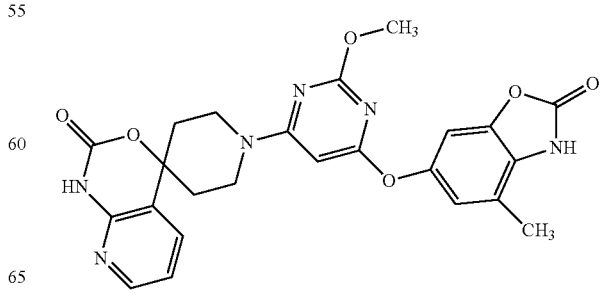

58 mg (0.23 mmol) spiro[piperidin-4,4'-pyrido[2,3-d][1,3]oxazin]-2'(1'H)-one hydrochloride, 70 mg (0.20 mmol) 6-(6-chloro-2-methoxypyrimidin-4-yloxy)-4-methylbenzo[d]oxazol-2(3H)-one and 0.10 mL DIPEA (0.57 mmol) in 1.0 mL DMF were stirred for 3 h at 90° C. The reaction mixture was mixed with water, the precipitate w suction filtered, washed and dried. The residue was purified by preparative HPLC-MS. The fractions containing product were combined and freeze-dried.

Yield: 45 mg (43% of theory)
ESI-MS: m/z=491 (M+H)$^+$
R$_t$ (HPLC): 1.26 min (method B)

Example 42

3-{1-[6-(2-cyclopropyl-4-methyl-1H-benzo[d]imidazol-6-yloxy)pyrimidin-4-yl]piperidin-4-yl}-7-methoxy-4,5-dihydro-1H-benzo[d][1,3]diazepin-2(3H)-one

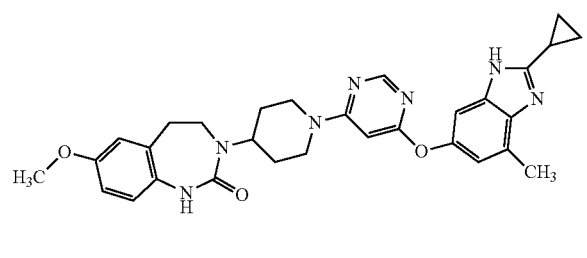 [SMILES: COc1ccc2c(c1)CCN(C1CCN(c3cc(Oc4cc(C)c5nc(C6CC6)[nH]c5c4)ncn3)CC1)C(=O)N2]

44 mg (0.16 mmol) 7-methoxy-3-piperidin-4-yl-1,3,4,5-tetrahydro-1,3-benzodiazepin-2-one, 40 mg (0.13 mmol) 6-(6-chloropyrimidin-4-yloxy)-2-cyclopropyl-4-methyl-1H-benzo[d]imidazole and 0.06 mL (0.32 mmol) DIPEA in 2.0 mL DMF were stirred overnight at RT. The reaction mixture was purified by preparative HPLC-MS. The fractions containing the product were partially evaporated down i.vac. and neutralised with 4M sodium hydroxide solution. The precipitate formed was suction filtered, washed and dried.

Yield: 26 mg (30% of theory)
ESI-MS: m/z=540 (M+H)$^+$
R$_t$ (HPLC): 1.17 min (method B)

Example 43

1-(1-(6-(2-cyclopropyl-4-methyl-1H-benzo[d]imidazol-6-yloxy)pyrimidin-4-yl)piperidin-4-yl)-1H-imidazol-[4,5-b]pyridin-2(3H)-one

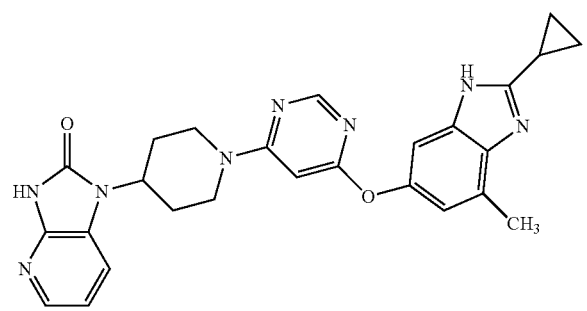 [SMILES: Cc1cc(Oc2cc(N3CCC(n4c(=O)[nH]c5ncccc54)CC3)ncn2)cc2[nH]c(C3CC3)nc12]

35 mg (0.16 mmol) 1-piperidin-4-yl-1,3-dihydroimidazo[4,5-b]pyridin-2-one, 40 mg (0.13 mmol) 6-(6-chloropyrimidin-4-yloxy)-2-cyclopropyl-4-methyl-1H-benzo[d]imidazole and 0.06 mL (0.32 mmol) DIPEA in 2.0 mL DMF were stirred overnight at RT and for 2 h at 40° C. The reaction mixture was purified by preparative HPLC-MS. The fractions containing product were partially evaporated down i.vac. and neutralised with 1M sodium hydroxide solution. The precipitate formed was suction filtered, washed and dried.

Yield: 30 mg (39% of theory)
ESI-MS: m/z=483 (M+H)$^+$
R$_t$ (HPLC): 1.06 min (method B)

Example 44

1-(6-(2-cyclopropyl-4-methyl-1H-benzo[d]imidazol-6-yloxy)pyrimidin-4-yl)spiro[piperidin-4,4'-pyrido[2,3-d][1,3]oxazin]-2'(1'H)-one

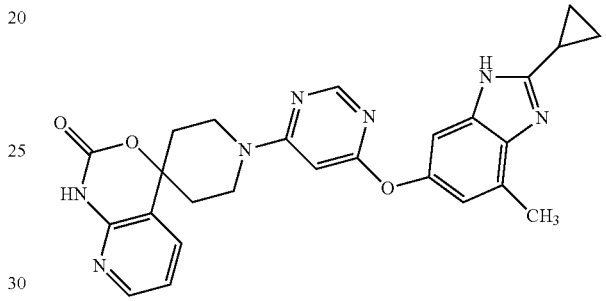

41 mg (0.16 mmol) spiro[piperidin-4,4'-pyrido[2,3-d][1,3]oxazin]-2'(1'H)-one hydrochloride, 40 mg (0.13 mmol) 6-(6-chloropyrimidin-4-yloxy)-2-cyclopropyl-4-methyl-1H-benzo[d]-imidazole and 0.08 mL (0.48 mmol) DIPEA in 2.0 mL DMF were stirred overnight at 40° C. The reaction mixture was purified by preparative HPLC-MS. The fractions containing product were partially evaporated down i.vac. and neutralised with 4M sodium hydroxide solution. The precipitate formed was suction filtered, washed and dried.

Yield: 30 mg (39% of theory)
ESI-MS: m/z=484 (M+H)$^+$
R$_t$ (HPLC): 1.04 min (method B)

Example 45

6-(2-cyclopropyl-6-(4-(7-methoxy-2-oxo-4,5-dihydro-1H-benzo[d][1,3]diazepin-3(2H)-yl)piperidin-1-yl)pyrimidin-4-yloxy)-4-methylbenzo[d]oxazol-2(3H)-one

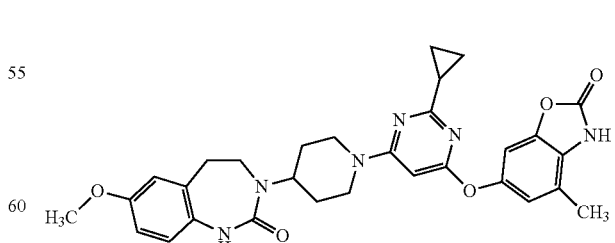

39 mg (0.14 mmol) 7-methoxy-3-piperidin-4-yl-1,3,4,5-tetrahydro-1,3-benzodiazepin-2-one, 39 mg (0.12 mmol) 6-(6-chloro-2-cyclopropylpyrimidin-4-yloxy)-4-methylbenzo[d]oxazol-2(3H)-one and 0.10 mL (0.57 mmol) DIPEA in 1.0 mL DMF were stirred for 2 h at 90° C. The reaction mixture was mixed with water. The precipitate formed was suction filtered, washed and dried.

Yield: 45 mg (63% of theory)
ESI-MS: m/z=557 (M+H)+
$R_t$ (HPLC): 1.43 min (method B)

Example 46

6-(6-chloro-2-(4-(7-methoxy-2-oxo-4,5-dihydro-1H-benzo[d][1,3]diazepin-3(2H)-yl)piperidin-1-yl)pyrimidin-4-yloxy)-4-methylbenzo[d]oxazol-2(3H)-one

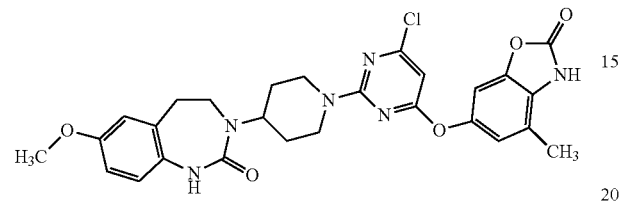

180 mg (0.65 mmol) 7-methoxy-3-piperidin-4-yl-1,3,4,5-tetrahydro-1,3-benzodiazepin-2-one, 205 mg (0.66 mmol) 6-(2,6-dichloropyrimidin-4-yloxy)-4-methylbenzo[d]oxazol-2(3H)-one and 0.25 mL (1.44 mmol) DIPEA in 5.0 mL DMF were stirred for 2 h at RT. The reaction mixture was mixed with water. The precipitate formed was suction filtered, washed and dried. The substance was purified by preparative HPLC-MS. The fractions containing product were partially evaporated down i.vac. and neutralised with sodium hydroxide solution. The precipitate formed was suction filtered, washed and dried.

Yield: 115 mg (32% of theory)
ESI-MS: m/z=551/553 (Cl) (M+H)+
$R_t$ (HPLC): 1.64 min (method B)

Example 47

6-(6-(4-(7-methoxy-2-oxo-4,5-dihydro-1H-benzo[d][1,3]diazepin-3(2H)-yl)piperidin-1-yl)pyrimidin-4-yloxy)benzo[d]oxazol-2(3H)-one

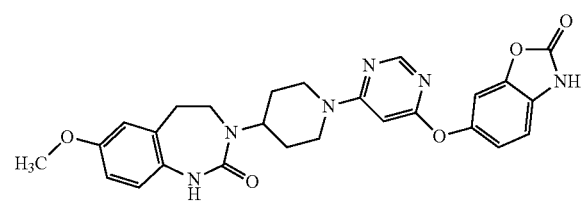 [SMILES: COc1ccc2c(c1)CCN(C1CCN(c3cc(Oc4ccc5[nH]c(=O)oc5c4)ncn3)CC1)C(=O)N2]

100 mg (0.36 mmol) 7-methoxy-3-piperidin-4-yl-1,3,4,5-tetrahydro-1,3-benzodiazepin-2-one, 90 mg (0.34 mmol) 6-(6-chloropyrimidin-4-yloxy)benzo[d]oxazol-2(3H)-one and 0.07 mL (0.41 mmol) DIPEA in 2.0 mL DMF were stirred overnight at RT and for 4 h at 40° C. The reaction mixture was purified by preparative HPLC-MS. The fractions containing product were partially evaporated down i.vac. The precipitate formed was suction filtered, washed and dried.

Yield: 65 mg (38% of theory)
ESI-MS: m/z=503 (M+H)+
$R_t$ (HPLC): 1.28 min (method B)

Example 48

N-(4-(6-(4-(7-methoxy-2-oxo-4,5-dihydro-1H-benzo[d][1,3]diazepin-3(2H)-yl)piperidin-1-yl)pyrimidin-4-yloxy)-2-methylphenyl)acetamide

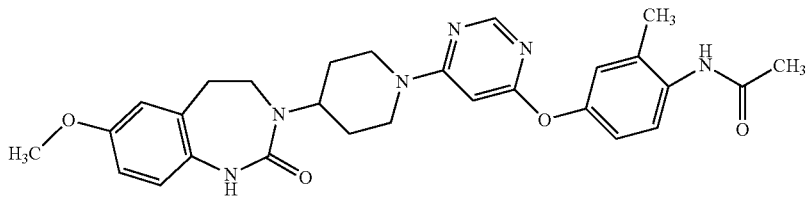 [SMILES: COc1ccc2c(c1)CCN(C1CCN(c3cc(Oc4ccc(NC(C)=O)c(C)c4)ncn3)CC1)C(=O)N2]

80 mg (0.17 mmol) 3-(1-(6-(4-amino-3-methylphenoxy)pyrimidin-4-yl)piperidin-4-yl)-7-methoxy-4,5-dihydro-1H-benzo[d][1,3]diazepin-2(3H)-one, 0.02 mL (0.35 mmol) AcOH, 120 mg (0.37 mmol) TBTU and 0.06 mL (0.43 mmol) TEA in 2.0 mL DMF were stirred for 2 h at RT. Water was added to the reaction mixture. The precipitate was suction filtered and purified by preparative HPLC-MS. The fractions containing product were combined and freeze-dried.

Yield: 20 mg (23% of theory)
ESI-MS: m/z=517 (M+H)+
$R_t$ (HPLC): 1.28 min (method B)

Example 49

3-(1-(6-(4-amino-3-methylphenoxy)pyrimidin-4-yl)piperidin-4-yl)-7-methoxy-4,5-dihydro-1H-benzo[d][1,3]diazepin-2(3H)-one

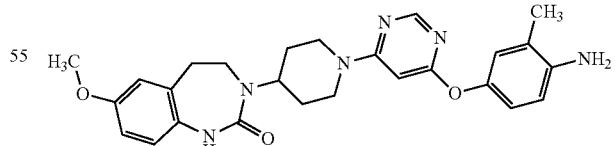

930 mg (1.84 mmol) 7-methoxy-3-(1-(6-(3-methyl-4-nitrophenoxy)pyrimidin-4-yl)piperidin-4-yl)-4,5-dihydro-1H-benzo[d][1,3]diazepin-2(3H)-one were placed in 20 mL THF and 20 mL MeOH and hydrogenated under a hydrogen atmosphere with the addition of 150 mg Pd/C (10%) at RT and a hydrogen pressure of 3 bar until all the hydrogen had been taken up. The catalyst was filtered off. Everything was distilled off from the filtrate to leave a residual volume of 15 mL. DIPE was added. The precipitate was suction filtered, washed and dried.

Yield: 680 mg (78% of theory)
ESI-MS: m/z=475 (M+H)⁺
R$_t$(HPLC): 1.25 min (method B)

Example 50

3-(1-(6-(7-chloro-2-methyl-1H-benzo[d]imidazol-5-yloxy)pyrimidin-4-yl)piperidin-4-yl)-7-methoxy-4,5-dihydro-1H-benzo[d][1,3]diazepin-2(3H)-one

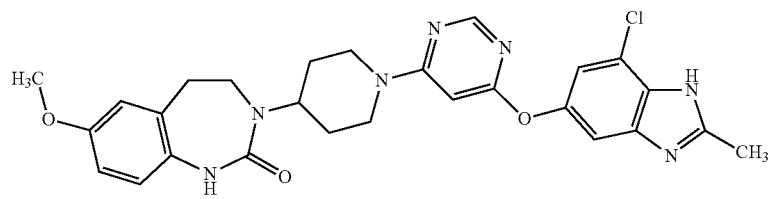

100 mg (0.36 mmol) 7-methoxy-3-piperidin-4-yl-1,3,4,5-tetrahydro-1,3-benzodiazepin-2-one, 110 mg (0.37 mmol) 7-chloro-5-(6-chloropyrimidin-4-yloxy)-2-methyl-1H-benzo[d]-imidazole and 0.14 mL (0.81 mmol) DIPEA in 2.0 mL DMF were stirred for 3 h at RT and 4 h at 40° C. The reaction mixture was mixed with water. The precipitate formed was suction filtered, washed and dried. The substance was purified by preparative HPLC-MS. The fractions containing product were combined and freeze-dried.

Yield: 90 mg (46% of theory)

ESI-MS: m/z=534/536 (Cl) (M+H)⁺

R$_t$(HPLC): 1.29 min (method B)

Example 51

1-(6-(7-chloro-2-methyl-1H-benzo[d]imidazol-5-yloxy)pyrimidin-4-yl)spiro[piperidin-4,4'-pyrido[2,3-d][1,3]oxazin]-2'(1'H)-one

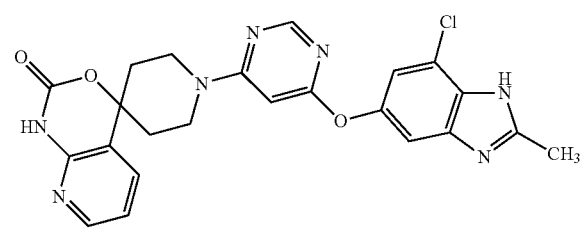 [SMILES: Cc1nc2cc(Oc3cc(N4CCC5(CC4)OC(=O)Nc4ncccc45)ncn3)cc(Cl)c2[nH]1]

90 mg (0.35 mmol) spiro[piperidin-4,4'-pyrido[2,3-d][1,3]oxazin]-2'(1'H)-one hydrochloride, 110 mg (0.37 mmol) 7-chloro-5-(6-chloropyrimidin-4-yloxy)-2-methyl-1H-benzo[d]imidazole and 0.14 mL (0.81 mmol) DIPEA in 2.0 mL DMF were stirred for 3 h at RT and 4 h at 40° C. The reaction mixture was purified by preparative HPLC-MS. The fractions containing product were combined and freeze-dried.

Yield: 50 mg (30% of theory)
ESI-MS: m/z=478/480 (Cl) (M+H)⁺
R$_t$ (HPLC): 1.07 min (method B)

Example 52

(S)-1-(1-(6-(4-methyl-2-(tetrahydrofuran-2-yl)-1H-benzo[d]imidazol-6-yloxy)pyrimidin-4-yl)-piperidin-4-yl)-1H-imidazo[4,5-b]pyridin-2(3H)-one

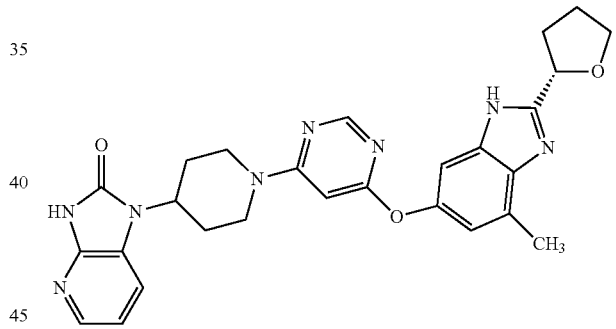

50 mg (0.23 mmol) 1-piperidin-4-yl-1,3-dihydroimidazo[4,5-b]pyridin-2-one, 70 mg (0.21 mmol) (S)-6-(6-chloropyrimidin-4-yloxy)-4-methyl-2-(tetrahydrofuran-2-yl)-1H-benzo[d]-imidazole and 0.08 mL (0.46 mmol) DIPEA in 2.0 mL DMF were stirred overnight at RT and for 2 h at 40° C. The reaction mixture was purified by preparative HPLC-MS. The fractions containing product were partially evaporated down i.vac. and neutralised with 1M sodium hydroxide solution. The precipitate formed was suction filtered, washed and dried.

Yield: 36 mg (31% of theory)
ESI-MS: m/z=513 (M+H)⁺
R$_t$ (HPLC): 1.13 min (method B)

Example 53

(S)-7-methoxy-3-(1-(6-(4-methyl-2-(tetrahydrofuran-2-yl)-1H-benzo[d]imidazol-6-yloxy)-pyrimidin-4-yl)piperidin-4-yl)-4,5-dihydro-1H-benzo[d][1,3]diazepin-2(3H)-one

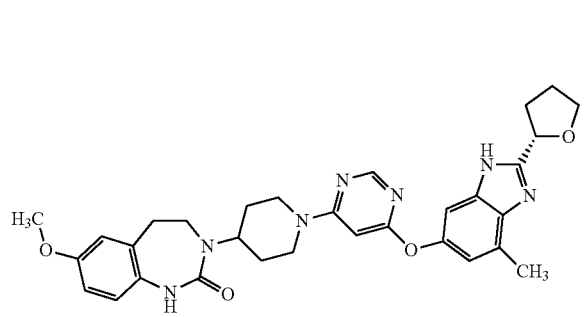 [SMILES: COc1ccc2c(c1)CCN(C1CCN(c3cc(Oc4cc(C)c5nc([C@@H]6CCCO6)[nH]c5c4)ncn3)CC1)C(=O)N2]

63 mg (0.23 mmol) 7-methoxy-3-piperidin-4-yl-1,3,4,5-tetrahydro-1,3-benzodiazepin-2-one, 70 mg (0.21 mmol) (S)-6-(6-chloropyrimidin-4-yloxy)-4-methyl-2-(tetrahydrofuran-2-yl)-1H-benzo[d]imidazole and 0.08 mL (0.46 mmol) DIPEA in 2.0 mL DMF were stirred overnight at RT and for 2 h at 40° C. The reaction mixture was purified by preparative HPLC-MS. The fractions containing product were partially evaporated down i.vac. and neutralised with 4M sodium hydroxide solution. The precipitate formed was suction filtered, washed and dried.

Yield: 22 mg (17% of theory)

ESI-MS: m/z=570 (M+H)$^+$

R$_t$ (HPLC): 3.15 min (method C)

Example 54

(S)-1-(6-(4-methyl-2-(tetrahydrofuran-2-yl)-1H-benzo[d]imidazol-6-yloxy)pyrimidin-4-yl)-spiro[piperidin-4,4'-pyrido[2,3-d][1,3]oxazin]-2'(1'H)-one

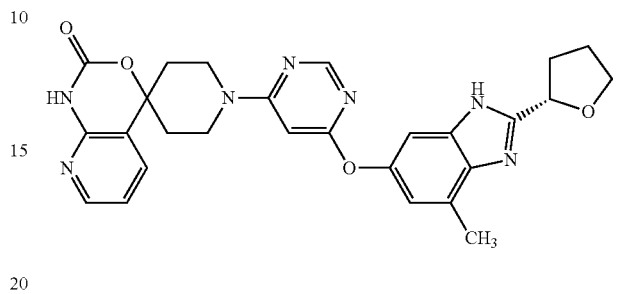

59 mg (0.23 mmol) spiro[piperidin-4,4'-pyrido[2,3-d][1,3]oxazin]-2'(1'H)-one hydrochloride, 70 mg (0.21 mmol) (S)-6-(6-chloropyrimidin-4-yloxy)-4-methyl-2-(tetrahydrofuran-2-yl)-1H-benzo[d]imidazole and 0.12 mL (0.70 mmol) DIPEA in 2.0 mL DMF were stirred overnight at 40° C. The reaction mixture was purified by preparative HPLC-MS. The fractions containing product were partially evaporated down i.vac. and neutralised with 4M sodium hydroxide solution. The precipitate formed was suction filtered, washed and dried.

Yield: 21 mg (18% of theory)

ESI-MS: m/z=514 (M+H)$^+$

R$_t$ (HPLC): 1.09 min (method B)

Example 55

7-methoxy-3-(1-(6-(2-methyl-1H-benzo[d]imidazol-5-yloxy)pyrimidin-4-yl)piperidin-4-yl)-4,5-dihydro-1H-benzo[d][1,3]diazepin-2(3H)-one

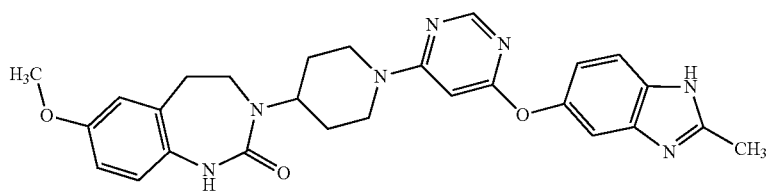

90 mg (0.17 mmol) 3-(1-(6-(4-chloro-2-methyl-1H-benzo[d]imidazol-5-yloxy)pyrimidin-4-yl)piperidin-4-yl)-7-methoxy-4,5-dihydro-1H-benzo[d][1,3]diazepin-2(3H)-one and 0.10 mL (0.71 mmol) TEA were placed in 10 mL methanol and hydrogenated under hydrogen atmosphere and with the addition of 10 mg Pd/C (10%) at 50° C. and a hydrogen pressure of 3 bar until the uptake of hydrogen had ended. The catalyst was filtered off and the filtrate was evaporated down i.vac. The residue was purified by preparative HPLC-MS. The fractions containing product were combined and freeze-dried.

Yield: 10 mg (12% of theory)
ESI-MS: m/z=500 (M+H)+
$R_f$(HPLC): 2.12 (method J)

Example 56

3-(1-(6-(4-chloro-2-methyl-1H-benzo[d]imidazol-5-yloxy)pyrimidin-4-yl)piperidin-4-yl)-7-methoxy-4,5-dihydro-1H-benzo[d][1,3]diazepin-2(3H)-one

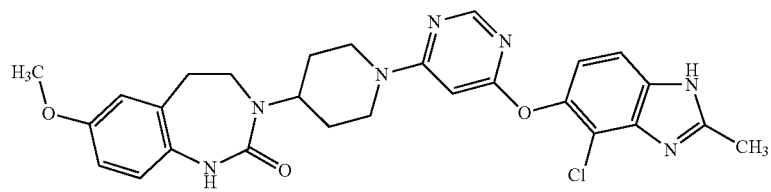

100 mg (0.36 mmol) 7-methoxy-3-piperidin-4-yl-1,3,4,5-tetrahydro-1,3-benzodiazepin-2-one, 110 mg (0.37 mmol) 4-chloro-5-(6-chloropyrimidin-4-yloxy)-2-methyl-1H-benzo[d]-imidazole and 0.14 mL (0.81 mmol) DIPEA in 2.0 mL DMF were stirred for 3 h at RT and for 4 h at 40° C. The reaction mixture was mixed with water. The precipitate formed was suction filtered, washed and dried. The filtrate was again suction filtered, washed and dried.

Yield: 190 mg (98% of theory)
ESI-MS: m/z=534/536 (Cl) (M+H)+
$R_f$(HPLC): 1.25 min (method B)

Example 57

7-(6-(4-(7-methoxy-2-oxo-4,5-dihydro-1H-benzo[d][1,3]diazepin-3(2H)-yl)piperidin-1-yl)-pyrimidin-4-yloxy)-5-methyl-2H-benzo[b][1.4]oxazin-3(4H)-one

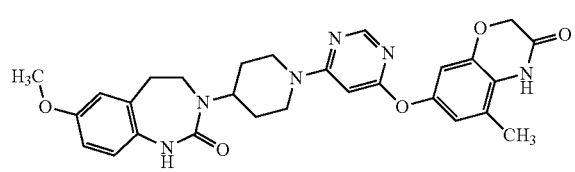 [SMILES: COc1ccc2c(c1)CCN(C1CCN(c3cc(Oc4cc(C)c5c(c4)OCC(=O)N5)ncn3)CC1)C(=O)N2]

70 mg (0.25 mmol) 7-methoxy-3-piperidin-4-yl-1,3,4,5-tetrahydro-1,3-benzodiazepin-2-one, 65 mg (0.20 mmol) 7-(6-chloropyrimidin-4-yloxy)-5-methyl-2H-benzo[b][1,4]oxazin-3(4H)-one and 50 µL (0.27 mmol) DIPEA in 2.0 mL DMF were stirred overnight at RT and for 3 h at 40° C. The reaction mixture was combined with water and methanol. The precipitate formed was suction filtered, washed and dried. The filtrate was again suction filtered, washed and dried.

Yield: 69 mg (62% of theory)

ESI-MS: m/z=531 (M+H)+

$R_f$(HPLC): 3.65 (method C)

Example 58

1-(6-(7-methyl-2-(tetrahydrofuran-3-yl)-1H-benzo[d]imidazol-5-yloxy)pyrimidin-4-yl)spiro-[piperidin-4,4'-pyrido[2,3-d][1,3]oxazin]-2'(1'H)-one

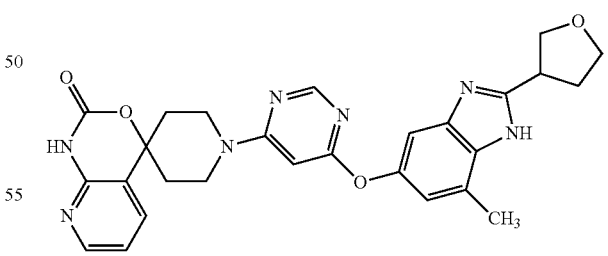

138 mg (0.54 mmol) spiro[piperidin-4,4'-pyrido[2,3-d][1,3]oxazin]-2'(1'H)-one hydrochloride, 180 mg (0.54 mmol) 5-(6-chloropyrimidin-4-yloxy)-7-methyl-2-(tetrahydrofuran-3-yl)-1H-benzo[d]imidazole and 280 µL (1.62 mmol) DIPEA in 5.0 mL DMF were stirred overnight at 60° C. The reaction mixture was combined with ice water. The precipitate formed was suction filtered and purified by chromatography. The fractions containing product were combined and evaporated down i.vac. to leave the aqueous residue. This was neutralised with an aqueous NaHCO₃ solution and extracted with ethyl acetate. The organic phase was dried and evaporated down i.vac.

Yield: 50 mg (18% of theory)
ESI-MS: m/z=514 (M+H)⁺
R$_t$(HPLC): 2.88 min (method L)

Example 59

(S)-1-(6-(7-methyl-2-(tetrahydrofuran-3-yl)-1H-benzo[d]imidazol-5-yloxy)pyrimidin-4-yl)-spiro[piperidin-4,4'-pyrido[2,3-d][1,3]oxazin]-2'(1'H)-one

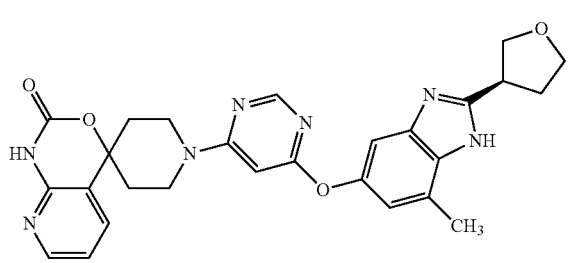 [SMILES: Cc1cc(Oc2cc(N3CCC4(CC3)OC(=O)Nc3ncccc34)ncn2)cc2nc([C@@H]3CCOC3)[nH]c12]

30 mg (60 mmol) 1-(6-(7-methyl-2-(tetrahydrofuran-3-yl)-1H-benzo[d]imidazol-5-yloxy)-pyrimidin-4-yl)spiro[piperidin-4,4'-pyrido[2,3-d][1,3]oxazin]-2'(1'H)-one were separated using chiral HPLC (method Daicel OJH, 250 mm×4.6 mm, 4 ml/min, 10 min, 25% MeOH with DEA). The fractions containing product were combined and evaporated down i.vac. The residue was dissolved in MeOH/H₂O and lyophilised.

Yield: 10 mg
ESI-MS: m/z=514 (M+H)⁺
R$_t$(HPLC): 4.29 min (method Daicel OJH, 250 mm×4.6 mm, 4 ml/min, 10 min, 25% MeOH with DEA)

Example 60

(R)-1-(6-(7-methyl-2-(tetrahydrofuran-3-yl)-1H-benzo[d]imidazol-5-yloxy)pyrimidin-4-yl)-spiro[piperidin-4,4'-pyrido[2,3-d][1,3]oxazin]-2'(1'H)-one

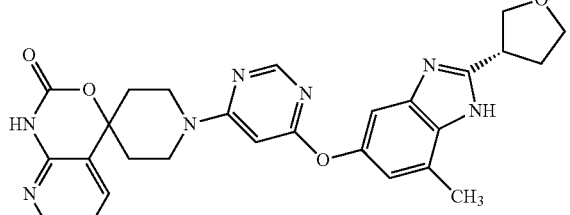

30 mg (60 mmol) 1-(6-(7-methyl-2-(tetrahydrofuran-3-yl)-1H-benzo[d]imidazol-5-yloxy)-pyrimidin-4-yl)spiro[piperidin-4,4'-pyrido[2,3-d][1,3]oxazin]-2'(1'H)-one were separated by chiral HPLC (method Daicel OJH, 250 mm×4.6 mm, 4 ml/min, 10 min, 25% MeOH with DEA). The fractions containing product were combined and evaporated down i.vac. The residue was dissolved in MeOH/H₂O and lyophilised.

Yield: 8 mg
ESI-MS: m/z=514 (M+H)⁺
R$_t$(HPLC): 5.53 min (method Daicel OJH, 250 mm×4.6 mm, 4 ml/min, 10 min, 25% MeOH with DEA)

Example 61

1-(6-(7-chloro-2-(tetrahydrofuran-3-yl)-1H-benzo[d]imidazol-5-yloxy)pyrimidin-4-yl)spiro-[piperidin-4,4'-pyrido[2,3-d][1,3]oxazin]-2'(1'H)-one

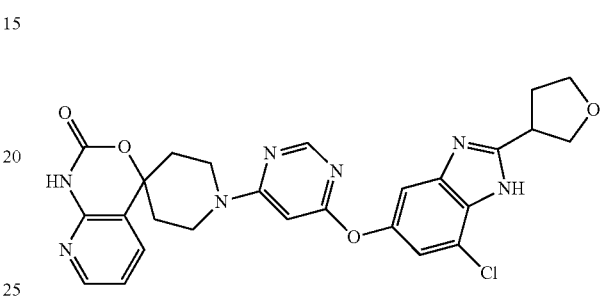

36 mg (0.14 mmol) spiro[piperidin-4,4'-pyrido[2,3-d][1,3]oxazin]-2'(1'H)-one hydrochloride, 50 mg (0.14 mmol) 7-chloro-5-(6-chloropyrimidin-4-yloxy)-2-(tetrahydrofuran-3-yl)-1H-benzo[d]imidazole and 50 µL (0.30 mmol) DIPEA in 2.0 mL DMF were stirred overnight at RT. The reaction mixture was purified by chromatography. The fractions containing product were combined and lyophilised.

Yield: 38 mg (51% of theory)
ESI-MS: m/z=534 (M+H)⁺
R$_t$(HPLC): 1.04 min (method B)

Example 62

1-(6-(7-chloro-2-(tetrahydro-2H-pyran-4-yl)-1H-benzo[d]imidazol-5-yloxy)pyrimidin-4-yl)-spiro[piperidin-4,4'-pyrido[2,3-d][1,3]oxazin]-2'(1'H)-one

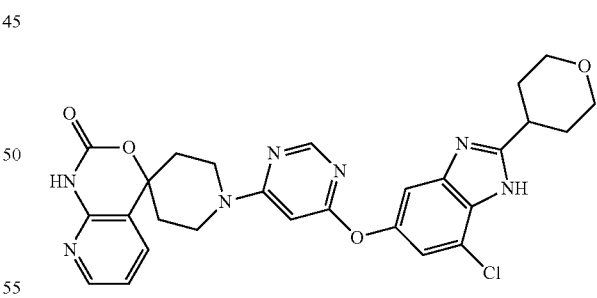

49 mg (0.19 mmol) spiro[piperidin-4,4'-pyrido[2,3-d][1,3]oxazin]-2'(1'H)-one hydrochloride, 70 mg (0.19 mmol) 7-chloro-5-(6-chloropyrimidin-4-yloxy)-2-(tetrahydro-2H-pyran-4-yl)-1H-benzo[d]imidazole and 70 µL (0.40 mmol) DIPEA in 2.0 mL DMF were stirred for 3 h at RT and for 3 h at 40° C. The reaction mixture was purified by chromatography. The fractions containing product were combined and evaporated down i.vac.

Yield: 8 mg (8% of theory)
ESI-MS: m/z=548 (M+H)⁺
R$_t$(HPLC): 1.07 min (method B)

Example 63

1-(6-(7-methyl-2-(trifluoromethyl)-1H-benzo[d]imi-dazol-5-yloxy)pyrimidin-4-yl)spiro-[piperidin-4,4'-pyrido[2,3-d][1,3]oxazin]-2'(1'H)-one

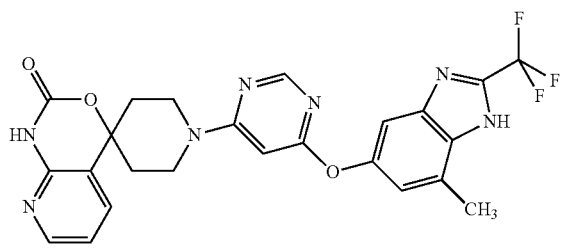 [SMILES: Cc1cc(Oc2cc(N3CCC4(CC3)OC(=O)Nc3ncccc34)ncn2)cc2nc(C(F)(F)F)[nH]c12]

21 mg (0.08 mmol) spiro[piperidin-4,4'-pyrido[2,3-d][1,3] oxazin]-2'(1'H)-one hydrochloride, 22 mg (0.07 mmol) 5-(6-chloropyrimidin-4-yloxy)-7-methyl-2-(trifluoromethyl)-1H-benzo[d]-imidazole and 40 µL (0.24 mmol) DIPEA in 2.0 mL DMF were stirred at 50° C. over the weekend. The reaction mixture was purified by chromatography. The fractions containing product were combined and evaporated down i.vac. to leave the aqueous residue. This was neutralised with a 1M aqueous NaOH solution. The precipitate formed was suction filtered, washed and dried.

Yield: 18 mg (44% of theory)

ESI-MS: m/z=512 (M+H)$^+$ $R_f$(HPLC): 1.30 min (method B)

Example 64

1-(6-(4-methyl-2-oxo-2,3-dihydrobenzo[d]thiazol-6-yloxy)pyrimidin-4-yl)spiro[piperidin-4,4'-pyrido[2,3-d][1,3]oxazin]-2'(1'H)-one

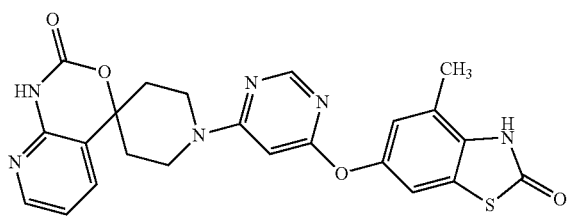 [SMILES: Cc1cc(Oc2cc(N3CCC4(CC3)OC(=O)Nc3ncccc34)ncn2)cc2sc(=O)[nH]c12]

90 mg (0.35 mmol) spiro[piperidin-4,4'-pyrido[2,3-d][1,3] oxazin]-2'(1'H)-one hydrochloride, 105 mg (0.36 mmol) 6-(6-chloropyrimidin-4-yloxy)-4-methylbenzo[d]thiazol-2 (3H)-one and 200 µL (1.16 mmol) DIPEA in 2.0 mL DMF were stirred for 14 h at 60° C. The reaction mixture was cooled, mixed with water and stirred for 30 min. The precipitate formed was suction filtered, stirred with methanol, suction filtered again and dried.

Yield: 120 mg (72% of theory)

ESI-MS: m/z=477 (M+H)$^+$ $R_f$(HPLC): 3.25 min (method C)

Example 65

1-(6-(7-methyl-2-(tetrahydro-2H-pyran-4-yl)-1H-benzo[d]imidazol-5-yloxy)pyrimidin-4-yl)-spiro[piperidin-4,4'-pyrido[2,3-d][1,3]oxazin]-2'(1'H)-one

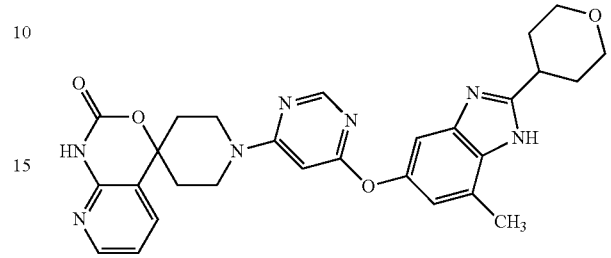

33 mg (0.13 mmol) spiro[piperidin-4,4'-pyrido[2,3-d][1,3] oxazin]-2'(1'H)-one hydrochloride, 40 mg (0.12 mmol) 7-methyl-5-(6-chloropyrimidin-4-yloxy)-2-(tetrahydro-2H-pyran-4-yl)-1H-benzo[d]imidazole and 70 µL (0.39 mmol) DIPEA in 2.0 mL DMF were stirred overnight at 60° C. The reaction mixture was poured onto ice water and the precipitate formed was suction filtered. The precipitate was dissolved and then purified by chromatography. The fractions containing product were combined and evaporated down i.vac. to leave the aqueous residue. This was neutralised with an aqueous NaHCO$_3$ solution. The precipitate formed was suction filtered, washed and dried.

Yield: 35 mg (51% of theory)

ESI-MS: m/z=528 (M+H)$^+$ $R_f$(HPLC): 0.96 min (method B)

Example 66

1-(6-(2-(2-methoxyethyl)-4-methyl-1H-benzo[d]imidazol-6-yloxy)pyrimidin-4-yl)spiro-[piperidin-4,4'-pyrido[2,3-d][1,3]oxazin]-2'(1'H)-one

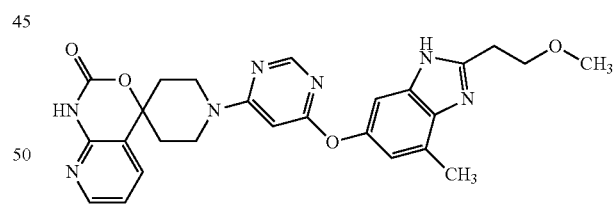

29 mg (0.11 mmol) spiro[piperidin-4,4'-pyrido[2,3-d][1,3] oxazin]-2'(1'H)-one hydrochloride, 29 mg (0.09 mmol) 6-(6-chloropyrimidin-4-yloxy)-2-(2-methoxyethyl)-4-methyl-1H-benzo-[d]imidazole and 50 µL (0.39 mmol) DIPEA in 2.0 mL DMF were stirred at 50° C. The reaction mixture was purified by chromatography. The fractions containing product were combined and evaporated down i.vac. to leave the aqueous residue. This was neutralised with a 1M aqueous NaOH solution. The precipitate formed was suction filtered, washed and dried.

Yield: 55 mg (51% of theory)

ESI-MS: m/z=502 (M+H)$^+$ $R_f$(HPLC): 2.72 min (method C)

Example 67

1-(6-(2-methoxy-7-methyl-1H-benzo[d]imidazol-5-yloxy)pyrimidin-4-yl)spiro[piperidin-4,4'-pyrido[2,3-d][1,3]oxazin]-2'(1'H)-one

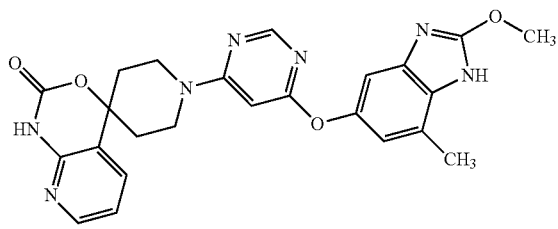 [SMILES: COc1nc2cc(Oc3cc(N4CCC5(CC4)OC(=O)Nc4ncccc45)ncn3)cc(C)c2[nH]1]

64 mg (0.25 mmol) spiro[piperidin-4,4'-pyrido[2,3-d][1,3]oxazin]-2'(1'H)-one hydrochloride, 57 mg (0.20 mmol) 5-(6-chloropyrimidin-4-yloxy)-2-methoxy-7-methyl)-1H-benzo[d]-imidazole and 130 μL (0.75 mmol) DIPEA in 2.0 mL DMF were stirred overnight at 60° C. The reaction mixture was purified by chromatography. The fractions containing product were combined and evaporated down i.vac. to leave the aqueous residue. This was neutralised with a 1M aqueous NaOH solution. The precipitate formed was suction filtered, washed and dried.

Yield: 20 mg (17% of theory)
ESI-MS: m/z=474 (M+H)$^+$
R$_t$(HPLC): 1.10 min (method B)

Example 68

1-(6-(7-methyl-1H-indazol-5-yloxy)pyrimidin-4-yl)spiro[piperidin-4,4'-pyrido[2,3-d]-[1,3]oxazin]-2'(1'H)-one

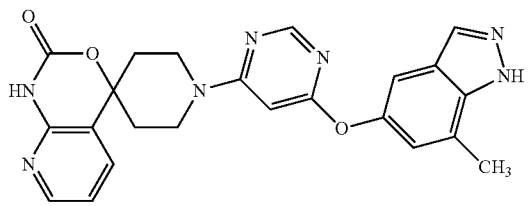 [SMILES: Cc1cc(Oc2cc(N3CCC4(CC3)OC(=O)Nc3ncccc34)ncn2)cc2cn[nH]c12]

60 mg (0.23 mmol) spiro[piperidin-4,4'-pyrido[2,3-d][1,3]oxazin]-2'(1'H)-one hydrochloride, 60 mg (0.23 mmol) 5-(6-chloropyrimidin-4-yloxy)-7-methyl-1H-indazole and 100 μL (0.58 mmol) DIPEA in 0.8 mL DMF were stirred at RT over the weekend. The reaction mixture was purified by chromatography. The fractions containing product were combined and evaporated down i.vac. to leave the aqueous residue. This was neutralised with an aqueous saturated NaHCO$_3$ solution. The precipitate formed was suction filtered and dried.

Yield: 40 mg (38% of theory)
ESI-MS: m/z=444 (M+H)$^+$
R$_t$(HPLC): 3.06 min (method C)

Example 69

5-methyl-7-(6-(2'-oxo-1'.2'-dihydrospiro[piperidin-4,4'-pyrido[2,3-d][1,3]oxazin]-1-yl)-pyrimidin-4-yloxy)-2H-benzo[b][1.4]oxazin-3(4H)-one

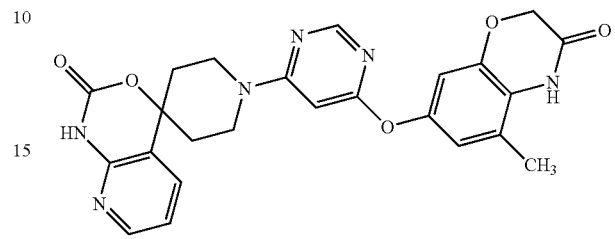

72 mg (0.28 mmol) spiro[piperidin-4,4'-pyrido[2,3-d][1,3]oxazin]-2'(1'H)-one hydrochloride, 70 mg (0.22 mmol) 7-(6-chloropyrimidin-4-yloxy)-5-methyl-2H-benzo[b][1.4]oxazin-3(4H)-one and 100 μL (0.58 mmol) DIPEA in 2.0 mL DMF were stirred overnight at RT. The reaction mixture was combined with methanol and water. The precipitate formed was suction filtered, washed with methanol and dried.

Yield: 75 mg (73% of theory)
ESI-MS: m/z=475 (M+H)$^+$
R$_t$(HPLC): 1.18 min (method B)

Example 70

(R)-1-(6-(4-methyl-2-(tetrahydrofuran-2-yl)-1H-benzo[d]imidazol-6-yloxy)pyrimidin-4-yl)-spiro[piperidin-4,4'-pyrido[2,3-d][1,3]oxazin]-2'(1'H)-one

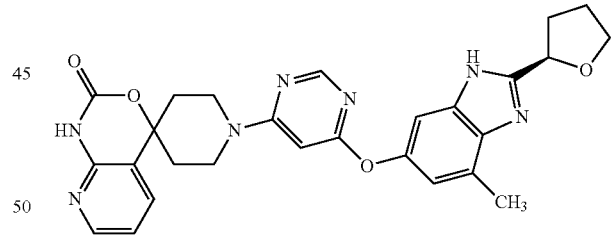

166 mg (0.65 mmol) spiro[piperidin-4,4'-pyrido[2,3-d][1,3]oxazin]-2'(1'H)-one hydrochloride, 205 mg (0.62 mmol) (R)-6-(6-chloropyrimidin-4-yloxy)-4-methyl-2-(tetrahydrofuran-2-yl)-1H-benzo[d]imidazole and 320 μL (1.86 mmol) DIPEA in 5.0 mL DMF were stirred overnight at 50° C. The reaction mixture was purified by chromatography. The fractions containing product were combined and evaporated down i.vac. to leave the aqueous residue. This was neutralised with an aqueous NaHCO$_3$ solution. The precipitate formed was suction filtered, washed and dried.

Yield: 110 mg (35% of theory)
ESI-MS: m/z=514 (M+H)$^+$
R$_t$(HPLC): 0.98 min (method B)

Example 71

4-methyl-6-(2-methyl-6-(2'-oxo-1'.2'-dihydrospiro[piperidin-4,4'-pyrido[2,3-d][1,3]oxazin]-1-yl)pyrimidin-4-yloxy)benzo[d]oxazol-2(3H)-one

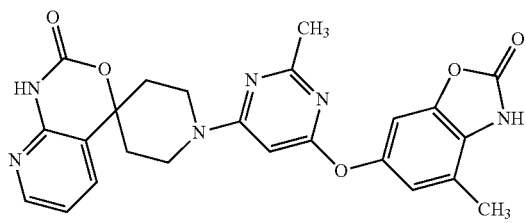 [SMILES: Cc1nc(Oc2cc(C)c3[nH]c(=O)oc3c2)cc(N2CCC3(CC2)OC(=O)Nc2ncccc23)n1]

90 mg (0.35 mmol) spiro[piperidin-4,4'-pyrido[2,3-d][1,3]oxazin]-2'(1'H)-one hydrochloride, 90 mg (0.31 mmol) 6-(6-chloro-2-methylpyrimidin-4-yloxy)-4-methylbenzo[d]oxazol-2(3H)-one and 200 μL (1.16 mmol) DIPEA in 1.5 mL DMF were stirred overnight at RT. Another 90 mg (0.35 mmol) spiro[piperidin-4,4'-pyrido[2,3-d][1,3]oxazin]-2'(1'H)-one hydrochloride and 200 μL (1.16 mmol) DIPEA were added and the mixture was stirred for 8 h at 60° C. The reaction mixture was mixed with water and stirred overnight. Then DCM was added and the mixture was stirred for a further 30 min. DCM was removed and the aqueous phase was suction filtered. The precipitate was washed with EtOH and dried.

Yield: 100 mg (68% of theory)
ESI-MS: m/z=475 (M+H)$^+$
R$_f$(HPLC): 1.04 min (method B)

Example 72

6-(6-(4-(7-methoxy-2-oxo-4,5-dihydro-1H-benzo[d][1,3]diazepin-3(2H)-yl)piperidin-1-yl)-pyrimidin-4-yloxy)-4-methylbenzo[d]thiazol-2(3H)-one

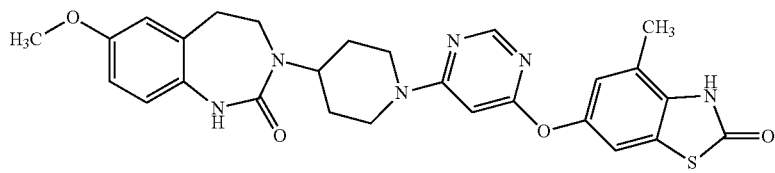 [SMILES: COc1ccc2c(c1)CCN(C1CCN(c3cc(Oc4cc(C)c5[nH]c(=O)sc5c4)ncn3)CC1)C(=O)N2]

100 mg (0.36 mmol) 7-methoxy-3-(piperidin-4-yl)-4,5-dihydro-1H-benzo[d][1,3]diazepin-2(3H)-one, 110 mg (0.36 mmol) 6-(6-chloropyrimidin-4-yloxy)-4-methylbenzo[d]thiazol-2(3H)-one and 140 μL (0.81 mmol) DIPEA in 2.0 mL DMF were stirred for 14 h at 60° C. The reaction mixture was cooled, mixed with water and stirred for 30 min. The precipitate formed was suction filtered and dried.

Yield: 160 mg (72% of theory)
ESI-MS: m/z=533 (M+H)$^+$
R$_f$(HPLC): 1.37 min (method B)

Example 73

7-methoxy-3-(1-(6-(4-methyl-2-(tetrahydrofuran-3-yl)-1H-benzo[d]imidazol-6-yloxy)-pyrimidin-4-yl)piperidin-4-yl)-4,5-dihydro-1H-benzo[d][1,3]diazepin-2(3H)-one

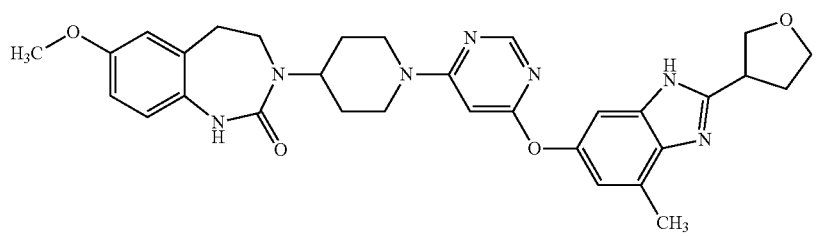 [SMILES: COc1ccc2c(c1)CCN(C1CCN(c3cc(Oc4cc(C)c5nc(C6CCOC6)[nH]c5c4)ncn3)CC1)C(=O)N2]

28 mg (0.10 mmol) 7-methoxy-3-(piperidin-4-yl)-4,5-dihydro-1H-benzo[d][1,3]diazepin-2(3H)-one, 33 mg (0.10 mmol) 6-(6-chloropyrimidin-4-yloxy)-4-methyl-2-(tetrahydrofuran-3-yl)-1H-benzo[d]imidazole and 30 μL (0.20 mmol) DIPEA in 2.0 mL DMF were stirred at 50° C. over the weekend. The reaction mixture was purified by chromatography. The fractions containing product were combined and evaporated down i.vac. to leave the aqueous residue. This was neutralised with a 4 M aqueous NaOH solution. The precipitate formed was suction filtered, washed and dried.
Yield: 16 mg (28% of theory)
ESI-MS: m/z=570 (M+H)$^+$
R$_f$(HPLC): 3.22 min (method C)

Example 74

1-(6-(4-methyl-2-oxo-2,3-dihydrobenzo[d]oxazol-6-yloxy)-2-(trifluoromethyl)pyrimidin-4-yl)-spiro[piperidin-4,4'-pyrido[2,3-d][1,3]oxazin]-2'(1'H)-one

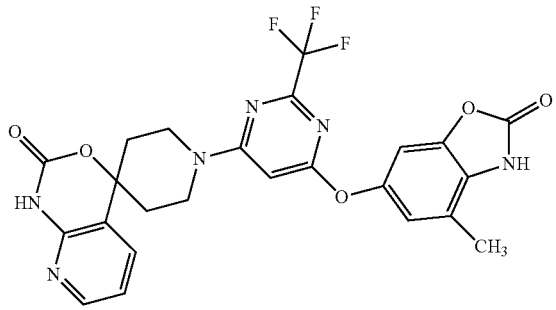 [SMILES: Cc1cc(Oc2cc(N3CCC4(CC3)OC(=O)Nc3ncccc34)nc(C(F)(F)F)n2)cc2oc(=O)[nH]c12]

90 mg (0.35 mmol) spiro[piperidin-4,4'-pyrido[2,3-d][1,3]oxazin]-2'(1'H)-one hydrochloride, 125 mg (0.36 mmol) 6-(6-chloro-2-trifluoromethyl-pyrimidin-4-yloxy)-4-methyl-3H-benzoxazol-2-one and 0.20 mL (1.16 mmol) DIPEA in 2.0 mL NMP were stirred for 14 h at 60° C. After cooling the reaction mixture was mixed with water and stirred for 30 min. The precipitate formed was suction filtered and dried.
Yield: 0.18 mg (97% of theory)
ESI-MS: m/z=529 (M+H)$^+$
R$_f$(HPLC): 1.40 min (method B)

Example 75

4-(4-methyl-2-oxo-2,3-dihydrobenzo[d]oxazol-6-yloxy)-6-(2'-oxo-1',2'-dihydrospiro-[piperidin-4,4'-pyrido[2,3-d][1,3]oxazin]-1-yl)nicotinonitrile

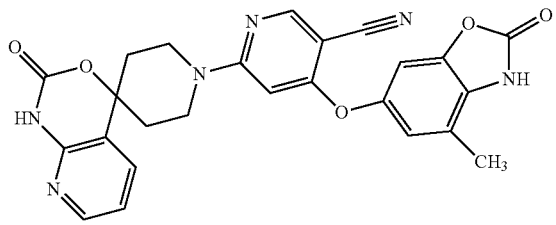 [SMILES: Cc1cc(Oc2cc(N3CCC4(CC3)OC(=O)Nc3ncccc34)ncc2C#N)cc2oc(=O)[nH]c12]

40 mg (0.16 mmol) spiro[piperidin-4,4'-pyrido[2,3-d][1,3]oxazin]-2'(1'H)-one hydrochloride, 40 mg (0.12 mmol) 6-chloro-4-(4-methyl-2-oxo-2,3-dihydro-benzoxazol-6-yloxy)-nicotinonitrile and 0.08 mL (0.47 mmol) DIPEA in 0.80 mL NMP were stirred for 1 h at 140° C. The reaction mixture was purified by preparative HPLC-MS. The fractions containing product were partially evaporated down i.vac. and neutralised with aqueous NaHCO$_3$ solution. The precipitate formed was suction filtered and dried.
Yield: 47 mg (36% of theory)
ESI-MS: m/z=485 (M+H)$^+$
R$_f$(HPLC): 1.34 min (method B)

Example 76

4-methyl-6-(2-methyl-6-(2-oxo-2,3-dihydro-1H-spiro[[1,8]naphthyridin-4,4'-piperidin]-1'-yl)pyrimidin-4-yloxy)benzo[d]oxazol-2(3H)-one

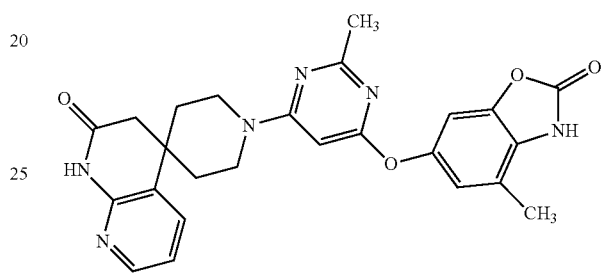

26 mg (0.12 mmol) 1H-spiro[[1,8]naphthyridin-4,4'-piperidin]-2(3H)-one, 35 mg (0.12 mmol) 6-(6-chloro-2-methylpyrimidin-4-yloxy)-4-methylbenzo[d]oxazol-2(3H)-one and 42 μL (0.24 mmol) DIPEA in 2.0 mL DMF were stirred for 4 days at 60° C. The reaction mixture was purified by preparative HPLC-MS. The fractions containing product were combined and lyophilised.
Yield: 19 mg (34% of theory)
ESI-MS: m/z=4739 (M+H)$^+$
R$_f$(HPLC): 1.40 min (method B)

Example 77

4-methyl-6-(2-methyl-6-(2'-oxo-1'.2'-dihydrospiro[piperidin-4.3'-pyrrolo[2,3-b]pyridin]-1-yl)-pyrimidin-4-yloxy)benzo[d]oxazol-2(3H)-one

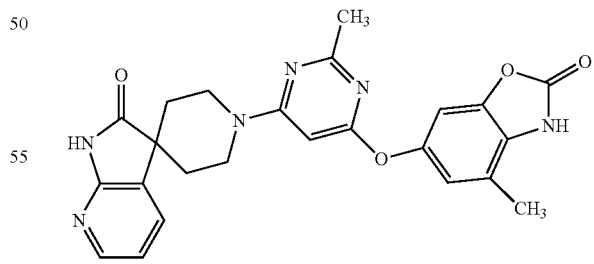

36 mg (0.15 mmol) spiro[piperidin-4.3'-pyrrolo[2,3-b]pyridin]-2'(1'H)-one, 44 mg (0.15 mmol) 6-(6-chloro-2-methylpyrimidin-4-yloxy)-4-methylbenzo[d]oxazol-2(3H)-one and 91 μL (0.536 mmol) DIPEA in 2.0 mL DMF were stirred for 48 h at RT. The reaction mixture was purified by preparative HPLC-MS. The fractions containing product were combined and lyophilised.

Yield: 0.13 mg (18% of theory)
ESI-MS: m/z=459 (M+H)+
R$_t$(HPLC): 1.06 min (method B)

Example 78

1-{1-[6-(2.7-dimethyl-3H-benzimidazol-5-yloxy)-pyrimidin-4-yl]-spiro[piperidin-4,4'-pyrido-[2,3-d][1,3]oxazin]-2'(1'H)-one

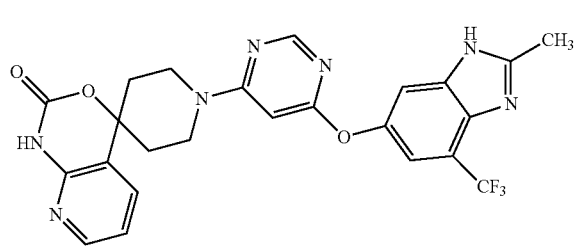 [SMILES: Cc1nc2c(C(F)(F)F)cc(Oc3cc(N4CCC5(CC4)OC(=O)Nc4ncccc45)ncn3)cc2[nH]1]

128 mg (0.500 mmol) spiro[piperidin-4,4'-pyrido[2,3-d][1,3]oxazin]-2'(1'H)-one hydrochloride, 167 mg (0.500 mmol) 6-(6-chloro-pyrimidin-4-yloxy)-2-methyl-4-trifluoromethyl-1H-benzimidazole and 0.261 mL (1.50 mmol) DIPEA in 1.5 mL DMF were stirred for 10 h at RT. The reaction mixture was purified by preparative HPLC-MS. The fractions containing product were combined and freeze-dried.

Yield: 65 mg (25% of theory)
ESI-MS: m/z=512 (M+H)+
R$_t$ (HPLC): 3.0 min (method C)

Example 79

7-methoxy-3-{1-[6-(2-methyl-7-trifluoromethyl-3H-benzimidazol-5-yloxy)-pyrimidin-4-yl]-piperidin-4-yl}-1,3,4,5-tetrahydro-benzo[d][1,3]diazepin-2-one

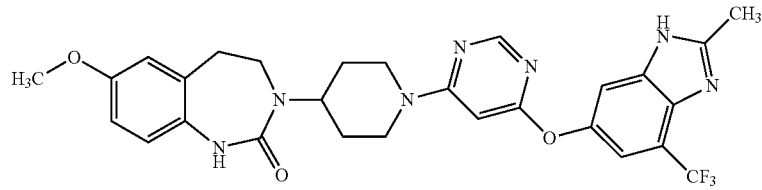

140 mg (0.510 mmol) 7-methoxy-3-piperidin-4-yl-1,3,4,5-tetrahydro-1,3-benzodiazepin-2-one, 167 mg (0.500 mmol) 6-(6-chloro-pyrimidin-4-yloxy)-2-methyl-4-trifluoromethyl-1H-benzimidazole and 0.261 mL (1.50 mmol) DIPEA in 1.5 mL DMF were stirred for 10 h at RT. The reaction mixture was purified by preparative HPLC-MS. The fractions containing product were combined and freeze-dried.

Yield: 106 mg (37% of theory)
ESI-MS: m/z=568 (M+H)+
R$_t$ (HPLC): 3.5 min (method C)

Example 80

7-methoxy-3-[4'-(4-methyl-2-oxo-2,3-dihydro-benzoxazol-6-yloxy)-1'-oxy-3.4.5.6-tetrahydro-2H-[1.2']bipyridinyl-4-yl]-1,3,4,5-tetrahydro-benzo[d][1,3]diazepin-2-one

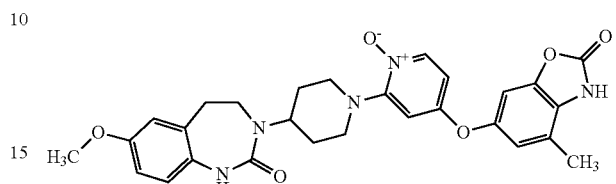

A mixture of 75 mg (0.18 mmol) 7-methoxy-3-(4'-nitro-1'-oxy-3.4.5.6-tetrahydro-2H-[1.2']bipyridinyl-4-yl)-1,3,4,5-tetrahydro-benzo[d][1,3]diazepin-2-one, 35 mg (0.21 mmol) 6-hydroxy-4-methyl-3H-benzoxazol-2-one and 50 mg (0.44 mmol) potassium-tert-butoxide in 1.0 mL NMP was stirred for 20 min in the microwave at 150° C. After cooling to RT the reaction mixture was filtered and purified by preparative HPLC-MS. The fractions containing product were combined and freeze-dried.

Yield: 3.0 mg (3% of theory)
ESI-MS: m/z=532 (M+H)+
R$_t$ (HPLC): 1.31 min (method B)

The following Examples describe the preparation of pharmaceutical formulations which contain as active substance any desired compound of general formula I:

Example I

Capsules for Powder Inhalation Containing 1 mg of Active Ingredient

Composition:
1 capsule for powder inhalation contains:

| | |
|---|---|
| active ingredient | 1.0 mg |
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

Example II

Inhalable Solution for Respimat® Containing 1 mg of Active Ingredient

Composition:
1 puff contains:

| | |
|---|---|
| active ingredient | 1.0 mg |
| benzalkonium chloride | 0.002 mg |
| disodium edetate | 0.0075 mg |
| purified water ad | 15.0 µl |

Method of Preparation:

The active ingredient and benzalkonium chloride are dissolved in water and transferred into Respimat® cartridges.

Example III

Inhalable Solution for Nebulisers Containing 1 mg of Active Ingredient

Composition:
1 vial contains:

| | |
|---|---|
| active ingredient | 0.1 g |
| sodium chloride | 0.18 g |
| benzalkonium chloride | 0.002 g |
| purified water ad | 20.0 ml |

Method of Preparation:

The active ingredient, sodium chloride and benzalkonium chloride are dissolved in water.

Example IV

Propellant Gas-Operated Metered Dose Aerosol Containing 1 mg of Active Ingredient Composition:
1 puff contains:

| | |
|---|---|
| active ingredient | 1.0 mg |
| lecithin | 0.1% |
| propellant gas ad | 50.0 µl |

Method of Preparation:

The micronised active ingredient is homogeneously suspended in the mixture of lecithin and propellant gas. The suspension is transferred into a pressurised container with a metering valve.

Example V

Nasal Spray Containing 1 mg of Active Ingredient

Composition:

| | |
|---|---|
| active ingredient | 1.0 mg |
| sodium chloride | 0.9 mg |
| benzalkonium chloride | 0.025 mg |
| disodium edetate | 0.05 mg |
| purified water ad | 0.1 ml |

Method of Preparation:

The active ingredient and the excipients are dissolved in water and transferred into a suitable container.

Example VI

Injectable Solution Containing 5 mg of Active Substance Per 5 ml

Composition:

| | |
|---|---|
| active substance | 5 mg |
| glucose | 250 mg |
| human serum albumin | 10 mg |
| glycofurol | 250 mg |
| water for injections ad | 5 ml |

Preparation:

Glycofurol and glucose are dissolved in water for injections (Wfl); human serum albumin is added; active ingredient is dissolved with heating; made up to specified volume with Wfl; transferred into ampoules under nitrogen gas.

Example VII

Injectable Solution Containing 100 mg of Active Substance Per 20 ml

Composition:

| | |
|---|---|
| active substance | 100 mg |
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections ad | 10 ml |

Preparation:

Polysorbate 80, sodium chloride, monopotassium dihydrogen phosphate and disodium hydrogen phosphate are dissolved in water for injections (Wfl); human serum albumin is added; active ingredient is dissolved with heating; made up to specified volume with Wfl; transferred into ampoules.

Example VIII

Lyophilisate Containing 10 mg of Active Substance

Composition:

| Active substance | 10 mg |
|---|---|
| Mannitol | 300 mg |
| human serum albumin | 20 mg |
| water for injections ad | 2 ml |

Preparation:

Mannitol is dissolved in water for injections (Wfl); human serum albumin is added; active ingredient is dissolved with heating; made up to specified volume with Wfl; transferred into vials; freeze-dried.

Solvent for Lyophilisate:

| Polysorbate 80 = Tween 80 | 20 mg |
|---|---|
| mannitol | 200 mg |
| water for injections ad | 10 ml |

Preparation:

Polysorbate 80 and mannitol are dissolved in water for injections (Wfl); transferred into ampoules.

Example IX

Tablets Containing 20 mg of Active Substance

Composition:

| active substance | 20 mg |
|---|---|
| lactose | 120 mg |
| corn starch | 40 mg |
| magnesium stearate | 2 mg |
| Povidone K 25 | 18 mg |

Preparation:

Active substance, lactose and corn starch are homogeneously mixed; granulated with an aqueous solution of Povidone; mixed with magnesium stearate; compressed in a tablet press; weight of tablet 200 mg.

Example X

Capsules Containing 20 mg Active Substance

Composition:

| active substance | 20 mg |
|---|---|
| corn starch | 80 mg |
| highly dispersed silica | 5 mg |
| magnesium stearate | 2.5 mg |

Preparation:

Active substance, corn starch and silica are homogeneously mixed; mixed with magnesium stearate; the mixture is packed into size 3 hard gelatine capsules in a capsule filling machine.

Example XI

Suppositories Containing 50 mg of Active Substance

Composition:

| active substance | 50 mg |
|---|---|
| hard fat (Adeps solidus) q.s. Ad | 1700 mg |

Preparation:

Hard fat is melted at about 38° C.; ground active substance is homogeneously dispersed in the molten hard fat; after cooling to about 35° C. it is poured into chilled moulds.

Example XII

Injectable Solution Containing 10 mg of Active Substance Per 1 ml

Composition:

| active substance | 10 mg |
|---|---|
| mannitol | 50 mg |
| human serum albumin | 10 mg |
| water for injections ad | 1 ml |

Preparation:

Mannitol is dissolved in water for injections (Wfl); human serum albumin is added; active ingredient is dissolved with heating; made up to specified volume with Wfl; transferred into ampoules under nitrogen gas.

The invention claimed is:

1. A compound of the formula

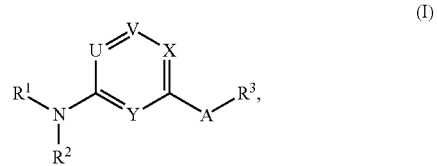

(I)

wherein

A denotes —NH, —N(C(O)—$C_{1-3}$-alkyl), S, O, SO, $SO_2$, $R^1$ and $R^2$ together with the nitrogen atom to which they are attached denote a moiety selected from the group consisting of

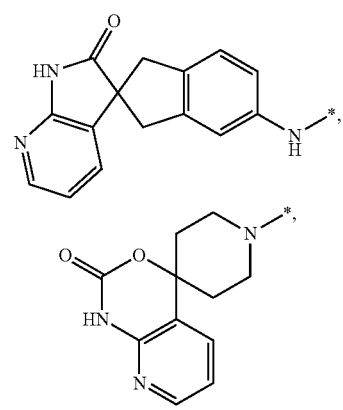

-continued
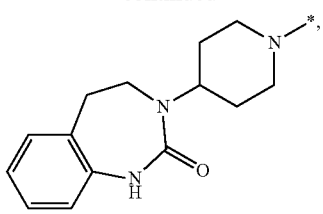
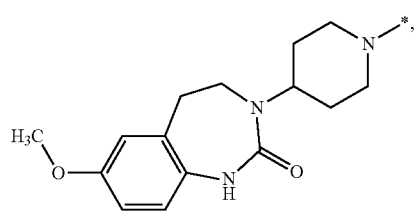
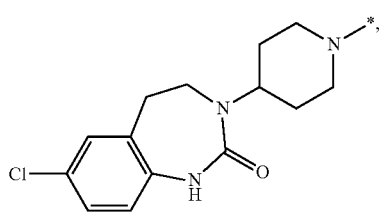
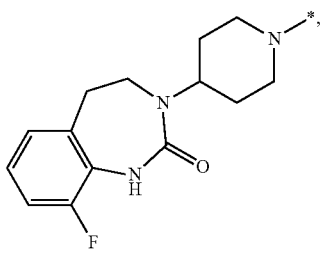
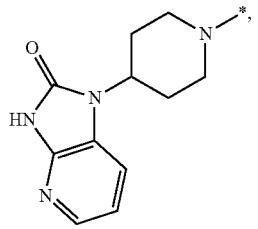
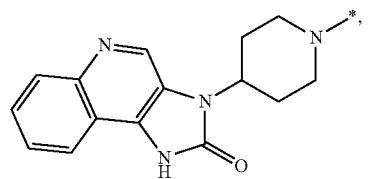
and,
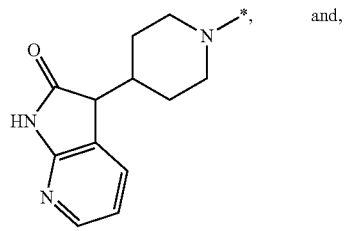
-continued
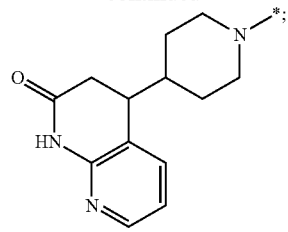
R³ denotes a group moiety selected from the group consisting of
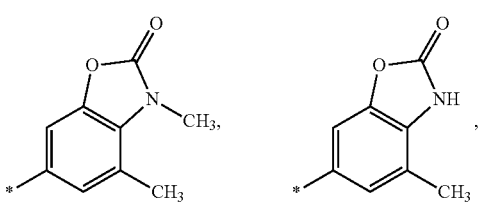
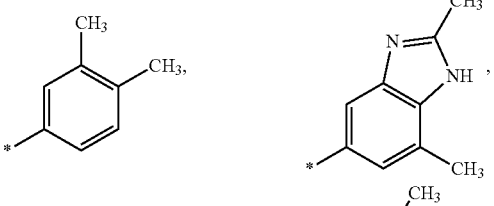
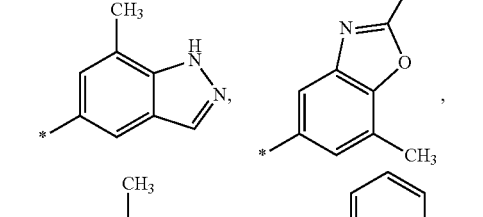
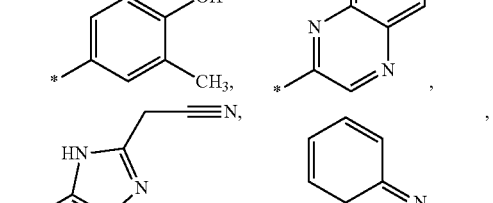
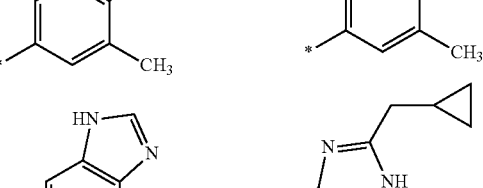
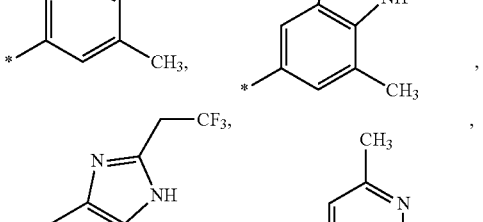

-continued
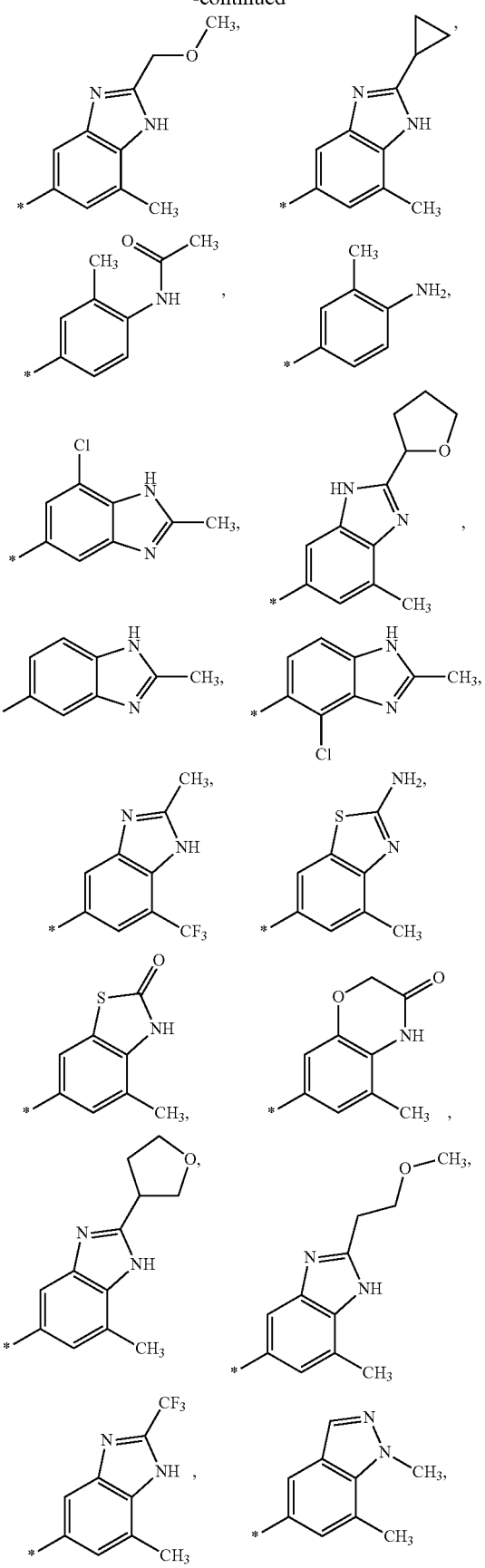
-continued
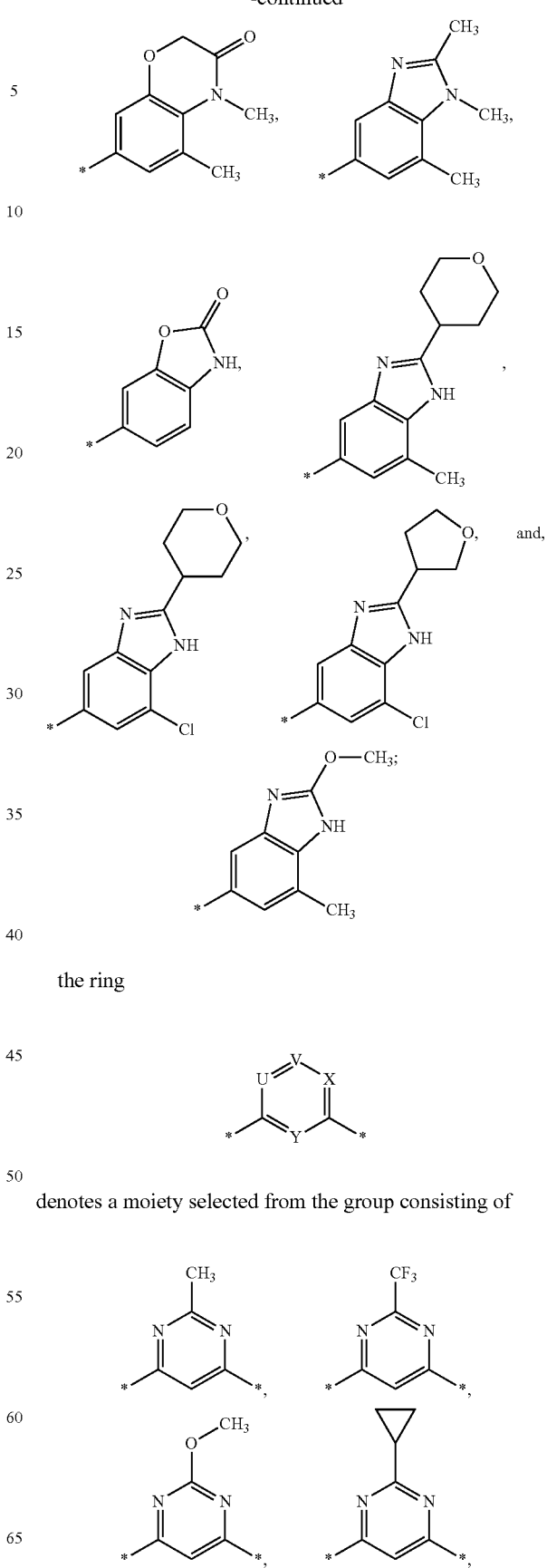
the ring
denotes a moiety selected from the group consisting of Y denotes N or CH, R$^5$ denotes
  (a) H,
  (b) —NR$^{5.1}$R$^{5.2}$,
  (c) halogen,
  (d) a C$_{1-3}$-alkyl or C$_{1-3}$-alkyl-O— group wherein each methylene group is substituted by up to two fluorine atoms and each methyl group is substituted by up to three fluorine atoms, R$^{5.1}$ denotes H, R$^{5.2}$ denotes H, and R$^6$ denotes
  (a) H, or a tautomer or salt thereof.

2. A compound of the formula I according to claim 1, wherein

A denotes —O— or —NH—, or a tautomer or salt thereof.

3. A compound of the formula Ia (Ia)

wherein

A denotes —NH— or —O—,

R$^1$ and R$^2$ together with the nitrogen atom to which they are attached denote a group selected from $R^3$ denotes a group selected from
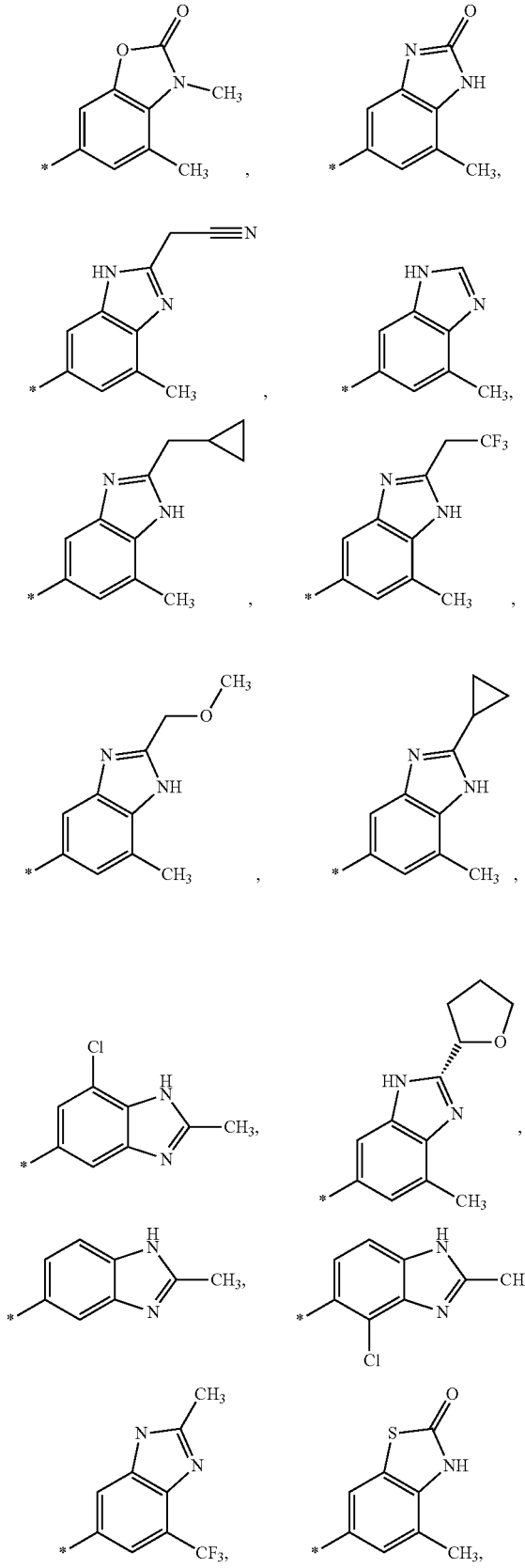
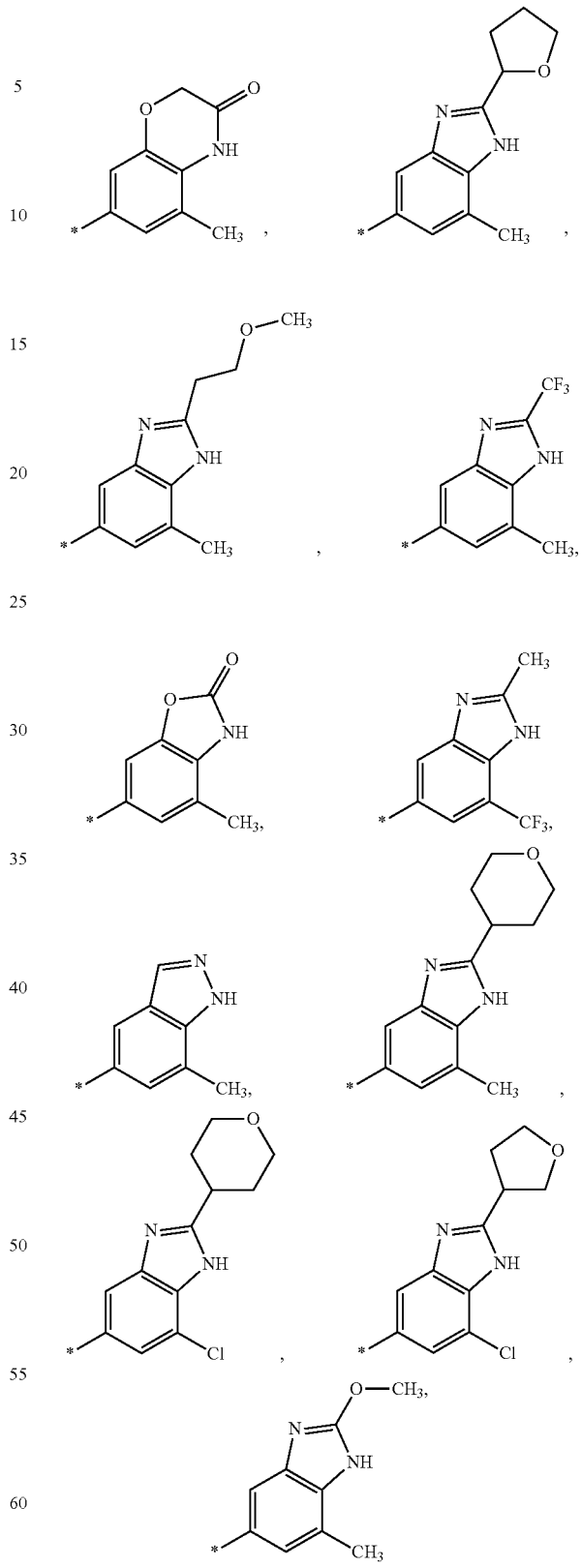
$R^5$ denotes H, Cl, $CH_3$, —O—$CH_3$ or cyclopropyl,
or a tautomer or salt thereof.

4. A compound of the formula I according to claim 1 selected from the group consisting of:
| No. | Structure |
|---|---|
| (1) | 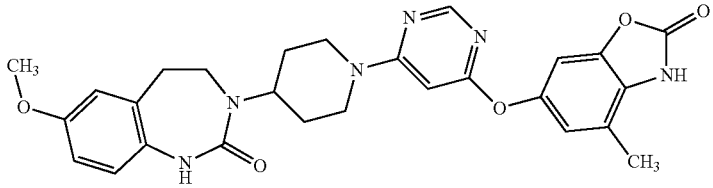 [SMILES: COc1ccc2c(c1)CCN(C1CCN(c3cc(Oc4cc(C)c5[nH]c(=O)oc5c4)ncn3)CC1)C(=O)N2] |
| (2) | 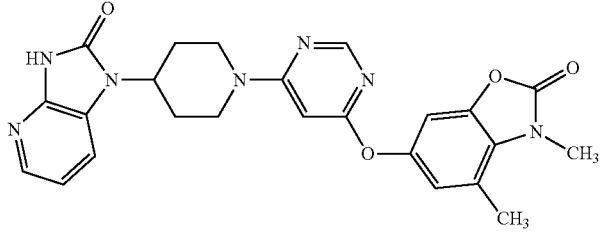 [SMILES: Cc1cc(Oc2cc(N3CCC(n4c(=O)[nH]c5ncccc54)CC3)ncn2)cc2oc(=O)n(C)c12] |
| (3) | 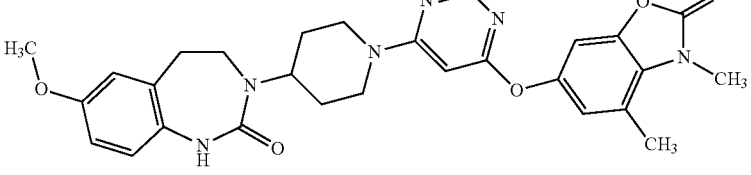 |
| (4) | 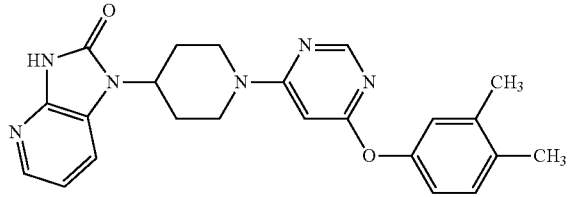 [SMILES: Cc1ccc(Oc2cc(N3CCC(n4c(=O)[nH]c5ncccc54)CC3)ncn2)cc1C] |
| (5) | 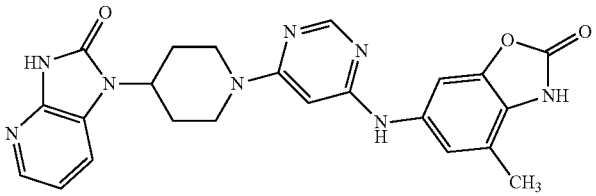 [SMILES: Cc1cc(Nc2cc(N3CCC(n4c(=O)[nH]c5ncccc54)CC3)ncn2)cc2oc(=O)[nH]c12] |
| (6) | 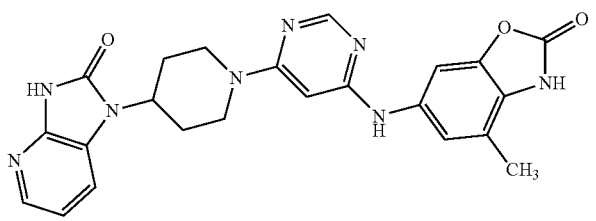 [SMILES: Cc1cc(Nc2cc(N3CCC(n4c(=O)[nH]c5ncccc54)CC3)ncn2)cc2oc(=O)[nH]c12] |
| (7) | 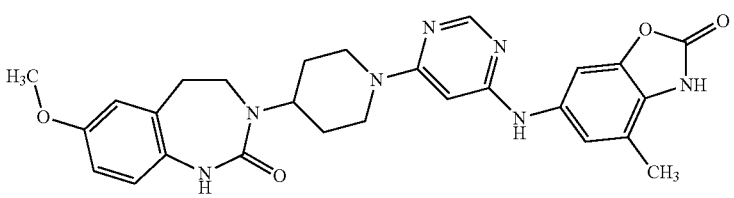 [SMILES: COc1ccc2c(c1)CCN(C1CCN(c3cc(Nc4cc(C)c5[nH]c(=O)oc5c4)ncn3)CC1)C(=O)N2] |

-continued
| No. | Structure |
|---|---|
| (8) | 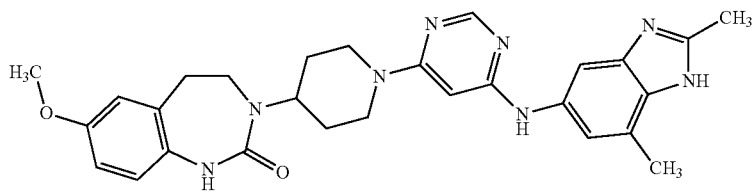 |
| (9) | 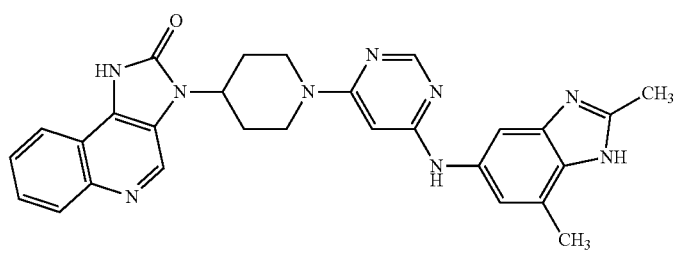 [SMILES: Cc1nc2cc(Nc3cc(N4CCC(n5c(=O)[nH]c6c7ccccc7ncc65)CC4)ncn3)cc(C)c2[nH]1] |
| (10) | 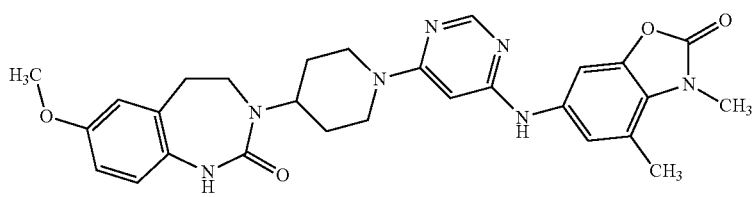 |
| (11) | 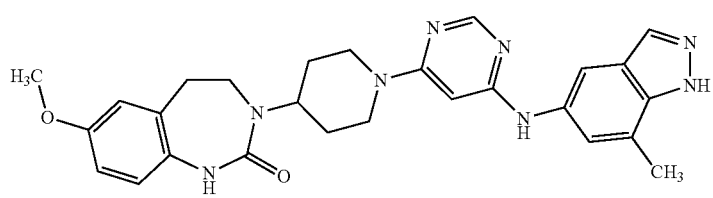 [SMILES: COc1ccc2c(c1)CCN(C1CCN(c3cc(Nc4cc(C)c5[nH]ncc5c4)ncn3)CC1)C(=O)N2] |
| (12) | 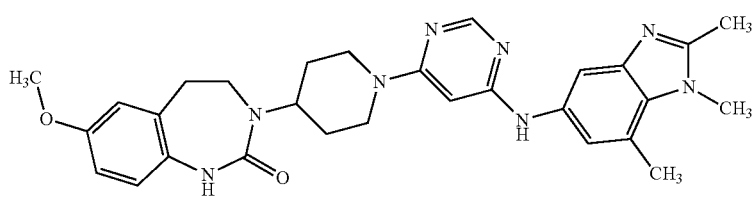 |
| (13) | 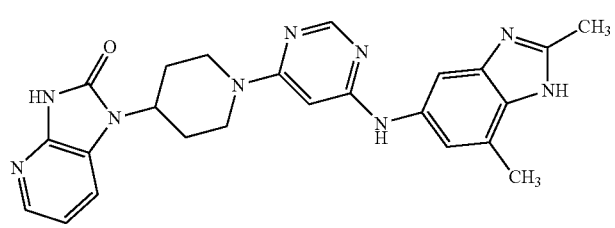 [SMILES: Cc1nc2cc(Nc3cc(N4CCC(n5c(=O)[nH]c6ncccc65)CC4)ncn3)cc(C)c2[nH]1] |
| (14) | 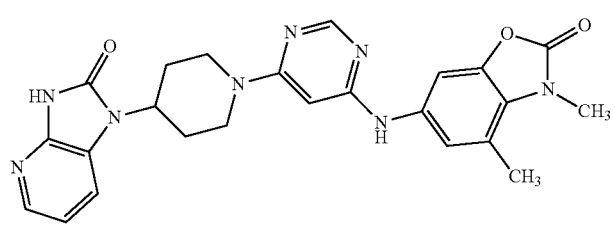 [SMILES: Cc1cc(Nc2cc(N3CCC(n4c(=O)[nH]c5ncccc54)CC3)ncn2)cc2oc(=O)n(C)c12] |

| No. | Structure |
|---|---|
| (15) | 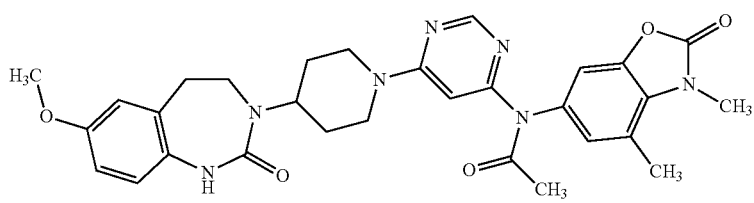 |
| (16) | 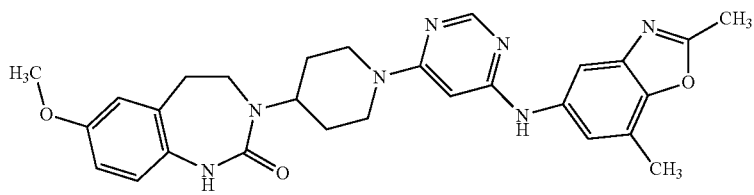 |
| (17) | 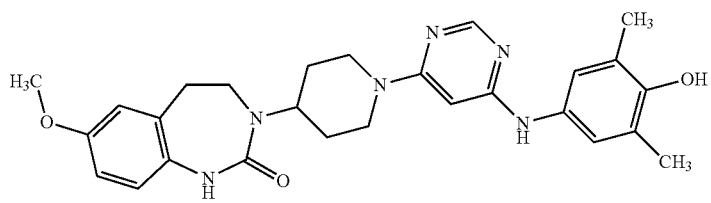 [SMILES: COc1ccc2c(c1)CCN(C1CCN(c3cc(Nc4cc(C)c(O)c(C)c4)ncn3)CC1)C(=O)N2] |
| (18) | 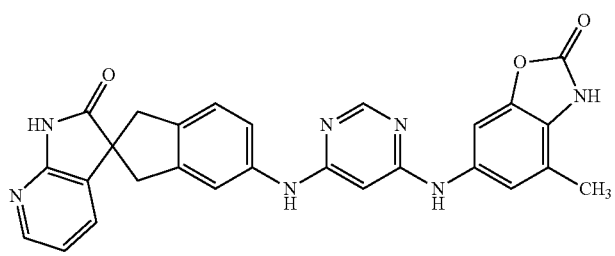 [SMILES: Cc1cc(Nc2cc(Nc3ccc4c(c3)CC3(C4)C(=O)Nc4ncccc43)ncn2)cc2oc(=O)[nH]c12] |
| (19) | 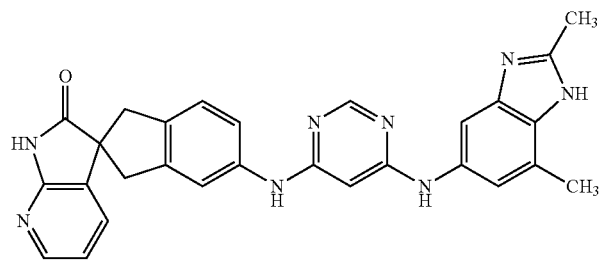 [SMILES: Cc1nc2cc(Nc3cc(Nc4ccc5c(c4)CC4(C5)C(=O)Nc5ncccc54)ncn3)cc(C)c2[nH]1] |
| (20) | 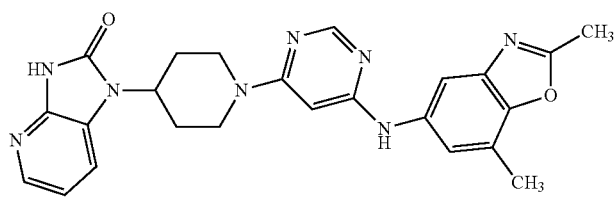 [SMILES: Cc1nc2cc(Nc3cc(N4CCC(n5c(=O)[nH]c6ncccc65)CC4)ncn3)cc(C)c2o1] |
| (21) | 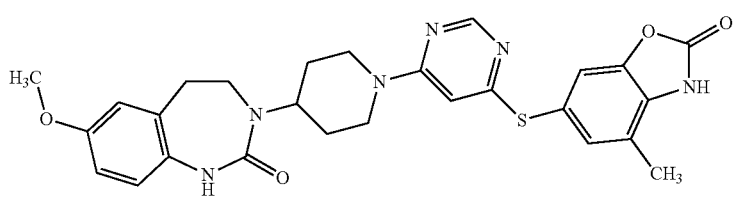 [SMILES: COc1ccc2c(c1)CCN(C1CCN(c3cc(Sc4cc(C)c5[nH]c(=O)oc5c4)ncn3)CC1)C(=O)N2] |

-continued
| No. | Structure |
|---|---|
| (22) | 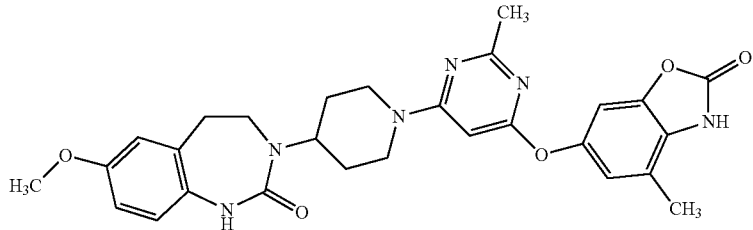 [SMILES: COc1ccc2c(c1)CCN(C1CCN(c3cc(Oc4cc(C)c5[nH]c(=O)oc5c4)nc(C)n3)CC1)C(=O)N2] |
| (23) | 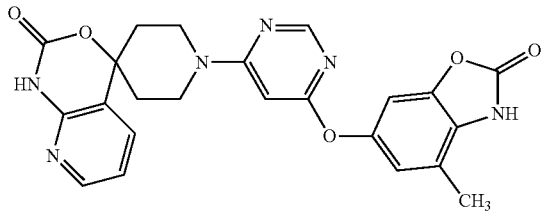 [SMILES: Cc1cc(Oc2cc(N3CCC4(CC3)OC(=O)Nc3ncccc34)ncn2)cc2oc(=O)[nH]c12] |
| (24) | 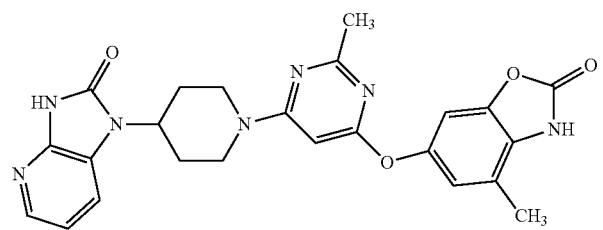 [SMILES: Cc1nc(Oc2cc(C)c3[nH]c(=O)oc3c2)cc(N2CCC(n3c(=O)[nH]c4ncccc43)CC2)n1] |
| (25) | 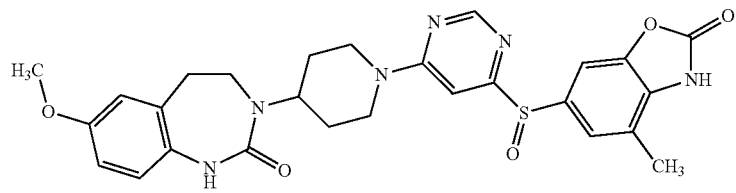 |
| (26) | 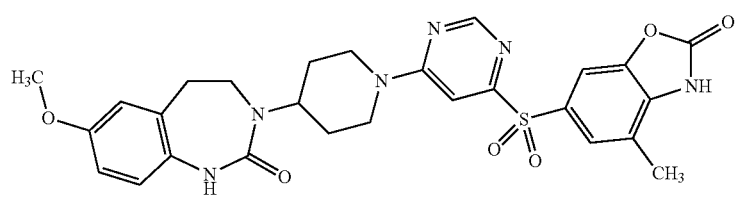 [SMILES: COc1ccc2c(c1)CCN(C1CCN(c3cc(S(=O)(=O)c4cc(C)c5[nH]c(=O)oc5c4)ncn3)CC1)C(=O)N2] |
| (27) | 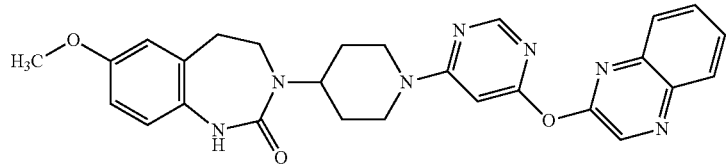 [SMILES: COc1ccc2c(c1)CCN(C1CCN(c3cc(Oc4cnc5ccccc5n4)ncn3)CC1)C(=O)N2] |
| (28) | 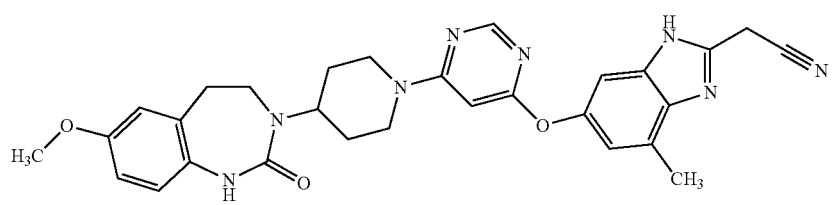 [SMILES: COc1ccc2c(c1)CCN(C1CCN(c3cc(Oc4cc(C)c5nc(CC#N)[nH]c5c4)ncn3)CC1)C(=O)N2] |

-continued
| No. | Structure |
|---|---|
| (29) | 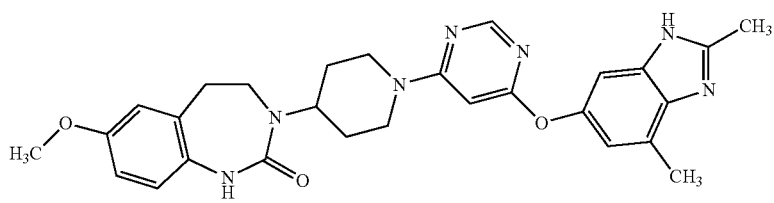 |
| (30) | 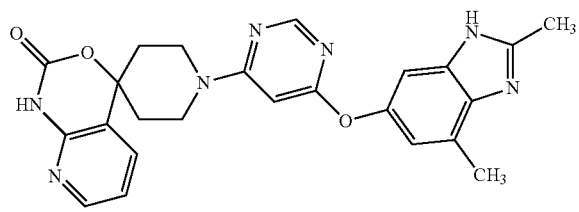 [SMILES: Cc1nc2c(C)cc(Oc3cc(N4CCC5(CC4)OC(=O)Nc4ncccc45)ncn3)cc2[nH]1] |
| (31) | 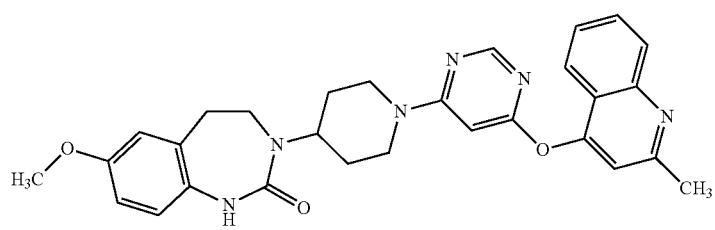 |
| (32) | 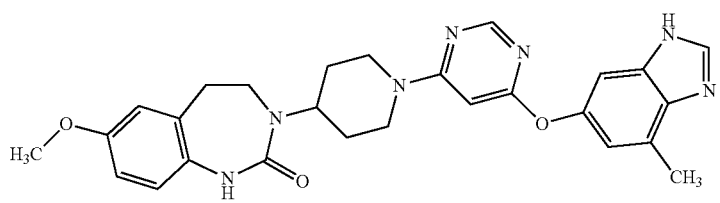 [SMILES: COc1ccc2c(c1)CCN(C1CCN(c3cc(Oc4cc(C)c5nc[nH]c5c4)ncn3)CC1)C(=O)N2] |
| (33) | 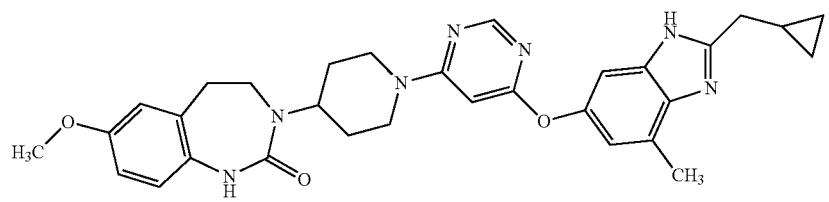 [SMILES: COc1ccc2c(c1)CCN(C1CCN(c3cc(Oc4cc(C)c5nc(CC6CC6)[nH]c5c4)ncn3)CC1)C(=O)N2] |
| (34) | 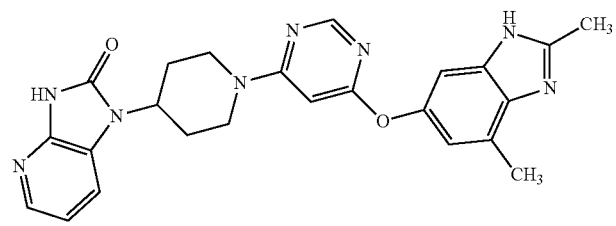 [SMILES: Cc1nc2c(C)cc(Oc3cc(N4CCC(n5c(=O)[nH]c6ncccc65)CC4)ncn3)cc2[nH]1] |
| (35) | 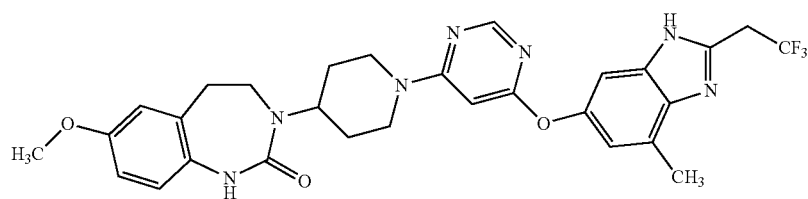 [SMILES: COc1ccc2c(c1)CCN(C1CCN(c3cc(Oc4cc(C)c5nc(CC(F)(F)F)[nH]c5c4)ncn3)CC1)C(=O)N2] |

-continued
| No. | Structure |
|---|---|
| (36) | 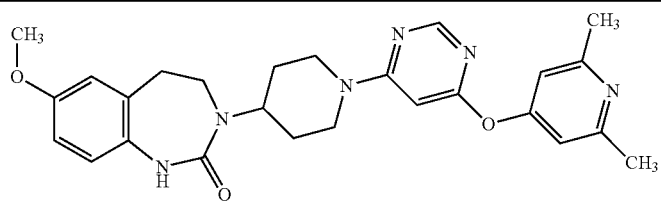 |
| (37) | 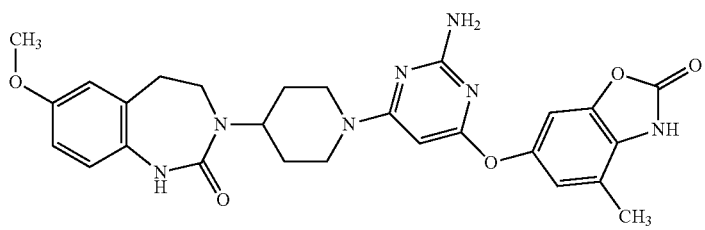 [SMILES: COc1ccc2c(c1)CCN(C1CCN(c3cc(Oc4cc(C)c5[nH]c(=O)oc5c4)nc(N)n3)CC1)C(=O)N2] |
| (38) | 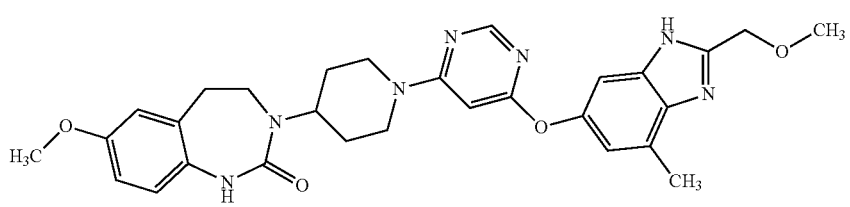 |
| (39) | 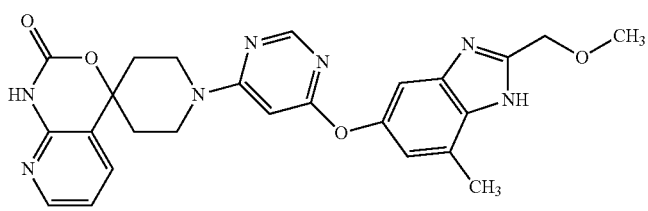 [SMILES: COCc1nc2cc(Oc3cc(N4CCC5(CC4)OC(=O)Nc4ncccc45)ncn3)cc(C)c2[nH]1] |
| (40) | 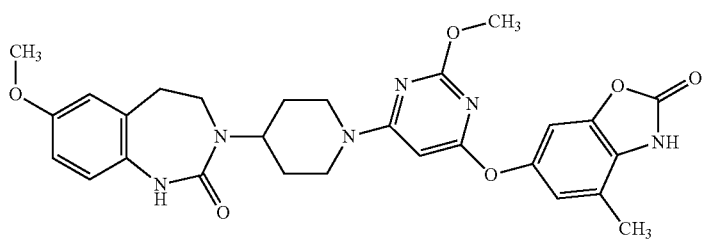 [SMILES: COc1ccc2c(c1)CCN(C1CCN(c3cc(Oc4cc(C)c5[nH]c(=O)oc5c4)nc(OC)n3)CC1)C(=O)N2] |
| (41) | 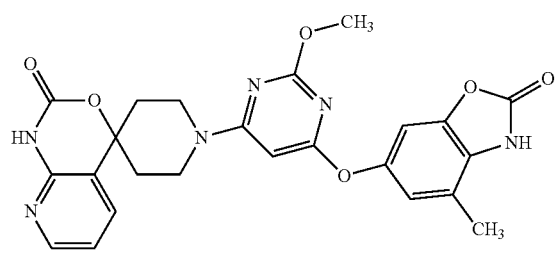 [SMILES: COc1nc(Oc2cc(C)c3[nH]c(=O)oc3c2)cc(N2CCC3(CC2)OC(=O)Nc2ncccc23)n1] |
| (42) | 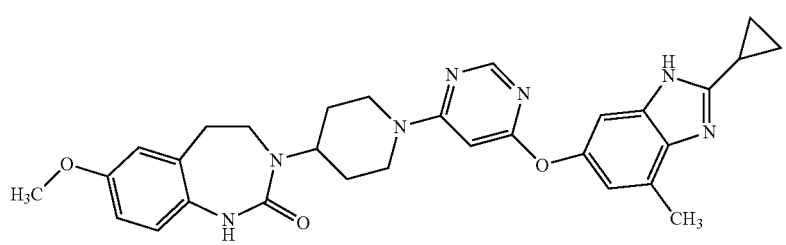 [SMILES: COc1ccc2c(c1)CCN(C1CCN(c3cc(Oc4cc(C)c5nc(C6CC6)[nH]c5c4)ncn3)CC1)C(=O)N2] |

| No. | Structure |
|---|---|
| (43) | 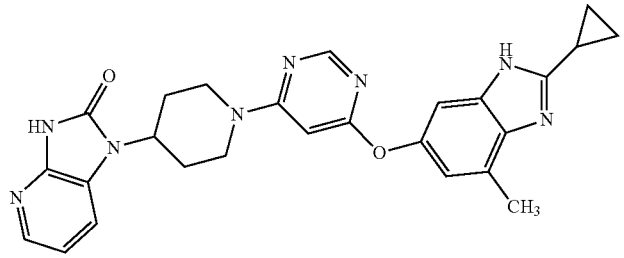 [SMILES: Cc1cc(Oc2cc(N3CCC(n4c(=O)[nH]c5ncccc54)CC3)ncn2)cc2[nH]c(C3CC3)nc12] |
| (44) | 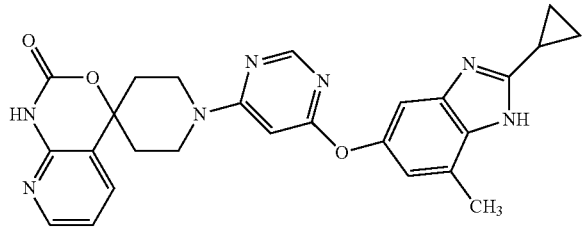 [SMILES: Cc1cc(Oc2cc(N3CCC4(CC3)OC(=O)Nc3ncccc34)ncn2)cc2nc(C3CC3)[nH]c12] |
| (45) | 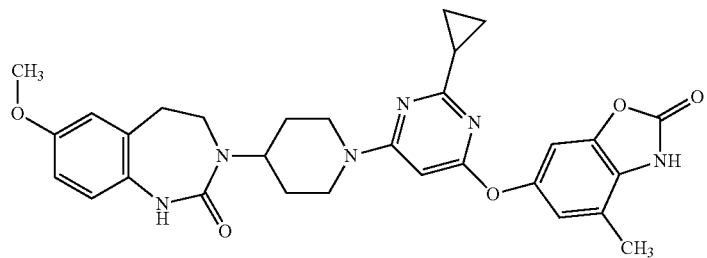 [SMILES: COc1ccc2c(c1)CCN(C1CCN(c3cc(Oc4cc(C)c5[nH]c(=O)oc5c4)nc(C4CC4)n3)CC1)C(=O)N2] |
| (46) | 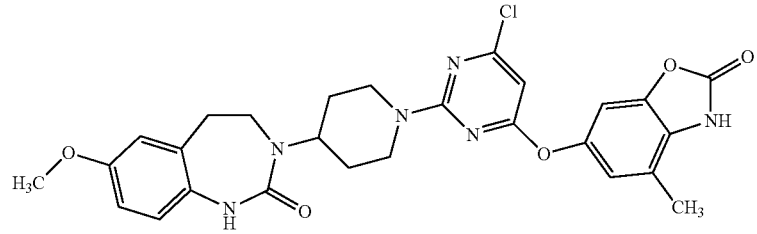 [SMILES: COc1ccc2c(c1)CCN(C1CCN(c3nc(Cl)cc(Oc4cc(C)c5[nH]c(=O)oc5c4)n3)CC1)C(=O)N2] |
| (47) | 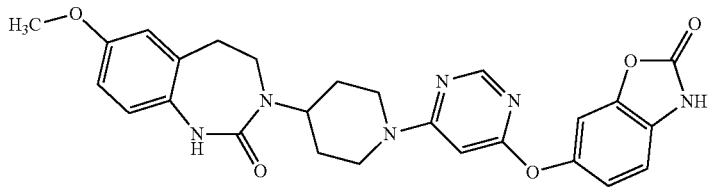 [SMILES: COc1ccc2c(c1)CCN(C1CCN(c3cc(Oc4ccc5[nH]c(=O)oc5c4)ncn3)CC1)C(=O)N2] |
| (48) | 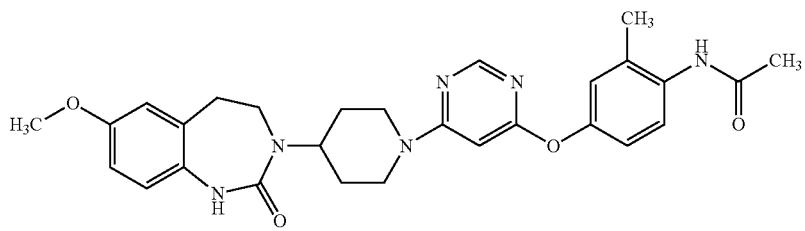 [SMILES: COc1ccc2c(c1)CCN(C1CCN(c3cc(Oc4ccc(NC(C)=O)c(C)c4)ncn3)CC1)C(=O)N2] |

-continued
| No. | Structure |
|---|---|
| (49) | 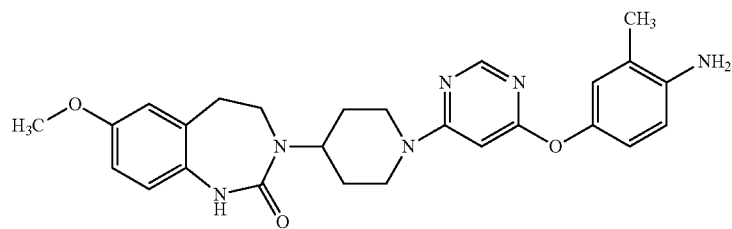 [SMILES: COc1ccc2c(c1)CCN(C1CCN(c3cc(Oc4ccc(N)c(C)c4)ncn3)CC1)C(=O)N2] |
| (50) | 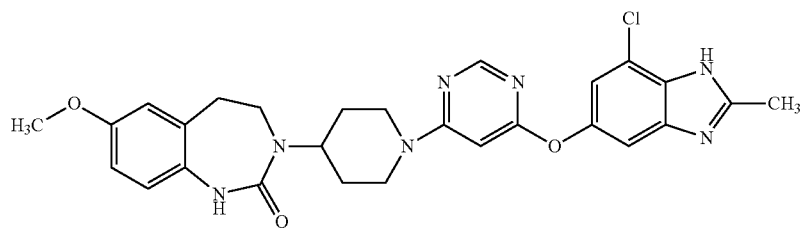 |
| (51) | 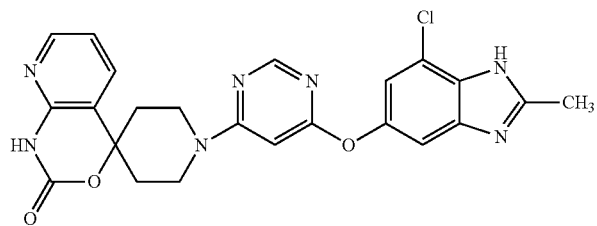 [SMILES: Cc1nc2cc(Oc3cc(N4CCC5(CC4)OC(=O)Nc4ncccc45)ncn3)cc(Cl)c2[nH]1] |
| (52) | 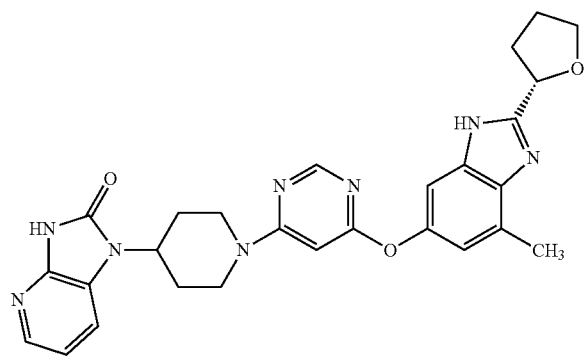 [SMILES: Cc1cc(Oc2cc(N3CCC(n4c(=O)[nH]c5ncccc54)CC3)ncn2)cc2[nH]c([C@@H]3CCCO3)nc12] |
| (53) | 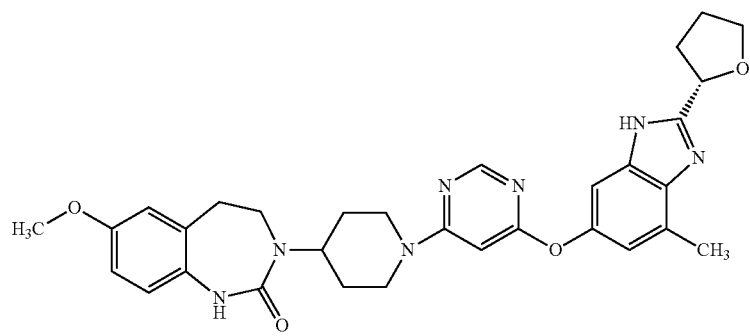 [SMILES: COc1ccc2c(c1)CCN(C1CCN(c3cc(Oc4cc(C)c5nc([C@@H]6CCCO6)[nH]c5c4)ncn3)CC1)C(=O)N2] |

225
226
-continued
| No. | Structure |
|---|---|
| (54) | 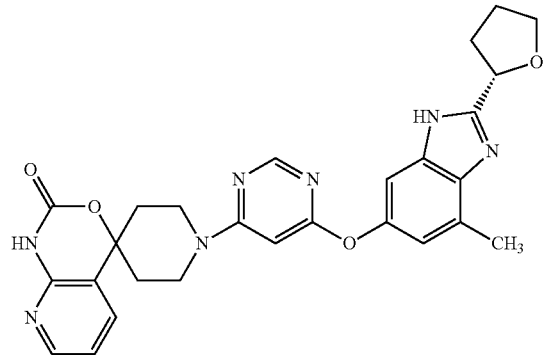 [SMILES: Cc1cc(Oc2cc(N3CCC4(CC3)OC(=O)Nc3ncccc34)ncn2)cc2[nH]c([C@@H]3CCCO3)nc12] |
| (55) | 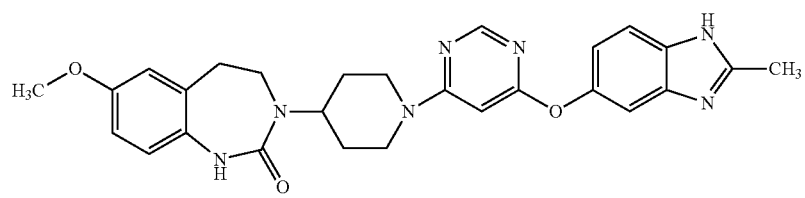 |
| (56) | 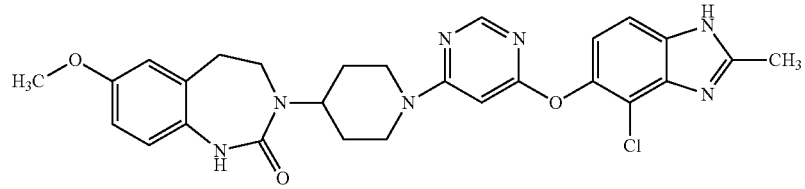 |
| (57) | 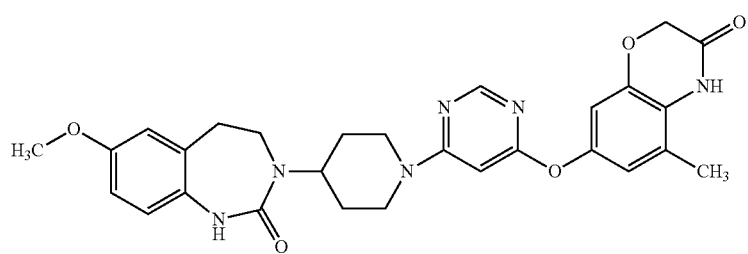 [SMILES: COc1ccc2c(c1)CCN(C1CCN(c3cc(Oc4cc(C)c5c(c4)OCC(=O)N5)ncn3)CC1)C(=O)N2] |
| (58) | 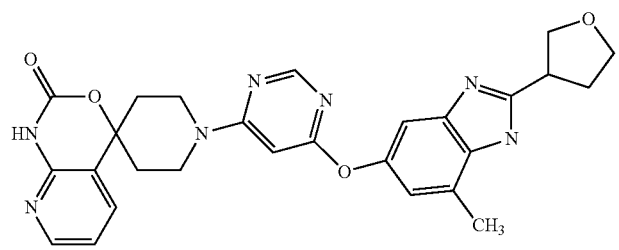 [SMILES: Cc1cc(Oc2cc(N3CCC4(CC3)OC(=O)Nc3ncccc34)ncn2)cc2nc(C3CCOC3)[nH]c12] |
| (59) | 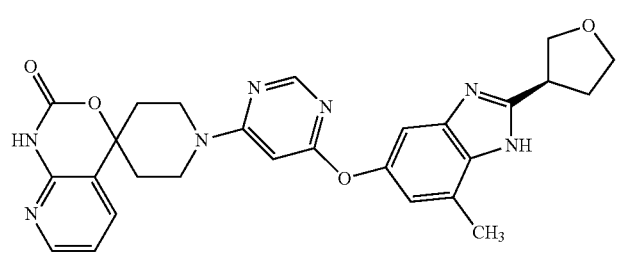 [SMILES: Cc1cc(Oc2cc(N3CCC4(CC3)OC(=O)Nc3ncccc34)ncn2)cc2nc([C@@H]3CCOC3)[nH]c12] |

| No. | Structure |
|---|---|
| (60) | 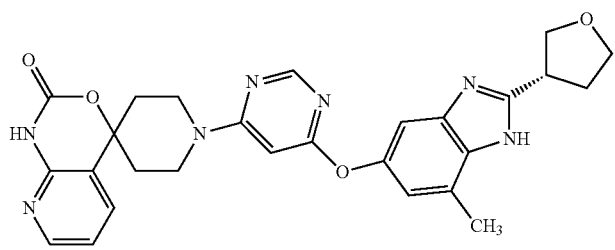 [SMILES: Cc1cc(Oc2cc(N3CCC4(CC3)OC(=O)Nc3ncccc34)ncn2)cc2nc([C@H]3CCOC3)[nH]c12] |
| (61) | 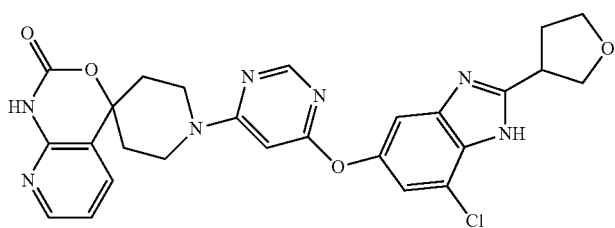 [SMILES: O=C1Nc2ncccc2C2(CCN(c3cc(Oc4cc(Cl)c5[nH]c(C6CCOC6)nc5c4)ncn3)CC2)O1] |
| (62) | 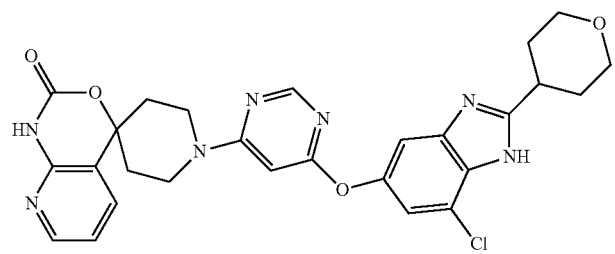 [SMILES: O=C1Nc2ncccc2C2(CCN(c3cc(Oc4cc(Cl)c5[nH]c(C6CCOCC6)nc5c4)ncn3)CC2)O1] |
| (63) | 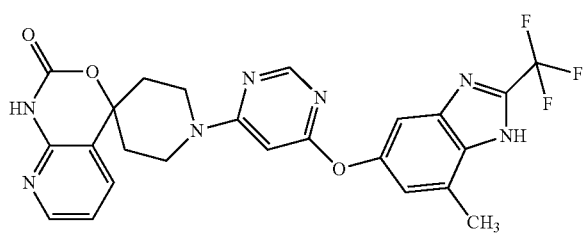 [SMILES: Cc1cc(Oc2cc(N3CCC4(CC3)OC(=O)Nc3ncccc34)ncn2)cc2nc(C(F)(F)F)[nH]c12] |
| (64) | 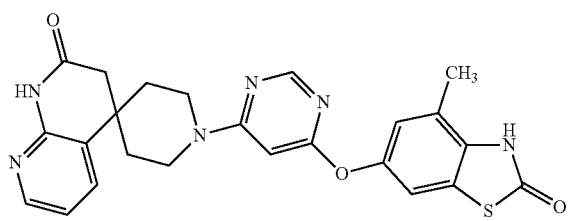 [SMILES: Cc1cc(Oc2cc(N3CCC4(CC3)CC(=O)Nc3ncccc34)ncn2)cc2sc(=O)[nH]c12] |
| (65) | 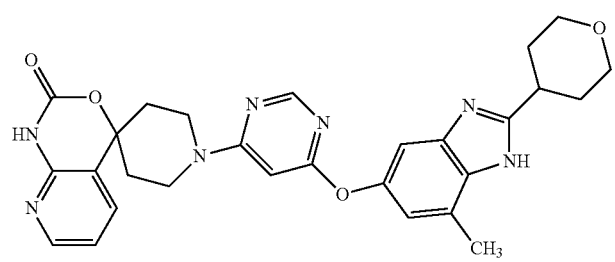 [SMILES: Cc1cc(Oc2cc(N3CCC4(CC3)OC(=O)Nc3ncccc34)ncn2)cc2nc(C3CCOCC3)[nH]c12] |

| No. | Structure |
|---|---|
| (66) | 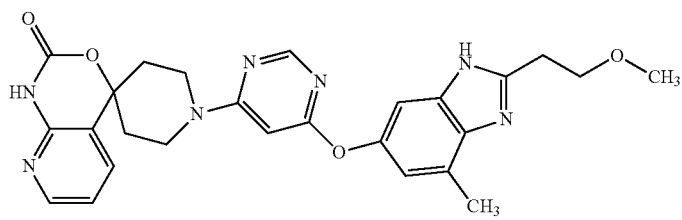 [SMILES: COCCc1nc2c(C)cc(Oc3cc(N4CCC5(CC4)OC(=O)Nc4ncccc45)ncn3)cc2[nH]1] |
| (67) | 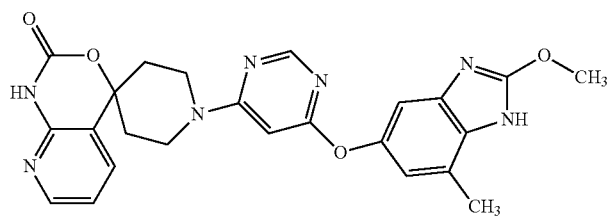 [SMILES: COc1nc2cc(Oc3cc(N4CCC5(CC4)OC(=O)Nc4ncccc45)ncn3)cc(C)c2[nH]1] |
| (68) | 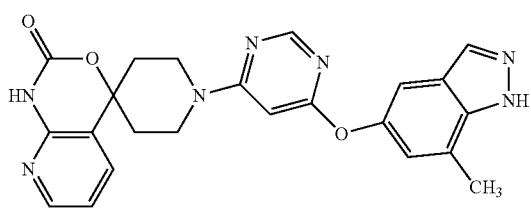 [SMILES: Cc1cc(Oc2cc(N3CCC4(CC3)OC(=O)Nc3ncccc34)ncn2)cc2cn[nH]c12] |
| (69) | 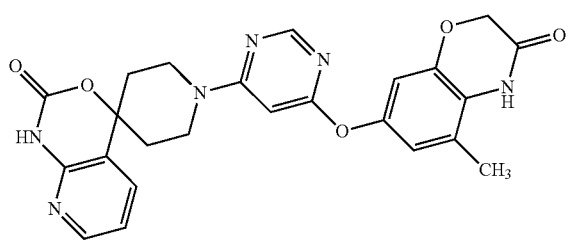 [SMILES: Cc1cc(Oc2cc(N3CCC4(CC3)OC(=O)Nc3ncccc34)ncn2)cc2c1NC(=O)CO2] |
| (70) | 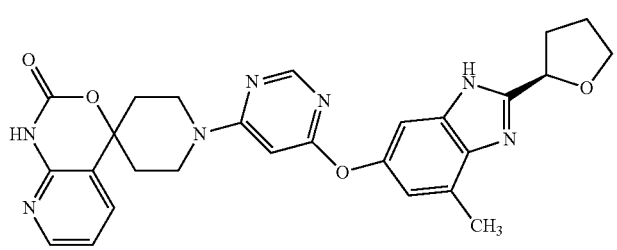 [SMILES: Cc1cc(Oc2cc(N3CCC4(CC3)OC(=O)Nc3ncccc34)ncn2)cc2[nH]c([C@H]3CCCO3)nc12] |
| (71) | 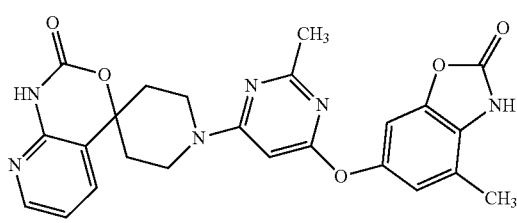 [SMILES: Cc1nc(Oc2cc(C)c3[nH]c(=O)oc3c2)cc(N2CCC3(CC2)OC(=O)Nc2ncccc23)n1] |
| (72) | 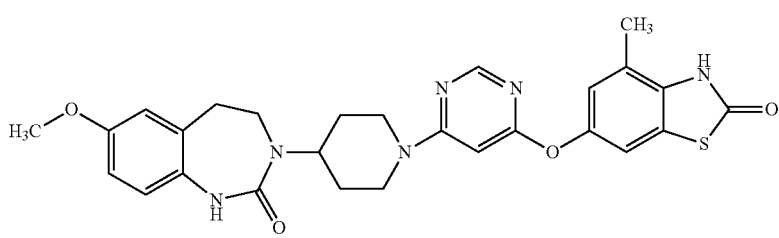 [SMILES: COc1ccc2c(c1)CCN(C1CCN(c3cc(Oc4cc(C)c5[nH]c(=O)sc5c4)ncn3)CC1)C(=O)N2] |

| No. | Structure |
|---|---|
| (73) | 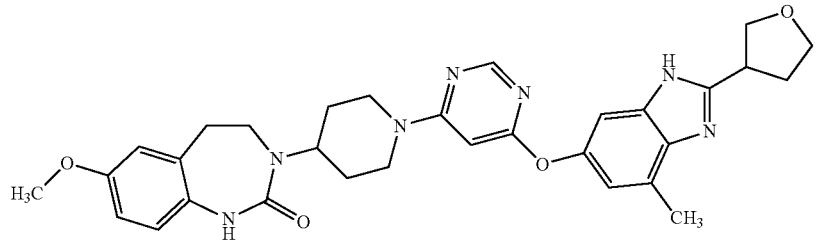 [SMILES: COc1ccc2c(c1)CCN(C1CCN(c3cc(Oc4cc(C)c5nc(C6CCOC6)[nH]c5c4)ncn3)CC1)C(=O)N2] |
| (74) | 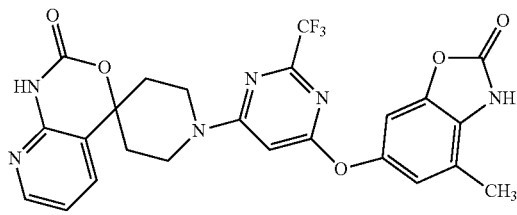 [SMILES: Cc1cc(Oc2cc(N3CCC4(CC3)OC(=O)Nc3ncccc34)nc(C(F)(F)F)n2)cc2oc(=O)[nH]c12] |
| (75) | 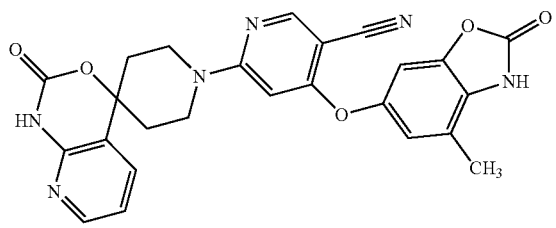 [SMILES: Cc1cc(Oc2cc(N3CCC4(CC3)OC(=O)Nc3ncccc34)ncc2C#N)cc2oc(=O)[nH]c12] |
| (76) | 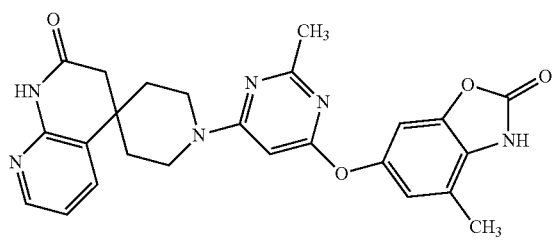 [SMILES: Cc1nc(Oc2cc(C)c3[nH]c(=O)oc3c2)cc(N2CCC3(CC2)CC(=O)Nc2ncccc23)n1] |
| (77) | 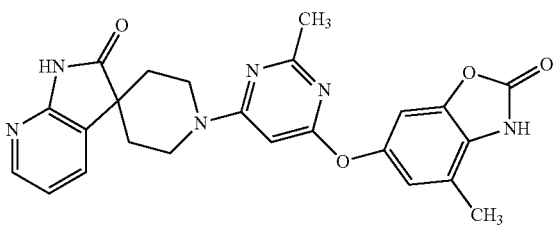 [SMILES: Cc1nc(Oc2cc(C)c3[nH]c(=O)oc3c2)cc(N2CCC3(CC2)C(=O)Nc2ncccc23)n1] |
| (78) | 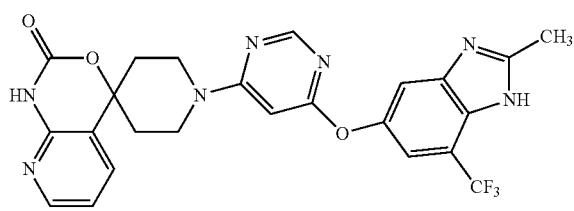 |

| No. | Structure |
|---|---|
| (79) | 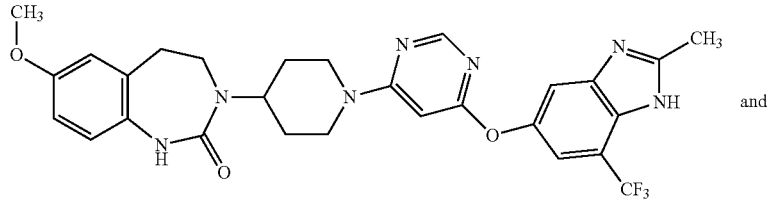 [SMILES: COc1ccc2c(c1)CCN(C1CCN(c3cc(Oc4cc(C(F)(F)F)c5[nH]c(C)nc5c4)ncn3)CC1)C(=O)N2] and |
| (80) | 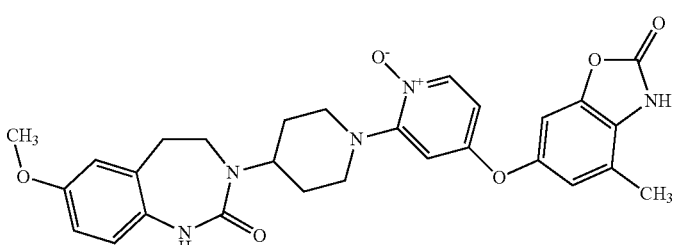 | or a tautomer or salt thereof.

5. A physiologically acceptable salt of a compound according to claim 1.

6. A pharmaceutical composition comprising a compound according to claim 1 or a pharmaceutically acceptable salt thereof together with a carrier or diluent.

7. A method for treating headache, including migraine and cluster headache, in a host suffering from such condition, comprising the administration of a therapeutically effective amount of a compound according to claim 1 or a pharmaceutically acceptable salt thereof.

8. The method of claim 7 wherein the condition to be treated is migraine or cluster headache.

* * * * *